US011603544B2

(12) United States Patent
Adair et al.

(10) Patent No.: US 11,603,544 B2
(45) Date of Patent: Mar. 14, 2023

(54) GENOMIC SAFE HARBORS FOR GENETIC THERAPIES IN HUMAN STEM CELLS AND ENGINEERED NANOPARTICLES TO PROVIDE TARGETED GENETIC THERAPIES

(71) Applicant: Fred Hutchinson Cancer Center, Seattle, WA (US)

(72) Inventors: Jennifer E. Adair, Seattle, WA (US); Reza Shahbazi, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 398 days.

(21) Appl. No.: 16/619,211

(22) PCT Filed: Jun. 5, 2018

(86) PCT No.: PCT/US2018/036154
§ 371 (c)(1),
(2) Date: Dec. 4, 2019

(87) PCT Pub. No.: WO2018/226762
PCT Pub. Date: Dec. 13, 2018

(65) Prior Publication Data
US 2021/0171983 A1 Jun. 10, 2021

Related U.S. Application Data

(60) Provisional application No. 62/515,474, filed on Jun. 5, 2017, provisional application No. 62/564,129, filed on Sep. 27, 2017, provisional application No. 62/664,045, filed on Apr. 27, 2018.

(51) Int. Cl.
| | |
|---|---|
| C07H 21/02 | (2006.01) |
| C12N 15/90 | (2006.01) |
| A61K 47/69 | (2017.01) |
| C12N 5/078 | (2010.01) |
| C12N 9/22 | (2006.01) |
| C12N 15/113 | (2010.01) |

(52) U.S. Cl.
CPC ........ *C12N 15/907* (2013.01); *A61K 47/6929* (2017.08); *C12N 5/0634* (2013.01); *C12N 9/22* (2013.01); *C12N 15/113* (2013.01); *C12N 2510/00* (2013.01)

(58) Field of Classification Search
CPC .......................... C12N 15/111; C12N 2310/20
See application file for complete search history.

(56) References Cited

U.S. PATENT DOCUMENTS

| | | |
|---|---|---|
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,580,701 B2 | 2/2017 | May et al. |
| 2001/0005581 A1 | 6/2001 | Grant |
| 2003/0053983 A1 | 3/2003 | Tamarkin et al. |
| 2003/0118657 A1 | 6/2003 | West et al. |
| 2008/0050774 A1 | 2/2008 | Berka et al. |
| 2016/0208243 A1 | 7/2016 | Zhang et al. |
| 2017/0058272 A1 | 3/2017 | Carter et al. |
| 2017/0106025 A1 | 4/2017 | Kovarik |
| 2018/0030425 A1 | 2/2018 | Joung et al. |
| 2019/0345450 A1 | 11/2019 | Radtke et al. |

FOREIGN PATENT DOCUMENTS

| | | |
|---|---|---|
| WO | WO2014018423 A2 | 1/2014 |
| WO | WO2014093595 A1 | 6/2014 |
| WO | WO2014093622 A2 | 6/2014 |
| WO | WO2014093635 A1 | 6/2014 |
| WO | WO2014093655 A2 | 6/2014 |
| WO | WO2014093661 A2 | 6/2014 |
| WO | WO2014093694 A1 | 6/2014 |
| WO | WO2014093701 A1 | 6/2014 |
| WO | WO2014093709 A1 | 6/2014 |
| WO | WO2014093712 A1 | 6/2014 |
| WO | WO2014093718 A1 | 6/2014 |
| WO | WO2014145599 A2 | 9/2014 |
| WO | WO2014204723 A1 | 12/2014 |
| WO | WO2014204724 A1 | 12/2014 |
| WO | WO2014204725 A1 | 12/2014 |
| WO | WO2014204726 A1 | 12/2014 |
| WO | WO2014204727 A1 | 12/2014 |
| WO | WO2014204728 A1 | 12/2014 |
| WO | WO2014204729 A1 | 12/2014 |
| WO | WO2015048577 A2 | 4/2015 |
| WO | WO2015065964 A1 | 5/2015 |
| WO | WO2015089351 A1 | 6/2015 |
| WO | WO2015089354 A1 | 6/2015 |
| WO | WO2015089364 A1 | 6/2015 |

(Continued)

OTHER PUBLICATIONS

Bedel, et al., "Metabolic Correction of Congenital Erythropoietic Porphyria with iPSCs Free of Reprogramming Factors", The American Journal of Human Genetics, vol. 91, No. 1, 2012, pp. 109-121.
Corrigan-Curay, et al., "Genome Editing Technologies: Defining a Path to Clinic", Molecular Therapy, vol. 23, No. 5, 1 2015, pp. 796-806.

(Continued)

*Primary Examiner* — Amy H Bowman
(74) *Attorney, Agent, or Firm* — Lee & Hayes PC; C. Rachal Winger

(57) ABSTRACT

Genomic safe harbors (GSH) for genetic therapies in human stem cells and engineered nanoparticles to provide targeted genetic therapies are described. The GSH and/or associated nanoparticles can be used to safely and efficiently treat a variety of genetic, infectious, and malignant diseases.

20 Claims, 72 Drawing Sheets

Specification includes a Sequence Listing.

(56) References Cited

FOREIGN PATENT DOCUMENTS

| | | |
|---|---|---|
| WO | WO2015089419 A2 | 6/2015 |
| WO | WO2015089427 A1 | 6/2015 |
| WO | WO2015089462 A1 | 6/2015 |
| WO | WO2015089465 A1 | 6/2015 |
| WO | WO2015089473 A1 | 6/2015 |
| WO | WO2015089486 A2 | 6/2015 |
| WO | WO2016094874 A1 | 6/2016 |
| WO | WO2016118780 A1 | 7/2016 |
| WO | WO2016205711 A1 | 12/2016 |
| WO | WO2017004261 A1 | 1/2017 |
| WO | WO2017015015 A1 | 1/2017 |
| WO | WO2017053312 A1 | 3/2017 |
| WO | WO2017053713 A1 | 3/2017 |
| WO | WO2016115179 A1 | 4/2017 |
| WO | WO2017062983 A1 | 4/2017 |
| WO | WO2017066588 A2 | 4/2017 |
| WO | WO2017106657 A1 | 6/2017 |
| WO | WO2017127807 A1 | 7/2017 |
| WO | WO2017184768 A1 | 10/2017 |
| WO | WO2017218948 A2 | 12/2017 |

OTHER PUBLICATIONS

Extended European Search Report dated Feb. 11, 2021 for European Patent Application No. 18812653.6, 9 pages.
Pellenz, et al., "New Human Chromosomal Sites with Safe Harbor Potential for Targeted Transgene Insertion", Human Gene Therapy, vol. 30, No. 7, 2019, 15 pages.
Sadelain, et al., "Safe Harbours for the Integration of New DNA in the Human Genome", Nature Reviews Cancer, vol. 12, No. 1, 2011, pp. 51-58.
Sayandip, et al., "Gene Therapy for PIDs: Progress, Pitfalls and Prospects", Gene, Elsevier, Amsterdam, NL, vol. 525, No. 2, 2013, pp. 174-181.
Supplementary Table XP55767862, "Nucleotide Sequence Variants in mCreI Genomic Target Sites, Together with Predicted Effect on mCreI Cleavage Sensitivity", retrieved on Jan. 22, 2021 from https://www.ncbi.nlm.nih.gov/pmc/articles/PMC6648220/ Jul. 16, 2019, 8 pages.
Ding et al, "Gold Nanoparticles for Nucleic Acid Delivery," Molecular Therapy, vol. 22, No. 6, 2014, pp. 1075-1083.
Genbank, "*Homo sapiens* genomic DNA, chromosome 11q clone:RP11-655M14, complete sequences", retrieved on Sep. 27, 2018 at <<https://www.ncbi.nlm.nih.gov/nuccore/AP003385.2/>>, GenBank Accession No. AP003385.2, 2 pages.
Jiang, et al., "CRISPR-Cpf1 assisted genome editing of Corynebacterium glutamicum," Nat. Commun., vol. 8, No. 15179, 2017, pp. 1-11.
Kim, et al., "CRISPR/Cpf1-mediated DNA-free plant genome editing," Nat. Comm., vol. 8, No. 14406, 2017, pp. 1-7.
Lee, et al., "Nanoparticle delivery of Cas9 ribonucleoprotein and donor DNA in vivo induces homology-directed DNA repair," Nat. Biomed. Eng., vol. 1, 2017, pp. 889-901.
Invitation to Pay Additional Fees Dated Aug. 14, 2018 in International Application No. PCT/US18/36154, 3 pages.
Search Report and Written Opinion Dated Oct. 26, 2018 for International Application No. PCT/US18/36154, 17 pages.
Wisniewski, et al., "Further phenotypic characterization of the primitive lineage—CD34 + CD38-CD90 + CD45RA-hematopoietic stem cell/progenitor cell sub-population isolated from cord blood, mobilized peripheral blood and patients with chronic myelogenous leukemia," Blood Cancer Journal, vol. 1, No. 9, 2011, pp. 1-11.
Xu, et al., "Generation of targeted mutant rice using a CRISPR-Cpf1 system," Plant Biotechnol. J., vol. 15, No. 6, 2017, pp. 713-717.
Fin, et al., "CRISPR-Cas9 and CRISPR-Cpf1 mediated targeting of a stomatai developmental gene EPFL9 in rice," Plant Cell Rep., vol. 36, No. 5, 2017, pp. 745-757.
Yin, et al., "Delivery technologies for genome editing," Nat. Rev., vol. 16, 2017, pp. 387-399.
Zaidi, et al., "CRISPR-Cpf1: A New Tool for Plant Genome Editing," Cell Press, vol. 22, No. 7, 2017, pp. 550-553.
Zetsche, et al., "Multiplex gene editing by CRISPR-Cpf1 through autonomous processing of a single crRNA array," Nat. Biotechnol., vol. 35, No. 1, 2017, pp. 31-34.
Zhang, et al., "CRISPR-Cpf1 correction of muscular dystrophy mutations in human cardiomycocytes and mice," Sci. Adv., vol. 3, No. 4, 2017, pp. 1-10.
Zhang, et al., "Multiplex gene regulation by CRISPR-ddCpf1," Cell Discovery, vol. 3, 2017, pp. 1-9.
Zhong, et al., "Cpf1 proteins excise CRISPR RNAs from mRNA transcripts in mammalian cells," Nat. Chern. Biol, vol. 13, No. 8, 2017, pp. 834-841.
Bibikova, et al., "Enhancing Gene Targeting with Designed Zinc Finger Nucleases," Science, vol. 300, 2003, 1 page.
Bibikova, et al., "Targeted Chromosomal Cleavage and Mutagenesis in Drosophila Using Zinc-Finger Nucleases," Genetics, vol. 161, 2002, pp. 1169-1175.
Boch, et al., "Breaking the Code of DNA Binding Specificity of TAL-Type III Effectors," Science, vol. 326, 2009, pp. 1509-1512.
Bonifant, et al., "Toxicity and management in CAR T-cell therapy," Mol. Ther. Oncolytics, vol. 3, 2016, 7 pages.
Chang & Wilson, "Modification of DNA ends can decrease end joining relative to homologous recombination in mammalian cells," PNAS, vol. 84, No. 14, 1987, pp. 4959-4963.
Choudhary, et al., "Knockdown of HPRT for Selection of Genetically Modified Human Hematopoietic Progenitor Cells," PLoS One, vol. 8, No. 3, 2013, 9 pages.
Christian, et al., "Targeting DNA Double-Strand Breaks with TAL Effector Nucleases," Genetics, vol. 186, 2010, pp. 757-761.
De Ravin et al., "CRISPR-Cas9 Gene Repair of Hematopoietic Stem Cells From Patients With X-linked Chronic Granulomatous Disease," Sci. Transl. Med., vol. 9, No. 372, 2017, 10 pages.
Dong, et al., "The Crystal Structure of Cpf1 in Complex With CRISPR RNA," Nature, vol. 532, No. 7600, 2016, pp. 522-526.
Gori, et al., "In vivo Selection of Autologous MGMT Gene-Modified Cells Following Reduced Intensity Conditioning with BCNU and Temozolomide in the Dog Model," Cancer Gene. Ther., vol. 19, No. 8, 2012, pp. 523-529.
Hakkinen, "The Gold-Sulfur Interface at the Nanoscale," Nat. Chem., vol. 4, No. 6, 2012, pp. 443-455.
Huang, et al., "Cancer Cell Targeting Using Multiple Aptamers Conjugated on Nanorods," Anal. Chem., vol. 80, No. 3, 2008, pp. 567-572.
Kennedy, et al., "Ex Vivo y-Retroviral Gene Therapy of Dogs with X-linked Severe Combined Immunodeficiency and the Development of a Thymic T Cell Lymphoma," Vet. Immunol. Immunopathol., vol. 142, No. 1-2, 2011, pp. 36-48.
Kim, et al., "Efficient Transcriptional Gene Repression by Type V-A CRISPR-Cpf1 from Eubacterium eligens," ACS. Synth. Biol., vol. 6, No. 7, 2017, pp. 1273-1282.
Kim, et al., "Genome-wide Analysis Reveals Specificities of Cpf1 Endonucleases in Human Cells," Nat. Biotechnol., vol. 34, No. 8, 2016, pp. 863-868.
Kim, et al., "Hybrid restriction enzymes Zinc finger fusion to Fok I cleavage domain," PNAS, vol. 93, 1996, pp. 1156-1160.
Li, et al., "Engineering CRISPR-Cpf1 crRNAs and mRNAs to maximize genome editing efficiency," Nat. Biomed. Eng., vol. 1, No. 5, 2017, 21 pages.
Mirkin, et al., "A DNA-based Method for Rationally Assembling Nanoparticles Into Macroscopic Materials," Nature, vol. 382, No. 6592, 1996, pp. 607-609.
Miller, et al., "A TALE nuclease architecture for efficient genome editing," Nat. Biotechl., vol. 29, No. 2, 2011, pp. 143-150.
Miller, et al., "An improved zinc-finger nuclease architecture for highly specific genome editing," Nat. Biotechnol., vol. 25, No. 7, 2007, pp. 778-785.
Miller, et al., "Repetitive Zinc-Binding Domains in the Protein Transcription Factor IHA From Xenopus Oocytes," EMBO J., vol. 4, No. 6, 1985, pp. 1609-1614.
Moscou & Bogdanove, "A Simple Cipher Governs DNA Recognition by TAL Effectors," Science, vol. 326, 2009, pp. 1501.

(56) References Cited

OTHER PUBLICATIONS

Nehls, et al., "Two Genetically Separable Steps in the Differentiation of Thymic Epithelium," Science, vol. 272, No. 5263, 1996, pp. 886-889.

Papapetrou & Schambach, "Gene Insertion Into Genomic Safe Harbors for Human Gene Therapy," Mol. Ther., vol. 24, No. 4, 2016. pp. 678-684.

Papapetrou, et al., "Genomic safe harbors permit high beta-globin transgene expression in thalassemia induced pluripotent stem cells," Nat. Biotechnol., vol. 29, No. 1, 2011, pp. 73-78.

Perrault & Chan, "Synthesis and Surface Modification of Highly Monodispersed, Spherical Gold Nanoparticles of 50-200 Nm," J. Am. Chem. Soc., vol. 131, No. 47, 2009, pp. 17042-17043.

Radtke, et al., "A distinct hematopoietic stem cell population for rapid multilineage engraftment in nonhuman primates," Sci. Transl. Med., vol. 9, No. 414, 2017, 22 pages.

Ran, et al., "Double Nicking by RNA-guided CRISPR Cas9 for Enhanced Genome Editing Specificity," Cell, vol. 154, No. 6, 2013, 1380-1389.

Richardson, et al., "Enhancing homology-directed genome editing by catalytically active and inactive CRISPR-Cas9 using asymmetric donor DNA," Nat. Biotechnol., vol. 34, No. 3, 2016, pp. 339-344.

Shahbazi, et al., "Functionalized Gold Nanoparticles Manifested as Potent Carriers for Nucleolar Targeting," Nanotechnology, vol. 28, No. 2, 2017, 12 pages.

Shahbazi, et al., "Modified Gold-Based siRNA Nanotherapeutics for Targeted Therapy of Triple-Negative Breast Cancer," Nanomedicine, vol. 12, No. 16, 2017, pp. 1961-1973.

Tang, et al., "A CRISP-Cpf1 system for efficient genome editing and transcriptional repression in plants," Nat. Plants., vol. 3, No. 17018, 2017, 21 pages.

Turkevich, et al., "A study of the nucleation and growth processes in the synthesis of colloidal gold," Discussions of the Faraday Society, vol. 11, No. 0, 1951, pp. 55-75.

Wolfe, et al., "DNA Recognition By Cys2His2 Zinc Finger Proteins," Ann. Rev. Biophy. Biomol., vol. 29, 2000, pp. 183-212.

Yan, et al., "BLISS is a versatile and quantitative method for genome-wide profiling of DNA double-strand breaks." Nat. Commun., vol. 8, 2017, 9 pages.

Zetsche, et al., "Cpf1 Is a Single RNA-Guided Endonuclease of a Class 2 CRISPR-Cas System," Cell, vol. 163, No. 3, 2015, pp. 795-771.

Zhang, et al., "Instantaneous and Quantitative Functionalization of Gold Nanoparticles With Thiolated DNA Using a pH-assisted and Surfactant-Free Route," J. Am. Chem. Soc., vol. 134. No. 17, 2012, pp. 7266-7269.

FIG. 4

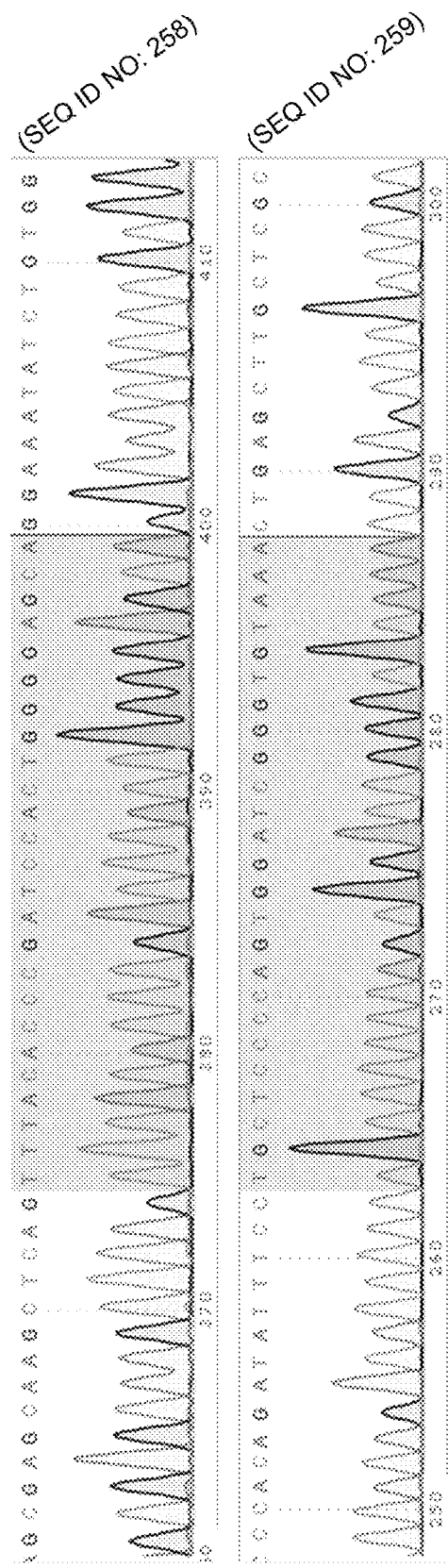

crRNA:

5'-/AltR1/rUrA rArUrU rUrCrU rArCrU rCrUrU rGrArU rCrArC rCrCrG rArUrC rUrGrG rGrGrA rGrCrA /iSp18//3ThioMC3-D/-3' (SEQ ID NO: 260)

Homology template for non-target strand:

CCACTTGAGTCCGTGTCACAAGCCCACAGATATTTCCTGGCGGCCGCTCCCCAGTGGATCGGGTGTAAACTGAGCTTGC
TCGCTCGG (SEQ ID NO: 261)    NotI restriction site (bold, underline)

Homology template for target strand:

CGAGCAAGCTCAGTTCACACCCGATCCACTGGGGAGCAGGGCCGCAAATATCTGTGGCTTGTGACACGGACTCAAG
TGGGCTGG (SEQ ID NO: 262)

FIG. 10A
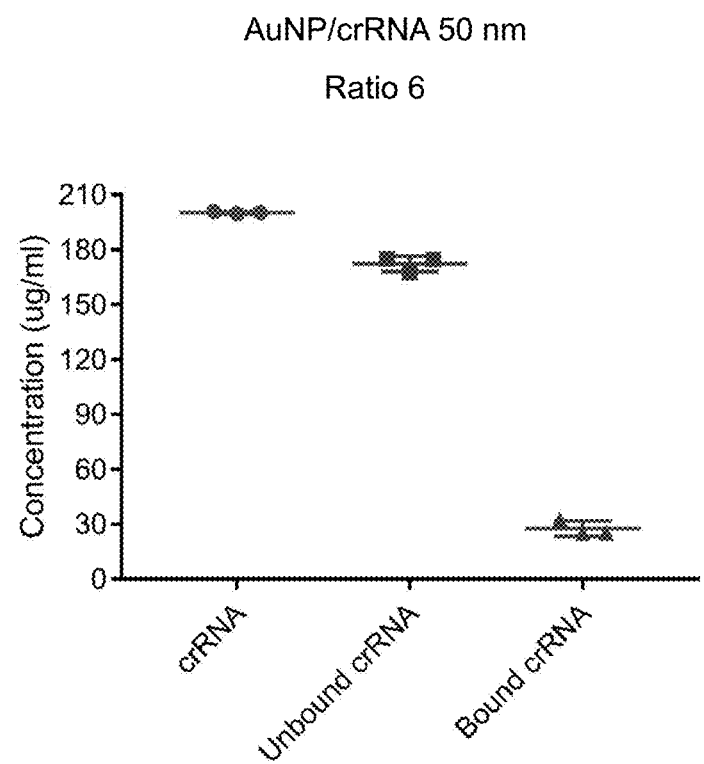
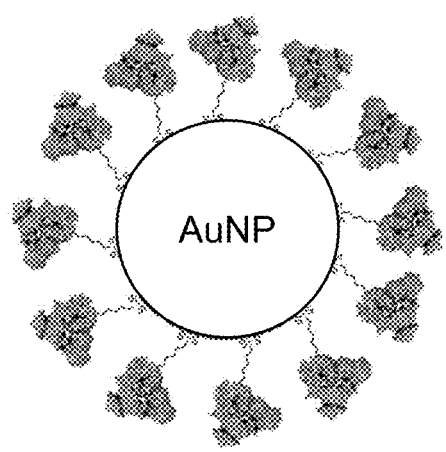

FIG. 10A cont'd
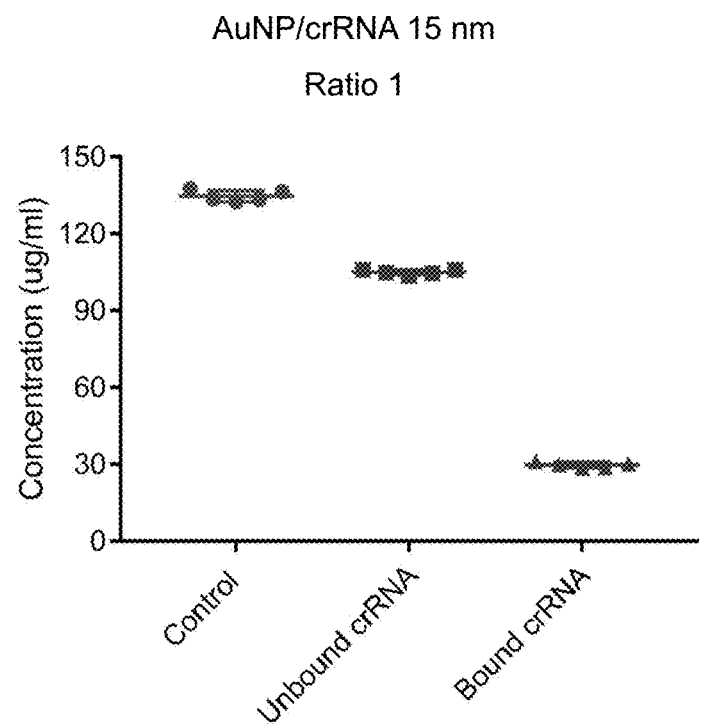
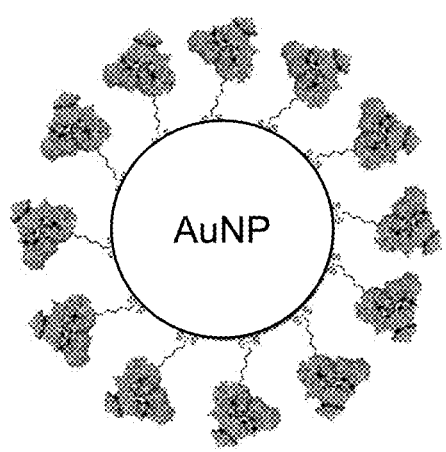

FIG. 10A cont'd
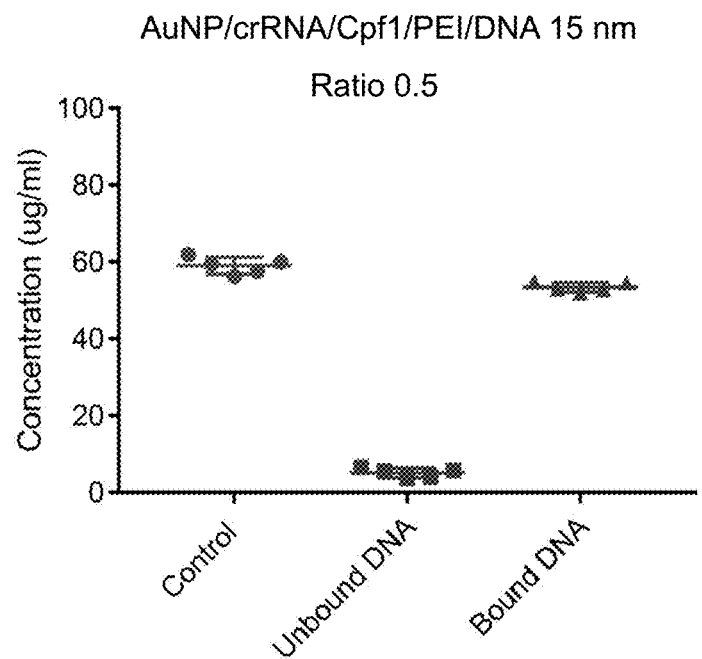
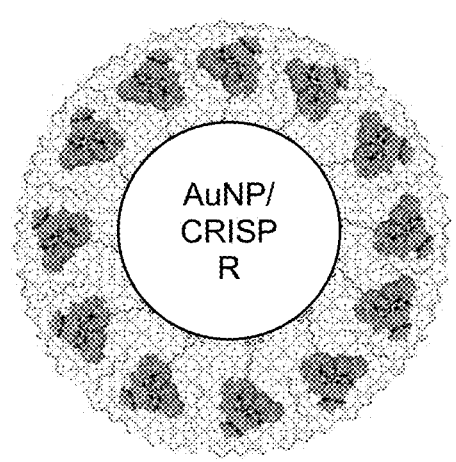

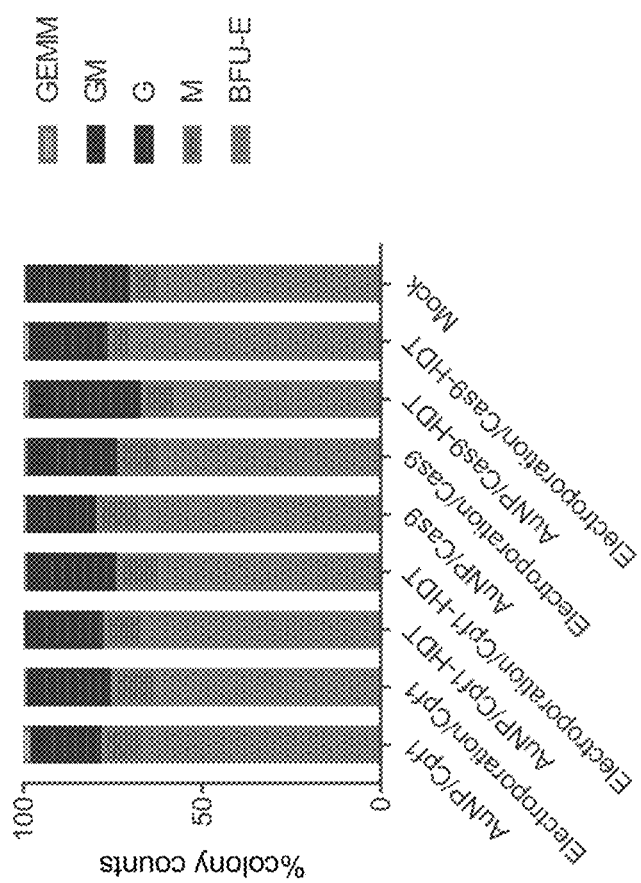
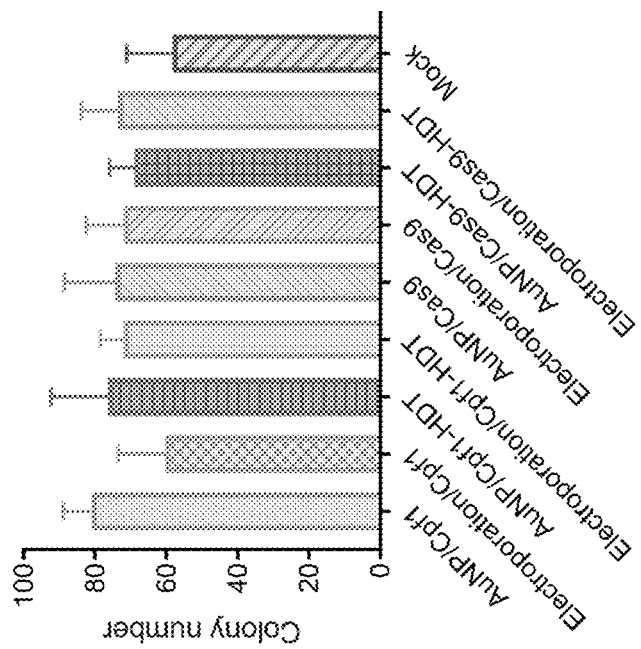
FIG. 18A

FIG. 23

>PGK promoter
GGGGTTGGGGTTGCGCCTTTTCCAAGGCAGCCCTGGGTTTGCGCAGGGACGCGGCTGCT
CTGGGCGTGGTTCCGGGAAACGCAGCGGCGCCGACCCTGGGTCTCGCACATTCTTCACG
TCCGTTCGCAGCGTCACCCGGATCTTCGCCGCTACCCTTGTGGGCCCCCCGGCGACGCTT
CCTGCTCCGCCCCTAAGTCGGGAAGGTTCCTTGCGGTTCGCGGCGTGCCGGACGTGACA
AACGGAAGCCGCACGTCTCACTAGTACCCTCGCAGACGGACAGCGCCAGGGAGCAATGG
CAGCGCGCCGACCGCGATGGGCTGTGGCCAATAGCGGCTGCTCAGCGGGGCGCGCCGA
GAGCAGCGGCCGGGAAGGGGCGGTGCGGGAGGCGGGGTGTGGGGCGGTAGTGTGGGC
CCTGTTCCTGCCCGCGCGGTGTTCCGCATTCTGCAAGCCTCCGGAGCGCACGTCGGCAG
TCGGCTCCCTCGTTGACCGAATCACCGACCTCTCTCCCCAG (SEQ ID NO: 214)

>Streptococcus pyogenes serotype M1 Cas9 cds (nucleotides 854751-858857 of NCBI
Reference Sequence: NC_002737.2)
ATGGATAAGAAATACTCAATAGGCTTAGATATCGGCACAAATAGCGTCGGATGGGCGGTGA
TCACTGATGAATATAAGGTTCCGTCTAAAAAGTTCAAGGTTCTGGGAAATACAGACCGCCA
CAGTATCAAAAAAATCTTATAGGGGCTCTTTTATTTGACAGTGGAGAGACAGCGGAAGCG
ACTCGTCTCAAACGGACAGCTCGTAGAAGGTATACACGTCGGAAGAATCGTATTTGTTATC
TACAGGAGATTTTTTCAAATGAGATGGCGAAAGTAGATGATAGTTTCTTTCATCGACTTGAA
GAGTCTTTTTTGGTGGAAGAAGACAAGAAGCATGAACGTCATCCTATTTTTGGAAATATAGT
AGATGAAGTTGCTTATCATGAGAAATATCCAACTATCTATCATCTGCGAAAAAATTGGTAG
ATTCTACTGATAAAGCGGATTTGCGCTTAATCTATTTGGCCTTAGCGCATATGATTAAGTTT
CGTGGTCATTTTTTGATTGAGGGAGATTTAAATCCTGATAATAGTGATGTGGACAAACTATT
TATCCAGTTGGTACAAACCTACAATCAATTATTTGAAGAAAACCCTATTAACGCAAGTGGAG
TAGATGCTAAAGCGATTCTTTCTGCACGATTGAGTAAATCAAGACGATTAGAAAATCTCATT
GCTCAGCTCCCCGGTGAGAAGAAAAATGGCTTATTTGGGAATCTCATTGCTTTGTCATTGG
GTTTGACCCCTAATTTTAAATCAAATTTTGATTTGGCAGAAGATGCTAAATTACAGCTTTCAA
AAGATACTTACGATGATGATTTAGATAATTTATTGGCGCAAATTGGAGATCAATATGCTGAT
TTGTTTTTGGCAGCTAAGAATTTATCAGATGCTATTTTACTTTCAGATATCCTAAGAGTAAAT
ACTGAAATAACTAAGGCTCCCCTATCAGCTTCAATGATTAAACGCTACGATGAACATCATCA
AGACTTGACTCTTTTAAAAGCTTTAGTTCGACAACAACTTCCAGAAAAGTATAAAGAAATCTT
TTTTGATCAATCAAAAAACGGATATGCAGGTTATATTGATGGGGGAGCTAGCCAAGAAGAA
TTTTATAAATTTATCAAACCAATTTTAGAAAAAATGGATGGTACTGAGGAATTATTGGTGAAA
CTAAATCGTGAAGATTTGCTGCGCAAGCAACGGACCTTTGACAACGGCTCTATTCCCCATC
AAATTCACTTGGGTGAGCTGCATGCTATTTTGAGAAGACAAGAAGACTTTTATCCATTTTTA
AAAGACAATCGTGAAGATGAAAAATCTTGACTTTTCGAATTCCTTATTATGTTGGTCC
ATTGGCGCGTGGCAATAGTCGTTTTGCATGGATGACTCGGAAGTCTGAAGAAACAATTACC
CCATGGAATTTTGAAGAAGTTGTCGATAAAGGTGCTTCAGCTCAATCATTTATTGAACGCAT
GACAAACTTTGATAAAAATCTTCCAAATGAAAAGTACTACCAAAACATAGTTTGCTTTATGA
GTATTTACGGTTTATAACGAATTGACAAAGGTCAAATATGTTACTGAAGGAATGCGAAAAC
CAGCATTTCTTTCAGGTGAACAGAAGAAAGCCATTGTTGATTACTCTTCAAAACAAATCGA
AAAGTAACCGTTAAGCAATTAAAGAAGATTATTTCAAAAAATAGAATGTTTTGATAGTGTT
GAAATTTCAGGAGTTGAAGATAGATTTAATGCTTCATTAGGTACCTACCATGATTTGCTAAA
AATTATTAAAGATAAAGATTTTTTGGATAATGAAGAAATGAAGATATCTTAGAGGATATTGT
TTTAACATTGACCTTATTTGAAGATAGGGAGATGATTGAGGAAAGACTTAAACATATGCTC
ACCTCTTTGATGATAAGGTGATGAAACAGCTTAAACGTCGCCGTTATACTGGTTGGGGACG
TTTGTCTCGAAAATTGATTAATGGTATTAGGGATAAGCAATCTGGCAAAACAATATTAGATTT
TTTGAAATCAGATGGTTTTGCCAATCGCAATTTTATGCAGCTGATCCATGATGATAGTTTGA
CATTTAAAGAAGACATTCAAAAAGCACAAGTGTCTGGACAAGGCGATAGTTTACATGAACAT
ATTGCAAATTTAGCTGGTAGCCCTGCTATTAAAAAAGGTATTTTACAGACTGTAAAAGTTGT

FIG. 23 cont'd.

TGATGAATTGGTCAAAGTAATGGGGCGGCATAAGCCAGAAAATATCGTTATTGAAATGGCA
CGTGAAAATCAGACAACTCAAAAGGGCCAGAAAAATTCGCGAGAGCGTATGAAACGAATC
GAAGAAGGTATCAAAGAATTAGGAAGTCAGATTCTTAAAGAGCATCCTGTTGAAAATACTCA
ATTGCAAAATGAAAAGCTCTATCTCTATTATCTCCAAAATGGAAGAGACATGTATGTGGACC
AAGAATTAGATATTAATCGTTAAGTGATTATGATGTCGATCACATTGTTCCACAAAGTTTCC
TTAAAGACGATTCAATAGACAATAAGGTCTTAACGCGTTCTGATAAAAATCGTGGTAAATCG
GATAACGTTCCAAGTGAAGAAGTAGTCAAAAAGATGAAAAACTATTGGAGACAACTTCTAAA
CGCCAAGTTAATCACTCAACGTAAGTTTGATAATTTAACGAAAGCTGAACGTGGAGGTTTGA
GTGAACTTGATAAAGCTGGTTTTATCAAACGCCAATTGGTTGAAACTCGCCAAATCACTAAG
CATGTGGCACAAATTTTGGATAGTCGCATGAATACTAAATACGATGAAAATGATAAACTTAT
TCGAGAGGTTAAAGTGATTACCTTAAAATCTAAATTAGTTTCTGACTTCCGAAAAGATTTCCA
ATTCTATAAAGTACGTGAGATTAACAATTACCATCATGCCCATGATGCGTATCTAAATGCCG
TCGTTGGAACTGCTTTGATTAAGAAATATCCAAAACTTGAATCGGAGTTTGTCTATGGTGAT
TATAAAGTTTATGATGTTCGTAAAATGATTGCTAAGTCTGAGCAAGAAATAGGCAAAGCAAC
CGCAAATATTTCTTTTACTCTAATATCATGAACTTCTTCAAAACAGAAATTACACTTGCAAA
TGGAGAGATTCGCAAACGCCCTCTAATCGAAACTAATGGGGAAACTGGAGAAATTGTCTGG
GATAAAGGGCGAGATTTTGCCACAGTGCGCAAAGTATTGTCCATGCCCCAAGTCAATATTG
TCAAGAAAACAGAAGTACAGACAGGCGGATTCTCCAAGGAGTCAATTTTACCAAAAGAAA
TTCGGACAAGCTTATTGCTCGTAAAAAAGACTGGGATCCAAAAAAATATGGTGGTTTTGATA
GTCCAACGGTAGCTTATTCAGTCCTAGTGGTTGCTAAGGTGGAAAAAGGGAAATCGAAGAA
GTTAAAATCCGTTAAAGAGTTACTAGGGATCACAATTATGGAAAGAAGTTCCTTTGAAAAAA
ATCCGATTGACTTTTAGAAGCTAAAGGATATAAGGAAGTTAAAAAGACTTAATCATTAAAC
TACCTAAATATAGTCTTTTTGAGTTAGAAAACGGTCGTAAACGGATGCTGGCTAGTGCCGG
AGAATTACAAAAGGAAATGAGCTGGCTCTGCCAAGCAAATATGTGAATTTTTTATATTTAG
CTAGTCATTATGAAAAGTTGAAGGGTAGTCCAGAAGATAACGAACAAAAACAATTGTTTGTG
GAGCAGCATAAGCATTATTTAGATGAGATTATTGAGCAAATCAGTGAATTTTCTAAGCGTGT
TATTTTAGCAGATGCCAATTTAGATAAAGTTCTTAGTGCATATAACAAACATAGAGACAAAC
CAATACGTGAACAAGCAGAAAATATTATTCATTTATTTACGTTGACGAATCTTGGAGCTCCC
GCTGCTTTTAAATATTTTGATACAACAATTGATCGTAAACGATATACGTCTACAAAAGAAGTT
TTAGATGCCACTCTTATCCATCAATCCATCACTGGTCTTTATGAAACACGCATTGATTTGAG
TCAGCTAGGAGGTGACTGA (SEQ ID NO: 215)

FIG. 23 cont'd.

\>Francisella tularensis type V CRISPR-associated Cpf1 cds (nucleotides 652838-656740 of NCBI Reference Sequence: NZ_CP009633.1)
ATGTCAATTTATCAAGAATTTGTTAATAAATATAGTTTAAGTAAAACTCTAAGATTTGAGTTAA
TCCCACAGGGTAAAACACTTGAAAACATAAAAGCAAGAGGTTTGATTTTAGATGATGAGAAA
AGAGCTAAAGACTACAAAAAGGCTAAACAAATAATTGATAAATATCATCAGTTTTTTATAGAG
GAGATATTAAGTTCGGTTTGTATTAGCGAAGATTTATTACAAAACTATTCTGATGTTTATTTT
AAACTTAAAAGAGTGATGATGATAATCTACAAAAGATTTTAAAAGTGCAAAAGATACGAT
AAAGAAACAAATATCTGAATATATAAAGGACTCAGAGAAATTTAAGAATTTGTTTAATCAAAA
CCTTATCGATGCTAAAAAAGGGCAAGAGTCAGATTTAATTCTATGGCTAAAGCAATCTAAGG
ATAATGGTATAGAACTATTTAAAGCCAATAGTGATATCACAGATATAGATGAGGCGTTAGAA
ATAATCAAATCTTTTAAAGGTTGGACAACTTATTTTAAGGGTTTTCATGAAAATAGAAAAAAT
GTTTATAGTAGCAATGATATTCCTACATCTATTATTTATAGGATAGTAGATGATAATTTGCCT
AAATTTCTAGAAAATAAAGCTAAGTATGAGAGTTTAAAAGACAAAGCTCCAGAAGCTATAAA
CTATGAACAAATTAAAAAAGATTTGGCAGAAGAGCTAACCTTTGATATTGACTACAAAACAT
CTGAAGTTAATCAAAGAGTTTTTCACTTGATGAAGTTTTGAGATAGCAAACTTTAATAATT
ATCTAAATCAAAGTGGTATTACTAAATTTAATACTATTATTGGTGGTAAATTTGTAAATGGTG
AAAATACAAAGAGAAAAGGTATAAATGAATATATAAATCTATACTCACAGCAAATAAATGATA
AAACACTCAAAAAATATAAAATGAGTGTTTTATTTAAGCAAATTTTAAGTGATACAGAATCTA
AATCTTTTGTAATTGATAAGTTAGAAGATGATAGTGATGTAGTTACAACGATGCAAAGTTTTT
ATGAGCAAATAGCAGCTTTTAAAACAGTAGAAGAAAATCTATTAAAGAAACACTATCTTTAT
TATTTGATGATTTAAAAGCTCAAAAACTTGATTTGAGTAAAATTTATTTTAAAAATGATAAATC
TCTTACTGATCTATCACAACAAGTTTTTGATGATTATAGTGTTATTGGTACAGCGGTACTAGA
ATATATAACTCAACAAATAGCACCTAAAAATCTTGATAACCCTAGTAAGAAAGAGCAAGAAT
TAATAGCCAAAAAACTGAAAAAGCAAAATACTTATCTCTAGAAACTATAAAGCTTGCCTTA
GAAGAATTTAATAAGCATAGAGATATAGATAAACAGTGTAGGTTTGAAGAAATACTTGCAAA
CTTTGCGGCTATTCCGATGATATTTGATGAAATAGCTCAAAACAAAGACAATTTGGCACAGA
TATCTATCAAATATCAAAATCAAGGTAAAAAGACCTACTTCAAGCTAGTGCGGAAGATGAT
GTTAAAGCTATCAAGGATCTTTTAGATCAAACTAATAATCTCTTACATAAACTAAAAATATTT
CATATTAGTCAGTCAGAAGATAAGGCAAATATTTTAGACAAGGATGAGCATTTTTATCTAGT
ATTTGAGGAGTGCTACTTTGAGCTAGCGAATATAGTGCCTCTTTATAACAAAATTAGAAACT
ATATAACTCAAAAGCCATATAGTGATGAGAAATTTAAGCTCAATTTTGAGAACTCGACTTTG
GCTAATGGTTGGGATAAAAATAAAGAGCCTGACAATACGGCAATTTTATTTATCAAAGATGA
TAAATATTATCTGGGTGTGATGAATAAGAAAAATAACAAAATATTTGATGATAAAGCTATCAA
AGAAAATAAAGGCGAGGGTTATAAAAAAATTGTTTATAAACTTTTACCTGGCGCAAATAAAA
TGTTACCTAAGGTTTTCTTTTCTGCTAAATCTATAAAATTTTATAATCCTAGTGAAGATATACT
TAGAATAAGAAATCATTCCACACATACAAAAAATGGTAGTCCTCAAAAAGGATATGAAAAAT
TTGAGTTTAATATTGAAGATTGCCGAAAATTTATAGATTTTATAAACAGTCTATAAGTAAGC
ATCCGGAGTGGAAAGATTTTGGATTTAGATTTTCTGATACTCAAAGATATAATTCTATAGATG
AATTTTATAGAGAAGTTGAAAATCAAGGCTACAAACTAACTTTTGAAAATATATCAGAGAGCT
ATATTGATAGCGTAGTTAATCAGGGTAAATTGTACCTATTCCAAATCTATAATAAAGATTTTT
CAGCTTATAGCAAAGGGCGACCAAATCTACATACTTTATATTGGAAAGCGCTGTTTGATGA
GAGAAATCTTCAAGATGTGGTTTATAAGCTAAATGGTGAGGCAGAGCTTTTTATCGTAAAC
AATCAATACCTAAAAAATCACTCACCCAGCTAAAGAGGCAATAGCTAATAAAACAAAGAT
AATCCTAAAAAGAGAGTGTTTTTGAATATGATTTAATCAAAGATAAACGCTTTACTGAAGAT
AAGTTTTTCTTTCACTGTCCTATTACAATCAATTTTAAATCTAGTGGAGCTAATAAGTTTAAT
GATGAAATCAATTTATTGCTAAAGAAAAGCAAATGATGTTCATATATTAAGTATAGATAGA
GGTGAAAGACATTTAGCTTACTATACTTTGGTAGATGGTAAAGGCAATATCATCAAACAAGA
TACTTTCAACATCATTGGTAATGATAGAATGAAAACAAACTACCATGATAAGCTTGCTGCAA
TAGAGAAAGATAGGGATTCAGCTAGGAAAGACTGGAAAAAGATAAATAACATCAAAGAGAT

FIG. 23 cont'd.

GAAAGAGGGCTATCTATCTCAGGTAGTTCATGAAATAGCTAAGCTAGTTATAGAGTATAATG
CTATTGTGGTTTTTGAGGATTTAAATTTTGGATTTAAAAGAGGGCGTTTCAAGGTAGAGAAG
CAGGTCTATCAAAAGTTAGAAAAAATGCTAATTGAGAAACTAAACTATCTAGTTTTCAAAGAT
AATGAGTTTGATAAAACTGGGGGAGTGCTTAGAGCTTATCAGCTAACAGCACCTTTTGAGA
CTTTTAAAAAGATGGGTAAACAAACAGGTATTATCTACTATGTACCAGCTGGTTTTACTTCAA
AAATTTGTCCTGTAACTGGTTTTGTAAATCAGTTATATCCTAAGTATGAAAGTGTCAGCAAAT
CTCAAGAGTTCTTTAGTAAGTTTGACAAGATTTGTTATAACCTTGATAAGGGCTATTTTGAGT
TTAGTTTTGATTATAAAAACTTTGGTGACAAGGCTGCCAAAGGCAAGTGGACTATAGCTAGC
TTTGGGAGTAGATTGATTAACTTTAGAAATTCAGATAAAAATCATAATTGGGATACTCGAGA
AGTTTATCCAACTAAAGAGTTGGAGAAATTGCTAAAAGATTATTCTATCGAATATGGGCATG
GCGAATGTATCAAAGCAGCTATTTGCGGTGAGAGCGACAAAAAGTTTTTTGCTAAGCTAAC
TAGTGTCCTAAATACTATCTTACAAATGCGTAACTCAAAAACAGGTACTGAGTTAGATTATCT
AATTTCACCAGTAGCAGATGTAAATGGCAATTTCTTTGATTCGCGACAGGCGCCAAAAAATA
TGCCTCAAGATGCTGATGCCAATGGTGCTTATCATATTGGGCTAAAAGGTCTGATGCTACT
AGGTAGGATCAAAAATAATCAAGAGGGCAAAAAACTCAATTTGGTTATCAAAAATGAAGAGT
ATTTTGAGTTCGTGCAGAATAGGAATAACTAA (SEQ ID NO: 216)

FIG. 23 cont'd.

>Acidaminococcus sp. BV3L6 Cpf1 (AsCpf1) cds from Zetsche 2015
ATGACACAGTTCGAGGGCTTTACCAACCTGTATCAGGTGAGCAAGACACTGCGGTTTGAG
CTGATCCCACAGGGCAAGACCCTGAAGCACATCCAGGAGCAGGGCTTCATCGAGGAGGA
CAAGGCCCGCAATGATCACTACAAGGAGCTGAAGCCCATCATCGATCGGATCTACAAGAC
CTATGCCGACCAGTGCCTGCAGCTGGTGCAGCTGGATTGGGAGAACCTGAGCGCCGCCA
TCGACTCCTATAGAAAGGAGAAAACCGAGGAGACAAGGAACGCCCTGATCGAGGAGCAGG
CCACATATCGCAATGCCATCCACGACTACTTCATCGGCCGGACAGACAACCTGACCGATG
CCATCAATAAGAGACACGCCGAGATCTACAAGGGCCTGTTCAAGGCCGAGCTGTTTAATG
GCAAGGTGCTGAAGCAGCTGGGCACCGTGACCACAACCGAGCACGAGAACGCCCTGCTG
CGGAGCTTCGACAAGTTTACAACCTACTTCTCCGGCTTTTATGAGAACAGGAAGAACGTGT
TCAGCGCCGAGGATATCAGCACAGCCATCCCACACCGCATCGTGCAGGACAACTTCCCCA
AGTTTAAGGAGAATTGTCACATCTTCACACGCCTGATCACCGCCGTGCCCAGCCTGCGGG
AGCACTTTGAGAACGTGAAGAAGGCCATCGGCATCTTCGTGAGCACCTCCATCGAGGAGG
TGTTTTCCTTCCCTTTTTATAACCAGCTGCTGACACAGACCCAGATCGACCTGTATAACCAG
CTGCTGGGAGGAATCTCTCGGGAGGCAGGCACCGAGAAGATCAAGGGCCTGAACGAGGT
GCTGAATCTGGCCATCCAGAAGAATGATGAGACAGCCCACATCATCGCCTCCCTGCCACA
CAGATTCATCCCCCTGTTTAAGCAGATCCTGTCCGATAGGAACACCCTGTCTTTCATCCTG
GAGGAGTTTAAGAGCGACGAGGAAGTGATCCAGTCCTTCTGCAAGTACAAGACACTGCTG
AGAAACGAGAACGTGCTGGAGACAGCCGAGGCCCTGTTTAACGAGCTGAACAGCATCGAC
CTGACACACATCTTCATCAGCCACAAGAAGCTGGAGACAATCAGCAGCGCCCTGTGCGAC
CACTGGGATACACTGAGGAATGCCCTGTATGAGCGGAGAATCTCCGAGCTGACAGGCAAG
ATCACCAAGTCTGCCAAGGAGAAGGTGCAGCGCAGCCTGAAGCACGAGGATATCAACCTG
CAGGAGATCATCTCTGCCGCAGGCAAGGAGCTGAGCGAGGCCTTCAAGCAGAAAACCAG
CGAGATCCTGTCCCACGCACACGCCGCCCTGGATCAGCCACTGCCTACAACCCTGAAGAA
GCAGGAGGAGAAGGAGATCCTGAAGTCTCAGCTGGACAGCCTGCTGGGCCTGTACCACC
TGCTGGACTGGTTTGCCGTGGATGAGTCCAACGAGGTGGACCCCGAGTTCTCTGCCCGGC
TGACCGGCATCAAGCTGGAGATGGAGCCTTCTCTGAGCTTCTACAACAAGGCCAGAAATTA
TGCCACCAAGAAGCCCTACTCCGTGGAGAAGTTCAAGCTGAACTTTCAGATGCCTACACTG
GCCTCTGGCTGGGACGTGAATAAGGAGAAGAACAATGGCGCCATCCTGTTTGTGAAGAAC
GGCCTGTACTATCTGGGCATCATGCCAAAGCAGAAGGGCAGGTATAAGGCCCTGAGCTTC
GAGCCCACAGAGAAAACCAGCGAGGGCTTTGATAAGATGTACTATGACTACTTCCCTGATG
CCGCCAAGATGATCCCAAAGTGCAGCACCCAGCTGAAGGCCGTGACAGCCCACTTTCAGA
CCCACACAACCCCCATCCTGCTGTCCAACAATTTCATCGAGCCTCTGGAGATCACAAAGGA
GATCTACGACCTGAACAATCCTGAGAAGGAGCCAAAGAAGTTTCAGACAGCCTACGCCAA
GAAAACCGGCGACCAGAAGGGCTACAGAGAGGCCCTGTGCAAGTGGATCGACTTCACAA
GGGATTTTCTGTCCAAGTATACCAAGACAACCTCTATCGATCTGTCTAGCCTGCGGCCATC
CTCTCAGTATAAGGACCTGGGCGAGTACTATGCCGAGCTGAATCCCCTGCTGTACCACATC
AGCTTCCAGAGAATCGCCGAGAAGGAGATCATGGATGCCGTGGAGACAGGCAAGCTGTAC
CTGTTCCAGATCTATAACAAGGACTTTGCCAAGGGCCACCACGGCAAGCCTAATCTGCACA
CACTGTATTGGACCGGCCTGTTTTCTCCAGAGAACCTGGCCAAGACAAGCATCAAGCTGAA
TGGCCAGGCCGAGCTGTTCTACCGCCCTAAGTCCAGGATGAAGAGGATGGCACACCGGC
TGGGAGAGAAGATGCTGAACAAGAAGCTGAAGGATCAGAAAACCCCAATCCCCGACACCC
TGTACCAGGAGCTGTACGACTATGTGAATCACAGACTGTCCCACGACCTGTCTGATGAGG
CCAGGGCCCTGCTGCCCAACGTGATCACCAAGGAGGTGTCTCACGAGATCATCAAGGATA
GGCGCTTTACCAGCGACAAGTTCTTTTTCCACGTGCCTATCACACTGAACTATCAGGCCGC
CAATTCCCCATCTAAGTTCAACCAGAGGGTGAATGCCTACCTGAAGGAGCACCCCGAGAC
ACCTATCATCGGCATCGATCGGGGCGAGAGAAACCTGATCTATATACAGTGATCGACTCC
ACCGGCAAGATCCTGGAGCAGCGGAGCCTGAACACCATCCAGCAGTTTGATTACCAGAAG
AAGCTGGACAACAGGGAGAAGGAGAGGGTGGCAGCAAGGCAGGCCTGGTCTGTGGTGG

FIG. 23 cont'd.

GCACAATCAAGGATCTGAAGCAGGGCTATCTGAGCCAGGTCATCCACGAGATCGTGGACC
TGATGATCCACTACCAGGCCGTGGTGGTGCTGGAGAACCTGAATTTCGGCTTTAAGAGCA
AGAGGACCGGCATCGCCGAGAAGGCCGTGTACCAGCAGTTCGAGAAGATGCTGATCGATA
AGCTGAATTGCCTGGTGCTGAAGGACTATCCAGCAGAGAAAGTGGGAGGCGTGCTGAACC
CATACCAGCTGACAGACCAGTTCACCTCCTTTGCCAAGATGGGCACCCAGTCTGGCTTCCT
GTTTTACGTGCCTGCCCCATATACATCTAAGATCGATCCCCTGACCGGCTTCGTGGACCCC
TTCGTGTGGAAAACCATCAAGAATCACGAGAGCCGCAAGCACTTCCTGGAGGGCTTCGAC
TTTCTGCACTACGACGTGAAAACCGGCGACTTCATCCTGCACTTTAAGATGAACAGAAATC
TGTCCTTCCAGAGGGGCCTGCCCGGCTTTATGCCTGCATGGGATATCGTGTTCGAGAAGA
ACGAGACACAGTTTGACGCCAAGGGCACCCCTTTCATCGCCGGCAAGAGAATCGTGCCAG
TGATCGAGAATCACAGATTCACCGGCAGATACCGGGACCTGTATCCTGCCAACGAGCTGA
TCGCCCTGCTGGAGGAGAAGGGCATCGTGTTCAGGGATGGCTCCAACATCCTGCCAAAGC
TGCTGGAGAATGACGATTCTCACGCCATCGACACCATGGTGGCCCTGATCCGCAGCGTGC
TGCAGATGCGGAACTCCAATGCCGCCACAGGCGAGGACTATATCAACAGCCCCGTGCGC
GATCTGAATGGCGTGTGCTTCGACTCCCGGTTTCAGAACCCAGAGTGGCCCATGGACGCC
GATGCCAATGGCGCCTACCACATCGCCCTGAAGGGCCAGCTGCTGCTGAATCACCTGAAG
GAGAGCAAGGATCTGAAGCTGCAGAACGGCATCTCCAATCAGGACTGGCTGGCCTACATC
CAGGAGCTGCGCAAC (SEQ ID NO: 217)

FIG. 23 cont'd.

>Lachnospiraceae bacterium MC2017 Cpf1 (Lb3Cpf1) cds from Zetsche 2015
ATGGATTACGGCAACGGCCAGTTTGAGCGGAGAGCCCCCTGACCAAGACAATCACCCTG
CGCCTGAAGCCTATCGGCGAGACACGGGAGACAATCCGCGAGCAGAAGCTGCTGGAGCA
GGACGCCGCCTTCAGAAAGCTGGTGGAGACAGTGACCCCTATCGTGGACGATTGTATCAG
GAAGATCGCCGATAACGCCCTGTGCCACTTTGGCACCGAGTATGACTTCAGCTGTCTGGG
CAACGCCATCTCTAAGAATGACAGCAAGGCCATCAAGAAGGAGACAGAGAAGGTGGAGAA
GCTGCTGGCCAAGGTGCTGACCGAGAATCTGCCAGATGGCCTGCGCAAGGTGAACGACA
TCAATTCCGCCGCCTTTATCCAGGATACACTGACCTCTTTCGTGCAGGACGATGCCGACAA
GCGGGTGCTGATCCAGGAGCTGAAGGGCAAGACCGTGCTGATGCAGCGGTTCCTGACCA
CACGGATCACAGCCCTGACCGTGTGGCTGCCCGACAGAGTGTTCGAGAACTTTAATATCTT
CATCGAGAACGCCGAGAAGATGAGAATCCTGCTGGACTCCCTCTGAATGAAGATCAT
GAAGTTTGACCCAGATGCCGAGCAGTACGCCTCTCTGGAGTTCTATGGCCAGTGCCTGTC
TCAGAAGGACATCGATAGCTACAACCTGATCATCTCCGGCATCTATGCCGACGATGAGGTG
AAGAACCCTGGCATCAATGAGATCGTGAAGGAGTACAATCAGCAGATCCGGGGCGACAAG
GATGAGTCCCCACTGCCCAAGCTGAAGAAGCTGCACAAGCAGATCCTGATGCCAGTGGAG
AAGGCCTTCTTTGTGCGCGTGCTGTCTAACGACAGCGATGCCCGGAGCATCCTGGAGAAG
ATCCTGAAGGACACAGAGATGCTGCCCTCCAAGATCATCGAGGCCATGAAGGAGGCAGAT
GCAGGCGACATCGCCGTGTACGGCAGCCGGCTGCACGAGCTGAGCCACGTGATCTACGG
CGATCACGGCAAGCTGTCCCAGATCATCTATGACAAGGAGTCCAAGAGGATCTCTGAGCT
GATGGAGACACTGTCTCCAAAGGAGCGCAAGGAGAGCAAGAAGCGGCTGGAGGGCCTGG
AGGAGCACATCAGAAAGTCTACATACACCTTCGACGAGCTGAACAGGTATGCCGAGAAGA
ATGTGATGGCAGCATACATCGCAGCAGTGGAGGAGTCTTGTGCCGAGATCATGAGAAAGG
AGAAGGATCTGAGGACCCTGCTGAGCAAGGAGGACGTGAAGATCCGGGGCAACAGACAC
AATACACTGATCGTGAAGAACTACTTTAATGCCTGGACCGTGTTCCGGAACCTGATCAGAA
TCCTGAGGCGCAAGTCCGAGGCCGAGATCGACTCTGACTTCTACGATGTGCTGGACGATT
CCGTGGAGGTGCTGTCTCTGACATACAAGGGCGAGAATCTGTGCCGCAGCTATATCACCA
AGAAGATCGGCTCCGACCTGAAGCCCGAGATCGCCACATACGGCAGCGCCCTGAGGCCT
AACAGCCGCTGGTGGTCCCCAGGAGAGAAGTTTAATGTGAAGTTCCACACCATCGTGCGG
AGAGATGGCCGGCTGTACTATTTCATCCTGCCCAAGGGCGCCAAGCCTGTGGAGCTGGAG
GACATGGATGGCGACATCGAGTGTCTGCAGATGAGAAAGATCCCTAACCCAACAATCTTTC
TGCCCAAGCTGGTGTTCAAGGACCCTGAGGCCTTCTTTAGGGATAATCCAGAGGCCGACG
AGTTCGTGTTTCTGAGCGGCATGAAGGCCCCGTGACAATCACCAGAGAGACATACGAGG
CCTACAGGTATAAGCTGTATACCGTGGGCAAGCTGCGCGATGGCGAGGTGTCCGAAGAG
GAGTACAAGCGGGCCCTGCTGCAGGTGCTGACCGCCTACAAGGAGTTTCTGGAGAACAGA
ATGATCTATGCCGACCTGAATTTCGGCTTTAAGGATCTGGAGGAGTATAAGGACAGCTCCG
AGTTTATCAAGCAGGTGGAGACACACAACACCTTCATGTGCTGGGCCAAGGTGTCTAGCTC
CCAGCTGGACGATCTGGTGAAGTCTGGCAACGGCCTGCTGTTCGAGATCTGGAGCGAGC
GCCTGGAGTCCTACTATAAGTACGGCAATGAGAAGGTGCTGCGGGGCTATGAGGGCGTG
CTGCTGAGCATCCTGAAGGATGAGAACCTGGTGTCCATGCGGACCCTGCTGAACAGCCGG
CCCATGCTGGTGTACCGGCCAAAGGAGTCTAGCAAGCCTATGGTGGTGCACCGGGATGG
CAGCAGAGTGGTGGACAGGTTTGATAAGGACGGCAAGTACATCCCCCCTGAGGTGCACGA
CGAGCTGTATCGCTTCTTTAACAATCTGCTGATCAAGGAGAAGCTGGGCGAGAAGGCCCG
GAAGATCCTGGACAACAAGAAGGTGAAGGTGAAGGTGCTGGAGAGCGAGAGAGTGAAGT
GGTCCAAGTTCTACGATGAGCAGTTTGCCGTGACCTTCAGCGTGAAGAAGAACGCCGATT
GTCTGGACACCACAAAGGACCTGAATGCCGAAGTGATGGAGCAGTATAGCGAGTCCAACA
GACTGATCCTGATCAGGAATACCACAGATATCCTGTACTATCTGGTGCTGGACAAGAATGG
CAAGGTGCTGAAGCAGAGATCCCTGAACATCATCAATGACGGCGCCAGGGATGTGGACTG
GAAGGAGAGGTTCCGCCAGGTGACAAAGGATAGAAACGAGGGCTACAATGAGTGGGATTA
TTCCAGGACCTCTAACGACCTGAAGGAGGTGTACCTGAATTATGCCCTGAAGGAGATCGC

FIG. 23 cont'd.

CGAGGCCGTGATCGAGTACAACGCCATCCTGATCATCGAGAAGATGTCTAATGCCTTTAAG
GACAAGTATAGCTTCCTGGACGACGTGACCTTCAAGGGCTTCGAGACAAAGCTGCTGGCC
AAGCTGAGCGATCTGCACTTTAGGGGCATCAAGGACGGCGAGCCATGTTCCTTCACAAAC
CCCCTGCAGCTGTGCCAGAACGATTCTAATAAGATCCTGCAGGACGGCGTGATCTTTATGG
TGCCAAATTCTATGACACGGAGCCTGGACCCCGACACCGGCTTCATCTTTGCCATCAACGA
CCACAATATCAGGACCAAGAAGGCCAAGCTGAACTTTCTGAGCAAGTTCGATCAGCTGAAG
GTGTCCTCTGAGGGCTGCCTGATCATGAAGTACAGCGGCGATTCCCTGCCTACACACAAC
ACCGACAATCGCGTGTGGAACTGCTGTTGCAATCACCCAATCACAAACTATGACCGGGAG
ACAAAGAAGGTGGAGTTCATCGAGGAGCCCGTGGAGGAGCTGTCCCGCGTGCTGGAGGA
GAATGGCATCGAGACAGACACCGAGCTGAACAAGCTGAATGAGCGGGAGAACGTGCCTG
GCAAGGTGGTGGATGCCATCTACTCTCTGGTGCTGAATTATCTGCGCGGCACAGTGAGCG
GAGTGGCAGGACAGAGGGCCGTGTACTATAGCCCTGTGACCGGCAAGAAGTACGATATCT
CCTTTATCCAGGCCATGAACCTGAATAGGAAGTGTGACTACTATAGGATCGGCTCCAAGGA
GAGGGGAGAGTGGACCGATTTCGTGGCCCAGCTGATCAAC (SEQ ID NO: 218)

>Lachnospiraceae bacterium ND2006 type V CRISPR-associated protein Cpf1 coding
ATGAGCAAGCTGGAGAAGTTTACAAACTGCTACTCCCTGTCTAAGACCCTGAGGTTCAAGG
CCATCCCTGTGGGCAAGACCCAGGAGAACATCGACAATAAGCGGCTGCTGGTGGAGGAC
GAGAAGAGAGCCGAGGATTATAAGGGCGTGAAGAAGCTGCTGGATCGCTACTATCTGTCT
TTTATCAACGACGTGCTGCACAGCATCAAGCTGAAGAATCTGAACAATTACATCAGCCTGTT
CCGGAAGAAAACCAGAACCGAGAAGGAGAATAAGGAGCTGGAGAACCTGGAGATCAATCT
GCGGAAGGAGATCGCCAAGGCCTTCAAGGGCAACGAGGGCTACAAGTCCCTGTTTAAGAA
GGATATCATCGAGACAATCCTGCCAGAGTTCCTGGACGATAAGGACGAGATCGCCCTGGT
GAACAGCTTCAATGGCTTTACCACAGCCTTCACCGGCTTCTTTGATAACAGAGAGAATATG
TTTTCCGAGGAGGCCAAGAGCACATCCATCGCCTTCAGGTGTATCAACGAGAATCTGACCC
GCTACATCTCTAATATGGACATCTTCGAGAAGGTGGACGCCATCTTTGATAAGCACGAGGT
GCAGGAGATCAAGGAGAAGATCCTGAACAGCGACTATGATGTGGAGGATTTCTTTGAGGG
CGAGTTCTTTAACTTTGTGCTGACACAGGAGGGCATCGACGTGTATAACGCCATCATCGGC
GGCTTCGTGACCGAGAGCGGCGAGAAGATCAAGGGCCTGAACGAGTACATCAACCTGTAT
AATCAGAAAACCAAGCAGAAGCTGCCTAAGTTTAAGCCACTGTATAAGCAGGTGCTGAGCG
ATCGGGAGTCTCTGAGCTTCTACGGCGAGGGCTATACATCCGATGAGGAGGTGCTGGAGG
TGTTTAGAAACACCCTGAACAAGAACAGCGAGATCTTCAGCTCCATCAAGAAGCTGGAGAA
GCTGTTCAAGAATTTTGACGAGTACTCTAGCGCCGGCATCTTTGTGAAGAACGGCCCCGC
CATCAGCACAATCTCCAAGGATATCTTCGGCGAGTGGAACGTGATCCGGGACAAGTGGAA
TGCCGAGTATGACGATATCCACCTGAAGAAGAAGGCCGTGGTGACCGAGAAGTACGAGGA
CGATCGGAGAAAGTCCTTCAAGAAGATCGGCTCCTTTTCTCTGGAGCAGCTGCAGGAGTA
CGCCGACGCCGATCTGTCTGTGGTGGAGAAGCTGAAGGAGATCATCATCCAGAAGGTGGA
TGAGATCTACAAGGTGTATGGCTCCTCTGAGAAGCTGTTCGACGCCGATTTTGTGCTGGAG
AAGAGCCTGAAGAAGAACGACGCCGTGGTGGCCATCATGAAGGACCTGCTGGATTCTGTG
AAGAGCTTCGAGAATTACATCAAGGCCTTCTTTGGCGAGGGCAAGGAGACAAACAGGGAC
GAGTCCTTCTATGGCGATTTTGTGCTGGCCTACGACATCCTGCTGAAGGTGGACCACATCT
ACGATGCCATCCGCAATTATGTGACCCAGAAGCCCTACTCTAAGGATAAGTTCAAGCTGTA
TTTTCAGAACCCTCAGTTCATGGGCGGCTGGGACAAGGATAAGGAGACAGACTATCGGGC
CACCATCCTGAGATACGGCTCCAAGTACTATCTGGCCATCATGGATAAGAAGTACGCCAAG
TGCCTGCAGAAGATCGACAAGGACGATGTGAACGGCAATTACGAGAAGATCAACTATAAG
CTGCTGCCCGGCCCTAATAAGATGCTGCCAAAGGTGTTCTTTTCTAAGAAGTGGATGGCCT
ACTATAACCCCAGCGAGGACATCCAGAAGATCTACAAGAATGGCACATTCAAGAAGGGCG
ATATGTTTAACCTGAATGACTGTCACAAGCTGATCGACTTCTTTAAGGATAGCATCTCCCGG

FIG. 23 cont'd.

TATCCAAAGTGGTCCAATGCCTACGATTTCAACTTTTCTGAGACAGAGAAGTATAAGGACAT
CGCCGGCTTTTACAGAGAGGTGGAGGAGCAGGGCTATAAGGTGAGCTTCGAGTCTGCCA
GCAAGAAGGAGGTGGATAAGCTGGTGGAGGAGGGCAAGCTGTATATGTTCCAGATCTATA
ACAAGGACTTTTCCGATAAGTCTCACGGCACACCCAATCTGCACACCATGTACTTCAAGCT
GCTGTTTGACGAGAACAATCACGGACAGATCAGGCTGAGCGGAGGAGCAGAGCTGTTCAT
GAGGCGCGCCTCCCTGAAGAAGGAGGAGCTGGTGGTGCACCCAGCCAACTCCCCTATCG
CCAACAAGAATCCAGATAATCCCAAGAAACCACAACCCTGTCCTACGACGTGTATAAGGA
TAAGAGGTTTTCTGAGGACCAGTACGAGCTGCACATCCCAATCGCCATCAATAAGTGCCCC
AAGAACATCTTCAAGATCAATACAGAGGTGCGCGTGCTGCTGAAGCACGACGATAACCCCT
ATGTGATCGGCATCGATAGGGGCGAGCGCAATCTGCTGTATATCGTGGTGGTGGACGGCA
AGGGCAACATCGTGGAGCAGTATTCCCTGAACGAGATCATCAACAACTTCAACGGCATCAG
GATCAAGACAGATTACCACTCTCTGCTGGACAAGAAGGAGAAGGAGAGGTTCGAGGCCCG
CCAGAACTGGACCTCCATCGAGAATATCAAGGAGCTGAAGGCCGGCTATATCTCTCAGGT
GGTGCACAAGATCTGCGAGCTGGTGGAGAAGTACGATGCCGTGATCGCCCTGGAGGACC
TGAACTCTGGCTTTAAGAATAGCCGCGTGAAGGTGGAGAAGCAGGTGTATCAGAAGTTCG
AGAAGATGCTGATCGATAAGCTGAACTACATGGTGGACAAGAAGTCTAATCCTTGTGCAAC
AGGCGGCGCCCTGAAGGGCTATCAGATCACCAATAAGTTCGAGAGCTTTAAGTCCATGTCT
ACCCAGAACGGCTTCATCTTTTACATCCCTGCCTGGCTGACATCCAAGATCGATCCATCTA
CCGGCTTTGTGAACCTGCTGAAAACCAAGTATACCAGCATCGCCGATTCCAAGAAGTTCAT
CAGCTCCTTTGACAGGATCATGTACGTGCCCGAGGAGGATCTGTTCGAGTTTGCCCTGGA
CTATAAGAACTTCTCTCGCACAGACGCCGATTACATCAAGAAGTGGAAGCTGTACTCCTAC
GGCAACCGGATCAGAATCTTCCGGAATCCTAAGAAGAACAACGTGTTCGACTGGGAGGAG
GTGTGCCTGACCAGCGCCTATAAGGAGCTGTTCAACAAGTACGGCATCAATTATCAGCAG
GGCGATATCAGAGCCCTGCTGTGCGAGCAGTCCGACAAGGCCTTCTACTCTAGCTTTATG
GCCCTGATGAGCCTGATGCTGCAGATGCGGAACAGCATCACAGGCCGCACCGACGTGGA
TTTTCTGATCAGCCCTGTGAAGAACTCCGACGGCATCTTCTACGATAGCCGGAACTATGAG
GCCCAGGAGAATGCCATCCTGCCAAAGAACGCCGACGCCAATGGCGCCTATAACATCGCC
AGAAAGGTGCTGTGGGCCATCGGCCAGTTCAAGAAGGCCGAGGACGAGAAGCTGGATAA
GGTGAAGATCGCCATCTCTAACAAGGAGTGGCTGGAGTACGCCCAGACCAGCGTGAAGCA
C (SEQ ID NO: 219)

>Francisella tularensis subsp. Novicida U112 Cpf1 (FnCpf1) coding
ATGAGCATCTACCAGGAGTTCGTCAACAAGTATTCACTGAGTAAGACACTGCGGTTCGAGC
TGATCCCACAGGGCAAGACACTGGAGAACATCAAGGCCCGAGGCCTGATTCTGGACGATG
AGAAGCGGGCAAAAGACTATAAGAAAGCCAAGCAGATCATTGATAAATACCACCAGTTCTT
TATCGAGGAAATTCTGAGCTCCGTGTGCATCAGTGAGGATCTGCTGCAGAATTACTCAGAC
GTGTACTTCAAGCTGAAGAAGAGCGACGATGACAACCTGCAGAAGGACTTCAAGTCCGCC
AAGGACACCATCAAGAAACAGATTAGCGAGTACATCAAGGACTCCGAAAAGTTTAAAAATC
TGTTCAACCAGAATCTGATCGATGCTAAGAAAGGCCAGGAGTCCGACCTGATCCTGTGGCT
GAAACAGTCTAAGGACAATGGGATTGAACTGTTCAAGGCTAACTCCGATATCACTGATATT
GACGAGGCACTGGAAATCATCAAGAGCTTCAAGGGATGGACCACATACTTTAAAGGCTTCC
ACGAGAACCGCAAGAACGTGTACTCCAGCAACGACATTCCTACCTCCATCATCTACCGAAT
CGTCGATGACAATCTGCCAAAGTTCCTGGAGAACAAGGCCAAATATGAATCTCTGAAGGAC
AAAGCTCCCGAGGCAATTAATTACGAACAGATCAAGAAAGATCTGGCTGAGGAACTGACAT
TCGATATCGACTATAAGACTAGCGAGGTGAACCAGAGGGTCTTTTCCCTGGACGAGGTGTT
TGAAATCGCCAATTTCAACAATTACCTGAACCAGTCCGGCATTACTAAATTCAATACCATCA
TTGGCGGGAAGTTTGTGAACGGGGAGAATACCAAGCGCAAGGGAATTAACGAATACATCA
ATCTGTATAGCCAGCAGATCAACGACAAAACTCTGAAGAAATACAAGATGTCTGTGCTGTT
CAAACAGATCCTGAGTGATACCGAGTCCAAGTCTTTTGTCATTGATAAACTGGAAGATGACT

FIG. 23 cont'd.

CAGACGTGGTCACTACCATGCAGAGCTTTTATGAGCAGATCGCCGCTTTCAAGACAGTGGA
GGAAAAATCTATTAAGGAAACTCTGAGTCTGCTGTTCGATGACCTGAAAGCCCAGAAGCTG
GACCTGAGTAAGATCTACTTCAAAAACGATAAGAGTCTGACAGACCTGTCACAGCAGGTGT
TTGATGACTATTCCGTGATTGGGACCGCCGTCCTGGAGTACATTACACAGCAGATCGCTCC
AAAGAACCTGGATAATCCCTCTAAGAAAGAGCAGGAACTGATCGCTAAGAAACCGAGAAG
GCAAAATATCTGAGTCTGGAAACAATTAAGCTGGCACTGGAGGAGTTCAACAAGCACAGG
GATATTGACAAACAGTGCCGCTTTGAGGAAATCCTGGCCAACTTCGCAGCCATCCCCATGA
TTTTTGATGAGATCGCCCAGAACAAAGACAATCTGGCTCAGATCAGTATTAAGTACCAGAA
CCAGGGCAAGAAAGACCTGCTGCAGGCTTCAGCAGAAGATGACGTGAAAGCCATCAAGGA
TCTGCTGGACCAGACCAACAATCTGCTGCACAAGCTGAAAATCTTCCATATTAGTCAGTCA
GAGGATAAGGCTAATATCCTGGATAAAGACGAACACTTCTACCTGGTGTTCGAGGAATGTT
ACTTCGAGCTGGCAAACATTGTCCCCTGTATAACAAGATTAGGAACTACATCACACAGAA
GCCTTACTCTGACGAGAAGTTTAAACTGAACTTCGAAAATAGTACCCTGGCCAACGGGTGG
GATAAGAACAAGGAGCCTGACAACACAGCTATCCTGTTCATCAAGGATGACAAGTACTATC
TGGGAGTGATGAATAAGAAAACAATAAGATCTTCGATGACAAAGCCATTAAGGAGAACAA
AGGGGAAGGATACAAGAAAATCGTGTATAAGCTGCTGCCCGGCGCAAATAAGATGCTGCC
TAAGGTGTTCTTCAGCGCCAAGAGTATCAAATTCTACAACCCATCCGAGGACATCCTGCGG
ATTAGAAATCACTCAACACATACTAAGAACGGGAGCCCCAGAAGGGATATGAGAAATTTG
AGTTCAACATCGAGGATTGCAGGAAGTTTATTGACTTCTACAAGCAGAGCATCTCCAAACA
CCCTGAATGGAAGGATTTTGGCTTCCGGTTTTCCGACACACAGAGATATAACTCTATCGAC
GAGTTCTACCGCGAGGTGGAAAATCAGGGGTATAAGCTGACTTTTGAGAACATTTCTGAAA
GTTACATCGACAGCGTGGTCAATCAGGGAAAGCTGTACCTGTTCCAGATCTATAACAAAGA
TTTTTCAGCATACAGCAAGGGCAGACCAAACCTGCATACACTGTACTGGAAGGCCCTGTTC
GATGAGAGGAATCTGCAGGACGTGGTCTATAAACTGAACGGAGAGGCCGAACTGTTTTAC
CGGAAGCAGTCTATTCCTAAGAAAATCACTCACCCAGCTAAGGAGGCCATCGCTAACAAGA
ACAAGGACAATCCTAAGAAAGAGAGCGTGTTCGAATACGATCTGATTAAGGACAAGCGGTT
CACCGAAGATAAGTTCTTTTTCCATTGTCCAATCACCATTAACTTCAAGTCAAGCGGCGCTA
ACAAGTTCAACGACGAGATCAATCTGCTGCTGAAGGAAAAGCAAACGATGTGCACATCCT
GAGCATTGACCGAGGAGAGCGGCATCTGGCCTACTATACCCTGGTGGATGGCAAAGGGAA
TATCATTAAGCAGGATACATTCAACATCATTGGCAATGACCGGATGAAAACCAACTACCAC
GATAAACTGGCTGCAATCGAGAAGGATAGAGACTCAGCTAGGAAGGACTGGAAGAAAATC
AACAACATTAAGGAGATGAAGGAAGGCTATCTGAGCCAGGTGGTCCATGAGATTGCAAAG
CTGGTCATCGAATACAATGCCATTGTGGTGTTCGAGGATCTGAACTTCGGCTTTAAGAGGG
GGCGCTTTAAGGTGGAAAAACAGGTCTATCAGAAGCTGGAGAAAATGCTGATCGAAAAGCT
GAATTACCTGGTGTTTAAAGATAACGAGTTCGACAAGACCGGAGGCGTCCTGAGAGCCTA
CCAGCTGACAGCTCCCTTTGAAACTTTCAAGAAAATGGGAAAACAGACAGGCATCATCTAC
TATGTGCCAGCCGGATTCACTTCCAAGATCTGCCCCGTGACCGGCTTTGTCAACCAGCTGT
ACCCTAAATATGAGTCAGTGAGCAAGTCCAGGAATTTTTCAGCAAGTTCGATAAGATCTGT
TATAATCTGGACAAGGGGTACTTCGAGTTTTCCTTCGATTACAAGAACTTCGGCGACAAGG
CCGCTAAGGGGAAATGGACCATTGCCTCCTTCGGATCTCGCCTGATCAACTTTCGAAATTC
CGATAAAAACCACAATTGGGACACTAGGGAGGTGTACCCAACCAAGGAGCTGGAAAAGCT
GCTGAAAGACTACTCTATCGAGTATGGACATGGCAATGCATCAAGGCAGCCATCTGTGG
CGAGAGTGATAAGAAATTTTTCGCCAAGCTGACCTCAGTGCTGAATACAATCCTGCAGATG
CGGAACTCAAAGACCGGGACAGAACTGGACTATCTGATTAGCCCCGTGGCTGATGTCAAC
GGAAACTTCTTCGACAGCAGACAGGCACCCAAAAATATGCCTCAGGATGCAGACGCCAAC
GGGGCCTACCACATCGGGCTGAAGGGACTGATGCTGCTGGGCCGGATCAAGAACAATCA
GGAGGGGAAGAAGCTGAACCTGGTCATTAAGAACGAGGAATACTTCGAGTTTGTCCAGAA
TAGAAATAAC (SEQ ID NO: 220)

FIG. 23 cont'd.

>Peregrinibacteria bacterium GW2011_GWA_33_10 Cpf1 (PeCpf1) coding
ATGTCCAACTTCTTTAAGAATTTCACCAACCTGTATGAGCTGTCCAAGACACTGAGGTTTGA
GCTGAAGCCCGTGGGCGACACCCTGACAAACATGAAGGACCACCTGGAGTACGATGAGAA
GCTGCAGACCTTCCTGAAGGATCAGAATATCGACGATGCCTATCAGGCCCTGAAGCCTCA
GTTCGACGAGATCCACGAGGAGTTTATCACAGATTCTCTGGAGAGCAAGAAGGCCAAGGA
GATCGACTTCTCCGAGTACCTGGATCTGTTTCAGGAGAAGAAGGAGCTGAACGACTCTGA
GAAGAAGCTGCGCAACAAGATCGGCGAGACATTCAACAAGGCCGGCGAGAAGTGGAAGA
AGGAGAAGTACCCTCAGTATGAGTGGAAGAAGGGCTCCAAGATCGCCAATGGCGCCGACA
TCCTGTCTTGCCAGGATATGCTGCAGTTTATCAAGTATAAGAACCCAGAGGATGAGAAGAT
CAAGAATTACATCGACGATACACTGAAGGGCTTCTTTACCTATTTCGGCGGCTTTAATCAGA
ACAGGGCCAACTACTATGAGACAAAGAAGGAGGCCTCCACCGCAGTGGCAACAAGGATCG
TGCACGAGAACCTGCCAAAGTTCTGTGACAATGTGATCCAGTTTAAGCACATCATCAAGCG
GAAGAAGGATGGCACCGTGGAGAAACCGAGAGAAGACCGAGTACCTGAACGCCTACCA
GTATCTGAAGAACAATAACAAGATCACACAGATCAAGGACGCCGAGACAGAGAAGATGATC
GAGTCTACACCCATCGCCGAGAAGATCTTCGACGTGTACTACTTCAGCAGCTGCCTGAGC
CAGAAGCAGATCGAGGAGTACAACCGGATCATCGGCCACTATAATCTGCTGATCAACCTGT
ATAACCAGGCCAAGAGATCTGAGGGCAAGCACCTGAGCGCCAACGAGAAGAAGTATAAGG
ACCTGCCTAAGTTCAAGACCCTGTATAAGCAGATCGGCTGCGGCAAGAAGAAGGACCTGT
TTTACACAATCAAGTGTGATACCGAGGAGGAGGCCAATAAGTCCCGGAACGAGGGCAAGG
AGTCCCACTCTGTGGAGGAGATCATCAACAAGGCCCAGGAGGCCATCAATAAGTACTTCAA
GTCTAATAACGACTGTGAGAATATCAACACCGTGCCCGACTTCATCAACTATATCCTGACAA
AGGAGAATTACGAGGGCGTGTATTGGAGCAAGGCCGCCATGAACACCATCTCCGACAAGT
ACTTCGCCAATTATCACGACCTGCAGGATAGACTGAAGGAGGCCAAGGTGTTTCAGAAGG
CCGATAAGAAGTCCGAGGACGATATCAAGATCCCAGAGGCCATCGAGCTGTCTGGCCTGT
TCGGCGTGCTGGACAGCCTGGCCGATTGGCAGACCACACTGTTTAAGTCTAGCATCCTGA
GCAACGAGGACAAGCTGAAGATCATCACAGATTCCCAGACCCCCTCTGAGGCCCTGCTGA
AGATGATCTTCAATGACATCGAGAAGAACATGGAGTCCTTTCTGAAGGAGACAAACGATAT
CATCACCCTGAAGAAGTATAAGGGCAATAAGGAGGGCACCGAGAAGATCAAGCAGTGGTT
CGACTATACACTGGCCATCAACCGGATGCTGAAGTACTTTCTGGTGAAGGAGAATAAGATC
AAGGGCAACTCCCTGGATACCAATATCTCTGAGGCCCTGAAAACCCTGATCTACAGCGAC
GATGCCGAGTGGTTCAAGTGGTACGACGCCCTGAGAAACTATCTGACCCAGAAGCCTCAG
GATGAGGCCAAGGAGAATAAGCTGAAGCTGAATTTCGACAACCCATCTCTGGCCGGCGGC
TGGGATGTGAACAAGGAGTGCAGCAATTTTTGCGTGATCCTGAAGGACAAGAACGAGAAG
AAGTACCTGGCCATCATGAAGAAGGGCGAGAATACCCTGTTCCAGAAGGAGTGGACAGAG
GGCCGGGGCAAGAACCTGACAAAGAAGTCTAATCCACTGTTCGAGATCAATAACTGCGAG
ATCCTGAGCAAGATGGAGTATGACTTTTGGGCCGACGTGAGCAAGATGATCCCCAAGTGT
AGCACCCAGCTGAAGGCCGTGGTGAACCACTTCAAGCAGTCCGACAATGAGTTCATCTTTC
CTATCGGCTACAAGGTGACAAGCGGCGAGAAGTTTAGGGAGGAGTGCAAGATCTCCAAGC
AGGACTTCGAGCTGAATAACAAGGTGTTTAATAAGAACGAGCTGAGCGTGACCGCCATGC
GCTACGATCTGTCCTCTACACAGGAGAAGCAGTATATCAAGGCCTTCCAGAAGGAGTACTG
GGAGCTGCTGTTTAAGCAGGAGAAGCGGGACACCAAGCTGACAAATAACGAGATCTTCAA
CGAGTGGATCAATTTTGCAACAAGAAGTATAGCGAGCTGCTGTCCTGGGAGAGAAAGTAC
AAGGATGCCCTGACCAATTGGATCAACTTCTGTAAGTACTTTCTGAGCAAGTATCCCAAGA
CCACACTGTTCAACTACTCTTTTAAGGAGAGCGAGAATTATAACTCCCTGGACGAGTTCTAC
CGGGACGTGGATATCTGTTCTTACAAGCTGAATATCAACACCACAATCAATAAGAGCATCC
TGGATAGACTGGTGGAGGAGGGCAAGCTGTACCTGTTTGAGATCAAGAATCAGGACAGCA
ACGATGGCAAGTCCATCGGCCACAAGAATAACCTGCACACCATCTACTGGAACGCCATCTT
CGAGAATTTTGACAACAGGCCTAAGCTGAATGGCGAGGCCGAGATCTTCTATCGCAAGGC

FIG. 23 cont'd.

CATCTCCAAGGATAAGCTGGGCATCGTGAAGGGCAAGAAAACCAAGAACGGCACCGAGAT
CATCAAGAATTACAGATTCAGCAAGGAGAAGTTTATCCTGCACGTGCCAATCACCCTGAAC
TTCTGCTCCAATAACGAGTATGTGAATGACATCGTGAACACAAAGTTCTACAATTTTTCCAA
CCTGCACTTTCTGGGCATCGATAGGGGCGAGAAGCACCTGGCCTACTATTCTCTGGTGAA
TAAGAACGGCGAGATCGTGGACCAGGGCACACTGAACCTGCCTTTCACCGACAAGGATGG
CAATCAGCGCAGCATCAAGAAGGAGAAGTACTTTTATAACAAGCAGGAGGACAAGTGGGA
GGCCAAGGAGGTGGATTGTTGGAATTATAACGACCTGCTGGATGCCATGGCCTCTAACCG
GGACATGGCCAGAAAGAATTGGCAGAGGATCGGCACCATCAAGGAGGCCAAGAACGGCT
ACGTGAGCCTGGTCATCAGGAAGATCGCCGATCTGGCCGTGAATAACGAGCGCCCCGCCT
TCATCGTGCTGGAGGACCTGAATACAGGCTTTAAGCGGTCCAGACAGAAGATCGATAAGA
GCGTGTACCAGAAGTTCGAGCTGGCCCTGGCCAAGAAGCTGAACTTTCTGGTGGACAAGA
ATGCCAAGCGCGATGAGATCGGCTCCCTACAAAGGCCCTGCAGCTGACCCCCCCTGTGA
ATAACTACGGCGACATTGAGAACAAGAAGCAGGCCGGCATCATGCTGTATACCCGGGCCA
ATTATACCTCTCAGACAGATCCAGCCACAGGCTGGAGAAAGACCATCTATCTGAAGGCCG
GCCCCGAGGAGACAACATACAAGAAGGACGGCAAGATCAAGAACAAGAGCGTGAAGGAC
CAGATCATCGAGACATTCACCGATATCGGCTTTGACGGCAAGGATTACTATTTCGAGTACG
ACAAGGGCGAGTTTGTGGATGAGAAAACCGGCGAGATCAAGCCCAAGAAGTGGCGGCTG
TACTCCGGCGAGAATGGCAAGTCCCTGGACAGGTTCCGCGGAGAGAGGGAGAAGGATAA
GTATGAGTGGAAGATCGACAAGATCGATATCGTGAAGATCCTGGACGATCTGTTCGTGAAT
TTTGACAAGAACATCAGCCTGCTGAAGCAGCTGAAGGAGGGCGTGGAGCTGACCCGGAAT
AACGAGCACGGCACAGGCGAGTCCCTGAGATTCGCCATCAACCTGATCCAGCAGATCCGG
AATACCGGCAATAACGAGAGAGACAACGATTTCATCCTGTCCCAGTGAGGGACGAGAAT
GGCAAGCACTTTGACTCTCGCGAGTACTGGGATAAGGAGACAAAGGGCGAGAAGATCAGC
ATGCCCAGCTCCGGCGATGCCAATGGCGCCTTCAACATCGCCCGGAAGGGCATCATCATG
AACGCCCACATCCTGGCCAATAGCGACTCCAAGGATCTGTCCCTGTTCGTGTCTGACGAG
GAGTGGGATCTGCACCTGAATAACAAGACCGAGTGGAAGAAGCAGCTGAACATCTTTTCTA
GCAGGAAGGCCATGGCCAAGCGCAAGAAG (SEQ ID NO: 221)

>Parcubacteria bacterium GWC2011_GWC2_44_17 Cpf1 (PbCpf1) coding
ATGGAGAACATCTTCGACCAGTTTATCGGCAAGTACAGCCTGTCCAAGACCCTGAGATTCG
AGCTGAAGCCCGTGGGCAAGACAGAGGACTTCCTGAAGATCAACAAGGTGTTTGAGAAGG
ATCAGACCATCGACGATAGCTACAATCAGGCCAAGTTCTATTTTGATTCCCTGCACCAGAA
GTTTATCGACGCCGCCCTGGCCTCCGATAAGACATCCGAGCTGTCTTTCCAGAACTTTGCC
GACGTGCTGGAGAAGCAGAATAAGATCATCCTGGATAAGAAGAGAGAGATGGGCGCCCTG
AGGAAGCGCGACAAGAACGCCGTGGGCATCGATAGGCTGCAGAAGGAGATCAATGACGC
CGAGGATATCATCCAGAAGGAGAAGGAGAAGATCTACAAGGACGTGCGCACCCTGTTCGA
TAACGAGGCCGAGTCTTGGAAAACCTACTATCAGGAGCGGGAGGTGGACGGCAAGAAGAT
CACCTTCAGCAAGGCCGACCTGAAGCAGAAGGGCGCCGATTTCTGACAGCCGCCGGCAT
CCTGAAGGTGCTGAAGTATGAGTTCCCCGAGGAGAAGGAGAAGGAGTTTCAGGCCAAGAA
CCAGCCCTCCCTGTTCGTGGAGGAGAAGGAGAATCCTGGCCAGAAGAGGTACATCTTCGA
CTCTTTTGATAAGTTCGCCGGCTATCTGACCAAGTTTCAGCAGACAAAGAAGAATCTGTAC
GCAGCAGACGGCACCAGCACAGCAGTGGCCACCCGCATCGCCGATAACTTTATCATCTTC
CACCAGAATACCAAGGTGTTCCGGGACAAGTACAAGAACAATCACACAGACCTGGGCTTC
GATGAGGAGAACATCTTTGAGATCGAGAGGTATAAGAATTGCCTGCTGCAGCGCGAGATC
GAGCACATCAAGAATGAGAATAGCTACAACAAGATCATCGGCCGGATCAATAAGAAGATCA
AGGAGTATCGGGACCAGAAGGCCAAGGATACCAAGCTGACAAAGTCCGACTTCCCTTTCT
TTAAGAACCTGGATAAGCAGATCCTGGGCGAGGTGGAGAAGGAGAAGCAGCTGATCGAGA
AAACCCGGGAGAAAACCGAGGAGGACGTGCTGATCGAGCGGTTCAAGGAGTTCATCGAG
AACAATGAGGAGAGGTTCACCGCCGCCAAGAAGCTGATGAATGCCTTCTGTAACGGCGAG

FIG. 23 cont'd.

TTTGAGTCCGAGTACGAGGGCATCTATCTGAAGAATAAGGCCATCAACACAATCTCCCGGA
GATGGTTCGTGTCTGACAGAGATTTTGAGCTGAAGCTGCCTCAGCAGAAGTCCAAGAACAA
GTCTGAGAAGAATGAGCCAAAGGTGAAGAAGTTCATCTCCATCGCCGAGATCAAGAACGC
CGTGGAGGAGCTGGACGGCGATATCTTTAAGGCCGTGTTCTACGACAAGAAGATCATCGC
CCAGGGCGGCTCTAAGCTGGAGCAGTTCCTGGTCATCTGGAAGTACGAGTTTGAGTATCT
GTTCCGGGACATCGAGAGAGAGAACGGCGAGAAGCTGCTGGGCTATGATAGCTGCCTGA
AGATCGCCAAGCAGCTGGGCATCTTCCACAGGAGAAGGAGGCCCGCGAGAAGGCAACC
GCCGTGATCAAGAATTACGCCGACGCCGGCCTGGGCATCTTCCAGATGATGAAGTATTTTT
CTCTGGACGATAAGGATCGGAAGAACACCCCGGCCAGCTGAGCACAAATTTCTACGCCG
AGTATGACGGCTACTACAAGGATTTCGAGTTTATCAAGTACTACAACGAGTTTAGGAACTTC
ATCACCAAGAAGCCTTTCGACGAGGATAAGATCAAGCTGAACTTTGAGAATGGCGCCCTGC
TGAAGGGCTGGGACGAGAACAAGGAGTACGATTTCATGGGCGTGATCCTGAAGAAGGAG
GGCCGCCTGTATCTGGGCATCATGCACAAGAACCACCGGAAGCTGTTCAGTCCATGGGC
AATGCCAAGGCGACAACGCCAATAGATACCAGAAGATGATCTATAAGCAGATCGCCGAC
GCCTCTAAGGATGTGCCCAGGCTGCTGCTGACCAGCAAGAAGGCCATGGAGAAGTTCAAG
CCTTCCCAGGAGATCCTGAGAATCAAGAAGGAGAAAACCTTCAAGCGGGAGAGCAAGAAC
TTTTCCCTGAGAGATCTGCACGCCCTGATCGAGTACTATAGGAACTGCATCCCTCAGTACA
GCAATTGGTCCTTTTATGACTTCCAGTTTCAGGATACCGGCAAGTACCAGAATATCAAGGA
GTTCACAGACGATGTGCAGAAGTACGGCTATAAGATCTCCTTTCGCGACATCGACGATGAG
TATATCAATCAGGCCCTGAACGAGGGCAAGATGTACCTGTTCGAGGTGGTGAACAAGGAT
ATCTATAACACCAAGAATGGCTCCAAGAATCTGCACACTGTACTTTGAGCACATCCTGTC
TGCCGAGAACCTGAATGACCCAGTGTTCAAGCTGTCTGGCATGGCCGAGATCTTTCAGCG
GCAGCCCAGCGTGAACGAAAGAGAAGATCACCACACAGAAGAATCAGTGTATCCTGGA
CAAGGGCGATAGAGCCTACAAGTATAGGCGCTACACCGAGAAGAAGATCATGTTCCACAT
GAGCCTGGTGCTGAACACAGGCAAGGGCGAGATCAAGCAGGTGCAGTTTAATAAGATCAT
CAACCAGAGGATCAGCTCCTCTGACAACGAGATGAGGGTGAATGTGATCGGCATCGATCG
CGGCGAGAAGAACCTGCTGTACTATAGCGTGGTGAAGCAGAATGGCGAGATCATCGAGCA
GGCCTCCCTGAACGAGATCAATGGCGTGAACTACCGGGACAAGCTGATCGAGAGGGAGA
AGGAGCGCCTGAAGAACCGGCAGAGCTGGAAGCCTGTGGTGAAGATCAAGGATCTGAAG
AAGGGCTACATCTCCCACGTGATCCACAAGATCTGCCAGCTGATCGAGAAGTATTCTGCCA
TCGTGGTGCTGGAGGACCTGAATATGAGATTCAAGCAGATCAGGGGAGGAATCGAGCGGA
GCGTGTACCAGCAGTTCGAGAAGGCCCTGATCGATAAGCTGGGCTATCTGGTGTTTAAGG
ACAACAGGGATCTGAGGGCACCAGGAGGCGTGCTGAATGGCTACCAGCTGTCTGCCCCC
TTTGTGAGCTTCGAGAAGATGCGCAAGCAGACCGGCATCCTGTTCTACACACAGGCCGAG
TATACCAGCAAGACAGACCCAATCACCGGCTTTCGGAAGAACGTGTATATCTCTAATAGCG
CCTCCCTGGATAAGATCAAGGAGGCCGTGAAGAAGTTCGACGCCATCGGCTGGGATGGCA
AGGAGCAGTCTTACTTCTTTAAGTACAACCCTTACAACCTGGCCGACGAGAAGTATAAGAA
CTCTACCGTGAGCAAGGAGTGGGCCATCTTTGCCAGCGCCCCAAGAATCCGGAGACAGAA
GGGCGAGGACGGCTACTGGAAGTATGATAGGGTGAAAGTGAATGAGGAGTTCGAGAAGCT
GCTGAAGGTCTGGAATTTTGTGAACCCAAAGGCCACAGATATCAAGCAGGAGATCATCAAG
AAGGAGAAGGCAGGCGACCTGCAGGGAGAAGGAGCTGGATGGCCGGCTGAGAAACTT
TTGGCACTCTTTCATCTACCTGTTTAACCTGGTGCTGGAGCTGCGCAATTCTTTCAGCCTG
CAGATCAAGATCAAGGCAGGAGAAGTGATCGCAGTGGACGAGGGCGTGGACTTCATCGC
CAGCCCAGTGAAGCCCTTCTTTACCACACCCAACCCTTACATCCCCTCCAACCTGTGCTGG
CTGGCCGTGGAGAATGCAGACGCAAACGGAGCCTATAATATCGCCAGGAAGGGCGTGAT
GATCCTGAAGAAGATCCGCGAGCACGCCAAGAAGGACCCCGAGTTCAAGAAGCTGCCAAA
CCTGTTTATCAGCAATGCAGAGTGGGACGAGGCAGCCCGGGATTGGGGCAAGTACGCAG
GCACCACAGCCCTGAACCTGGACCAC (SEQ ID NO: 222)

FIG. 23 cont'd.

>Lachnospiraceae bacterium MA2020 (Lb2Cpf1) coding
ATGTACTATGAGTCCCTGACCAAGCAGTACCCCGTGTCTAAGACAATCCGGAATGAGCTGA
TCCCTATCGGCAAGACACTGGATAACATCCGCCAGAACAATATCCTGGAGAGCGACGTGA
AGCGGAAGCAGAACTACGAGCACGTGAAGGGCATCCTGGATGAGTATCACAAGCAGCTGA
TCAACGAGGCCCTGGACAATTGCACCCTGCCATCCCTGAAGATCGCCGCCGAGATCTACC
TGAAGAATCAGAAGGAGGTGTCTGACAGAGAGGATTTCAACAAGACACAGGACCTGCTGA
GGAAGGAGGTGGTGGAGAAGCTGAAGGCCCACGAGAACTTTACCAAGATCGGCAAGAAG
GACATCCTGGATCTGCTGGAGAAGCTGCCTTCCATCTCTGAGGACGATTACAATGCCCTG
GAGAGCTTCCGCAACTTTTACACCTATTTCACATCCTACAACAAGGTGCGGGAGAATCTGT
ATTCTGATAAGGAGAAGAGCTCCACAGTGGCCTACAGACTGATCAACGAGAATTTCCCAAA
GTTTCTGGACAATGTGAAGAGCTATAGGTTTGTGAAAACCGCAGGCATCCTGGCAGATGG
CCTGGGAGAGGAGGAGCAGGACTCCCTGTTCATCGTGGAGACATTCAACAAGACCCTGAC
ACAGGACGGCATCGATACCTACAATTCTCAAGTGGGCAAGATCAACTCTAGCATCAATCTG
TATAACCAGAAGAATCAGAAGGCCAATGGCTTCAGAAAGATCCCCAAGATGAAGATGCTGT
ATAAGCAGATCCTGTCCGATAGGGAGGAGTCTTTCATCGACGAGTTTCAGAGCGATGAGG
TGCTGATCGACAACGTGGAGTCTTATGGCAGCGTGCTGATCGAGTCTCTGAAGTCCTCTAA
GGTGAGCGCCTTCTTTGATGCCCTGAGAGAGTCTAAGGGCAAGAACGTGTACGTGAAGAA
TGACCTGGCCAAGACAGCCATGAGCAACATCGTGTTCGAGAATTGGAGGACCTTTGACGA
TCTGCTGAACCAGGAGTACGACCTGGCCAACGAGAACAAGAAGAAGGACGATAAGTATTT
CGAGAAGCGCCAGAAGGAGCTGAAGAAGAATAAGAGCTACTCCCTGGAGCACCTGTGCAA
CCTGTCCGAGGATTCTTGTAACCTGATCGAGAATTATATCCACCAGATCTCCGACGATATC
GAGAATATCATCATCAACAATGAGACATTCCTGCGCATCGTGATCAATGAGCACGACAGGT
CCCGCAAGCTGGCCAAGAACCGGAAGGCCGTGAAGGCCATCAAGGACTTTCTGGATTCTA
TCAAGGTGCTGGAGCGGGAGCTGAAGCTGATCAACAGCTCCGGCCAGGAGCTGGAGAAG
GATCTGATCGTGTACTCTGCCCACGAGGAGCTGCTGGTGGAGCTGAAGCAGGTGGACAG
CCTGTATAACATGACCAGAAATTATCTGACAAAGAAGCCTTTCTCTACCGAGAAGGTGAAG
CTGAACTTTAATCGCAGCACACTGCTGAACGGCTGGGATCGGAATAAGGAGACAGACAAC
CTGGGCGTGCTGCTGCTGAAGGACGGCAAGTACTATCTGGGCATCATGAACACAAGCGCC
AATAAGGCCTTCGTGAATCCCCCTGTGGCCAAGACCGAGAAGGTGTTTAAGAAGGTGGAT
TACAAGCTGCTGCCAGTGCCCAACCAGATGCTGCCAAAGGTGTTCTTTGCCAAGAGCAATA
TCGACTTCTATAACCCCTCTAGCGAGATCTACTCCAATTATAAGAAGGGCACCCACAAGAA
GGGCAATATGTTTTCCCTGGAGGATTGTCACAACCTGATCGACTTCTTTAAGGAGTCTATCA
GCAAGCACGAGGACTGGAGCAAGTTCGGCTTTAAGTTCAGCGATACAGCCTCCTACAACG
ACATCTCCGAGTTCTATCGCGAGGTGGAGAAGCAGGGCTACAAGCTGACCTATACAGACA
TCGATGAGACATACATCAATGATCTGATCGAGCGGAACGAGCTGTACCTGTTCCAGATCTA
TAATAAGGACTTTAGCATGTACTCCAAGGGCAAGCTGAACCTGCACACACTGTATTTCATG
ATGCTGTTTGATCAGCGCAATATCGACGACGTGGTGTATAAGCTGAACGGAGAGGCAGAG
GTGTTCTATAGGCCAGCCTCCATCTCTGAGGACGAGCTGATCATCCACAAGGCCGGCGAG
GAGATCAAGAACAAGAATCCTAACCGGGCCAGAACCAAGGAGACAAGCACCTTCAGCTAC
GACATCGTGAAGGATAAGCGGTATAGCAAGGATAAGTTTACCCTGCACATCCCCATCACAA
TGAACTTCGGCGTGGATGAGGTGAAGCGGTTCAACGACGCCGTGAACAGCGCCATCCGG
ATCGATGAGAATGTGAACGTGATCGGCATCGACCGGGGCGAGAGAAATCTGCTGTACGTG
GTGGTCATCGACTCTAAGGGCAACATCCTGGAGCAGATCTCCCTGAACTCTATCATCAATA
AGGAGTACGACATCGAGACAGATTATCACGCACTGCTGGATGAGAGGGGGAGGGCGGCAGA
GATAAGGCCCGGAAGGACTGGAACACCGTGGAGAATATCAGGGACCTGAAGGCCGGCTA
CCTGAGCCAGGTGGTGAACGTGGTGGCCAAGCTGGTGCTGAAGTATAATGCCATCATCTG
CCTGGAGGACCTGAACTTTGGCTTCAAGAGGGGCCGCCAGAAGGTGGAGAAGCAGGTGT
ACCAGAAGTTCGAGAAGATGCTGATCGATAAGCTGAATTACCTGGTCATCGACAAGAGCCG
CGAGCAGACATCCCCTAAGGAGCTGGGAGGCGCCCTGAACGCACTGCAGCTGACCTCTA

FIG. 23 cont'd.

AGTTCAAGAGCTTTAAGGAGCTGGGCAAGCAGTCCGGCGTGATCTACTATGTGCCTGCCT
ACCTGACCTCTAAGATCGATCCAACCACAGGCTTCGCCAATCTGTTTTATATGAAGTGTGA
GAACGTGGAGAAGTCCAAGAGATTCTTTGACGGCTTTGATTTCATCAGGTTCAACGCCCTG
GAGAACGTGTTCGAGTTCGGCTTTGACTACCGGAGCTTCACCCAGAGGGCCTGCGGCATC
AATTCCAAGTGGACCGTGTGCACCAACGGCGAGCGCATCATCAAGTATCGGAATCCAGAT
AAGAACAATATGTTCGACGAGAAGGTGGTGGTGGTGACCGATGAGATGAAGAACCTGTTT
GAGCAGTACAAGATCCCCTATGAGGATGGCAGAAATGTGAAGGACATGATCATCAGCAAC
GAGGAGGCCGAGTTCTACCGGAGACTGTATAGGCTGCTGCAGCAGACCCTGCAGATGAG
AAACAGCACCTCCGACGGCACAAGGGATTACATCATCTCCCTGTGAAGAATAAGAGAGA
GGCCTACTTCAACAGCGAGCTGTCCGACGGCTCTGTGCCAAAGGACGCCGATGCCAACG
GCGCCTACAATATCGCCAGAAAGGGCCTGTGGGTGCTGGAGCAGATCAGGCAGAAGAGC
GAGGGCGAGAAGATCAATCTGGCCATGACCAACGCCGAGTGGCTGGAGTATGCCCAGAC
ACACCTGCTG (SEQ ID NO: 223)

>Candidatus Methanoplasma termitum Cpf1 (CMtCpf1) coding
ATGAACAATTACGACGAGTTCACCAAGCTGTATCCTATCCAGAAACCATCCGGTTTGAGC
TGAAGCCACAGGGCAGAACCATGGAGCACCTGGAGACATTCAACTTCTTTGAGGAGGACC
GGGATAGAGCCGAGAAGTATAAGATCCTGAAGGAGGCCATCGACGAGTACCACAAGAAGT
TTATCGATGAGCACCTGACCAATATGTCCCTGGATTGGAACTCTCTGAAGCAGATCAGCGA
GAAGTACTATAAGAGCAGGGAGGAGAAGGACAAGAAGGTGTTCCTGTCCGAGCAGAAGAG
GATGCGCCAGGAGATCGTGTCTGAGTTTAAGAAGGACGATCGCTTCAAGGACCTGTTTTCC
AAGAAGCTGTTCTCTGAGCTGCTGAAGGAGGAGATCTACAAGAAGGGCAACCACCAGGAG
ATCGACGCCCTGAAGAGCTTCGATAAGTTTTCCGGCTATTTCATCGGCCTGCACGAGAATA
GGAAGAACATGTACTCCGACGGCGATGAGATCACCGCCATCTCCAATCGCATCGTGAATG
AGAACTTCCCCAAGTTTCTGGATAACCTGCAGAAGTACCAGGAGGCCAGGAAGAAGTATC
CTGAGTGGATCATCAAGGCCGAGAGCGCCCTGGTGGCCCACAATATCAAGATGGACGAG
GTGTTCTCCCTGGAGTACTTTAATAAGGTGCTGAACCAGGAGGGCATCCAGCGGTACAAC
CTGGCCCTGGGCGGCTATGTGACCAAGAGCGGCGAGAAGATGATGGGCCTGAATGATGC
CCTGAACCTGGCCCACCAGTCCGAGAAGAGCTCCAAGGGCAGAATCCACATGACCCCCCT
GTTCAAGCAGATCCTGTCCGAGAAGGAGTCCTTCTCTTACATCCCCGACGTGTTTACAGAG
GATTCTCAGCTGCTGCCTAGCATCGGCGGCTTCTTTGCCCAGATCGAGAATGACAAGGAT
GGCAACATCTTCGACCGGGCCCTGGAGCTGATCTCTAGCTACGCCGAGTATGATACCGAG
CGGATCTATATCAGACAGGCCGACATCAATAGAGTGTCCAACGTGATCTTTGGAGAGTGG
GGCACCCTGGGAGGCCTGATGAGGGAGTACAAGGCCGACTCTATCAATGATATCAACCTG
GAGCGCACATGCAAGAAGGTGGACAAGTGGCTGGATTCTAAGGAGTTTGCCCTGAGCGAT
GTGCTGGAGGCCATCAAGAGGACCGGCAACAATGACGCCTTCAACGAGTATATCTCCAAG
ATGCGGACAGCCAGAGAGAAGATCGATGCCGCCCGCAAGGAGATGAAGTTCATCAGCGA
GAAGATCTCCGGCGATGAGGAGTCTATCCACATCATCAAGACCCTGCTGGACAGCGTGCA
GCAGTTCCTGCACTTCTTTAATCTGTTTAAGGCAAGGCAGGACATCCCACTGGATGGAGCC
TTCTACGCCGAGTTTGACGAGGTGCACAGCAAGCTGTTTGCCATCGTGCCCCTGTATAACA
AGGTGCGGAACTATCTGACCAAGAACAATCTGAACACAAAGAAGATCAAGCTGAATTTCAA
GAACCCTACACTGGCCAATGGCTGGGACCAGAACAAGGTGTACGATTATGCCTCCCTGAT
CTTTCTGCGGGACGGCAATTACTATCTGGGCATCATCAATCCTAAGAGAAAGAAGAACATC
AAGTTCGAGCAGGGCTCTGGCAACGGCCCCTTCTACCGGAAGATGGTGTATAAGCAGATC
CCCGGCCCTAATAAGAACCTGCCAAGAGTGTTCCTGACCTCCACAAAGGGCAAGAAGGAG
TATAAGCCCTCTAAGGAGATCATCGAGGGCTACGAGGCCGACAAGCACATCAGGGGCGAT
AAGTTCGACCTGGATTTTGTCACAAGCTGATCGATTTCTTTAAGGAGTCCATCGAGAAGCA
CAAGGACTGGTCTAAGTTCAACTTCTACTTCAGCCCAACCGAGAGCTATGGCGACATCTCT
GAGTTCTACCTGGATGTGGAGAAGCAGGGCTATCGCATGCACTTTGAGAATATCAGCGCC

FIG. 23 cont'd.

GAGACAATCGACGAGTATGTGGAGAAGGGCGATCTGTTTCTGTTCCAGATCTACAACAAGG
ATTTTGTGAAGGCCGCCACCGGCAAGAAGGACATGCACACAATCTACTGGAATGCCGCCT
TCAGCCCCGAGAACCTGCAGGACGTGGTGGTGAAGCTGAACGGCGAGGCCGAGCTGTTT
TATAGGGACAAGTCCGATATCAAGGAGATCGTGCACCGCGAGGGCGAGATCCTGGTGAAT
AGGACCTACAACGGCCGCACACCAGTGCCCGACAAGATCCACAAGAAGCTGACCGATTAT
CACAATGGCCGGACAAAGGACCTGGGCGAGGCCAAGGAGTACCTGGATAAGGTGAGATA
CTTCAAGGCCCACTATGACATCACCAAGGATCGGAGATACCTGAACGACAAGATCTATTTC
CACGTGCCTCTGACCCTGAACTTCAAGGCCAACGGCAAGAAGAATCTGAACAAGATGGTC
ATCGAGAAGTTCCTGTCCGATGAGAAGGCCCACATCATCGGCATCGACAGGGGCGAGCG
CAATCTGCTGTACTATTCCATCATCGACAGGTCTGGCAAGATCATCGATCAGCAGAGCCTG
AATGTGATCGACGGCTTTGATTATCGGGAGAAGCTGAACCAGAGAGAGATCGAGATGAAG
GATGCCCGCCAGTCTTGGAACGCCATCGGCAAGATCAAGGACCTGAAGGAGGGCTACCT
GAGCAAGGCCGTGCACGAGATCACCAAGATGGCCATCCAGTATAATGCCATCGTGGTCAT
GGAGGAGCTGAACTACGGCTTCAAGCGGGGCCGGTTCAAGGTGGAGAAGCAGATCTATC
AGAAGTTCGAGAATATGCTGATCGATAAGATGAACTACCTGGTGTTTAAGGACGCACCTGA
TGAGTCCCCAGGAGGCGTGCTGAATGCCTACCAGCTGACAAACCCACTGGAGTCTTTCGC
CAAGCTGGGCAAGCAGACCGGCATCCTGTTTTACGTGCCAGCCGCCTATACATCCAAGAT
CGACCCCACCACAGGCTTCGTGAATCTGTTTAACACCTCCTCTAAGACAAACGCCCAGGAG
CGGAAGGAGTTCCTGCAGAAGTTTGAGAGCATCTCCTATTCTGCCAAGGATGGCGGCATC
TTTGCCTTCGCCTTTGACTACAGAAAGTTCGGCACCAGCAAGACAGATCACAAGAACGTGT
GGACCGCCTATACAAACGGCGAGAGGATGCGCTACATCAAGGAGAAGAAGCGGAATGAG
CTGTTTGACCCTTCTAAGGAGATCAAGGAGGCCCTGACCAGCTCCGGCATCAAGTACGAT
GGCGGCCAGAACATCCTGCCAGACATCCTGAGGAGCAACAATAACGGCCTGATCTACACA
ATGTATTCTAGCTTCATCGCCGCCATCCAGATGCGCGTGTACGACGGCAAGGAGGATTATA
TCATCAGCCCCATCAAGAACTCCAAGGGCGAGTTCTTTAGGACCGACCCCAAGAGGCGCG
AGCTGCCTATCGACGCCGATGCCAATGGCGCCTACAACATCGCCCTGAGGGGAGAGCTG
ACAATGAGGGCAATCGCAGAGAAGTTCGACCCTGATAGCGAGAAGATGGCCAAGCTGGAG
CTGAAGCACAAGGATTGGTTCGAGTTTATGCAGACCAGAGGCGAC (SEQ ID NO: 224)

>Eubacterium eligens Cpf1 (EeCpf1) coding
ATGAACGGCAATAGGTCCATCGTGTACCGCGAGTTCGTGGGCGTGATCCCCGTGGCCAAG
ACCCTGAGGAATGAGCTGCGCCCTGTGGGCCACACACAGGAGCACATCATCCAGAACGG
CCTGATCCAGGAGGACGAGCTGCGGCAGGAGAAGAGCACCGAGCTGAAGAACATCATGG
ACGATTACTATAGAGAGTACATCGATAAGTCTCTGAGCGGCGTGACCGACCTGGACTTCAC
CCTGCTGTTCGAGCTGATGAACCTGGTGCAGAGCTCCCCTCCAAGGACAATAAGAAGGC
CCTGGAGAAGGAGCAGTCTAAGATGAGGGAGCAGATCTGCACCCACCTGCAGTCCGACTC
TAACTACAAGAATATCTTTAACGCCAAGCTGCTGAAGGAGATCCTGCCTGATTTCATCAAGA
ACTACAATCAGTATGACGTGAAGGATAAGGCCGGCAAGCTGGAGACACTGGCCCTGTTTA
ATGGCTTCAGCACATACTTTACCGACTTCTTTGAAGAGGAAGAACGTGTTCACCAAGGA
GGCCGTGAGCACATCCATCGCCTACCGCATCGTGCACGAGAACCTCCTGATCTTCCTGGC
CAATATGACCTCTTATAAGAAGATCAGCGAGAAGGCCCTGGATGAGATCGAAGTGATCGAG
AAGAACAATCAGGACAAGATGGGCGATTGGGAGCTGAATCAGATCTTTAACCCTGACTTCT
ACAATATGGTGCTGATCCAGTCCGGCATCGACTTCTACAACGAGATCTGCGGCGTGGTGA
ATGCCCACATGAACCTGTACTGTCAGCAGACCAAGAACAATTATAACCTGTTCAAGATGCG
GAAGCTGCACAAGCAGATCCTGGCCTACACCAGCACCAGCTTCGAGGTGCCAAGATGTT
CGAGGACGATATGAGCGTGTATAACGCCGTGAACGCCTTCATCGACGAGACAGAGAAGGG
CAACATCATCGGCAAGCTGAAGGATATCGTGAATAAGTACGACGAGCTGGATGAGAAGAG
AATCTATATCAGCAAGGACTTTACGAGACACTGAGCTGCTTCATGTCCGGCAACTGGAAT
CTGATCACAGGCTGCGTGGAGAACTTCTACGATGAGAACATCCACGCCAAGGGCAAGTCC

FIG. 23 cont'd.

AAGGAGGAGAAGGTGAAGAAGGCCGTGAAGGAGGACAAGTACAAGTCTATCAATGACGTG
AACGATCTGGTGGAGAAGTATATCGATGAGAAGGAGAGGAATGAGTTCAAGAACAGCAAT
GCCAAGCAGTACATCCGCGAGATCTCCAACATCATCACCGACACAGAGACAGCCCACCTG
GAGTATGACGATCACATCTCTCTGATCGAGAGCGAGGAGAAGGCCGACGAGATGAAGAAG
CGGCTGGATATGTATATGAACATGTACCACTGGGCCAAGGCCTTTATCGTGGACGAGGTG
CTGGACAGAGATGAGATGTTCTACAGCGATATCGACGATATCTATAATATCCTGGAGAACA
TCGTGCCACTGTATAATCGGGTGAGAAACTACGTGACCCAGAAGCCCTACAACTCTAAGAA
GATCAAGCTGAATTTCCAGAGCCCTACACTGGCCAATGGCTGGTCCAGTCTAAGGAGTTC
GACAACAATGCCATCATCCTGATCAGAGATAACAAGTACTATCTGGCCATCTTCAATGCCAA
GAACAAGCCAGACAAGAAGATCATCCAGGGCAACTCCGATAAGAAGAACGACAACGATTA
CAAGAAGATGGTGTATAACCTGCTGCCAGGCGCCAACAAGATGCTGCCCAAGGTGTTTCT
GTCTAAGAAGGGCATCGAGACATTCAAGCCCTCCGACTATATCATCTCTGGCTACAACGCC
CACAAGCACATCAAGACAAGCGAGAATTTTGATATCTCCTTCTGTCGGGACCTGATCGATT
ACTTCAAGAACAGCATCGAGAAGCACGCCGAGTGGAGAAAGTATGAGTTCAAGTTTTCCGC
CACCGACAGCTACTCCGATATCTCTGAGTTCTATCGGGAGGTGGAGATGCAGGGCTACAG
AATCGACTGGACATATATCAGCGAGGCCGACATCAACAAGCTGGATGAGGAGGGCAAGAT
CTATCTGTTTCAGATCTACAATAAGGATTTCGCCGAGAACAGCACCGGCAAGGAGAATCTG
CACACAATGTACTTTAAGAACATCTTCTCCGAGGAGAATCTGAAGGACATCATCATCAAGCT
GAACGGCCAGGCCGAGCTGTTTTATCGGAGAGCCTCTGTGAAGAATCCCGTGAAGCACAA
GAAGGATAGCGTGCTGGTGAACAAGACCTACAAGAATCAGCTGGACAACGGCGACGTGGT
GAGAATCCCCATCCCTGACGATATCTATAACGAGATCTACAAGATGTATAATGGCTACATCA
AGGAGTCCGACCTGTCTGAGGCCGCCAAGGAGTACCTGGATAAGGTGGAGGTGAGGACC
GCCCAGAAGGACATCGTGAAGGATTACCGCTATACAGTGGACAAGTACTTCATCCACACAC
CTATCACCATCAACTATAAGGTGACCGCCCGCAACAATGTGAATGATATGGTGGTGAAGTA
CATCGCCCAGAACGACGATATCCACGTGATCGGCATCGACCGGGGCGAGAGAAACCTGAT
CTACATCTCCGTGATCGATTCTCACGGCAACATCGTGAAGCAGAAATCCTACAACATCCTG
AACAACTACGACTACAAGAAGAAGCTGGTGGAGAAGGAGAAAACCCGGGAGTACGCCAGA
AAGAACTGGAAGAGCATCGGCAATATCAAGGAGCTGAAGGAGGGCTATATCTCCGGCGTG
GTGCACGAGATCGCCATGCTGATCGTGGAGTACAACGCCATCATCGCCATGGAGGACCTG
AATTATGGCTTTAAGAGGGGCCGCTTCAAGGTGGAGCGGCAGGTGTACCAGAAGTTTGAG
AGCATGCTGATCAATAAGCTGAACTATTTCGCCAGCAAGGAGAAGTCCGTGGACGAGCCA
GGAGGCCTGCTGAAGGGCTATCAGCTGACCTACGTGCCCGATAATATCAAGAACCTGGGC
AAGCAGTGCGGCGTGATCTTTTACGTGCCTGCCGCCTTCACCAGCAAGATCGACCCATCC
ACAGGCTTTATCTCTGCCTTCAACTTTAAGTCTATCAGCACAAATGCCTCTCGGAAGCAGTT
CTTTATGCAGTTTGACGAGATCAGATACTGTGCCGAGAAGGATATGTTCAGCTTTGGCTTC
GACTACAACAACTTCGATACCTACAACATCACAATGGGCAAGACACAGTGGACCGTGTATA
CAAACGGCGAGAGACTGCAGTCTGAGTTCAACAATGCCAGGCGCACCGGCAAGACAAAGA
GCATCAATCTGACAGAGACAATCAAGCTGCTGCTGGAGGACAATGAGATCAACTACGCCG
ACGGCCACGATATCAGGATCGATATGGAGAAGATGGACGAGGATAAGAAGAGCGAGTTCT
TTGCCCAGCTGCTGAGCCTGTATAAGCTGACCGTGCAGATGCGCAATTCCTATACAGAGG
CCGAGGAGCAGGAGAACGGCATCTCTTACGACAAGATCATCAGCCCTGTGATCAATGATG
AGGGCGAGTTCTTTGACTCCGATAACTATAAGGAGTCTGACGATAAGGAGTGCAAGATGCC
AAAGGACGCCGATGCCAACGGCGCCTACTGTATCGCCCTGAAGGGCCTGTATGAGGTGCT
GAAGATCAAGAGCGAGTGGACCGAGGACGGCTTTGATAGGAATTGCCTGAAGCTGCCACA
CGCAGAGTGGCTGGACTTCATCCAGAACAAGCGGTACGAG (SEQ ID NO: 225)

FIG. 23 cont'd.

>Moraxella bovoculi 237 Cpf1 (MbCpf1) coding
ATGCTGTTCCAGGACTTTACCCACCTGTATCCACTGTCCAAGACAGTGAGATTTGAGCTGA
AGCCCATCGATAGGACCCTGGAGCACATCCACGCCAAGAACTTCCTGTCTCAGGACGAGA
CAATGGCCGATATGCACCAGAAGGTGAAAGTGATCCTGGACGATTACCACCGCGACTTCA
TCGCCGATATGATGGGCGAGGTGAAGCTGACCAAGCTGGCCGAGTTCTATGACGTGTACC
TGAAGTTTCGGAAGAACCCAAAGGACGATGAGCTGCAGAAGCAGCTGAAGGATCTGCAGG
CCGTGCTGAGAAAGGAGATCGTGAAGCCCATCGGCAATGGCGGCAAGTATAAGGCCGGC
TACGACAGGCTGTTCGGCGCCAAGCTGTTTAAGGACGGCAAGGAGCTGGGCGATCTGGC
CAAGTTCGTGATCGCACAGGAGGGAGAGCTCCCCAAAGCTGGCCCACCTGGCCCACTT
CGAGAAGTTTTCCACCTATTTCACAGGCTTTCACGATAACCGGAAGAATATGTATTCTGACG
AGGATAAGCACACCGCCATCGCCTACCGCCTGATCCACGAGAACCTGCCCCGGTTTATCG
ACAATCTGCAGATCCTGACCACAATCAAGCAGAAGCACTCTGCCCTGTACGATCAGATCAT
CAACGAGCTGACCGCCAGCGGCCTGGACGTGTCTCTGGCCAGCCACCTGGATGGCTATC
ACAAGCTGCTGACACAGGAGGGCATCACCGCCTACAATACACTGCTGGGAGGAATCTCCG
GAGAGGCAGGCTCTCCTAAGATCCAGGGCATCAACGAGCTGATCAATTCTCACCACAACC
AGCACTGCCACAAGAGCGAGAGAATCGCCAAGCTGAGGCCACTGCACAAGCAGATCCTGT
CCGACGGCATGAGCGTGTCCTTCCTGCCCTCTAAGTTTGCCGACGATAGCGAGATGTGCC
AGGCCGTGAACGAGTTCTATCGCCACTACGCCGACGTGTTCGCCAAGGTGCAGAGCCTGT
TCGACGGCTTTGACGATCACCAGAAGGATGGCATCTACGTGGAGCACAAGAACCTGAATG
AGCTGTCCAAGCAGGCCTTCGGCGACTTTGCACTGCTGGGACGCGTGCTGGACGGATACT
ATGTGGATGTGGTGAATCCAGAGTTCAACGAGCGGTTTGCCAAGGCCAAGACCGACAATG
CCAAGGCCAAGCTGACAAAGGAGAAGGATAAGTTCATCAAGGGCGTGCACTCCCTGGCCT
CTCTGGAGCAGGCCATCGAGCACTATACCGCAAGGCACGACGATGAGAGCGTGCAGGCA
GGCAAGCTGGGACAGTACTTCAAGCACGGCCTGGCCGGAGTGGACAACCCCATCCAGAA
GATCCACAACAATCACAGCACCATCAAGGGCTTTCTGGAGAGGGAGCGCCCTGCAGGAGA
GAGAGCCCTGCCAAAGATCAAGTCCGGCAAGAATCCTGAGATGACACAGCTGAGGCAGCT
GAAGGAGCTGCTGGATAACGCCCTGAATGTGGCCCACTTCGCCAAGCTGCTGACCACAAA
GACCACACTGGACAATCAGGATGGCAACTTCTATGGCGAGTTTGGCGTGCTGTACGACGA
GCTGGCCAAGATCCCCACCCTGTATAACAAGGTGAGAGATTACCTGAGCCAGAAGCCTTT
CTCCACCGAGAAGTACAAGCTGAACTTTGGCAATCCAACACTGCTGAATGGCTGGGACCT
GAACAAGGAGAAGGATAATTTCGGCGTGATCCTGCAGAAGGACGGCTGCTACTATCTGGC
CCTGCTGGACAAGGCCCACAAGAAGGTGTTTGATAACGCCCCTAATACAGGCAAGAGCAT
CTATCAGAAGATGATCTATAAGTACCTGGAGGTGAGGAAGCAGTTCCCCAAGGTGTTCTTT
TCCAAGGAGGCCATCGCCATCAACTACCACCCTTCTAAGGAGCTGGTGGAGATCAAGGAC
AAGGGCCGGCAGAGATCCGACGATGAGCGCCTGAAGCTGTATCGGTTTATCCTGGAGTGT
CTGAAGATCCACCCTAAGTACGATAAGAAGTTCGAGGGCGCCATCGGCGACATCCAGCTG
TTTAAGAAGGATAAGAAGGGCAGAGAGGTGCCAATCAGCGAGAAGGACCTGTTCGATAAG
ATCAACGGCATCTTTTCTAGCAAGCCTAAGCTGGAGATGGAGGACTTCTTTATCGGCGAGT
TCAAGAGGTATAACCCAAGCCAGGACCTGGTGGATCAGTATAATATCTACAAGAAGATCGA
CTCCAACGATAATCGCAAGAAGGAGAATTTCTACAACAATCACCCCAAGTTTAAGAAGGAT
CTGGTGCGGTACTATTACGAGTCTATGTGCAAGCACGAGGAGTGGGAGGAGAGCTTCGAG
TTTTCCAAGAAGCTGCAGGACATCGGCTGTTACGTGGATGTGAACGAGCTGTTTACCGAGA
TCGAGACACGGAGACTGAATTATAAGATCTCCTTCTGCAACATCAATGCCGACTACATCGA
TGAGCTGGTGGAGCAGGGCCAGCTGTATCTGTTCCAGATCTACAACAAGGACTTTTCCCCA
AAGGCCCACGGCAAGCCCAATCTGCACACCCTGTACTTCAAGGCCCTGTTTCTGAGGAC
AACCTGGCCGATCCTATCTATAAGCTGAATGGCGAGGCCCAGATCTTCTACAGAAGGCCT
CCCTGGACATGAACGAGACAACAATCCACAGGGCCGGCGAGGTGCTGGAGAACAAGAAT
CCCGATAATCCTAAGAAGAGACAGTTCGTGTACGACATCATCAAGGATAAGAGGTACACAC
AGGACAAGTTCATGCTGCACGTGCCAATCACCATGAACTTTGGCGTGCAGGGCATGACAA

FIG. 23 cont'd.

TCAAGGAGTTCAATAAGAAGGTGAACCAGTCTATCCAGCAGTATGACGAGGTGAACGTGAT
CGGCATCGATCGGGGCGAGAGACACCTGCTGTACCTGACCGTGATCAATAGCAAGGGCG
AGATCCTGGAGCAGTGTTCCCTGAACGACATCACCACAGCCTCTGCCAATGGCACACAGA
TGACCACACCTTACCACAAGATCCTGGATAAGAGGGAGATCGAGCGCCTGAACGCCCGGG
TGGGATGGGGCGAGATCGAGACAATCAAGGAGCTGAAGTCTGGCTATCTGAGCCACGTG
GTGCACCAGATCAGCCAGCTGATGCTGAAGTACAACGCCATCGTGGTGCTGGAGGACCTG
AATTTCGGCTTTAAGAGGGGCCGCTTTAAGGTGGAGAAGCAGATCTATCAGAACTTCGAGA
ATGCCCTGATCAAGAAGCTGAACCACCTGGTGCTGAAGGACAAGGCCGACGATGAGATCG
GCTCTTACAAGAATGCCCTGCAGCTGACCAACAATTTCACAGATCTGAAGAGCATCGGCAA
GCAGACCGGCTTCCTGTTTTATGTGCCCGCCTGGAACACCTCTAAGATCGACCCTGAGAC
AGGCTTTGTGGATCTGCTGAAGCCAAGATACGAGAACATCGCCCAGAGCCAGGCCTTCTT
TGGCAAGTTCGACAAGATCTGCTATAATGCCGACAAGGATTACTTCGAGTTTCACATCGAC
TACGCCAAGTTTACCGATAAGGCCAAGAATAGCCGCCAGATCTGGACAATCGTTCCCACG
GCGACAAGCGGTACGTGTACGATAAGACAGCCAACCAGAATAAGGGCGCCGCCAAGGGC
ATCAACGTGAATGATGAGCTGAAGTCCCTGTTCGCCCGCCACCACATCAACGAGAAGCAG
CCCAACCTGGTCATGGACATCTGCCAGAACAATGATAAGGAGTTTCACAAGTCTCTGATGT
ACCTGCTGAAAACCCTGCTGGCCCTGCGGTACAGCAACGCCTCCTCTGACGAGGATTTCA
TCCTGTCCCCGTGGCAAACGACGAGGGCGTGTTCTTTAATAGCGCCCTGGCCGACGATA
CACAGCCTCAGAATGCCGATGCCAACGGCGCCTACCACATCGCCCTGAAGGGCCTGTGG
CTGCTGAATGAGCTGAAGAACTCCGACGATCTGAACAAGGTGAAGCTGGCCATCGACAAT
CAGACCTGGCTGAATTTCGCCCAGAACAGG (SEQ ID NO: 226)

>Prevotella disiens Cpf1 (PdCpf1) coding
ATGGAGAACTATCAGGAGTTCACCAACCTGTTTCAGCTGAATAAGACACTGAGATTCGAGC
TGAAGCCCATCGGCAAGACCTGCGAGCTGCTGGAGGAGGGCAAGATCTTCGCCAGCGGC
TCCTTTCTGGAGAAGGACAAGGTGAGGGCCGATAACGTGAGCTACGTGAAGAAGGAGATC
GACAAGAAGCACAAGATCTTTATCGAGGAGACACTGAGCTCCTTCTCTATCAGCAACGATC
TGCTGAAGCAGTACTTTGACTGCTATAATGAGCTGAAGGCCTTCAAGAAGGACTGTAAGAG
CGATGAGGAGGAGGTGAAGAAAACCGCCCTGCGCAACAAGTGTACCTCCATCCAGAGGG
CCATGCGCGAGGCCATCTCTCAGGCCTTTCTGAAGAGCCCCCAGAAGAAGCTGCTGGCCA
TCAAGAACCTGATCGAGAACGTGTTCAAGGCCGACGAGAATGTGCAGCACTTCTCCGAGT
TTACCAGCTATTTCTCCGGCTTTGAGACAAACAGAGAGAATTTCTACTCTGACGAGGAGAA
GTCCACATCTATCGCCTATAGGCTGGTGCACGATAACCTGCCTATCTTCATCAAGAACATC
TACATCTTCGAGAAGCTGAAGGAGCAGTTCGACGCCAAGACCCTGAGCGAGATCTTCGAG
AACTACAAGCTGTATGTGGCCGGCTCTAGCCTGGATGAGGTGTTCTCCCTGGAGTACTTTA
ACAATACCCTGACACAGAAGGGCATCGACAACTATAATGCCGTGATCGGCAAGATCGTGAA
GGAGGATAAGCAGGAGATCCAGGGCCTGAACGAGCACATCAACCTGTATAATCAGAAGCA
CAAGGACCGGAGACTGCCCTTCTTTATCTCCCTGAAGAAGCAGATCCTGTCCGATCGGGA
GGCCCTGTCTTGGCTGCCTGACATGTTCAAGAATGATTCTGAAGTGATCAAGGCCCTGAAG
GGCTTCTACATCGAGGACGGCTTTGAGAACAATGTGCTGACACCTCTGGCCACCCTGCTG
TCCTCTCTGGATAAGTACAACCTGAATGGCATCTTTATCCGCAACAATGAGGCCCTGAGCT
CCCTGTCCCAGAACGTGTATCGGAATTTTTCTATCGACGAGGCCATCGATGCCAACGCCGA
GCTGCAGACCTTCAACAATTACGAGCTGATCGCCAATGCCCTGCGCGCCAAGATCAAGAA
GGAGACAAAGCAGGGCCGGAAGTCTTTCGAGAAGTACGAGGAGTATATCGATAAGAAGGT
GAAGGCCATCGACAGCCTGTCCATCCAGGAGATCAACGAGCTGGTGGAGAATTACGTGAG
CGAGTTTAACTCTAATAGCGGCAACATGCCAAGAAGGTGGAGGACTACTTCAGCCTGATG
AGGAAGGGCGACTTCGGCTCCAACGATCTGATCGAAAATATCAAGACCAAGCTGAGCGCC
GCAGAGAAGCTGCTGGGCACAAAGTACCAGGAGACAGCCAAGGACATCTTCAAGAAGGAT
GAGAACTCCAAGCTGATCAAGGAGCTGCTGGACGCCACCAAGCAGTTCCAGCACTTTATC

FIG. 23 cont'd.

AAGCCACTGCTGGGCACAGGCGAGGAGGCAGATCGGGACCTGGTGTTCTACGGCGATTT
TCTGCCCCTGTATGAGAAGTTTGAGGAGCTGACCCTGCTGTATAACAAGGTGCGGAATAGA
CTGACACAGAAGCCCTATTCCAAGGACAAGATCCGCCTGTGCTTCAACAAGCCTAAGCTGA
TGACAGGCTGGGTGGATTCCAAGACCGAGAAGTCTGACAACGGCACACAGTACGGCGGC
TATCTGTTTCGGAAGAAGAATGAGATCGGCGAGTACGATTATTTCTGGGCATCTCTAGCA
AGGCCCAGCTGTTCAGAAAGAACGAGGCCGTGATCGGCGACTACGAGAGGCTGGATTACT
ATCAGCCAAAGGCCAATACCATCTACGGCTCTGCCTATGAGGGCGAGAACAGCTACAAGG
AGGACAAGAAGCGGCTGAACAAAGTGATCATCGCCTATATCGAGCAGATCAAGCAGACAA
ACATCAAGAAGTCTATCATCGAGTCCATCTCTAAGTATCCTAATATCAGCGACGATGACAAG
GTGACCCCATCCTCTCTGCTGGAGAAGATCAAGAAGGTGTCTATCGACAGCTACAACGGC
ATCCTGTCCTTCAAGTCTTTTCAGAGCGTGAACAAGGAAGTGATCGATAACCTGCTGAAAA
CCATCAGCCCCCTGAAGAACAAGGCCGAGTTTCTGGACCTGATCAATAAGGATTATCAGAT
CTTCACCGAGGTGCAGGCCGTGATCGACGAGATCTGCAAGCAGAAAACCTTCATCTACTTT
CCAATCTCCAACGTGGAGCTGGAGAAGGAGATGGGCGATAAGGACAAGCCCCTGTGCCT
GTTCCAGATCAGCAATAAGGATCTGTCCTTCGCCAAGACCTTTAGCGCCAACCTGCGGAAG
AAGAGAGGCGCCGAGAATCTGCACACAATGCTGTTTAAGGCCCTGATGGAGGGCAACCAG
GATAATCTGGACCTGGGCTCTGGCGCCATCTTCTACAGAGCCAAGAGCCTGGACGGCAAC
AAGCCCACACACCCTGCCAATGAGGCCATCAAGTGTAGGAACGTGGCCAATAAGGATAAG
GTGTCCCTGTTCACCTACGACATCTATAAGAACAGGCGCTACATGGAGAATAAGTTCCTGT
TTCACCTGAGCATCGTGCAGAACTATAAGGCCGCCAATGACTCCGCCCAGCTGAACAGCT
CCGCCACCGAGTATATCAGAAAGGCCGATGACCTGCACATCATCGGCATCGATAGGGGCG
AGCGCAATCTGCTGTACTATTCCGTGATCGATATGAAGGGCAACATCGTGGAGCAGGACT
CTCTGAATATCATCAGGAACAATGACCTGGAGACAGATTACCACGACCTGCTGGATAAGAG
GGAGAAGGAGCGCAAGGCCAACCGGCAGAATTGGGAGGCCGTGGAGGGCATCAAGGAC
CTGAAGAAGGGCTACCTGAGCCAGGCCGTGCACCAGATCGCCCAGCTGATGCTGAAGTAT
AACGCCATCATCGCCCTGGAGGATCTGGGCCAGATGTTTGTGACCCGCGGCCAGAAGATC
GAGAAGGCCGTGTACCAGCAGTTCGAGAAGAGCCTGGTGGATAAGCTGTCCTACCTGGTG
GACAAGAAGCGGCCTTATAATGAGCTGGGCGGCATCCTGAAGGCCTACCAGCTGGCCTCT
AGCATCACCAAGAACAATTCTGACAAGCAGAACGGCTTCCTGTTTTATGTGCCAGCCTGGA
ATACAAGCAAGATCGATCCCGTGACCGGCTTTACAGACCTGCTGCGGCCCAAGGCCATGA
CCATCAAGGAGGCCCAGGACTTCTTTGGCGCCTTCGATAACATCTCTTACAATGACAAGGG
CTATTTCGAGTTTGAGACAAACTACGACAAGTTTAAGATCAGAATGAAGAGCGCCCAGACC
AGGTGGACAATCTGCACCTTCGGCAATCGGATCAAGAGAAAGAAGGATAAGAACTACTGG
AATTATGAGGAGGTGGAGCTGACCGAGGAGTTCAAGAAGCTGTTTAAGGACAGCAACATC
GATTACGAGAACTGTAATCTGAAGGAGGAGATCCAGAACAAGGACAATCGCAAGTTCTTTG
ATGACCTGATCAAGCTGCTGCAGCTGACACTGCAGATGCGGAACTCCGATGACAAGGGCA
ATGATTATATCATCTCTCCTGTGGCCAACGCCGAGGGCCAGTTCTTTGACTCCCGCAATGG
CGATAAGAAGCTGCCACTGGATGCAGACGCAAACGGAGCCTACAATATCGCCCGCAAGGG
CCTGTGGAACATCCGGCAGATCAAGCAGACCAAGAACGACAAGAAGCTGAATCTGAGCAT
CTCCTCTACAGAGTGGCTGGATTTCGTGCGGGAGAAGCCTTACCTGAAG (SEQ ID NO: 227)

>Streptococcus pyogenes serotype M1 Cas9 protein (UniProt Accession Q99ZW2)
MDKKYSIGLDIGTNSVGWAVITDEYKVPSKKFKVLGNTDRHSIKKNLIGALLFDSGETAEATRLK
RTARRRYTRRKNRICYLQEIFSNEMAKVDDSFFHRLEESFLVEEDKKHERHPIFGNIVDEVAYH
EKYPTIYHLRKKLVDSTDKADLRLIYLALAHMIKFRGHFLIEGDLNPDNSDVDKLFIQLVQTYNQL
FEENPINASGVDAKAILSARLSKSRRLENLIAQLPGEKKNGLFGNLIALSLGLTPNFKSNFDLAED
AKLQLSKDTYDDDLDNLLAQIGDQYADLFLAAKNLSDAILLSDILRVNTEITKAPLSASMIKRYDE
HHQDLTLLKALVRQQLPEKYKEIFFDQSKNGYAGYIDGGASQEEFYKFIKPILEKMDGTEELLVK

FIG. 23 cont'd.

LNREDLLRKQRTFDNGSIPHQIHLGELHAILRRQEDFYPFLKDNREKIEKILTFRIPYYVGPLARG
NSRFAWMTRKSEETITPWNFEEVVDKGASAQSFIERMTNFDKNLPNEKVLPKHSLLYEYFTVY
NELTKVKYVTEGMRKPAFLSGEQKKAIVDLLFKTNRKVTVKQLKEDYFKKIECFDSVEISGVEDR
FNASLGTYHDLLKIIKDKDFLDNEENEDILEDIVLTLTLFEDREMIEERLKTYAHLFDDKVMKQLK
RRRYTGWGRLSRKLINGIRDKQSGKTILDFLKSDGFANRNFMQLIHDDSLTFKEDIQKAQVSGQ
GDSLHEHIANLAGSPAIKKGILQTVKVVDELVKVMGRHKPENIVIEMARENQTTQKGQKNSRER
MKRIEEGIKELGSQILKEHPVENTQLQNEKLYLYYLQNGRDMYVDQELDINRLSDYDVDHIVPQ
SFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFY
KVREINNYHHAHDAYLNAVVGTALIKKYPKLESEFVYGDYKVYDVRKMIAKSEQEIGKATAKYFF
YSNIMNFFKTEITLANGEIRKRPLIETNGETGEIVWDKGRDFATVRKVLSMPQVNIVKKTEVQTG
GFSKESILPKRNSDKLIARKKDWDPKKYGGFDSPTVAYSVLVVAKVEKGKSKKLKSVKELLGITI
MERSSFEKNPIDFLEAKGYKEVKKDLIIKLPKYSLFELENGRKRMLASAGELQKGNELALPSKYV
NFLYLASHYEKLKGSPEDNEQKQLFVEQHKHYLDEIIEQISEFSKRVILADANLDKVLSAYNKHR
DKPIREQAENIIHLFTLTNLGAPAAFKYFDTTIDRKRYTSTKEVLDATLIHQSITGLYETRIDLSQLG
GD (SEQ ID NO: 228)

>Francisella tularensis type V CRISPR-associated protein Cpf1 (NCBI Reference Sequence: WP_003040289.1)
MSIYQEFVNKYSLSKTLRFELIPQGKTLENIKARGLILDDEKRAKDYKKAKQIIDKYHQFFIEEILSS
VCISEDLLQNYSDVYFKLKKSDDDNLQKDFKSAKDTIKKQISEYIKDSEKFKNLFNQNLIDAKKG
QESDLILWLKQSKDNGIELFKANSDITDIDEALEIIKSFKGWTTYFKGFHENRKNVYSSNDIPTSII
YRIVDDNLPKFLENKAKYESLKDKAPEAINYEQIKKDLAEELTFDIDYKTSEVNQRVFSLDEVFEI
ANFNNYLNQSGITKFNTIIGGKFVNGENTKRKGINEYINLYSQQINDKTLKKYKMSVLFKQILSDT
ESKSFVIDKLEDDSDVVTTMQSFYEQIAAFKTVEEKSIKETLSLLFDDLKAQKLDLSKIYFKNDKS
LTDLSQQVFDDYSVIGTAVLEYITQQIAPKNLDNPSKKEQELIAKKTEKAKYLSLETIKLALEEFNK
HRDIDKQCRFEEILANFAAIPMIFDEIAQNKDNLAQISIKYQNQGKKDLLQASAEDDVKAIKDLLD
QTNNLLHKLKIFHISQSEDKANILDKDEHFYLVFEECYFELANIVPLYNKIRNYITQKPYSDEKFKL
NFENSTLANGWDKNKEPDNTAILFIKDDKYYLGVMNKKNNKIFDDKAIKENKGEGYKKIVYKLLP
GANKMLPKVFFSAKSIKFYNPSEDILRIRNHSTHTKNGSPQKGYEKFEFNIEDCRKFIDFYKQSIS
KHPEWKDFGFRFSDTQRYNSIDEFYREVENQGYKLTFENISESYIDSVVNQGKLYLFQIYNKDF
SAYSKGRPNLHTLYWKALFDERNLQDVVYKLNGEAELFYRKQSIPKKITHPAKEAIANKNKDNP
KKESVFEYDLIKDKRFTEDKFFFHCPITINFKSSGANKFNDEINLLLKEKANDVHILSIDRGERHLA
YYTLVDGKGNIIKQDTFNIIGNDRMKTNYHDKLAAIEKDRDSARKDWKKINNIKEMKEGYLSQVV
HEIAKLVIEYNAIVVFEDLNFGFKRGRFKVEKQVYQKLEKMLIEKLNYLVFKDNEFDKTGGVLRA
YQLTAPFETFKKMGKQTGIIYYVPAGFTSKICPVTGFVNQLYPKYESVSKSQEFFSKFDKICYNL
DKGYFEFSFDYKNFGDKAAKGKWTIASFGSRLINFRNSDKNHNWDTREVYPTKELEKLLKDYSI
EYGHGECIKAAICGESDKKFFAKLTSVLNTILQMRNSKTGTELDYLISPVADVNGNFFDSRQAPK
NMPQDADANGAYHIGLKGLMLLGRIKNNQEGKKLNLVIKNEEYFEFVQNRNN (SEQ ID NO: 229)

>Acidaminococcus sp. BV3L6 type V CRISPR-associated protein Cpf1 (AsCpf1) (NCBI Reference Sequence: WP_021736722.1)
MTQFEGFTNLYQVSKTLRFELIPQGKTLKHIQEQGFIEEDKARNDHYKELKPIIDRIYKTYADQCL
QLVQLDWENLSAAIDSYRKEKTEETRNALIEEQATYRNAIHDYFIGRTDNLTDAINKRHAEIYKGL
FKAELFNGKVLKQLGTVTTTEHENALLRSFDKFTTYFSGFYENRKNVFSAEDISTAIPHRIVQDN
FPKFKENCHIFTRLITAVPSLREHFENVKKAIGIFVSTSIEEVFSFPFYNQLLTQTQIDLYNQLLGGI
SREAGTEKIKGLNEVLNLAIQKNDETAHIIASLPHRFIPLFKQILSDRNTLSFILEEFKSDEEVIQSF
CKYKTLLRNENVLETAEALFNELNSIDLTHIFISHKKLETISSALCDHWDTLRNALYERRISELTGK

FIG. 23 cont'd.

ITKSAKEKVQRSLKHEDINLQEIISAAGKELSEAFKQKTSEILSHAHAALDQPLPTTLKKQEEKEIL
KSQLDSLLGLYHLLDWFAVDESNEVDPEFSARLTGIKLEMEPSLSFYNKARNYATKKPYSVEKF
KLNFQMPTLASGWDVNKEKNNGAILFVKNGLYYLGIMPKQKGRYKALSFEPTEKTSEGFDKMY
YDYFPDAAKMIPKCSTQLKAVTAHFQTHTTPILLSNNFIEPLEITKEIYDLNNPEKEPKKFQTAYA
KKTGDQKGYREALCKWIDFTRDFLSKYTKTTSIDLSSLRPSSQYKDLGEYYAELNPLLYHISFQR
IAEKEIMDAVETGKLYLFQIYNKDFAKGHHGKPNLHTLYWTGLFSPENLAKTSIKLNGQAELFYR
PKSRMKRMAHRLGEKMLNKKLKDQKTPIPDTLYQELYDYVNHRLSHDLSDEARALLPNVITKEV
SHEIIKDRRFTSDKFFFHVPITLNYQAANSPSKFNQRVNAYLKEHPETPIIGIDRGERNLIYITVIDS
TGKILEQRSLNTIQQFDYQKKLDNREKERVAARQAWSVVGTIKDLKQGYLSQVIHEIVDLMIHYQ
AVVVLENLNFGFKSKRTGIAEKAVYQQFEKMLIDKLNCLVLKDYPAEKVGGVLNPYQLTDQFTS
FAKMGTQSGFLFYVPAPYTSKIDPLTGFVDPFVWKTIKNHESRKHFLEGFDFLHYDVKTGDFIL
HFKMNRNLSFQRGLPGFMPAWDIVFEKNETQFDAKGTPFIAGKRIVPVIENHRFTGRYRDLYPA
NELIALLEEKGIVFRDGSNILPKLLENDDSHAIDTMVALIRSVLQMRNSNAATGEDYINSPVRDLN
GVCFDSRFQNPEWPMDADANGAYHIALKGQLLLNHLKESKDLKLQNGISNQDWLAYIQELRN
(SEQ ID NO: 230)

>Lachnospiraceae bacterium MC2017 type V CRISPR-associated protein Cpf1 (NCBI
Reference Sequence: WP_044910712.1)
MDYGNGQFERRAPLTKTITLRLKPIGETRETIREQKLLEQDAAFRKLVETVTPIVDDCIRKIADNA
LCHFGTEYDFSCLGNAISKNDSKAIKKETEKVEKLLAKVLTENLPDGLRKVNDINSAAFIQDTLTS
FVQDDADKRVLIQELKGKTVLMQRFLTTRITALTVWLPDRVFENFNIFIENAEKMRILLDSPLNEK
IMKFDPDAEQYASLEFYGQCLSQKDIDSYNLIISGIYADDEVKNPGINEIVKEYNQQIRGDKDESP
LPKLKKLHKQILMPVEKAFFVRVLSNDSDARSILEKILKDTEMLPSKIIEAMKEADAGDIAVYGSR
LHELSHVIYGDHGKLSQIIYDKESKRISELMETLSPKERKESKKRLEGLEEHIRKSTYTFDELNRY
AEKNVMAAYIAAVEESCAEIMRKEKDLRTLLSKEDVKIRGNRHNTLIVKNYFNAWTVFRNLIRILR
RKSEAEIDSDFYDVLDDSVEVLSLTYKGENLCRSYITKKIGSDLKPEIATYGSALRPNSRWWSP
GEKFNVKFHTIVRRDGRLYYFILPKGAKPVELEDMDGDIECLQMRKIPNPTIFLPKLVFKDPEAFF
RDNPEADEFVFLSGMKAPVTITRETYEAYRYKLYTVGKLRDGEVSEEEYKRALLQVLTAYKEFL
ENRMIYADLNFGFKDLEEYKDSSEFIKQVETHNTFMCWAKVSSSQLDDLVKSGNGLLFEIWSE
RLESYYKYGNEKVLRGYEGVLLSILKDENLVSMRTLLNSRPMLVYRPKESSKPMVVHRDGSRV
VDRFDKDGKYIPPEVHDELYRFFNNLLIKEKLGEKARKILDNKKVKVKVLESERVKWSKFYDEQ
FAVTFSVKKNADCLDTTKDLNAEVMEQYSESNRLILIRNTTDILYYLVLDKNGKVLKQRSLNIIND
GARDVDWKERFRQVTKDRNEGYNEWDYSRTSNDLKEVYLNYALKEIAEAVIEYNAILIIEKMSN
AFKDKYSFLDDVTFKGFETKLLAKLSDLHFRGIKDGEPCSFTNPLQLCQNDSNKILQDGVIFMVP
NSMTRSLDPDTGFIFAINDHNIRTKKAKLNFLSKFDQLKVSSEGCLIMKYSGDSLPTHNTDNRV
WNCCCNHPITNYDRETKKVEFIEEPVEELSRVLEENGIETDTELNKLNERENVPGKVVDAIYSLV
LNYLRGTVSGVAGQRAVYYSPVTGKKYDISFIQAMNLRKCDYYRIGSKERGEWTDFVAQLIN
(SEQ ID NO: 231)

>Lachnospiraceae bacterium ND2006 type V CRISPR-associated protein Cpf1 (NCBI
Reference Sequence: WP_051666128.1)
MLKNVGIDRLDVEKGRKNMSKLEKFTNCYSLSKTLRFKAIPVGKTQENIDNKRLLVEDEKRAED
YKGVKKLLDRYYLSFINDVLHSIKLKNLNNYISLFRKKTRTEKENKELENLEINLRKEIAKAFKGNE
GYKSLFKKDIIETILPEFLDDKDEIALVNSFNGFTTAFTGFFDNRENMFSEEAKSTSIAFRCINENL
TRYISNMDIFEKVDAIFDKHEVQEIKEKILNSDYDVEDFFEGEFFNFVLTQEGIDVYNAIIGGFVTE
SGEKIKGLNEYINLYNQKTKQKLPKFKPLYKQVLSDRESLSFYGEGYTSDEEVLEVFRNTLNKN
SEIFSSIKKLEKLFKNFDEYSSAGIFVKNGPAISTISKDIFGEWNVIRDKWNAEYDDIHLKKKAVVT
EKYEDDRRKSFKKIGSFSLEQLQEYADADLSVVEKLKEIIIQKVDEIYKVYGSSEKLFDADFVLEK

FIG. 23 cont'd.

SLKKNDAVVAIMKDLLDSVKSFENYIKAFFGEGKETNRDESFYGDFVLAYDILLKVDHIYDAIRNY
VTQKPYSKDKFKLYFQNPQFMGGWDKDKETDYRATILRYGSKYYLAIMDKKYAKCLQKIDKDD
VNGNYEKINYKLLPGPNKMLPKVFFSKKWMAYYNPSEDIQKIYKNGTFKKGDMFNLNDCHKLID
FFKDSISRYPKWSNAYDFNFSETEKYKDIAGFYREVEEQGYKVSFESASKKEVDKLVEEGKLY
MFQIYNKDFSDKSHGTPNLHTMYFKLLFDENNHGQIRLSGGAELFMRRASLKKEELVVHPANS
PIANKNPDNPKKTTTLSYDVYKDKRFSEDQYELHIPIAINKCPKNIFKINTEVRVLLKHDDNPYVIG
IDRGERNLLYIVVVDGKGNIVEQYSLNEIINNFNGIRIKTDYHSLLDKKEKERFEARQNWTSIENIK
ELKAGYISQVVHKICELVEKYDAVIALEDLNSGFKNSRVKVEKQVYQKFEKMLIDKLNYMVDKKS
NPCATGGALKGYQITNKFESFKSMSTQNGFIFYIPAWLTSKIDPSTGFVNLLKTKYTSIADSKKFI
SSFDRIMYVPEEDLFEFALDYKNFSRTDADYIKKWKLYSYGNRIRIFRNPKKNNVFDWEEVCLT
SAYKELFNKYGINYQQGDIRALLCEQSDKAFYSSFMALMSLMLQMRNSITGRTDVDFLISPVKN
SDGIFYDSRNYEAQENAILPKNADANGAYNIARKVLWAIGQFKKAEDEKLDKVKIAISNKEWLEY
AQTSVKH (SEQ ID NO: 232)

>amino acids 19-1246 of Lachnospiraceae bacterium ND2006 type V CRISPR-associated protein Cpf1
MSKLEKFTNCYSLSKTLRFKAIPVGKTQENIDNKRLLVEDEKRAEDYKGVKKLLDRYYLSFINDV
LHSIKLKNLNNYISLFRKKTRTEKENKELENLEINLRKEIAKAFKGNEGYKSLFKKDIIETILPEFLD
DKDEIALVNSFNGFTTAFTGFFDNRENMFSEEAKSTSIAFRCINENLTRYISNMDIFEKVDAIFDK
HEVQEIKEKILNSDYDVEDFFEGEFFNFVLTQEGIDVYNAIIGGFVTESGEKIKGLNEYINLYNQK
TKQKLPKFKPLYKQVLSDRESLSFYGEGYTSDEEVLEVFRNTLKNSEIFSSIKKLEKLFKNFDE
YSSAGIFVKNGPAISTISKDIFGEWNVIRDKWNAEYDDIHLKKKAVVTEKYEDDRRKSFKKIGSF
SLEQLQEYADADLSVVEKLKEIIIQKVDEIYKVYGSSEKLFDADFVLEKSLKKNDAVVAIMKDLLD
SVKSFENYIKAFFGEGKETNRDESFYGDFVLAYDILLKVDHIYDAIRNYVTQKPYSKDKFKLYFQ
NPQFMGGWDKDKETDYRATILRYGSKYYLAIMDKKYAKCLQKIDKDDVNGNYEKINYKLLPGP
NKMLPKVFFSKKWMAYYNPSEDIQKIYKNGTFKKGDMFNLNDCHKLIDFFKDSISRYPKWSNA
YDFNFSETEKYKDIAGFYREVEEQGYKVSFESASKKEVDKLVEEGKLYMFQIYNKDFSDKSHG
TPNLHTMYFKLLFDENNHGQIRLSGGAELFMRRASLKKEELVVHPANSPIANKNPDNPKKTTTL
SYDVYKDKRFSEDQYELHIPIAINKCPKNIFKINTEVRVLLKHDDNPYVIGIDRGERNLLYIVVVDG
KGNIVEQYSLNEIINNFNGIRIKTDYHSLLDKKEKERFEARQNWTSIENIKELKAGYISQVVHKICE
LVEKYDAVIALEDLNSGFKNSRVKVEKQVYQKFEKMLIDKLNYMVDKKSNPCATGGALKGYQIT
NKFESFKSMSTQNGFIFYIPAWLTSKIDPSTGFVNLLKTKYTSIADSKKFISSFDRIMYVPEEDLF
EFALDYKNFSRTDADYIKKWKLYSYGNRIRIFRNPKKNNVFDWEEVCLTSAYKELFNKYGINYQ
QGDIRALLCEQSDKAFYSSFMALMSLMLQMRNSITGRTDVDFLISPVKNSDGIFYDSRNYEAQE
NAILPKNADANGAYNIARKVLWAIGQFKKAEDEKLDKVKIAISNKEWLEYAQTSVKH (SEQ ID NO: 233)

>Francisella tularensis subsp. Novicida U112 Cpf1 (FnCpf1) protein
MSIYQEFVNKYSLSKTLRFELIPQGKTLENIKARGLILDDEKRAKDYKKAKQIIDKYHQF
FIEEILSSVCISEDLLQNYSDVYFKLKKSDDDNLQKDFKSAKDTIKKQISEYIKDSEKFK
NLFNQNLIDAKKGQESDLILWLKQSKDNGIELFKANSDITDIDEALEIIKSFKGWTTYFK
GFHENRKNVYSSNDIPTSIIYRIVDDNLPKFLENKAKYESLKDKAPEAINYEQIKKDLAE
ELTFDIDYKTSEVNQRVFSLDEVFEIANFNNYLNQSGITKFNTIIGGKFVNGENTKRKGI
NEYINLYSQQINDKTLKKYKMSVLFKQILSDTESKSFVIDKLEDDSDVVTTMQSFYEQIA
AFKTVEEKSIKETLSLLFDDLKAQKLDLSKIYFKNDKSLTDLSQQVFDDYSVIGTAVLEY
ITQQIAPKNLDNPSKKEQELIAKKTEKAKYLSLETIKLALEEFNKHRDIDKQCRFEEILA
NFAAIPMIFDEIAQNKDNLAQISIKYQNQGKKDLLQASAEDDVKAIKDLLDQTNNLLHKL
KIFHISQSEDKANILDKDEHFYLVFEECYFELANIVPLYNKIRNYITQKPYSDEKFKLNF

FIG. 23 cont'd.

ENSTLANGWDKNKEPDNTAILFIKDDKYYLGVMNKKNNKIFDDKAIKENKGEGYKKIVYK
LLPGANKMLPKVFFSAKSIKFYNPSEDILRIRNHSTHTKNGSPQKGYEKFEFNIEDCRKF
IDFYKQSISKHPEWKDFGRFSDTQRYNSIDEFYREVENQGYKLTFENISESYIDSVVNQ
GKLYLFQIYNKDFSAYSKGRPNLHTYWKALFDERNLQDVVYKLNGEAELFYRKQSIPKK
ITHPAKEAIANKNKDNPKKESVFEYDLIKDKRFTEDKFFFHCPITINFKSSGANKFNDEI
NLLLKEKANDVHILSIDRGERHLAYYTLVDGKGNIIKQDTFNIIGNDRMKTNYHDKLAAI
EKDRDSARKDWKKINNIKEMKEGYLSQVVHEIAKLVIEYNAIVVFEDLNFGFKRGRFKVE
KQVYQKLEKMLIEKLNYLVFKDNEFDKTGGVLRAYQLTAPFETFKKMGKQTGIIYYVPAG
FTSKICPVTGFVNQLYPKYESVSKSQEFFSKFDKICYNLDKGYFEFSFDYKNFGDKAAKG
KWTIASFGSRLINFRNSDKNHNWDTREVYPTKELEKLLKDYSIEYGHGECIKAAICGESD
KKFFAKLTSVLNTILQMRNSKTGTELDYLISPVADVNGNFFDSRQAPKNMPQDADANGAY
HIGLKGLMLLGRIKNNQEGKKLNLVIKNEEYFEFVQNRNN (SEQ ID NO: 234)

> Peregrinibacteria bacterium GW2011_GWA_33_10 (PeCpf1) protein
MSNFFKNFTNLYELSKTLRFELKPVGDTLTNMKDHLEYDEKLQTFLKDQNIDDAYQALKP
QFDEIHEEFITDSLESKKAKEIDFSEYLDLFQEKKELNDSEKKLRNKIGETFNKAGEKWK
KEKYPQYEWKKGSKIANGADILSCQDMLQFIKYKNPEDEKIKNYIDDTLKGFFTYFGGFN
QNRANYYETKKEASTAVATRIVHENLPKFCDNVIQFKHIIKRKKDGTVEKTERKTEYLNA
YQYLKNNNKITQIKDAETEKMIESTPIAEKIFDVYYFSSCLSQKQIEEYNRIIGHYNLLI
NLYNQAKRSEGKHLSANEKKYKDLPKFKTLYKQIGCGKKKDLFYTIKCDTEEEANKSRNE
GKESHSVEEIINKAQEAINKYFKSNNDCENINTVPDFINYILTKENYEGVYWSKAAMNTI
SDKYFANYHDLQDRLKEAKVFQKADKKSEDDIKIPEAIELSGLFGVLDSLADWQTTLFKS
SILSNEDKLKIITDSQTPSEALLKMIFNDIEKNMESFLKETNDIITLKKYKGNKEGTEKI
KQWFDYTLAINRMLKYFLVKENKIKGNSLDTNISEALKTLIYSDDAEWFKWYDALRNYLT
QKPQDEAKENKLKLNFDNPSLAGGWDVNKECSNFCVILKDKNEKKYLAIMKKGENTLFQK
EWTEGRGKNLTKKSNPLFEINNCEILSKMEYDFWADVSKMIPKCSTQLKAVVNHFQSDN
EFIFPIGYKVTSGEKFREECKISKQDFELNNKVFNKNELSVTAMRYDLSSTQEKQYIKAF
QKEYWELLFKQEKRDTKLTNNEIFNEWINFCNKKYSELLSWERKYKDALTNWINFCKYFL
SKYPKTTLFNYSFKESENYNSLDEFYRDVDICSYKLNINTTINKSILDRLVEEGKLYLFE
IKNQDSNDGKSIGHKNNLHTIYWNAIFENFDNRPKLNGEAEIFYRKAISKDKLGIVKGKK
TKNGTEIIKNYRFSKEKFILHVPITLNFCSNNEYVNDIVNTKFYNFSNLHFLGIDRGEKH
LAYYSLVNKNGEIVDQGTLNLPFTDKDGNQRSIKKEKYFYNKQEDKWEAKEVDCWNYNDL
LDAMASNRDMARKNWQRIGTIKEAKNGYVSLVIRKIADLAVNNERPAFIVLEDLNTGFKR
SRQKIDKSVYQKFELALAKKLNFLVDKNAKRDEIGSPTKALQLTPPVNNYGDIENKKQAG
IMLYTRANYTSQTDPATGWRKTIYLKAGPEETTYKKDGKIKNKSVKDQIIETFTDIGFDG
KDYYFEYDKGEFVDEKTGEIKPKKWRLYSGENGKSLDRFRGEREKDKYEWKIDKIDIVKI
LDDLFVNFDKNISLLKQLKEGVELTRNNEHGTGESLRFAINLIQQIRNTGNNERDNDFIL
SPVRDENGKHFDSREYWDKETKGEKISMPSSGDANGAFNIARKGIIMNAHILANSDSKDL
SLFVSDEEWDLHLNNKTEWKKQLNIFSSRKAMAKRKK (SEQ ID NO: 235)

>Parcubacteria bacterium GWC2011_GWC2_44_17 Cpf1 (PbCpf1) protein
MENIFDQFIGKYSLSKTLRFELKPVGKTEDFLKINKVFEKDQTIDDSYNQAKFYFDSLHQ
KFIDAALASDKTSELSFQNFADVLEKQNKIILDKKREMGALRKRDKNAVGIDRLQKEIND
AEDIIQKEKEKIYKDVRTLFDNEAESWKTYYQEREVDGKKITFSKADLKQKGADFLTAAG
ILKVLKYEFPEEKEKEFQAKNQPSLFVEEKENPGQKRYIFDSFDKFAGYLTKFQQTKKNL
YAADGTSTAVATRIADNFIIFHQNTKVFRDKYNNHTDLGFDEENIFEIERYKNCLLQRE
IEHIKNENSYNKIIGRINKKIKEYRDQKAKDTKLTKSDFPFFKNLDKQILGEVEKEKQLI
EKTREKTEEDVLIERFKEFIENNEERFTAAKKLMNAFCNGEFESEYEGIYLKNKAINTIS
RRWFVSDRDFELKLPQQKSKNKSEKNEPKVKKFISIAEIKNAVEELDGDIFKAVFYDKKI

FIG. 23 cont'd.

IAQGGSKLEQFLVIWKYEFEYLFRDIERENGEKLLGYDSCLKIAKQLGIFPQEKEAREKA
TAVIKNYADAGLGIFQMMKYFSLDDKDRKNTPGQLSTNFYAEYDGYYKDFEFIKYYNEFR
NFITKKPFDEDKIKLNFENGALLKGWDENKEYDFMGVILKKEGRLYLGIMHKNHRKLFQS
MGNAKGDNANRYQKMIYKQIADASKDVPRLLLTSKKAMEKFKPSQEILRIKKEKTFKRES
KNFSLRDLHALIEYYRNCIPQYSNWSFYDFQFQDTGKYQNIKEFTDDVQKYGYKISFRDI
DDEYINQALNEGKMYLFEVVNKDIYNTKNGSKNLHTLYFEHILSAENLNDPVFKLSGMAE
IFQRQPSVNEREKITTQKNQCILDKGDRAYKYRRYTEKKIMFHMSLVLNTGKGEIKQVQF
NKIINQRISSSDNEMRVNVIGIDRGEKNLLYYSVVKQNGEIIEQASLNEINGVNYRDKLI
EREKERLKNRQSWKPVVKIKDLKKGYISHVIHKICQLIEKYSAIVVLEDLNMRFKQIRGG
IERSVYQQFEKALIDKLGYLVFKDNRDLRAPGGVLNGYQLSAPFVSFEKMRKQTGILFYT
QAEYTSKTDPITGFRKNVYISNSASLDKIKEAVKKFDAIGWDGKEQSYFFKYNPYNLADE
KYKNSTVSKEWAIFASAPRIRRQKGEDGYWKYDRVKVNEEFEKLLKVWNFVNPKATDIKQ
EIIKKEKAGDLQGEKELDGRLRNFWHSFIYLFNLVLELRNSFSLQIKIKAGEVIAVDEGV
DFIASPVKPFFTTPNPYIPSNLCWLAVENADANGAYNIARKGVMILKKIREHAKKDPEFK
KLPNLFISNAEWDEAARDWGKYAGTTALNLDH (SEQ ID NO: 236)

>Lachnospiraceae bacterium MA2020 (Lb2Cpf1) protein
MYYESLTKQYPVSKTIRNELIPIGKTLDNIRQNNILESDVKRKQNYEHVKGILDEYHKQL
INEALDNCTLPSLKIAAEIYLKNQKEVSDREDFNKTQDLLRKEVVEKLKAHENFTKIGKK
DILDLLEKLPSISEDDYNALESFRNFYTYFTSYNKVRENLYSDKEKSSTVAYRLINENFP
KFLDNVKSYRFVKTAGILADGLGEEEQDSLFIVETFNKTLTQDGIDTYNSQVGKINSSIN
LYNQKNQKANGFRKIPKMKMLYKQILSDREESFIDEFQSDEVLIDNVESYGSVLIESLKS
SKVSAFFDALRESKGKNVYVKNDLAKTAMSNIVFENWRTFDDLLNQEYDLANENKKKDDK
YFEKRQKELKKNKSYSLEHLCNLSEDSCNLIENYIHQISDDIENIIINNETFLRIVINEH
DRSRKLAKNRKAVKAIKDFLDSIKVLERELKLINSSGQELEKDLIVYSAHEELLVELKQV
DSLYNMTRNYLTKKPFSTEKVKLNFNRSTLLNGWDRNKETDNLGVLLLKDGKYYLGIMNT
SANKAFVNPPVAKTEKVFKKVDYKLLPVPNQMLPKVFFAKSNIDFYNPSSEIYSNYKKGT
HKKGNMFSLEDCHNLIDFFKESISKHEDWSKFGFKFSDTASYNDISEFYREVEKQGYKLT
YTDIDETYINDLIERNELYLFQIYNKDFSMYSKGKLNLHTLYFMMLFDQRNIDDVVYKLN
GEAEVFYRPASISEDELIIHKAGEEIKNKNPNRARTKETSTFSYDIVKDKRYSKDKFTLH
IPITMNFGVDEVKRFNDAVNSAIRIDENVNVIGIDRGERNLLYVVVIDSKGNILEQISLN
SIINKEYDIETDYHALLDEREGGRDKARKDWNTVENIRDLKAGYLSQVVNVVAKLVLKYN
AIICLEDLNFGFKRGRQKVEKQVYQKFEKMLIDKLNYLVIDKSREQTSPKELGGALNALQ
LTSKFKSFKELGKQSGVIYYVPAYLTSKIDPTTGFANLFYMKCENVEKSKRFFDGFDFIR
FNALENVFEFGFDYRSFTQRACGINSKWTVCTNGERIIKYRNPDKNNMFDEKVVVVTDEM
KNLFEQYKIPYEDGRNVKDMIISNEEAEFYRRLYRLLQQTLQMRNSTSDGTRDYIISPVK
NKREAYFNSELSDGSVPKDADANGAYNIARKGLWVLEQIRQKSEGEKINLAMTNAEWLEY
AQTHLL (SEQ ID NO: 237)

>Candidatus Methanoplasma termitum Cpf1 (CMtCpf1) protein
MNNYDEFTKLYPIQKTIRFELKPQGRTMEHLETFNFFEEDRDRAEKYKILKEAIDEYHKK
FIDEHLTNMSLDWNSLKQISEKYYKSREEKDKKVFLSEQKRMRQEIVSEFKKDDRFKDLF
SKKLFSELLKEEIYKKGNHQEIDALKSFDKFSGYFIGLHENRKNMYSDGDEITAISNRIV
NENFPKFLDNLQKYQEARKKYPEWIIKAESALVAHNIKMDEVFSLEYFNKVLNQEGIQRY
NLALGGYVTKSGEKMMGLNDALNLAHQSEKSSKGRIHMTPLFKQILSEKESFSYIPDVFT
EDSQLLPSIGGFFAQIENDKDGNIFDRALELISSYAEYDTERIYIRQADINRVSNVIFGE
WGTLGGLMREYKADSINDINLERTCKKVDKWLDSKEFALSDVLEAIKRTGNNDAFNEYIS
KMRTAREKIDAARKEMKFISEKISGDEESIHIIKTLLDSVQQFLHFFNLFKARQDIPLDG
AFYAEFDEVHSKLFAIVPLYNKVRNYLTKNNLNTKKIKLNFKNPTLANGWDQNKVYDYAS

FIG. 23 cont'd.

LIFLRDGNYYLGIINPKRKKNIKFEQGSGNGPFYRKMVYKQIPGPNKNLPRVFLTSTKGK
KEYKPSKEIIEGYEADKHIRGDKFDLDFCHKLIDFFKESIEKHKDWSKFNFYFSPTESYG
DISEFYLDVEKQGYRMHFENISAETIDEYVEKGDLFLFQIYNKDFVKAATGKKDMHTIYW
NAAFSPENLQDVVVKLNGEAELFYRDKSDIKEIVHREGEILVNRTYNGRTPVPDKIHKKL
TDYHNGRTKDLGEAKEYLDKVRYFKAHYDITKDRRYLNDKIYFHVPLTLNFKANGKKNLN
KMVIEKFLSDEKAHIIGIDRGERNLLYYSIIDRSGKIIDQQSLNVIDGFDYREKLNQREI
EMKDARQSWNAIGKIKDLKEGYLSKAVHEITKMAIQYNAIVVMEELNYGFKRGRFKVEKQ
IYQKFENMLIDKMNYLVFKDAPDESPGGVLNAYQLTNPLESFAKLGKQTGILFYVPAAYT
SKIDPTTGFVNLFNTSSKTNAQERKEFLQKFESISYSAKDGGIFAFAFDYRKFGTSKTDH
KNVWTAYTNGERMRYIKEKKRNELFDPSKEIKEALTSSGIKYDGGQNILPDILRSNNNGL
IYTMYSSFIAAIQMRVYDGKEDYIISPIKNSKGEFFRTDPKRRELPIDADANGAYNIALR
GELTMRAIAEKFDPDSEKMAKLELKHKDWFEFMQTRGD (SEQ ID NO: 238)

>Eubacterium eligens Cpf1 (EeCpf1) protein
MNGNRSIVYREFVGVIPVAKTLRNELRPVGHTQEHIIQNGLIQEDELRQEKSTELKNIMD
DYYREYIDKSLSGVTDLDFTLLFELMNLVQSSPSKDNKKALEKEQSKMREQICTHLQSDS
NYKNIFNAKLLKEILPDFIKNYNQYDVKDKAGKLETLALFNGFSTYFTDFFEKRKNVFTK
EAVSTSIAYRIVHENSLIFLANMTSYKKISEKALDEIEVIEKNNQDKMGDWELNQIFNPD
FYNMVLIQSGIDFYNEICGVVNAHMNLYCQQTKNNYNLFKMRKLHKQILAYTSTSFEVPK
MFEDDMSVYNAVNAFIDETEKGNIIGKLKDIVNKYDELDEKRIYISKDFYETLSCFMSGN
WNLITGCVENFYDENIHAKGKSKEEKVKKAVKEDKYKSINDVNDLVEKYIDEKERNEFKN
SNAKQYIREISNIITDTETAHLEYDDHISLIESEEKADEMKKRLDMYMNMYHWAKAFIVD
EVLDRDEMFYSDIDDIYNILENIVPLYNRVRNYVTQKPYNSKKIKLNFQSPTLANGWSQS
KEFDNNAIILIRDNKYYLAIFNAKNKPDKKIIQGNSDKKNDNDYKKMVYNLLPGANKMLP
KVFLSKKGIETFKPSDYIISGYNAHKHIKTSENFDISFCRDLIDYFKNSIEKHAEWRKYE
FKFSATDSYSDISEFYREVEMQGYRIDWTYISEADINKLDEEGKIYLFQIYNKDFAENST
GKENLHTMYFKNIFSEENLKDIIIKLNGQAELFYRRASVKNPVKHKKDSVLVNKTYKNQL
DNGDVVRIPIPDDIYNEIYKMYNGYIKESDLSEAAKEYLDKVEVRTAQKDIVKDYRYTVD
KYFIHTPITINYKVTARNNVNDMVVKYIAQNDDIHVIGIDRGERNLIYISVIDSHGNIVK
QKSYNILNNYDYKKKLVEKEKTREYARKNWKSIGNIKELKEGYISGVVHEIAMLIVEYNA
IIAMEDLNYGFKRGRFKVERQVYQKFESMLINKLNYFASKEKSVDEPGGLLKGYQLTYVP
DNIKNLGKQCGVIFYVPAAFTSKIDPSTGFISAFNFKSISTNASRKQFFMQFDEIRYCAE
KDMFSFGFDYNNFDTYNITMGKTQWTVYTNGERLQSEFNNARRTGKTKSINLTETIKLLL
EDNEINYADGHDIRIDMEKMDEDKKSEFFAQLLSLYKLTVQMRNSYTEAEEQENGISYDK
IISPVINDEGEFFDSDNYKESDDKECKMPKDADANGAYCIALKGLYEVLKIKSEWTEDGF
DRNCLKLPHAEWLDFIQNKRYE (SEQ ID NO: 239)

>Moraxella bovoculi 237 Cpf1 (MbCpf1) protein
MLFQDFTHLYPLSKTVRFELKPIDRTLEHIHAKNFLSQDETMADMHQKVKVILDDYHRDF
IADMMGEVKLTKLAEFYDVYLKFRKNPKDDELQKQLKDLQAVLRKEIVKPIGNGGKYKAG
YDRLFGAKLFKDGKELGDLAKFVIAQEGESSPKLAHLAHFEKFSTYFTGFHDNRKNMYSD
EDKHTAIAYRLIHENLPRFIDNLQILTTIKQKHSALYDQIINELTASGLDVSLASHLDGY
HKLLTQEGITAYNTLLGGISGEAGSPKIQGINELINSHHNQHCHKSERIAKLRPLHKQIL
SDGMSVSFLPSKFADDSEMCQAVNEFYRHYADVFAKVQSLFDGFDDHQKDGIYVEHKNLN
ELSKQAFGDFALLGRVLDGYYVDVVNPEFNERFAKAKTDNAKAKLTKEKDKFIKGVHSLA
SLEQAIEHYTARHDDESVQAGKLGQYFKHGLAGVDNPIQKIHNNHSTIKGFLERERPAGE
RALPKIKSGKNPEMTQLRQLKELLDNALNVAHFAKLLTTKTTLDNQDGNFYGEFGVLYDE
LAKIPTLYNKVRDYLSQKPFSTEKYKLNFGNPTLLNGWDLNKEKDNFGVILQKDGCYYLA
LLDKAHKKVFDNAPNTGKSIYQKMIYKYLEVRKQFPKVFFSKEAIAINYHPSKELVEIKD

FIG. 23 cont'd.

KGRQRSDDERLKLYRFILECLKIHPKYDKKFEGAIGDIQLFKKDKKGREVPISEKDLFDK
INGIFSSKPKLEMEDFFIGEFKRYNPSQDLVDQYNIYKKIDSNDNRKKENFYNNHPKFKK
DLVRYYYESMCKHEEWEESFEFSKKLQDIGCYVDVNELFTEIETRRLNYKISFCNINADY
IDELVEQGQLYLFQIYNKDFSPKAHGKPNLHTLYFKALFSEDNLADPIYKLNGEAQIFYR
KASLDMNETTIHRAGEVLENKNPDNPKKRQFVYDIIKDKRYTQDKFMLHVPITMNFGVQG
MTIKEFNKKVNQSIQQYDEVNVIGIDRGERHLLYLTVINSKGEILEQCSLNDITTASANG
TQMTTPYHKILDKREIERLNARVGWGEIETIKELKSGYLSHVVHQISQLMLKYNAIVVLE
DLNFGFKRGRFKVEKQIYQNFENALIKKLNHLVLKDKADDEIGSYKNALQLTNNFTDLKS
IGKQTGFLFYVPAWNTSKIDPETGFVDLLKPRYENIAQSQAFFGKFDKICYNADKDYFEF
HIDYAKFTDKAKNSRQIWTICSHGDKRYVYDKTANQNKGAAKGINVNDELKSLFARHHIN
EKQPNLVMDICQNNDKEFHKSLMYLLKTLLALRYSNASSDEDFILSPVANDEGVFFNSAL
ADDTQPQNADANGAYHIALKGLWLLNELKNSDDLNKVKLAIDNQTWLNFAQNR (SEQ ID NO:
240)

>Prevotella disiens Cpf1 (PdCpf1) protein
MENYQEFTNLFQLNKTLRFELKPIGKTCELLEEGKIFASGSFLEKDKVRADNVSYVKKEI
DKKHKIFIEETLSSFSISNDLLKQYFDCYNELKAFKKDCKSDEEEVKKTALRNKCTSIQR
AMREAISQAFLKSPQKKLLAIKNLIENVFKADENVQHFSEFTSYFSGFETNRENFYSDEE
KSTSIAYRLVHDNLPIFIKNIYIFEKLKEQFDAKTLSEIFENYKLYVAGSSLDEVFSLEY
FNNTLTQKGIDNYNAVIGKIVKEDKQEIQGLNEHINLYNQKHKDRRLPFFISLKKQILSD
REALSWLPDMFKNDSEVIKALKGFYIEDGFENNVLTPLATLLSSLDKYNLNGIFIRNNEA
LSSLSQNVYRNFSIDEAIDANAELQTFNNYELIANALRAKIKKETKQGRKSFEKYEEYID
KKVKAIDSLSIQEINELVENYVSEFNSNSGNMPRKVEDYFSLMRKGDFGSNDLIENIKTK
LSAAEKLLGTKYQETAKDIFKKDENSKLIKELLDATKQFQHFIKPLLGTGEEADRDLVFY
GDFLPLYEKFEELTLLYNKVRNRLTQKPYSKDKIRLCFNKPKLMTGWVDSKTEKSDNGTQ
YGGYLFRKKNEIGEYDYFLGISSKAQLFRKNEAVIGDYERLDYYQPKANTIYGSAYEGEN
SYKEDKKRLNKVIIAYIEQIKQTNIKKSIIESISKYPNISDDDKVTPSSLLEKIKKVSID
SYNGILSFKSFQSVNKEVIDNLLKTISPLNKAEFLDLINKDYQIFTEVQAVIDEICKQK
TFIYFPISNVELEKEMGDKDKPLCLFQISNKDLSFAKTFSANLRKKRGAENLHTMLFKAL
MEGNQDNLDLGSGAIFYRAKSLDGNKPTHPANEAIKCRNVANKDKVSLFTYDIYKNRRYM
ENKFLFHLSIVQNYKAANDSAQLNSSATEYIRKADDLHIIGIDRGERNLLYYSVIDMKGN
IVEQDSLNIIRNNDLETDYHDLLDKREKERKANRQNWEAVEGIKDLKKGYLSQAVHQIAQ
LMLKYNAIIALEDLGQMFVTRGQKIEKAVYQQFEKSLVDKLSYLVDKKRPYNELGGILKA
YQLASSITKNNSDKQNGFLFYVPAWNTSKIDPVTGFTDLLRPKAMTIKEAQDFFGAFDNI
SYNDKGYFEFETNYDKFKIRMKSAQTRWTICTFGNRIKRKKDKNYWNYEEVELTEEFKKL
FKDSNIDYENCNLKEEIQNKDNRKFFDDLIKLLQLTQMRNSDDKGNDYIISPVANAEGQ
FFDSRNGDKKLPLDADANGAYNIARKGLWNIRQIKQTKNDKKLNLSISSTEWLDFVREKP
YLK (SEQ ID NO: 241)

GENOMIC SAFE HARBORS FOR GENETIC THERAPIES IN HUMAN STEM CELLS AND ENGINEERED NANOPARTICLES TO PROVIDE TARGETED GENETIC THERAPIES

CROSS-REFERENCE TO RELATED APPLICATIONS

This application is a U.S. National Phase Application based on International Patent Application No. PCT/US2018/036154 filed on Jun. 5, 2018, which claims priority to U.S. Provisional Patent Application No. 62/515,474 filed on Jun. 5, 2017, U.S. Provisional Patent Application No. 62/564,129 filed on Sep. 27, 2017, and U.S. Provisional Patent Application No. 62/664,045 filed on Apr. 27, 2018, each of which is incorporated by reference in its entirety as if fully set forth herein.

REFERENCE TO SEQUENCE LISTING

The Sequence Listing associated with this application is provided in text format in lieu of a paper copy, and is hereby incorporated by reference into the specification. The name of the text file containing the Sequence Listing is 2715363 ST25.txt. The text file is 259 KB, was created on Dec. 3, 2019, and is being submitted electronically via EFS-Web.

FIELD OF THE DISCLOSURE

The current disclosure provides genomic safe harbors (GSH) for genetic therapies in human stem cells and engineered nanoparticles to provide targeted genetic therapies. The disclosed GSH and/or associated nanoparticles can be used to safely and efficiently treat a variety of genetic, infectious, and malignant diseases.

BACKGROUND OF THE DISCLOSURE

Patient-specific gene therapy has great potential to treat genetic, infectious, and malignant diseases. For example, retrovirus-mediated gene addition into hematopoietic stem cells (HSC) and hematopoietic stem cells and progenitor cells (HSPC) has demonstrated curative outcomes for several genetic diseases over the last 10 years including inherited immunodeficiencies (e.g., X-linked and adenosine deaminase deficient severe combined immunodeficiency (SCID)), hemoglobinopathies, Wiskott-Aldrich syndrome and metachromatic leukodystrophy. Additionally, this treatment approach has also improved outcomes for poor prognosis diagnoses such as glioblastoma. The use of gene-corrected autologous, or "self", HSPC eliminates the risk of graft-host immune responses, negating the need for immunosuppressive drugs. However, effective implementation of HSPC gene therapy faces several major challenges. The current state-of-the-art includes the removal of cells from the patient via bone marrow aspirate or mobilized peripheral blood, sorting this bulk population for autologous HSPC by immunoselection of cells expressing the surface marker CD34, then culturing these cells in the presence of cytokines and the specified therapeutic retrovirus vector before harvesting. Re-administering cells to the patient may require cytoreductive conditioning to permit engraftment of the gene corrected cells. Currently, only centers with Good Manufacturing Practices (GMP) compliant facilities and the infrastructure to support them are capable of administering gene modified cell products. While a simplified manufacturing platform to automate this process in a small, mobile footprint has been developed, severely limited quantities of available therapeutic vectors have continued to create a significant bottleneck to widespread use of the technology.

In addition to the challenge of manufacturing sufficient therapeutic vector quantities, there remains a known risk of genotoxicity and other limitations associated with the use of viral vectors for gene transfer. For example, risks of genotoxicity are evidenced by the development of malignancy due to insertional mutagenesis in patients treated with HSPC gene therapy. This adverse side effect stems from the semi-random nature of retroviral-mediated transgene delivery into the host cell genome. Dysregulation of nearby genes by the inserted transgene sequence has been the molecular basis for clonal expansion and malignant transformation observed in some gene therapy patients, but reciprocal interactions between the inserted transgene and the surrounding genomic context can also cause transgene attenuation or silencing, diminishing therapeutic effects. Other limitations associated with the use of particular viral vectors include induction of immune responses, a decreased efficacy over time in dividing cells (e.g., adeno-associated vectors), an inability to adequately target selected cell types in vivo (e.g., retroviral vectors), and, as indicated, an inability to control insertion site and number of insertions (e.g., lentiviral vectors).

The last 5 years have seen an explosion in gene editing as a safer alternative to retrovirus-mediated gene transfer, made possible by the development of engineered guide RNA and nucleases which target specific DNA sequences and predictably generate DNA double strand breaks (DSB) at the targeted sequence. To date, these programmable complexes have been most effective at providing promising therapies when removal or silencing of a problematic gene (i.e., generating a loss-of-function mutation) is needed. This is because DSBs are most commonly repaired by error-prone non-homologous end joining (NHEJ) which results in oligonucleotide insertions and deletions (indels) at the DSB site.

For gene addition or correction of a specific mutation, less common homology-directed repair (HDR) of the DSB is required. In this situation, a more complex payload including the engineered guide RNA and nuclease as well as a homology-directed repair template must be co-delivered. Proof-of-concept for this approach has been demonstrated in HSPC but also required either tandem electroporation of some gene editing components followed by transduction with non-integrating viral vectors, particularly recombinant adeno-associated viral (rAAV) vectors to deliver DNA templates, or simultaneous electroporation of defined concentrations of engineered nuclease components with chemically modified, single-stranded oligonucleotide template at specified cell concentrations. Moreover, each engineered guide RNA, nuclease and homology-directed repair template had to be uniquely engineered for each specified genetic target, requiring separate evaluation of delivery, activity and specificity in cell lines and HSPC.

Thus, while there have been many exciting breakthroughs in the ability to perform genetic therapies at specific sites within the genome, the continued lack of a safe and potent delivery vehicle has hindered the clinical translation of gene editing systems, in particular, with HSPCs.

The concept of a genomic safe harbor (GSH) for genetic modification was first introduced in 2011 by Papapetrou and colleagues (Nature Biotechnology. 2011; 29(1):73-8). The major criteria proposed to define a GSH site are (1) the ability to accommodate new genetic material with, (2) predictable function, and (3) without potentially harmful alterations in host cell genomic activity. The benefit of identifying such a locus would greatly simplify development efforts for targeted gene addition approaches. Several loci have been evaluated in the human genome, but to date no bona fide validated GSH sites that meet the above criteria have been identified. Papapetrou et al., Mol. Ther. 2016; 24(4): 678-84.

SUMMARY OF THE DISCLOSURE

The current disclosure provides significant advances in the ability to perform genetic therapies for a variety of genetic, infectious, and malignant diseases by providing the identification of genomic safe harbors (GSH) within human hematopoietic stem cells (HSC) and hematopoietic stem cells and progenitor cells (HSPC). In particular embodiments, the GSH additionally qualify as the more rigorously defined universal HSC safe harbor loci, as described in additional detail herein.

The current disclosure also provides nanoparticles specifically engineered to deliver all components required for genetic editing, for example, at the GSH sites. The nanoparticles can be used for therapies where a loss-of-function mutation is needed, but importantly, can also provide all components needed for gene addition or correction of a specific mutation. The described approaches are safe (i.e., no off-target toxicity), reliable (targeted GSH cell chromatin is accessible and amenable to therapeutic cassette addition), scalable, easy to manufacture, synthetic, plug-and-play (i.e., the same basic platform can be used to deliver different therapeutic nucleic acids), and compatible with easy in vivo administration (through, for example, a syringe).

Particular embodiments include a nanoparticle with components to provide a targeted loss-of-function mutation. These embodiments include a targeting element (e.g., guide RNA) and a cutting element (e.g. a nuclease) associated with the surface of the nanoparticle. In particular embodiments, the targeting element is conjugated to the surface of the nanoparticle through a thiol linker. In particular embodiments, the targeting element and/or the cutting element are conjugated to the surface of the nanoparticle through a thiol linker. In particular embodiments, the targeting element is conjugated to the surface of the nanoparticle through a thiol linker and the cutting element is linked to the targeting element to form a ribonucleoprotein (RNP) complex. The targeting element targets the cutting element to a specific site for cutting and NHEJ repair.

Particular embodiments include a nanoparticle with components to provide a targeted gain-of-function mutation (e.g., gene addition or correction). In particular embodiments, these embodiments include a metal nanoparticle (e.g., a gold nanoparticle) associated with a targeting element, a cutting element, a homology-directed repair template, and a therapeutic DNA sequence. The targeting element targets the cutting element to a specific site for cutting, the homology-directed repair template provides for HDR repair, wherein following HDR repair the therapeutic DNA sequence has been inserted within the target site. Together, homology-directed repair templates and therapeutic DNA sequences can be referred to herein as donor templates. In particular embodiments, the targeting element is conjugated to the surface of the nanoparticle through a thiol linker. In particular embodiments, the targeting element and/or the cutting element are conjugated to the surface of the nanoparticle through a thiol linker. In particular embodiments, the targeting element is conjugated to the surface of the nanoparticle through a thiol linker and the cutting element is linked to the targeting element to form a ribonucleoprotein (RNP) complex. In these embodiments, the RNP complex is closer to the surface of the nanoparticle than donor template material. This configuration is beneficial when, for example, the targeting element and/or the cutting element are of bacterial origin. This is because many individuals who may receive nanoparticles described herein may have pre-existing immunity against bacterially-derived components such as bacterially-derived gene-editing components. Including bacterially-derived gene-editing components on an inner layer of the fully formulated nanoparticle allows non-bacterially-derived components (e.g., donor templates) to shield bacterially-derived components (e.g. targeting elements and/or cutting elements) from the patient's immune system. This protects the bacterially-derived components from attack and also avoids or reduces unwanted inflammatory responses against the nanoparticles following administration. In addition, this may allow for repeated administration of the nanoparticles in vivo without inactivation by the host immune response.

Particular embodiments utilize CRISPR gene editing. In particular embodiments, CRISPR gene editing can occur with CRISPR guide RNA (crRNA) and/or a CRISPR nuclease (e.g., Cpf1 (also referred to as Cas12a) or Cas9).

Particular embodiments adopt features that increase the efficiency and/or accuracy of HDR. For example, Cpf1 has a short single crRNA and cuts target DNA in staggered form with 5' 2-4 nucleotide (nt) overhangs called sticky ends. Sticky ends are favorable for HDR, Kim et al. (2016) Nat Biotechnol. 34(8): 863-8. Moreover, donor templates should be released from the nanoparticles before the genome cut by the RNP occurs to promote HDR. Accordingly, in particular embodiments disclosed herein donor templates are found farther from the surface of the nanoparticle than targeting elements and cutting elements. The current disclosure also unexpectedly found that delivery of gene-editing components on a gold nanoparticle increases the efficiency and/or accuracy of HDR. Accordingly, particular embodiments deliver gene-editing components utilizing gold nanoparticles.

In particular embodiments, targeting molecules can be used to target the nanoparticle to a specific cell so that activity of the gene editing system can be spatially or temporally controlled. For example, the activity and destination of the gene editing system may be controlled by a targeting molecule that selectively delivers the nanoparticle to targeted cells. In particular embodiments, the targeting molecule can include an antibody binding domain that binds CD34. In particular embodiments, pairs of targeting molecule can be used, for example, an antibody binding domain that binds CD34 and an antibody binding domain that binds CD90.

BRIEF DESCRIPTION OF THE SEVERAL VIEWS OF THE DRAWINGS

Many of the drawings submitted herein are better understood in color. Applicant considers the color versions of the drawings as part of the original submission and reserves the right to present color images of the drawings in later proceedings.

FIG. 4. Two GSH sites (SEQ ID NOs: 258, 259) within the human CCR5 gene within chromosome 3p21 along with crRNA (SEQ ID NO: 260) and HT (SEQ ID NOs: 261, 262) for a non-target and target strand. The purpose of choosing CCR5 was to validate the nanoformulation. A well-known naturally-occurring mutation in the CCR5 gene renders a person's blood cells resistant to HIV infection. For purposes of the present disclosure, this site provided a means to compare Cas9 and Cpf1 nucleases directly because there is a DNA sequence near the site of this naturally-occurring mutation that contains an identical cut site for both Cpf1 and Cas9. The PAM mutation in the homology template for the target strand is italicized, bolded, and underlined.

(FIG. 7A) Depiction of an exemplary AuNP configured with all components for gene addition within a GSH. Depicted components include crRNA, a Cpf1 nuclease, and ssDNA to provide a therapeutic nucleic acid sequence (e.g. a gene or corrected portion thereof). The embodiment depicted in FIG. 7A additionally includes a targeting molecule (e.g., an antibody binding domain or an aptamer). (FIG. 7B) Schematic representation of a synthesis process for creating and loading AuNP with exemplary gene editing components. (FIG. 7C) Schematic of a formulated "layered" AuNP which can be used to deliver large oligonucleotides, such as donor templates including homology-directed repair templates, therapeutic DNA sequences, and other potential elements. Donor templates are located farther from the AuNP surface than the depicted ribonucleoprotein complex (RNP) (FIG. 7D) Successful generation of 50 nm AuNP carrying all required gene editing components for insertion of a therapeutic DNA sequence. Transmission electron microscope images of AuNPs and AuNP/CRISPR nanoformulations. The depicted embodiment includes an AuNP associated with crRNA, Cpf1, ssDNA, thiol linkers, polyethylene glycol (PEG) spacers, and PEI2K. More particularly, thiol linkers are attached directly to the surface of the AuNP and crRNA. Use of such a linker allows conjugation of more crRNA to the surface of the AuNP, in part because the spaces reduces repulsion between the negative charge of RNA-based molecules and the negative charge of the AuNP surface. Cpf1 is linked to the crRNA to form an RNP. To improve the efficiency of HDR, ssDNA should be released from the AuNP before the genome cut occurs. Accordingly, ssDNA is found farther from the surface of the AuNP than the RNP.

(FIG. 9A) Localized surface plasmon resonance (LSPR) peaks of synthesized AuNPs. (FIG. 9B) LSPR peaks of the AuNP and AuNP/CRISPR nanoformulations. (FIG. 9C) Gel electrophoresis showing optimal AuNP/ssDNA w/w loading ratio. (FIG. 9D) Loading concentration of AuNP/CRISPR nanoformulations.

FIGS. 10A-10C. Optimal loading concentrations. (FIG. 10A) AuNP/crRNA 50 nm (Ratio 6); AuNP/crRNA 15 nm (Ratio 1); and AuNP/crRNA/Cpf1/PEI/DNA 15 nm (Ratio 0.5); (FIG. 10B) Optimal AuNP 50 nm/DNA w/w ratio; (FIG. 10C) Smaller AuNPs triple the available surface area with the same starting reagent amounts. By decreasing the size, surface area and conjugation ratio of the NPs increase.

(FIG. 11A) HSPC take up fully-loaded AuNPs in vitro. Time lapse imaging on spinning disc confocal microscope. Human mobilized CD34+ cells→Culture O/N→Add AuNPs (4 hours)→Analyze. (FIG. 11B) Confocal microscope imaging showing the uptake of CRISPR editing components into CD34+ cells.

(FIGS. 12A, 12B) Tracking Indels by Decomposition (TIDE) assay results showing percent cutting efficiency in K562 cells and CD34+ cells. (FIG. 12C) Percent viability after delivery with AuNPs and electroporation method. (FIG. 12D) Administration dose of CRISPR components.

(FIG. 15A) 10 µg/mL AuNP is an optimal concentration for HDR in CD34+ cells where maximum gene editing is achieved without loss in viability. The same protocol was used as described in relation to FIG. 13, except that CD34+ cells were initially obtained from a different human donor. (FIGS. 15B, 15C) Cell viability analysis by Live-Dead assay; (FIG. 15D) representative cell viability results in bar graph format.

FIGS. 18A, 18B. (FIG. 18A) There is no significant impact on HSPC fitness in vitro by any nuclease or delivery method as determined by a first colony-forming assay in methylcellulose (H4434). CD34+ cells were seeded at 200 cells per 35 mm plate with a total incubation time of 14 days. (FIG. 18B) Improved HSPC secondary plating fitness in vitro with AuNP/Cpf1. Colony plates from (FIG. 18A) were harvested and 10% of the resulting cell suspension was re-plated into a second colony-forming assay in Methylcellulose (H4434). This is a simple test to determine whether long-term colony-initiating cells were impacted by the experimental conditions. The total incubation time was 14 days. The only significant difference observed was in the number of colonies for the AuNP+Cpf1/crRNA treated cells, which displayed more long-term colonies-forming cells. No significant differences were observed in the type of colonies formed in each experimental group.

(FIG. 20A) 10% HDR was observed by TIDE without significant indels at the target locus in human CD34+ cells at the time of transplant. (FIG. 20B) Both T7E1 and NotI restriction digest were only observed in cells that received fully-loaded AuNP nanoformulations. (FIG. 20C) Interestingly, increased colony-forming capacity for this donor was noted only when cells were treated with AuNPs. No significant differences were observed in the types of colonies formed across each condition.

(FIGS. 21A, 21B) Mice transplanted with AuNP-treated cells displayed higher levels of human CD45+ cell engraftment than mice transplanted with mock cells. (FIGS. 21C, 21D) No significant differences in the frequency of human CD20+ cells were observed across groups. (FIGS. 21E, 21F) No significant differences in the frequency of human CD14+ cells were observed across groups. (FIGS. 21G, 21H) Significant differences in the frequency of human CD3+ cells were observed at 14 weeks and in the mice receiving fully-loaded AuNPs who displayed the lowest overall human engraftment. This result may be an artifact of low engraftment levels.

FIG. 23. Sequences supporting the disclosure.

DETAILED DESCRIPTION

Figure 1:
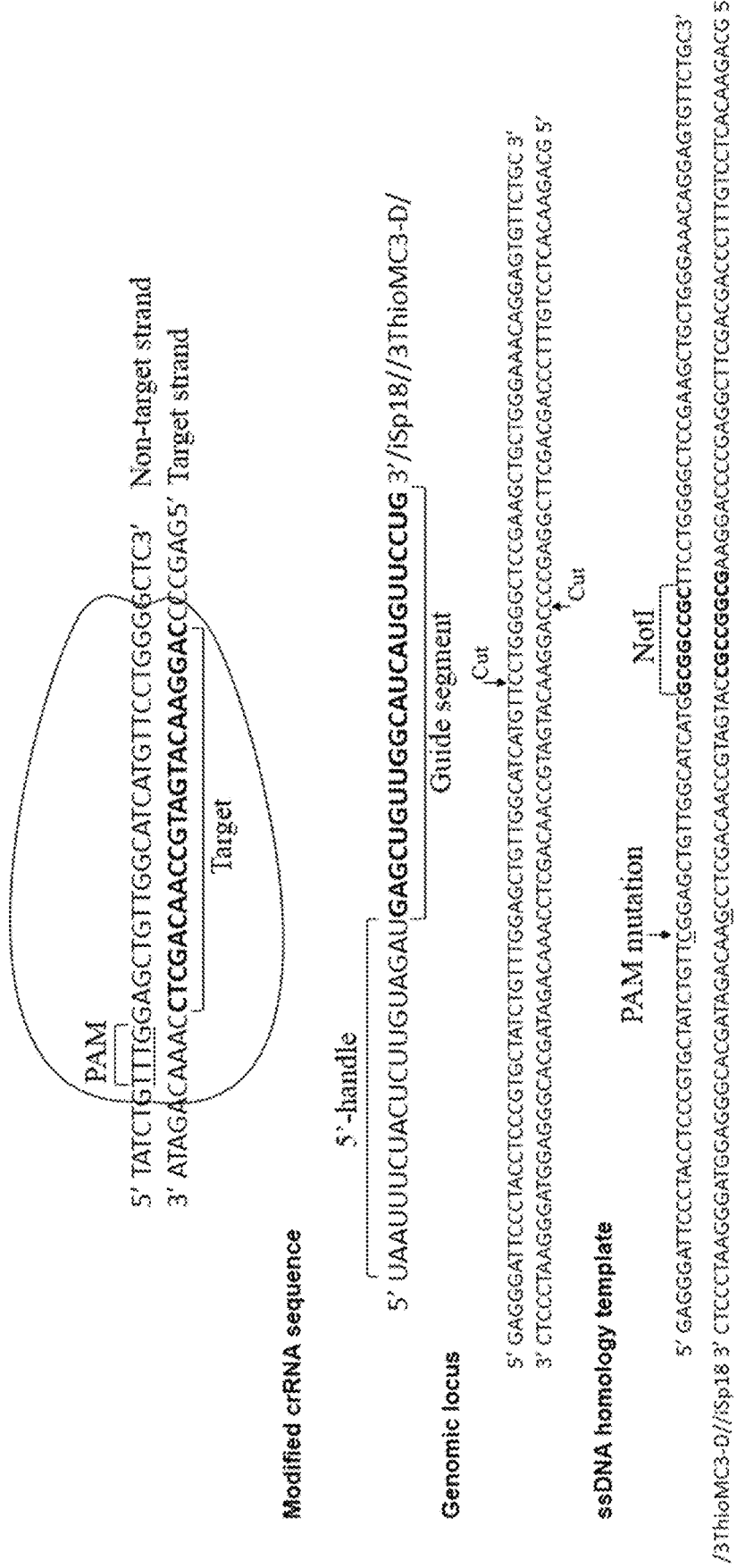
FIG. 1. Schematic showing the design and sequence of clustered regularly interspaced short palindromic repeat (CRISPR) RNA (crRNA) (SEQ ID NO: 244) and homology templates (HT) (SEQ ID NOs: 247, 248) for a genomic safe harbor (GSH) location (SEQ ID NOs: 242, 243, 245, 246) to allow targeted genome editing within human hematopoietic stem cells (HSC) and hematopoietic stem cells and progenitor cells (HSPC).

Patient-specific gene therapy has great potential to treat genetic, infectious, and malignant diseases. For example, retrovirus-mediated gene addition into hematopoietic stem cells (HSC) and hematopoietic stem cells and progenitor cells (HSPC) has demonstrated curative outcomes for several genetic diseases over the last 10 years including inherited immunodeficiencies (e.g., X-linked and adenosine deaminase deficient severe combined immunodeficiency (SCID)), hemoglobinopathies, Wiskott-Aldrich syndrome and metachromatic leukodystrophy. Additionally, this treatment approach has also improved outcomes for poor prognosis diagnoses such as glioblastoma. The use of gene-corrected autologous, or "self", HSPC eliminates the risk of graft-host immune responses, negating the need for immunosuppressive drugs. However, effective implementation of HSPC gene therapy faces several major challenges. The current state-of-the-art includes the removal of cells from the patient via bone marrow aspirate or mobilized peripheral blood, sorting this bulk population for autologous HSPC by immunoselection of cells expressing the surface marker CD34, then culturing these cells in the presence of cytokines and the specified therapeutic retrovirus vector before harvesting. Re-administering cells to the patient may require cytoreductive conditioning to permit engraftment of the gene corrected cells. Currently, only centers with Good Manufacturing Practices (GMP) compliant facilities and the infrastructure to support them are capable of administering gene modified cell products. While a simplified manufacturing platform to automate this process in a small, mobile footprint has been developed, severely limited quantities of available therapeutic vectors have continued to create a significant bottleneck to widespread use of the technology.

In addition to the challenge of manufacturing sufficient therapeutic vector quantities, there remains a known risk of genotoxicity associated with the use of retroviral vectors for gene transfer evidenced by the development of malignancy due to insertional mutagenesis in patients treated with HSPC gene therapy. This adverse side effect stems from the semi-random nature of retroviral-mediated transgene delivery into the host cell genome. Dysregulation of nearby genes by the inserted transgene sequence has been the molecular basis for clonal expansion and malignant transformation observed in some gene therapy patients, but reciprocal interactions between the inserted transgene and the surrounding genomic context can also cause transgene attenuation or silencing, diminishing therapeutic effects.

The last 5 years have seen an explosion in gene editing as a safer alternative to retrovirus-mediated gene transfer, made possible by the development of engineered guide RNA associated with nucleases which target specific DNA sequences and predictably generate DNA double strand breaks (DSB) at the targeted sequence. To date, these programmable complexes have been most effective at providing promising therapies when removal or silencing of a problematic gene (i.e., generating a loss-of-function mutation) is needed. This is because DSBs are most commonly repaired by error-prone non-homologous end joining (NHEJ) which results in oligonucleotide insertions and deletions (indels) at the DSB site.

For gene addition or correction of a specific mutation, less common homology-directed repair (HDR) of the DSB is required. In this situation, a more complex payload including the engineered guide RNA and nuclease, and a homology-directed repair template with homology to the target DSB locus must be co-delivered. Proof-of-concept for this approach has been demonstrated in HSPC but also required either tandem electroporation of genome editing components followed by transduction with non-integrating viral vectors, particularly recombinant adeno-associated viral (rAAV) vectors to deliver DNA templates, or simultaneous electroporation of defined concentrations of engineered nuclease components with chemically modified, single-stranded oligonucleotide template at specified cell concentrations. Moreover, each guide RNA, nuclease and homology-directed repair template had to be uniquely engineered for each specified genetic target, requiring separate evaluation of delivery, activity and specificity in cell lines and HSPC.

Thus, while there have been many exciting breakthroughs in the ability to perform genetic therapies at specific sites within the genome, the continued lack of a safe and potent delivery vehicle has hindered the clinical translation of gene editing systems, in particular, with HSPCs.

The concept of a genomic safe harbor (GSH) for genetic modification was first introduced in 2011 by Papapetrou and colleagues (Nature Biotechnology. 2011; 29(1):73-8). The major criteria proposed to define a GSH site are (1) the ability to accommodate new genetic material with, (2) predictable function, and (3) without potentially harmful alterations in host cell genomic activity. The benefit of identifying such a locus would greatly simplify development efforts for targeted gene addition approaches. Several loci have been evaluated in the human genome, but to date no bona fide validated GSH sites that meet the above criteria have been identified. Papapetrou et al., Mol. Ther. 2016; 24(4): 678-84.

The current disclosure provides significant advances in the ability to perform genetic therapies for a variety of genetic, infectious, and malignant diseases by providing the identification of genomic safe harbors (GSH) within human hematopoietic stem cells (HSC) and hematopoietic stem cells and progenitor cells (HSPC). Some of the identified GSH additionally qualify as the more rigorously defined universal HSC safe harbor loci, as described in additional detail herein.

The current disclosure also provides nanoparticles specifically engineered to deliver all components required for genetic editing, for example, at the GSH sites. The nanoparticles can be used for therapies where a loss-of-function mutation is needed, but importantly, can also provide all components needed for gene addition or correction of a specific mutation. The described approaches are safe (i.e., no off-target toxicity), reliable (targeted GSH cell chromatin is accessible and amenable to therapeutic additions), scalable, easy to manufacture, synthetic, plug-and-play (i.e., the same basic platform can be used to deliver different therapeutic nucleic acids), and compatible with easy in vivo administration (through, for example, a syringe).

Particular embodiments include a nanoparticle with components to provide a targeted loss-of-function mutation. These embodiments include a targeting element (e.g., guide RNA) and a cutting element (e.g. a nuclease) associated with the surface of the nanoparticle. In particular embodiments, the targeting element is conjugated to the surface of the nanoparticle through a thiol linker. In particular embodiments, the targeting element and/or the cutting element are conjugated to the surface of the nanoparticle through a thiol linker. In particular embodiments, the targeting element is conjugated to the surface of the nanoparticle through a thiol linker and the cutting element is linked to the targeting element to form a ribonucleoprotein (RNP) complex. The targeting element targets the cutting element to a specific site for cutting and NHEJ repair.

Particular embodiments include a nanoparticle with components to provide a targeted gain-of-function mutation (e.g., gene addition or correction). These embodiments include a targeting element, a cutting element, a homology-directed repair template, and a therapeutic DNA sequence associated with the surface of the nanoparticle. The targeting element targets the cutting element to a specific site for cutting, the homology-directed repair template provides for HDR repair, wherein following HDR repair the therapeutic DNA sequence has been inserted within the target site. Together, homology-directed repair templates and therapeutic DNA sequences can be referred to herein as donor templates. In particular embodiments, the targeting element is conjugated to the surface of the nanoparticle through a thiol linker. In particular embodiments, the targeting element and/or the cutting element are conjugated to the surface of the nanoparticle through a thiol linker. In particular embodiments, the targeting element is conjugated to the surface of the nanoparticle through a thiol linker and the cutting element is linked to the targeting element to form a ribonucleoprotein (RNP) complex. In these embodiments, the RNP complex is closer to the surface of the nanoparticle than donor template material. This configuration is beneficial when, for example, the targeting element and/or the cutting element are of bacterial origin. This is because many individuals who may receive nanoparticles described herein may have pre-existing immunity against bacterially-derived components, such as bacterially-derived gene-editing components. Including bacterially-derived gene-editing components on an inner layer of the fully formulated nanoparticle allows non-bacterially-derived components (e.g., donor templates) to shield bacterially-derived components (e.g. targeting elements and/or cutting elements) from the patient's immune system. This protects the bacterially-derived components from attack and also avoids or reduces unwanted inflammatory responses against the nanoparticles following administration. In addition, this may allow for repeated administration of the nanoparticles in vivo without inactivation by the host immune response.

Particular embodiments utilize CRISPR gene editing. In particular embodiments, CRISPR gene editing can occur with CRISPR guide RNA (crRNA) and/or a CRISPR nuclease (e.g., Cpf1 or Cas9).

Particular embodiments adopt features that increase the efficiency and/or accuracy of HDR. For example, Cpf1 has a short single crRNA and cuts target DNA in staggered form with 5' 2-4 nucleotide (nt) overhangs called sticky ends. Sticky ends are favorable for HDR, Kim et al. (2016) Nat Biotechnol. 34(8): 863-8. Moreover, donor templates should be released from the nanoparticles before the genome cut by the RNP occurs to promote HDR. Accordingly, in particular embodiments disclosed herein donor templates are found farther from the surface of the nanoparticle than targeting elements and cutting elements. The current disclosure also unexpectedly found that delivery of gene-editing components on a gold nanoparticle increases the efficiency and/or accuracy of HDR. Accordingly, particular embodiments deliver gene-editing components utilizing gold nanoparticles.

In particular embodiments, targeting molecules can be used to target the nanoparticle to a specific cell so that activity of the gene editing system can be spatially or temporally controlled. For example, the activity and destination of the gene editing system may be controlled by a targeting molecule that binds a cell surface marker, such as CD34 or CD90.

In embodiments utilizing gene-editing components of bacterial origin, the current disclosure also takes into account that many individuals who may receive nanoparticles described herein may have pre-existing immunity against such components. To address this potential preexisting immunity, gene-editing components of bacterial origin may be directly conjugated to the surface of nanoparticles followed by addition of donor templates. In this configuration, donor templates can shield the gene-editing components from immune attack and avoid or reduce unwanted inflammatory responses against the nanoparticles following administration.

The following aspects of the disclosure are now described with additional detail and options to support the teachings of the disclosure as follows: (I) Genomic Safe Harbors (GSH) and Universal HSC Safe Harbor Loci in Human HSC and HSPC; (II) Gene Editing Systems and Components to Target and Modify GSH Sites; (III) Nanoparticles; (IV) Conjugation of Active Components to Nanoparticles; (V) Gene Editing Efficiency; (VI) Nanoparticle Compositions and Cell Formulations; (VII) Exemplary Methods of Use; and (VIII) Reference Levels Derived from Control Populations; (IX) Kits; and (X) Exemplary Embodiments.

(I) Genomic Safe Harbors (GSH) and Universal HSC Safe Harbor Loci in Human HSC and HSPC. As indicated, one drawback with existing gene therapies is that the insertion site of retroviral vectors cannot be adequately controlled. Gene editing systems allow control over the target sites of genetic therapies, however, before the current disclosure, no bona fide validated GSH sites had been identified in the human genome (Papapetrou et al., Mol. Ther. 2016; 24(4): 678-84), as the concept had been proposed by Papapetrou and colleagues in Nature Biotechnology. 2011; 29(1):73-8) (i.e., (1) the ability to accommodate new genetic material with, (2) predictable function, and (3) without potentially harmful alterations in host cell genomic activity).

One of the challenges of the incorporation of genetic material in cells is determining where within the chromosomes the genetic material can be safely incorporated. The present disclosure solves this problem by providing chromatin-accessible regions in the CD34+ cell and CD34 subtype (CD45RA$^-$ and CD90$^+$) in human and non-human primate cells (see, e.g., WO 2017/218948 and Radtke et al., Sci. Transl. Med. 2017; 9 (414) which have high editing efficiency and low probability of disrupting cellular potential. In particular embodiments, the sites qualify as universal HSC safe harbor loci. In particular embodiments, to meet the criteria of a universal HSC safe harbor loci, chromatin sites must be >150 kb away from a known oncogene, >30 kb away from a known transcription start site; and have no overlap with coding mRNA. In particular embodiments, to meet the criteria of a universal HSC safe harbor loci, chromatin sites must be >200 kb away from a known oncogene, >40 kb away from a known transcription start site; and have no overlap with coding mRNA. In particular embodiments, to meet the criteria of a universal HSC safe harbor loci, chromatin sites must be >300 kb away from a known oncogene, >50 kb away from a known transcription start site; and have no overlap with coding mRNA. In particular embodiments, a universal HSC safe harbor loci meets the preceding criteria (>150 kb, >200 kb or >300 kb away from a known transcription start site; and have no overlap with coding mRNA >40 kb, or >50 kb away from a known transcription start site with no overlap with coding mRNA) and additionally is 100% homologous between the non-human primate and the human genome to permit rapid clinical translation of these gene edited populations. In particular embodiments, a universal HSC safe harbor loci meets the preceding criteria and demonstrates a 1:1 ratio of forward: reverse orientations of LV integration further demonstrating the loci does not impact surrounding genetic material.

The process to identify GSH within the human genome began by evaluating the biological outcome of long-term engraftment of lentivirus (LV) gene modified, autologous CD34$^+$ cells in the pigtailed macaque (*M. Nemestrina*), an established non-human primate model used for HSC and HSPC gene therapy preclinical evaluations. A high-throughput analysis of sites of LV integration was used to identify candidate GSH loci. LVs can transduce non-dividing cells, and integrate preferentially into active transcription units in the host cell genome. The locus of integration is determined at the time of gene transfer and is inherited by each daughter cell. 150,000 LV integration sites identified in blood cells collected from twelve animals over a period of 2-7 years after transplant were parsed into 1,077 25 kb genomic windows displaying significantly enriched frequencies of integration relative to the rest of the genome (Table 1).

TABLE 1

Identification of candidate GSH loci from LV integration sites identified in vivo in nonhuman primate recipients of autologous HSPC therapy

| Parsing Step Performed (Top to Bottom) | Number of Events |
| --- | --- |
| Total IS identified in 12 monkeys | 148,283 |
| Total number of 25 kb genomic windows containing IS | >95,000 |
| 25 kb genomic windows significantly enriched for IS | 1,077 |
| 25 kb genomic windows with 1:1 ratio of forward:reverse IS orientation | 664 |
| 25 kb genomic windows containing IS identified in 3 or more biological replicates | 662 |
| 25 kb windows with ≥90% homology to human genome | 171 |
| 25 kb windows ≥300 kb away from known oncogenes | 122 |
| 25 kb windows ≥50 kb away from TSS | 24 |
| 25 kb windows associated with constitutive transcriptional activity in whole blood | 2 |

IS: integration sites
TSS: transcription start site

A benign accessible locus would be expected to display a 1:1 ratio of forward: reverse orientations of LV integration. The list was thus further parsed into 664 genomic windows with equivalent forward and reverse orientation of integration events. Of these, 662 windows contained integration events which were represented by 3 or more biological replicates (≥3 of 12 monkeys analyzed).

The windows were filtered based on homology to the human genome (hg38) and a total of 171 windows were identified with ≥90% homology. To increase safety, these windows were cross-referenced against the COSMIC cancer gene database. Windows were only retained if they were >300 kb away from a known oncogene. This filter resulted in 122 windows. Any windows within 50 kb of a transcription start site were removed, which resulted in 24 windows, all of which were preferentially located in intronic sequences. Two genomic regions were highly enriched in these 24 windows: chromosome 11q13.2 and chromosome 16p12.1.

Both of these gene-rich loci are constitutively expressed in blood cells, indicating that (1) expression of transgenes is not expected to transactivate nearby genes which should be silenced in blood cells, and (2) inserted transgene sequences will not be attenuated or silenced during hematopoietic differentiation [University of California at Santa Cruz (UCSC) Genome Browser and ENCODE]. These two loci were further analyzed by the following criteria: target subdomains were identified as unique sequences with (1) 100% homology between the primate (RheMac3) and human (hg38) genomes, and (2) no overlap with coding mRNA. The latter criteria excluded chromosome 16p12.1 as a GSH locus because it overlaps with multiple mRNAs.

The following sites identified by the analysis are 100% homologous between the human genome and the rhesus genome.

TABLE 2

Sites Identified by Analysis that are 100% Homologous between the Human Genome and the Rhesus Genome

| Location on the Human Genome | Location on the Rhesus Genome |
| --- | --- |
| chr11: 67812226-67812252 | chr20: 5298821-5298847 |
| chr11: 67812280-67812306 | chr20: 5298873-5298899 |
| chr11: 67812349-67812375 | chr20: 5298938-5298964 |
| chr11: 67812179-67812205 | chr20: 5298774-5298800 |
| chr11: 67812443-67812469 | chr20: 5299024-5299050 |
| chr11: 67931439-67931465 | chr20: 5455480-5455506 |
| chr11: 67931473-67931499 | chr20: 5455446-5455472 |
| chr11: 67931516-67931542 | chr20: 5455403-5455429 |
| chr11: 67931362-67931388 | chr20: 5455557-5455583 |

These areas of chromosome 11q13.2 represent universal HSC safe harbor loci sites. The following sites also demonstrated permissiveness to genetic modification without adverse biological consequences, even under selective pressure in vivo and represent GSH sites: chr11:67523429-67533593; chr11:67681215-67741765; chr11:67805337-67845629; chr11:67895738-67941098; chr5:66425982-66457233; chr8: 28980753-29006178; chr16: 28151114-28175716; chr1: 39189118-39214131; chr17: 2149700-2174592; chr14: 35658075-35685512; chr18: 9198556-9223041; chr5: 140463887-140488886; chr11: 68563075-68588007; chr2: 43459415-43484174; chr11: 68517649-68542970; chr1: 8600474-8624530; chr12: 50609483-50635221; chr16: 28175717-28199134; chr17: 63329602-63353111; chr1 :107643312-107672400; chr17: 65870579-65895504; chr2: 224533608-224559225; chr14: 22272733-22296704; and chr15: 50094713-50119187. In particular embodiments, chr11:67681215-67741765, chr11:67805337-67845629, and/or chr11:67895738-67941098 are targeted for genetic modification.

Universal HSC safe harbor window loci on chr11 that are particularly relevant for gene editing (as described in more detail in relation to gene editing below) include: 67935219-67935243; 67911598-67911622; 67939901-67939925; 67927758-67927782; 67917930-67917954; 67918042-67918066; 67931473-67931497; 67936715-67936739; 67921126-7921150; 67914940-67914964; 67928284-67928308; 67936068-67936092; 67922372-67922396; 67811255-67811279; 67840351-67840375; 67821576-67821600; 67827279-67827303; 67822563-7822587; 67823914-67823938; 67818875-67818899; 67811907-67811931; 67811630-67811654; 7836644-67836668; 67806757-67806781; 67823923-67823947; 67841379-67841403; 67808086-7808110; 67823903-67823927; 67686904-67686928; 67692610-67692634; 67692462-67692486; 67692618-67692642; 67705405-67705429; 67686651-67686675; 67686788-67686812; 67684033-7684057; 67681565-67681589; 67704652-67704676; 67689328-67689352; 67688546-67688570; 67693464-67693488; 67682343-67682367; 67689948-67689972; 67684785-67684809; 67684738-67684762; 67684260-67684284; 67684173-67684197; 67687315-67687339; 67682671-67682695; 67691534-67691558; 67690743-67690767; 67693746-67693770; 67690174-67690198; 67692535-67692559; 67687605-67687629; 67694747-67694771; 67681441-67681465; 67691508-67691532; 67692057-67692081; 67692573-67692597; 67690331-67690355; 67697247-67697271; 67695745-67695769; 67695241-67695265; 67691931-67691955; 67691017-67691041; 67694689-67694713; 67721934-67721958; 67696164-67696188; 67736715-67736739; 67681498-67681522; 67690926-67690950; 67694271-67694295; 67682715-67682739; 67694107-67694131; 67692129-67692153; 67721153-67721177; 67726733-67726757; 67694551-67694575; 67684767-67684791; 67686717-67686741; 67692858-67692882; 67694890-67694914; 7706343-67706367; 67681596-67681620; 67684153-67684177; 67690025-67690049; 67691225-67691249; 67692361-67692385; 67692291-67692315; 67684752-67684776; 67690917-67690941; 67695354-67695378; 67685964-67685988; 67690852-67690876; 67698221-67698245; 67713445-67713469; 67693965-67693989; 67689830-67689854; 67690151-67690175; 67718079-67718103; 67692663-67692687; 67684143-67684167; 67702560-67702584; 67689807-67689831; 67734305-67734329; 67691410-67691434; 67691162-67691186; 67702695-67702719; 67689612-67689636; 67697284-67697308; 67691567-67691591; 67685635-67685659; 67689900-67689924; 67696035-67696059; 67687462-67687486; 67689863-67689887; 67690831-67690855; 67696956-67696980; 67703966-67703990; 67692382-67692406; 67693741-67693765; 67682707-67682731; 67689891-67689915; 67695833-67695857; 67689800-67689824; 67693566-67693590; 67681587-67681611; 67702113-67702137; 67701288-67701312; 67689761-67689785; 67723825-67723849; 67686892-67686916; 67698097-67698121; 67687614-67687638; 67703251-67703275; 67690109-67690133; 67719750-67719774; 67691762-67691786; 67691654-67691678; 67695445-67695469; 67694579-67694603; 67693002-67693026; 67731932-67731956; 67689608-67689632; 67691726-67691750; 67704995-67705019; 67694095-67694119; 67688285-67688309; 67692918-67692942; 67735442-67735466; 67694119-67694143; 67694791-67694815; 67695843-67695867; 67695032-67695056; 67703734-67703758; 67690809-67690833; 67697085-67697109; 67690629-67690653; 67701642-67701666; 67693639-67693663; 67703876-67703900; 67690054-67690078; 67695062-67695086; 67689878-67689902; 67696347-67696371; 67694806-67694830; 67690245-67690269; 67695377-67695401; 67694295-67694319; 67705602-67705626; 67693729-67693753; 67694696-67694720; 67694318-67694342; 67697768-67697792; 67694989-67695013; 67687551-67687575; 67694309-67694333; 67693926-67693950; 67693602-67693626; 67693896-67693920; 67718020-67718044; 67700346-67700370; 67696171-67696195; 67729142-67729166; 67684112-67684136; 67693375-67693399; 67691807-67691831; 67700198-67700222; 67697504-67697528; 67701370-67701394; 67703871-67703895; 67683323-67683347; and 67690737-67690761. These sites represent SEQ ID NOs. 1-194 as provided in Table 3 below.

While GSH loci described herein are ideally suited for genetic manipulation in HSC including a subset for CD34+ cells, CD34$^+$CD45RA$^-$CD90$^+$ HSC), other appropriate blood cells types include hematopoietic progenitor cells (HPC), hematopoietic stem and progenitor cell (HSPCs), T cells, natural killer (NK) cells, B cells, macrophages, monocytes, mesenchymal stem cells (MSC), white blood cell (WBC), mononuclear cell (MNC), endothelial cells (EC), stromal cells, and bone marrow fibroblasts. These cell types can collectively be referred to as "blood cells".

(II) Gene Editing Systems and Components to Target and Modify GSH Sites. Identification of the above-described GSH and more rigorously defined universal HSC safe harbor loci allows targeting with gene editing systems, greatly increasing the safety of genetic therapies. Within the teachings of the current disclosure, any gene editing system capable of precise sequence targeting and modification can be used. These systems typically include a targeting element for precise targeting and a cutting element for cutting the targeted genetic site. Guide RNA is one example of a targeting element while various nucleases provide examples of cutting elements. Targeting elements and cutting elements can be separate molecules or linked, for example, by a nanoparticle. Alternatively, a targeting element and a cutting element can be linked together into one dual purpose molecule. When insertion of a therapeutic nucleic acid sequence is intended, the systems also include a homology-directed repair template (which can include homology arms) associated with the therapeutic nucleic acid sequence. As detailed further below, however, different gene editing systems can adopt different components and configurations while maintaining the ability to precisely target, cut, and modify selected genomic sites.

Particular embodiments utilize zinc finger nucleases (ZFNs) as gene editing agents. ZFNs are a class of site-specific nucleases engineered to bind and cleave DNA at specific positions. ZFNs are used to introduce double strand breaks (DSBs) at a specific site in a DNA sequence which enables the ZFNs to target unique sequences within a genome in a variety of different cells. Moreover, subsequent to double-stranded breakage, homology-directed repair (HDR) or non-homologous end joining (NHEJ) takes place to repair the DSB, thus enabling genome editing.

ZFNs are synthesized by fusing a zinc finger DNA-binding domain to a DNA cleavage domain. The DNA-binding domain includes three to six zinc finger proteins which are transcription factors. The DNA cleavage domain includes the catalytic domain of, for example, FokI endonuclease. The FokI domain functions as a dimer requiring two constructs with unique DNA binding domains for sites on the target sequence. The FokI cleavage domain cleaves within a five or six base pair spacer sequence separating the two inverted half-sites.

For additional information regarding ZFNs, see Kim, et al. Proceedings of the National Academy of Sciences of the United States of America 93, 1156-1160 (1996); Wolfe, et al. Annual review of biophysics and biomolecular structure 29, 183-212 (2000); Bibikova, et al. Science 300, 764 (2003); Bibikova, et al. Genetics 161, 1169-1175 (2002); Miller, et al. The EMBO journal 4, 1609-1614 (1985); and Miller, et al. Nature biotechnology 25, 778-785 (2007)].

Particular embodiments can use transcription activator like effector nucleases (TALENs) as gene editing agents. TALENs refer to fusion proteins including a transcription activator-like effector (TALE) DNA binding protein and a DNA cleavage domain. TALENs are used to edit genes and genomes by inducing DSBs in the DNA, which induce repair mechanisms in cells. Generally, two TALENs must bind and flank each side of the target DNA site for the DNA cleavage domain to dimerize and induce a DSB. The DSB is repaired in the cell by NHEJ or HDR if an exogenous double-stranded donor DNA fragment is present.

As indicated, TALENs have been engineered to bind a target sequence of, for example, an endogenous genome, and cut DNA at the location of the target sequence. The TALEs of TALENs are DNA binding proteins secreted by *Xanthomonas* bacteria. The DNA binding domain of TALEs include a highly conserved 33 or 34 amino acid repeat, with divergent residues at the $12^{th}$ and $13^{th}$ positions of each repeat. These two positions, referred to as the Repeat Variable Diresidue (RVD), show a strong correlation with specific nucleotide recognition. Accordingly, targeting specificity can be improved by changing the amino acids in the RVD and incorporating nonconventional RVD amino acids.

Examples of DNA cleavage domains that can be used in TALEN fusions are wild-type and variant FokI endonucleases. For additional information regarding TALENs, see Boch, et al. Science 326, 1509-1512 (2009); Moscou, & Bogdanove, Science 326, 1501 (2009); Christian, et al. Genetics 186, 757-761 (2010); and Miller, et al. Nature biotechnology 29, 143-148 (2011).

Particular embodiments utilize MegaTALs as gene editing agents. MegaTALs have a single chain rare-cleaving nuclease structure in which a TALE is fused with the DNA cleavage domain of a meganuclease. Meganucleases, also known as homing endonucleases, are single peptide chains that have both DNA recognition and nuclease function in the same domain. In contrast to the TALEN, the megaTAL only requires the delivery of a single peptide chain for functional activity.

In particular embodiments, GSH can be targeted using CRISPR gene editing systems. The CRISPR nuclease system is a prokaryotic immune system that confers resistance to foreign genetic elements such as plasmids and phages and provides a form of acquired immunity. CRISPRs are DNA loci containing short repetitions of base sequences. In the context of a prokaryotic immune system, each repetition is followed by short segments of spacer DNA belonging to foreign genetic elements that the prokaryote was exposed to. This CRISPR array of repeats interspersed with spacers can be transcribed into RNA. The RNA can be processed to a mature form and associate with a cas (CRISPR-associated) nuclease. A CRISPR-Cas system including an RNA having a sequence that can hybridize to the foreign genetic elements and Cas nuclease can then recognize and cut these exogenous genetic elements in the genome.

A CRISPR-Cas system does not require the generation of customized proteins to target specific sequences, but rather a single Cas enzyme can be programmed by a short guide RNA molecule (crRNA) to recognize a specific DNA target. The CRISPR-Cas systems of bacterial and archaeal adaptive immunity show extreme diversity of protein composition and genomic loci architecture. The CRISPR-Cas system loci have more than 50 gene families and there are no strictly universal genes, indicating fast evolution and extreme diversity of loci architecture. So far, adopting a multi-pronged approach, there is comprehensive cas gene identification of 395 profiles for 93 Cas proteins. Classification includes signature gene profiles plus signatures of locus architecture. A new classification of CRISPR-Cas systems is proposed in which these systems are broadly divided into two classes, Class 1 with multi-subunit effector complexes and Class 2 with single-subunit effector modules exemplified by the Cas9 protein. Efficient gene editing in human CD34+ cells using electroporation of CRISPR/Cas9 mRNA and single-stranded oligodeoxyribonucleotide (ssODN) as a donor template for HDR has been demonstrated. De Ravin et al. Sci Transl Med. 2017; 9(372): eaah3480. Novel effector proteins associated with Class 2 CRISPR-Cas systems may be developed as powerful genome engineering tools and the prediction of putative novel effector proteins and their engineering and optimization is important. In addition to the Class 1 and Class 2 CRISPR-Cas systems, more recently a putative Class 2, Type V CRISPR-Cas class exemplified by Cpf1 has been identified Zetsche et al. (2015) Cell 163(3): 759-771.

Additional information regarding CRISPR-Cas systems and components thereof are described in, U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641 and applications related thereto; and WO2014/018423, WO2014/093595, WO2014/093622, WO2014/093635, WO2014/093655, WO2014/093661, WO2014/093694, WO2014/093701, WO2014/093709, WO2014/093712, WO2014/093718, WO2014/145599, WO2014/204723, WO2014/204724, WO2014/204725, WO2014/204726, WO2014/204727, WO2014/204728, WO2014/204729, WO2015/065964, WO2015/089351, WO2015/089354, WO2015/089364, WO2015/089419, WO2015/089427, WO2015/089462, WO2015/089465, WO2015/089473 and WO2015/089486, WO2016205711, WO2017/106657, WO2017/127807 and applications related thereto.

The Cpf1 nuclease particularly can provide added flexibility in target site selection by means of a short, three base pair recognition sequence (TTN), known as the protospacer-adjacent motif or PAM. Cpf1's cut site is at least 18 bp away from the PAM sequence, thus the enzyme can repeatedly cut a specified locus after indel (insertion and deletion) formation, increasing the efficiency of HDR. Moreover, staggered DSBs with sticky ends permit orientation-specific donor template insertion, which is advantageous in non-dividing cells.

Three windows of identified GSH sites on chromosome 11q13.2 were searched for Cpf1 target sites that contained the most preferred PAM sequence (TTTA) and an adjacent 21 bp of DNA which was completely unique to the human genome. A total of 194 target cut sites were identified by these criteria and are listed in Table 3. Each of these identified sequences provides a beneficial site to specifically target for gene therapy. The disclosed nucleic acid sequences are shown using standard letter abbreviations for nucleotide bases, as defined in 37 C.F.R. 1.822. Only one strand of each nucleic acid sequence is shown, but the complementary strand is understood as included by any reference to the displayed strand in the following Table 3 and/or as provided herein:

TABLE 3

Universal HSC Safe Harbor Loci with Cpf1 Target Sites that Contain the Most Preferred PAM Sequence with 21 Adjacent Base Pairs that are Unique to the Human Genome

| Universal HSC Safe Harbor‡ Window on chr11: | Cpf1 Target Sequence (TTTA = PAM†) | Number of Sequences Identified in the Human Genome (hg38)* | | |
|---|---|---|---|---|
| | | Exact Match | One bp Off | Two bp Off |
| 67935219-67935243 | TTTAAAAAAAGTCTTCATAA TAAAA (SEQ ID NO: 1) | 1 | 0 | 0 |
| 67911598-67911622 | TTTACTTCTGTGCACCCAT AGACTC (SEQ ID NO: 2) | 1 | 0 | 0 |
| 67939901-67939925 | TTTAACTCTGCCATGGGTG CCAGGA (SEQ ID NO: 3) | 1 | 0 | 0 |
| 67927758-67927782 | TTTAGCCACTGTGAGAAAC AGTTTA (SEQ ID NO: 4) | 1 | 0 | 0 |
| 67917930-67917954 | TTTATAAGGCTAAGTAGTA TTCTAT (SEQ ID NO: 5) | 1 | 0 | 0 |
| 67918042-67918066 | TTTATCCACTAATTGTTGAT GGGCA (SEQ ID NO: 6) | 1 | 0 | 0 |
| 67931473-67931497 | TTTATTTTCTTTTTGGTAAG AAGGA (SEQ ID NO: 7) | 1 | 0 | 0 |
| 67936715-67936739 | TTTAAAATAATCGTCATTCT TTTTG (SEQ ID NO: 8) | 1 | 0 | 0 |
| 67921126-67921150 | TTTATATTAATCCTTGTATG TCTGA (SEQ ID NO: 9) | 1 | 0 | 0 |
| 67914940-67914964 | TTTAAATGGATAAGTTAGG CTGGGC (SEQ ID NO: 10) | 1 | 0 | 0 |
| 67928284-67928308 | TTTACACAAACTGTACTTGT AGGTA (SEQ ID NO: 11) | 1 | 0 | 0 |
| 67936068-67936092 | TTTAGTGAGGAAAAACTAC ATTTAT (SEQ ID NO: 12) | 1 | 0 | 0 |
| 67922372-67922396 | TTTAAAAAGGGAAAATTAG GGAGAA (SEQ ID NO: 13) | 1 | 0 | 0 |
| 67811255-67811279 | TTTACTAAATGACCTCTTC GCCAAA (SEQ ID NO: 14) | 1 | 0 | 0 |
| 67840351-67840375 | TTTAGTGATATGAAAAGAA CCATGC (SEQ ID NO: 15) | 1 | 0 | 0 |
| 67821576-67821600 | TTTAAATTTTCCAGTGTCTC AGTGT (SEQ ID NO: 16) | 1 | 0 | 0 |
| 67827279-67827303 | TTTAAGCCTGAAAACCTAA AAAATG (SEQ ID NO: 17) | 1 | 0 | 0 |
| 67822563-67822587 | TTTAAAAATTAGCTGCGTT GGTGGT (SEQ ID NO: 18) | 1 | 0 | 0 |
| 67823914-67823938 | TTTAGCTGCTTTAAAATGT GAACTC (SEQ ID NO: 19) | 1 | 0 | 0 |
| 67818875-67818899 | TTTAATCTCAAGTCACTTCT CTAGG (SEQ ID NO: 20) | 1 | 0 | 0 |
| 67811907-67811931 | TTTAAACGCTCGTTAGATC ACTGGA (SEQ ID NO: 21) | 1 | 0 | 0 |
| 67811630-67811654 | TTTAAGGCAGGAATCAGGG TGCCAT (SEQ ID NO: 22) | 1 | 0 | 0 |

TABLE 3-continued

Universal HSC Safe Harbor Loci with Cpf1 Target Sites that Contain the Most Preferred PAM Sequence with 21 Adjacent Base Pairs that are Unique to the Human Genome

| Universal HSC Safe Harbor‡ Window on chr11: | Cpf1 Target Sequence (TTTA = PAM†) | Exact Match | One bp Off | Two bp Off |
|---|---|---|---|---|
| 67836644-67836668 | TTTAAAAAAATCCCAGGTG ACCCTA (SEQ ID NO: 23) | 1 | 0 | 0 |
| 67806757-67806781 | TTTAATCTTGCAGGGACAG GAAGGA (SEQ ID NO: 24) | 1 | 0 | 0 |
| 67823923-67823947 | TTTAAAATGTGAACTCCAA ATCAGG (SEQ ID NO: 25) | 1 | 0 | 0 |
| 67841379-67841403 | TTTATTATTTCGTTGTTTT CCTCT (SEQ ID NO: 26) | 1 | 0 | 0 |
| 67808086-67808110 | TTTATCTTGGTGTTTGAACT CGGAT (SEQ ID NO: 27) | 1 | 0 | 0 |
| 67823903-67823927 | TTTACTGCCCATTTAGCTG CTTTAA (SEQ ID NO: 28) | 1 | 0 | 0 |
| 67686904-67686928 | TTTAACTTGATTACCTTATA GTCAA (SEQ ID NO: 29) | 1 | 0 | 0 |
| 67692610-67692634 | TTTATATATTTAACTTCTGT ATTTT (SEQ ID NO: 30) | 1 | 0 | 0 |
| 67692462-67692486 | TTTATCTGCTATAGCTAACA AATTT (SEQ ID NO: 31) | 1 | 0 | 0 |
| 67692618-67692642 | TTTAACTTCTGTATTTTCTA AAACT (SEQ ID NO: 32) | 1 | 0 | 0 |
| 67705405-67705429 | TTTATAACACACCAGCATC AGTTAC (SEQ ID NO: 33) | 1 | 0 | 0 |
| 67686651-67686675 | TTTATTATCTTTCCTGTTTT CTAAT (SEQ ID NO: 34) | 1 | 0 | 0 |
| 67686788-67686812 | TTTAATATTAACATTTGCTA ATTTC (SEQ ID NO: 35) | 1 | 0 | 0 |
| 67684033-67684057 | TTTAAAAGGCCAGATGTCA ATTCAG (SEQ ID NO: 36) | 1 | 0 | 0 |
| 67681565-67681589 | TTTATGCAGATAGATATATA TTTTT (SEQ ID NO: 37) | 1 | 0 | 0 |
| 67704652-67704676 | TTTAATCACTGGATCATGG ACCTAA (SEQ ID NO: 38) | 1 | 0 | 0 |
| 67689328-67689352 | TTTAGTGTTTCTTAGAAACT TAACA (SEQ ID NO: 39) | 1 | 0 | 0 |
| 67688546-67688570 | TTTACAGCAGTGCCATTCA CAATGG (SEQ ID NO: 40) | 1 | 0 | 0 |
| 67693464-67693488 | TTTATAGGCCCAGGTCTAG ATCTGG (SEQ ID NO: 41) | 1 | 0 | 0 |
| 67682343-67682367 | TTTAGCCCTATCTTATCCAT ATGGA (SEQ ID NO: 42) | 1 | 0 | 0 |
| 67689948-67689972 | TTTATGTCTAGTACTTAGG GCAGTA (SEQ ID NO: 43) | 1 | 0 | 0 |
| 67684785-67684809 | TTTACAATTAATTGTAGTTC TTTGA (SEQ ID NO: 44) | 1 | 0 | 0 |
| 67684738-67684762 | TTTATTTTCTTAGATTTACT CTGTA (SEQ ID NO: 45) | 1 | 0 | 0 |
| 67684260-67684284 | TTTAAAAACTGGGTTTACA AATAAA (SEQ ID NO: 46) | 1 | 0 | 0 |
| 67684173-67684197 | TTTAAACATTTTGACTGTAG CCATT (SEQ ID NO: 47) | 1 | 0 | 0 |
| 67687315-67687339 | TTTATGACTGTTTCATGTGT GCTCA (SEQ ID NO: 48) | 1 | 0 | 0 |
| 67682671-67682695 | TTTATAACCTCACCTTTGG CTTTTA (SEQ ID NO: 49) | 1 | 0 | 0 |
| 67691534-67691558 | TTTAGAAGTCCATATAAGG GGATGC (SEQ ID NO: 50) | 1 | 0 | 0 |
| 67690743-67690767 | TTTACTGTTAATTAGTCCTT GCTTA (SEQ ID NO: 51) | 1 | 0 | 0 |
| 67693746-67693770 | TTTATCTATGAACCTCATAG GTCCT (SEQ ID NO: 52) | 1 | 0 | 0 |
| 67690174-67690198 | TTTACTATAGTTAATTGGAA CACTT (SEQ ID NO: 53) | 1 | 0 | 0 |
| 67692535-67692559 | TTTAACGTTAAATCTCTTTC TAACA (SEQ ID NO: 54) | 1 | 0 | 0 |
| 67687605-67687629 | TTTATCTCCTTTAAATTCCC ATGTT (SEQ ID NO: 55) | 1 | 0 | 0 |
| 67694747-67694771 | TTTAGTCCAAATAAAGCAA CAATAC (SEQ ID NO: 56) | 1 | 0 | 0 |
| 67681441-67681465 | TTTATCCATTCCCAACCAC AAAGAA (SEQ ID NO: 57) | 1 | 0 | 0 |
| 67691508-67691532 | TTTAATTTCTCCACTTGATT AACTT (SEQ ID NO: 58) | 1 | 0 | 0 |
| 67692057-67692081 | TTTAGCCAAAGGACATGCC TAAAAT (SEQ ID NO: 59) | 1 | 0 | 0 |
| 67692573-67692597 | TTTAGGAATTAATAAAAATT GTATA (SEQ ID NO: 60) | 1 | 0 | 0 |
| 67690331-67690355 | TTTAATGCATCCATAAACA GAACTG (SEQ ID NO: 61) | 1 | 0 | 0 |
| 67697247-67697271 | TTTAGGGTGGTTCTCCTGG GATTTT (SEQ ID NO: 62) | 1 | 0 | 0 |
| 67695745-67695769 | TTTATCCCTTACGCATGAG GTCCCT (SEQ ID NO: 63) | 1 | 0 | 0 |
| 67695241-67695265 | TTTACACAAGCAACACCAG CTGCAG (SEQ ID NO: 64) | 1 | 0 | 0 |

TABLE 3-continued

Universal HSC Safe Harbor Loci with Cpf1 Target Sites that Contain the Most Preferred PAM Sequence with 21 Adjacent Base Pairs that are Unique to the Human Genome

| Universal HSC Safe Harbor‡ Window on chr11: | Cpf1 Target Sequence (TTTA = PAM†) | Exact Match | One bp Off | Two bp Off |
|---|---|---|---|---|
| 67691931-67691955 | TTTAAATACTTGACAAAAAA GATTG (SEQ ID NO: 65) | 1 | 0 | 0 |
| 67691017-67691041 | TTTAAAAGGGGTCTCTACT AAATCT (SEQ ID NO: 66) | 1 | 0 | 0 |
| 67694689-67694713 | TTTAATCTTTATCTGACCTA AATTT (SEQ ID NO: 67) | 1 | 0 | 0 |
| 67721934-67721958 | TTTATAAAGAAATTCCGCA AGAACT (SEQ ID NO: 68) | 1 | 0 | 0 |
| 67696164-67696188 | TTTATGATTTAAAGGGGAA GCTTTG (SEQ ID NO: 69) | 1 | 0 | 0 |
| 67736715-67736739 | TTTAATGCTTTCAACATCGA TTGCT (SEQ ID NO: 70) | 1 | 0 | 0 |
| 67681498-67681522 | TTTACGGAGAGGATACAAA GATCCT (SEQ ID NO: 71) | 1 | 0 | 0 |
| 67690926-67690950 | TTTAAGATCTTCCTATAATT ATAGC (SEQ ID NO: 72) | 1 | 0 | 0 |
| 67694271-67694295 | TTTAATTTTGTTGGAGTCT TTTCT (SEQ ID NO: 73) | 1 | 0 | 0 |
| 67682715-67682739 | TTTATTTTTAAAACCAGAA CATTT (SEQ ID NO: 74) | 1 | 0 | 0 |
| 67694107-67694131 | TTTAGTTCTCTTTTTATACT CCAAA (SEQ ID NO: 75) | 1 | 0 | 0 |
| 67692129-67692153 | TTTACTAAGAATAGTGTAG GGGTTA (SEQ ID NO: 76) | 1 | 0 | 0 |
| 67721153-67721177 | TTTACTATTTCCCATCTTAT GTATA (SEQ ID NO: 77) | 1 | 0 | 0 |
| 67726733-67726757 | TTTAGCAGGTGTCTTGATC CCCCTT (SEQ ID NO: 78) | 1 | 0 | 0 |
| 67694551-67694575 | TTTATTTTCTAGTCCCCCTT TGATC (SEQ ID NO: 79) | 1 | 0 | 0 |
| 67684767-67684791 | TTTAAAATCATCTTATTGTT TACAA (SEQ ID NO: 80) | 1 | 0 | 0 |
| 67686717-67686741 | TTTAGAGAGATATATTTTCC TCTAG (SEQ ID NO: 81) | 1 | 0 | 0 |
| 67692858-67692882 | TTTAAAAGTGGTCACAAGT GGGGGA (SEQ ID NO: 82) | 1 | 0 | 0 |
| 67694890-67694914 | TTTACTAGAAACCTTTCCC ATATTG (SEQ ID NO: 83) | 1 | 0 | 0 |
| 67706343-67706367 | TTTATTGCTCTGTAACAGAT TACCA (SEQ ID NO: 84) | 1 | 0 | 0 |
| 67681596-67681620 | TTTACCAGCCATCTTAGAA CAAATT (SEQ ID NO: 85) | 1 | 0 | 0 |
| 67684153-67684177 | TTTACAGAATTCGCTTTCC CTTTAA (SEQ ID NO: 86) | 1 | 0 | 0 |
| 67690025-67690049 | TTTATTAAGCTAAACCTAG GTACAA (SEQ ID NO: 87) | 1 | 0 | 0 |
| 67691225-67691249 | TTTAGGATCACCTTAACTT GGTGAG (SEQ ID NO: 88) | 1 | 0 | 0 |
| 67692361-67692385 | TTTACTATTTCCCCTGGAG TCTTTA (SEQ ID NO: 89) | 1 | 0 | 0 |
| 67692291-67692315 | TTTAATAAGTCTTTTGATTA CAGGC (SEQ ID NO: 90) | 1 | 0 | 0 |
| 67684752-67684776 | TTTACTCTGTAGCTTTTTAA AATCA (SEQ ID NO: 91) | 1 | 0 | 0 |
| 67690917-67690941 | TTTACTTCTTTTAAGATCTT CCTAT (SEQ ID NO: 92) | 1 | 0 | 0 |
| 67695354-67695378 | TTTACTTTGCTCTGTGAAC AGAGTT (SEQ ID NO: 93) | 1 | 0 | 0 |
| 67685964-67685988 | TTTAATTCCTGTTTCATTTT CCCAT (SEQ ID NO: 94) | 1 | 0 | 0 |
| 67690852-67690876 | TTTAGGGCGTGACTGTGAA TAACTC (SEQ ID NO: 95) | 1 | 0 | 0 |
| 67698221-67698245 | TTTATTCAATTTCTCCTAAG TCTGC (SEQ ID NO: 96) | 1 | 0 | 0 |
| 67713445-67713469 | TTTAAAAATATTTAGCAACT GGGAC (SEQ ID NO: 97) | 1 | 0 | 0 |
| 67693965-67693989 | TTTACGTTCCCAGATCGTA TTTCTT (SEQ ID NO: 98) | 1 | 0 | 0 |
| 67689830-67689854 | TTTAGTTCATGGCAAGCAA GTCATT (SEQ ID NO: 99) | 1 | 0 | 0 |
| 67690151-67690175 | TTTAGGCCACCAATTGGGG GCATTT (SEQ ID NO: 100) | 1 | 0 | 0 |
| 67718079-67718103 | TTTACCAACCATCACTGCC ATCGTC (SEQ ID NO: 101) | 1 | 0 | 0 |
| 67692663-67692687 | TTTAACCCCAGAAACTGTT AATTCC (SEQ ID NO: 102) | 1 | 0 | 0 |
| 67684143-67684167 | TTTATAGTTATTTACAGAAT TCGCT (SEQ ID NO: 103) | 1 | 0 | 0 |
| 67702560-67702584 | TTTATTTGTGCAACAATGG GGAATT (SEQ ID NO: 104) | 1 | 0 | 0 |
| 67689807-67689831 | TTTAATAAAGCAATAGGAA GACGTT (SEQ ID NO: 105) | 1 | 0 | 0 |
| 67734305-67734329 | TTTAAGTCACAGGGGTGTA GACCCT (SEQ ID NO: 106) | 1 | 0 | 0 |

TABLE 3-continued

Universal HSC Safe Harbor Loci with Cpf1 Target Sites that Contain the Most Preferred PAM Sequence with 21 Adjacent Base Pairs that are Unique to the Human Genome

| Universal HSC Safe Harbor‡ Window on chr11: | Cpf1 Target Sequence (TTTA = PAM†) | Exact Match | One bp Off | Two bp Off |
|---|---|---|---|---|
| 67691410-67691434 | TTTAGTGACCACCCTACTC TATTGT (SEQ ID NO: 107) | 1 | 0 | 0 |
| 67691162-67691186 | TTTAATAGAATAGCCTCATA TTTTA (SEQ ID NO: 108) | 1 | 0 | 0 |
| 67702695-67702719 | TTTAACCACTCCCACTCCC AATTAC (SEQ ID NO: 109) | 1 | 0 | 0 |
| 67689612-67689636 | TTTAGATGGAACTAGCATT CCACAA (SEQ ID NO: 110) | 1 | 0 | 0 |
| 67697284-67697308 | TTTAAAAGTAGCAGCTTAA GCCAGA (SEQ ID NO: 111) | 1 | 0 | 0 |
| 67691567-67691591 | TTTAGTTAATTTCTTATATA AGAGC (SEQ ID NO: 112) | 1 | 0 | 0 |
| 67685635-67685659 | TTTAAGGTAGATCTGTGCA GGGGGA (SEQ ID NO: 113) | 1 | 0 | 0 |
| 67689900-67689924 | TTTACTCCTCCCGAAGAGG ATGGAT (SEQ ID NO: 114) | 1 | 0 | 0 |
| 67696035-67696059 | TTTAACATAGATATTGAAGT CAGAG (SEQ ID NO: 115) | 1 | 0 | 0 |
| 67687462-67687486 | TTTATCATATTACTATTTTG CCAGT (SEQ ID NO: 116) | 1 | 0 | 0 |
| 67689863-67689887 | TTTAGTTACATGATTTTAA GAGTT (SEQ ID NO: 117) | 1 | 0 | 0 |
| 67690831-67690855 | TTTACCTGGTTCTGTAAATA TTTTA (SEQ ID NO: 118) | 1 | 0 | 0 |
| 67696956-67696980 | TTTATTATGTGAGTGATAAA TTTGA (SEQ ID NO: 119) | 1 | 0 | 0 |
| 67703966-67703990 | TTTACACCCCCCACCCCCG AGGCCT (SEQ ID NO: 120) | 1 | 0 | 0 |
| 67692382-67692406 | TTTAACTGAACATGTGTTG GAGGAA (SEQ ID NO: 121) | 1 | 0 | 0 |
| 67693741-67693765 | TTTAATTTATCTATGAACCT CATAG (SEQ ID NO: 122) | 1 | 0 | 0 |
| 67682707-67682731 | TTTATTTTTTATTTTTTAAA ACCA (SEQ ID NO: 123) | 1 | 0 | 0 |
| 67689891-67689915 | TTTATCCTTTTTACTCCTCC CGAAG (SEQ ID NO: 124) | 1 | 0 | 0 |
| 67695833-67695857 | TTTAAACTTTTTTAAATAGG TAAAG (SEQ ID NO: 125) | 1 | 0 | 0 |
| 67689800-67689824 | TTTAATTTTTAATAAAGCAA TAGGA (SEQ ID NO: 126) | 1 | 0 | 0 |
| 67693566-67693590 | TTTACATATAGTTTTTGAGC ClIII (SEQ ID NO: 127) | 1 | 0 | 0 |
| 67681587-67681611 | TTTAAAAGTTTTACCAGCC ATCTTA (SEQ ID NO: 128) | 1 | 0 | 0 |
| 67702113-67702137 | TTTATTTGGGCTATTTGCC AAACAG (SEQ ID NO: 129) | 1 | 0 | 0 |
| 67701288-67701312 | TTTAACTATGGTTCCTTTAA ATCAG (SEQ ID NO: 130) | 1 | 0 | 0 |
| 67689761-67689785 | TTTATAAGGGGACAATCCA ACATCT (SEQ ID NO: 131) | 1 | 0 | 0 |
| 67723825-67723849 | TTTATTCGGACCCGTGCTA CAACTT (SEQ ID NO: 132) | 1 | 0 | 0 |
| 67686892-67686916 | TTTATTATCCATTTTAACTT GATTA (SEQ ID NO: 133) | 1 | 0 | 0 |
| 67698097-67698121 | TTTATCAGTTGTCCAATTTG TGGTG (SEQ ID NO: 134) | 1 | 0 | 0 |
| 67687614-67687638 | TTTAAATTCCCATGTTGCAA CCCTA (SEQ ID NO: 135) | 1 | 0 | 0 |
| 67703251-67703275 | TTTAATAATTTTTCTACTTA TACTT (SEQ ID NO: 136) | 1 | 0 | 0 |
| 67690109-67690133 | TTTACCCAGTGGGTAAAAT GATCTA (SEQ ID NO: 137) | 1 | 0 | 0 |
| 67719750-67719774 | TTTAGGTGTATGATACTTTT AGTGC (SEQ ID NO: 138) | 1 | 0 | 0 |
| 67691762-67691786 | TTTAGGTTCTACATATTGAA GCTTT (SEQ ID NO: 139) | 1 | 0 | 0 |
| 67691654-67691678 | TTTAAGTTCTTGTTTGGTTC GGGGC (SEQ ID NO: 140) | 1 | 0 | 0 |
| 67695445-67695469 | TTTATTCATCACAACAGGT AAGTCC (SEQ ID NO: 141) | 1 | 0 | 0 |
| 67694579-67694603 | TTTAAAGGATAAAGAATAAT ATAGG (SEQ ID NO: 142) | 1 | 0 | 0 |
| 67693002-67693026 | TTTATTTTCACATCCACAGC TCCTA (SEQ ID NO: 143) | 1 | 0 | 0 |
| 67731932-67731956 | TTTAGTCCCCGCATCGTGT GGGGGG (SEQ ID NO: 144) | 1 | 0 | 0 |
| 67689608-67689632 | TTTATTTAGATGGAACTAG CATTCC (SEQ ID NO: 145) | 1 | 0 | 0 |
| 67691726-67691750 | TTTATCTGCACTTATTAAAT GGCCT (SEQ ID NO: 146) | 1 | 0 | 0 |
| 67704995-67705019 | TTTATCCTTGGACATAATTA AAGAA (SEQ ID NO: 147) | 1 | 0 | 0 |
| 67694095-67694119 | TTTAACAGTGGCTTTAGTT CTCTTT (SEQ ID NO: 148) | 1 | 0 | 0 |

TABLE 3-continued

Universal HSC Safe Harbor Loci with Cpf1 Target Sites that Contain the Most Preferred PAM Sequence with 21 Adjacent Base Pairs that are Unique to the Human Genome

| Universal HSC Safe Harbor‡ Window on chr11: | Cpf1 Target Sequence (TTTA = PAM†) | Number of Sequences Identified in the Human Genome (hg38)* | | |
|---|---|---|---|---|
| | | Exact Match | One bp Off | Two bp Off |
| 67688285-67688309 | TTTAGTACAGCAGCCTGAACTGACT (SEQ ID NO: 149) | 1 | 0 | 0 |
| 67692918-67692942 | TTTAAAACGACCTGGTCTCCCGCAT (SEQ ID NO: 150) | 1 | 0 | 0 |
| 67735442-67735466 | TTTACTCTGTGACAATATATTCTAT (SEQ ID NO: 151) | 1 | 0 | 0 |
| 67694119-67694143 | TTTATACTCCAAACTTCAGACCCAG (SEQ ID NO: 152) | 1 | 0 | 0 |
| 67694791-67694815 | TTTAAATTTAGTTTTTTTATTATCT (SEQ ID NO: 153) | 1 | 0 | 0 |
| 67695843-67695867 | TTTAAATAGGTAAAGGCAGGGAGGA (SEQ ID NO: 154) | 1 | 0 | 0 |
| 67695032-67695056 | TTTAACTCCTCTTTTTCTTTCTGGA (SEQ ID NO: 155) | 1 | 0 | 0 |
| 67703734-67703758 | TTTAATTTGGGAATATTGGGTTAAT (SEQ ID NO: 156) | 1 | 0 | 0 |
| 67690809-67690833 | TTTAGAGTCAGTATAGATGGTTTTT (SEQ ID NO: 157) | 1 | 0 | 0 |
| 67697085-67697109 | TTTATGCTGGGAACCGGAGGGCTGG (SEQ ID NO: 158) | 1 | 0 | 0 |
| 67690629-67690653 | TTTAAAAGAAAAGTTAGGTTGGTGT (SEQ ID NO: 159) | 1 | 0 | 0 |
| 67701642-67701666 | TTTATGTTGTACATGCCACAAAAAA (SEQ ID NO: 160) | 1 | 0 | 0 |
| 67693639-67693663 | TTTAGTAATGTCTGGCCAACTGTGA (SEQ ID NO: 161) | 1 | 0 | 0 |
| 67703876-67703900 | TTTATTTCTTGTTGGGAGGATGAGG (SEQ ID NO: 162) | 1 | 0 | 0 |
| 67690054-67690078 | TTTAATTAAGGCTTTGACTGCATTA (SEQ ID NO: 163) | 1 | 0 | 0 |
| 67695062-67695086 | TTTACACTCTTCACTCGCTTTGTCC (SEQ ID NO: 164) | 1 | 0 | 0 |
| 67689878-67689902 | TTTAAGAGTTTGATTTATCCTTTTT (SEQ ID NO: 165) | 1 | 0 | 0 |
| 67696347-67696371 | TTTAGCTATTTGTTATGGCAGCAAC (SEQ ID NO: 166) | 1 | 0 | 0 |
| 67694806-67694830 | TTTATTATCTTTCCAATACTTTAAC (SEQ ID NO: 167) | 1 | 0 | 0 |
| 67690245-67690269 | TTTAAGGCTTGTTTATTTGTGTTTT (SEQ ID NO: 168) | 1 | 0 | 0 |
| 67695377-67695401 | TTTATCTGGTCCCCGAGGCAGTGCA (SEQ ID NO: 169) | 1 | 0 | 0 |
| 67694295-67694319 | TTTAAAGAAGGATATTTAGAATTTT (SEQ ID NO: 170) | 1 | 0 | 0 |
| 67705602-67705626 | TTTAAAGGTAGGCCTCAAAAGAAC (SEQ ID NO: 171) | 1 | 0 | 0 |
| 67693729-67693753 | TTTATTTGTTCTTTTAATTTATCTA (SEQ ID NO: 172) | 1 | 0 | 0 |
| 67694696-67694720 | TTTATCTGACCTAAATTTGACCAA (SEQ ID NO: 173) | 1 | 0 | 0 |
| 67694318-67694342 | TTTAGGCTCCTGGGATTCACAAGAA (SEQ ID NO: 174) | 1 | 0 | 0 |
| 67697768-67697792 | TTTACTGGCAAACTGGGAGGAGAGA (SEQ ID NO: 175) | 1 | 0 | 0 |
| 67694989-67695013 | TTTAACCTTAACGTGCTTGAGGTTT (SEQ ID NO: 176) | 1 | 0 | 0 |
| 67687551-67687575 | TTTATTTCTATATTTTGAGGACATG (SEQ ID NO: 177) | 1 | 0 | 0 |
| 67694309-67694333 | TTTAGAATTTTTAGGCTCCTGGGAT (SEQ ID NO: 178) | 1 | 0 | 0 |
| 67693926-67693950 | TTTATGATTTGCTGCCAGAACATTT (SEQ ID NO: 179) | 1 | 0 | 0 |
| 67693602-67693626 | TTTATTGATTTTTTAAATTTTCTAA (SEQ ID NO: 180) | 1 | 0 | 0 |
| 67693896-67693920 | TTTATCCCACTGCGGGTCCTGAGCA (SEQ ID NO: 181) | 1 | 0 | 0 |
| 67718020-67718044 | TTTATAATTTCCATGCTTTTTCAGT (SEQ ID NO: 182) | 1 | 0 | 0 |
| 67700346-67700370 | TTTATCTGTAATTCTGCAGACCCTC (SEQ ID NO: 183) | 1 | 0 | 0 |
| 67696171-67696195 | TTTAAAGGGAAGCTTTGAAGAGGA (SEQ ID NO: 184) | 1 | 0 | 0 |
| 67729142-67729166 | TTTACCTGCCGGTAGTCCTTGGTCC (SEQ ID NO: 185) | 1 | 0 | 0 |
| 67684112-67684136 | TTTACCAATGTGTTCTAAGTTTTCA (SEQ ID NO: 186) | 1 | 0 | 0 |
| 67693375-67693399 | TTTAAAAAAATAAATACTGACCTTG (SEQ ID NO: 187) | 1 | 0 | 0 |
| 67691807-67691831 | TTTATCTTGTAGGTGGTTAAGAACT (SEQ ID NO: 188) | 1 | 0 | 0 |
| 67700198-67700222 | TTTATTTCTTTTCACGAATTGCTGG (SEQ ID NO: 189) | 1 | 0 | 0 |
| 67697504-67697528 | TTTATGTGGTGTTCAGAGCCCCAGG (SEQ ID NO: 190) | 1 | 0 | 0 |

TABLE 3-continued

Universal HSC Safe Harbor Loci with Cpf1 Target Sites that Contain the Most Preferred PAM Sequence with 21 Adjacent Base Pairs that are Unique to the Human Genome

| Universal HSC Safe Harbor‡ Window on chr11: | Cpf1 Target Sequence (TTTA = PAM†) | Exact Match | Number of Sequences Identified in the Human Genome (hg38)* One bp Off | Two bp Off |
|---|---|---|---|---|
| 67701370-67701394 | TTTATCGGTGTTATTGATGATCATT (SEQ ID NO: 191) | 1 | 0 | 0 |
| 67703871-67703895 | TTTATTTTATTTCTTGTTGGGAGGA (SEQ ID NO: 192) | 1 | 0 | 0 |
| 67683323-67683347 | TTTAAATTGGCTATAAATCTTTGAC (SEQ ID NO: 193) | 1 | 0 | 0 |
| 67690737-67690761 | TTTACCTTTACTGTTAATTAGTCCT (SEQ ID NO: 194) | 1 | 0 | 0 |

‡GSH: loci identified by retrospective analysis of lentivirus integration sites in transplanted autologous gene modified blood stem and progenitor cells.
†PAM: protospacer adjacent motif sequence. TTTV is the denoted PAM recognition site for Cpf1; however, the strongest preference is for TTTA.
^ All sequences are depicted 5' to 3'.

crRNA for target SEQ ID NO: 132 includes (SEQ ID NO: 195)
UAAUUUCUACUCUUGUAGAUUUCGGACCCGUGCUACAACUU.

crRNA for target SEQ ID NO: 108 includes (SEQ ID NO: 196)
UAAUUUCUACUCUUGUAGAUAUAGAAUAGCCUCAUAUUUUA Cpf1 crRNA target sites and PAM sites within chr11:67681215-67741765 include (SEQ ID NO: 197)
TTTGTGTCCCCGTTTTGGTTGGTAAAC, (SEQ ID NO: 198)
TTTAAAAATCAATACCGATAATAATGA,
and (SEQ ID NO: 199)
TTTCTTAATATGAATATTAATATCGGT (PAM sites italicized).

Cpf1 crRNA target sites and PAM sites within chr11:67805337-67845629 include (SEQ ID NO: 200)
TTTCCGTATCTGGAAGGGGCATCTTGG
at 67812179-67812205, (SEQ ID NO: 201)
TTTCCTTAGGACCGGAAGGATTACAGC
at 67812226-67812252, (SEQ ID NO: 202)
TTTGCCTAAAAGGCACTATGTCAAATG
at 67812280-67812306, (SEQ ID NO: 203)
TTTGGAGCTGTTGGCATCATGTTCCTG
at 67812349-67812375,
and (SEQ ID NO: 204)
TTTGATTCTTTTCTATCTCAGGACAGA (PAM sites italicized).

Cpf1 crRNA target sites and PAM sites within chr11:67895738-67941098 include:

(SEQ ID NO: 205)
TTTATAGACATCCCACACTGTAGTTCT
at 67931362-67931388, (SEQ ID NO: 206)
TTTATTAATTTGAGAACCAACATAAGG
at 67931439-67931465, (SEQ ID NO: 207)
TTTATTTTCTTTTTGGTAAGAAGGAAC
at 67931473-67931499,
and (SEQ ID NO: 208)
TTTCACACACACACACACACACACACA
at 67931516-67931542

(PAM sites italicized).

In particular embodiments, a Cpf1 crRNA target sequence includes TTTGGAGCTGTTGGCATCATGTTCCTG (SEQ ID NO: 203), and a crRNA for the target includes (SEQ ID NO: 209)
UAAUUUCUACUCUUGUAGAUGAGCUGUUGGCAUCAUGUUCCUG.

In particular embodiments, a Cpf1 crRNA target sequence includes TTTATCCAAACCTCCTAAATGATAC (SEQ ID NO: 210) located at chr11:67839126-67839150, and a crRNA for the target includes:

(SEQ ID NO: 211)
UAAUUUCUACUCUUGUAGAUUCCAAACCUCCUAAAUGAUAC.

In particular embodiments, a Cpf1 crRNA target sequence includes TTTACACCCGATCCACTGGGGAGCA (SEQ ID NO: 212) located at chr3:46373915-46373939, and a crRNA for the target includes (SEQ ID NO: 260)
UAAUUUCUACUCUUGUAGAUCACCCGAUCCACUGGGGAGCA.

crRNAs were also designed based on the following 27 nt CRISPR/Cpf1 cut site sequence: TTTTTGATTCTTTTC-TATCTCAGGACA (SEQ ID NO: 213) located within chr11: 67812443-67812469.

Homology-directed repair templates for HDR were also designed for nuclease-guide pairs with symmetric or asymmetric homology arms as described by Richardson et al., Nat Biotechnol. 2016; 34(3):339-44. Each donor template included homology arms (homology-directed repair template) flanking a 20 bp random DNA barcode element for clone tracking, upstream of a human phosphoglycerate kinase (PGK) promoter (e.g., SEQ ID NO: 214) driving expression of an enhanced green fluorescent protein (GFP) reporter gene (for experimental purposes, but akin to a therapeutic DNA sequence in clinical use). Humanized Cpf1 protein was synthesized by a commercial manufactuer (Aldevron), and guide RNA with two modifications, an atom oligoehtylene glycol spacer and a 3' terminal thiol was also obtained from a commercial source (Integrated DNA Technologies). Single-stranded homology template DNA (ssODN) was also synthesized by a commercial manufacturer (Integrated DNA Technologies). For examples of such sequences, see FIGS. 1, 3, 4, and 16.

As indicated, in particular embodiments, gene editing systems to provide a genetic therapy within a GSH will include guide RNA and a nuclease. In particular embodiments, donor templates can be used, especially when performing a gain-of-function therapy or a precise loss-of-function therapy. In particular embodiments, gene editing systems include a homology-directed repair template and a therapeutic nucleic acid sequence.

All nucleic acid-based components of gene editing systems can be single stranded, double stranded, or may have mix of single stranded and double stranded regions. For example, guide RNA or a donor template may be a single-stranded DNA, a single-stranded RNA, a double-stranded DNA, or a double-stranded RNA. In particular embodiments utilizing nanoparticles described herein, the end of a nucleic acid farthest from the nanoparticle surface may be protected (e.g., from exonucleolytic degradation) by methods known to those of skill in the art. For example, one or more dideoxynucleotide residues can be added to the 3' terminus of a linear molecule and/or self-complementary oligonucleotides are ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include addition of terminal amino group(s) and the use of modified internucleotide linkages such as, for example, phosphorothioates, phosphoramidates, and O-methyl ribose or deoxyribose residues. Chemically modified mRNA can be used to increase intracellular stability, while asymmetric homology arms and phosphorothioate modification can be incorporated into the ssODN to improve HDR efficiency. In particular embodiments utilizing nanoparticles described herein, nucleic acids may be protected from electrostatic (charge-based) repulsions by, for example, addition of a charge shielding spacer. In particular embodiments, a charge shielding spacer can include an 18 atom oligoethylene glycol (OEG) spacer added to one or both ends. In particular embodiments, a charge shielding spacer can include a 10-26 atom oligoethylene glycol (OEG) spacer added to one or both ends.

Donor templates can be of any length, e.g., 10 nucleotides or more, 50 nucleotides or more, 100 nucleotides or more, 250 nucleotides or more, 500 nucleotides or more, 1000 nucleotides or more, 5000 nucleotides or more, etc.

In particular embodiments, a homology-directed repair template is designed to serve as a template in homologous recombination, such as within or near a target sequence nicked or cleaved by an enzyme (e.g., nuclease) of a gene editing system. A homology-directed repair template polynucleotide may be of any suitable length, such as 10, 15, 20, 25, 50, 75, 100, 150, 200, 500, 1000, 2000, 3000, 4000, 5000, or more nucleotides. In particular embodiments, the homology-directed repair template polynucleotide is complementary to a portion of a polynucleotide including the target sequence. When optimally aligned, a homology-directed repair template polynucleotide overlaps with one or more nucleotides of a target sequence (e.g., 1, 5, 10, 15, 20, 25, 30, 35, 40, 45, 50, 60, 70, 80, 90, 100 or more nucleotides).

In particular embodiments, the homology-directed repair template can include sufficient homology to a genomic sequence at the cleavage site, e.g. 70%, 80%, 85%, 90%, 95%, or 100% homology with the nucleotide sequences flanking the cleavage site, e.g., within 50 bases or less of the cleavage site, e.g., within 30 bases, within 15 bases, within 10 bases, within 5 bases, or immediately flanking the cleavage site, to support HDR between it and the genomic sequence to which it bears homology. 25, 50, 100, or 200 nucleotides, or more than 200 nucleotides of sequence homology between a homology-directed repair template and a targeted genomic sequence (or any integral value between 10 and 200 nucleotides, or more) can support HDR. Homology arms or flanking sequences are generally identical to the genomic sequence, for example, to the genomic region in which the double stranded break (DSB) occurs. However, absolute identity is not required.

In particular embodiments, the donor template includes a heterologous therapeutic nucleic acid sequence flanked by two regions of homology, such that homology-directed repair between the target DNA region and the two flanking sequences results in insertion of the heterologous therapeutic nucleic acid sequence at the target region.

In some examples, homology arms or flanking sequences of homology-directed repair templates are asymmetrical.

As indicated, in particular embodiments, donor templates include a therapeutic nucleic acid sequence. Therapeutic nucleic acid sequences can include a corrected gene sequence; a complete gene sequence and/or one or more regulatory elements associated with expression of the gene. A corrected gene sequence can be a portion of a gene requiring correction or can provide a complete replacement copy of a gene. A corrected gene sequence can provide a complete copy of a gene, without necessarily replacing an existing defective gene. One of ordinary skill in the art will recognize that removal of a defective gene when providing a corrected copy may or may not be required. When inserting a gene within a genetic safe harbor, a therapeutic nucleic acid sequence should include a coding region and all regulatory elements required for its expression.

Examples of therapeutic genes and gene products include skeletal protein 4.1, glycophorin, p55, the Duffy allele, globin family genes; WAS; phox; dystrophin; pyruvate kinase; CLN3; ABCD1; arylsulfatase A; SFTPB; SFTPC; NLX2.1; ABCA3; GATA1; ribosomal protein genes; TERT; TERC; DKC1; TINF2; CFTR; LRRK2; PARK2; PARK7; PINK1; SNCA; PSEN1; PSEN2; APP; SOD1; TDP43; FUS; ubiquilin 2; C9ORF72, α2β1; αvβ3; αvβ5; αvβ63; BOB/GPR15; Bonzo/STRL-33/TYMSTR; CCR2; CCR3; CCR5; CCR8; CD4; CD46; CD55; CXCR4; aminopeptidase-N; HHV-7; ICAM; ICAM-1; PRR2/HveB; HveA; α-dystroglycan; LDLR/α2MR/LRP; PVR; PRR1/HveC, laminin receptor, 101F6, 123F2, 53BP2, abl, ABLI, ADP, aFGF, APC, ApoAI, ApoAIV, ApoE, ATM, BAI-1, BDNF, Beta*(BLU), bFGF, BLC1, BLC6, BRCA1, BRCA2, CBFA1, CBL, C-CAM, CFTR, CNTF, COX-1, CSFIR, CTS-1, cytosine deaminase, DBCCR-1, DCC, Dp, DPC-4, E1A, E2F, EBRB2, erb, ERBA, ERBB, ETS1, ETS2, ETV6, Fab, FancA, FancB, FancC, FancD1, FancD2, FancE, FancF, FancG, FancI, FancJ, FancL, FancM, FancN, FancO, FancP, FancQ, FancR, FancS, FancT, FancU, FancV, and FancW, FCC, FGF, FGR, FHIT, fms, FOX, FUS 1, FUS1, FYN, G-CSF, GDAIF, Gene 21, Gene 26, GM-CSF, GMF, gsp, HCR, HIC-1, HRAS, hst, IGF, IL-1, IL-2, IL-3, IL-4, IL-5, IL-6, IL-7, IL-8, IL-9, IL-10, IL-11 IL-12, ING1, interferon α, interferon β, interferon γ, IRF-1, JUN, KRAS, LCK, LUCA-1, LUCA-2, LYN, MADH4, MADR2, MCC, mda7, MDM2, MEN-I, MEN-II, MLL, MMAC1, MYB, MYC, MYCL1, MYCN, neu, NF-1, NF-2, NGF, NOEY1, NOEY2, NRAS, NT3, NT5, OVCA1, p16, p21, p27, p53, p57, p73, p300, PGS, PIM1, PL6, PML, PTEN, raf, Rap1A, ras, Rb, RB1, RET, rks-3, ScFv, scFV ras, SEM A3, SRC, TAL1, TCL3, TFPI, thrombospondin, thymidine kinase, TNF, TP53, trk, T-VEC, VEGF, VHL, VVT1, WT-1, YES, zac1, iduronidase, IDS, GNS, HGSNAT, SGSH, NAGLU, GUSB, GALNS, GLB1, ARSB, HYAL1, F8, F9, HBB, CYB5R3, γC, JAK3, IL7RA, RAG1, RAG2, DCLRE1C, PRKDC, LIG4, NHEJ1, CD3D, CD3E, CD3Z, CD3G, PTPRC, ZAP70, LCK, AK2, ADA, PNP, WHN, CHD7, ORAI1, STIM1, CORO1A, CIITA, RFXANK, RFX5, RFXAP, RMRP, DKC1, TERT, TINF2, DCLRE1B, and SLC46A1.

In particular embodiments, a therapeutic gene includes a coding sequence for a therapeutic expression product (e.g., protein, RNA) and all associated regulatory elements (e.g., promoters, etc.) to result in expression of the gene product.

In particular embodiments, a therapeutic nucleic acid sequence (e.g., a gene) can be selected for incorporation into a GSH to provide for in vivo selection of the genetically modified cell. For example, in vivo selection using a cell-growth switch allows a minor population of genetically modified cells to be inducibly amplified. A strategy to achieve in vivo selection has been to employ drug selection while coexpressing a transgene that conveys chemoresistance, such as O6-methylguanine-DNA-methyltransferase (MGMT). An alternate approach is to confer an enhanced proliferative potential upon gene-modified HSC through the delivery of the homeobox transcription factor HOXB4. In particular embodiments, a suicide gene can be incorporated into the genetically modified cell so that such population of cells can be eliminated, for example, by administration of a drug that activities the suicide gene. See, for example, Cancer Gene Ther. 2012 August; 19(8):523-9; PLoS One. 2013; 8(3): e59594. and Molecular Therapy—Oncolytics (2016) 3, 16011.

Particular embodiments include contacting a blood cell with a gene editing system capable of inserting a donor template at a target blood cell GSH. In particular embodiments, the gene editing system includes crRNA capable of hybridizing to a target sequence within the GSH, and a nucleic acid encoding a nuclease enzyme such as Cpf1 or Cas9. In particular embodiments, Cas9 or Cpf1 coding sequences can include SEQ ID NOs: 215-227. In particular embodiments, Cas9 or Cpf1 amino acid sequences can include SEQ ID NOs: 228-241.

Figure 2:
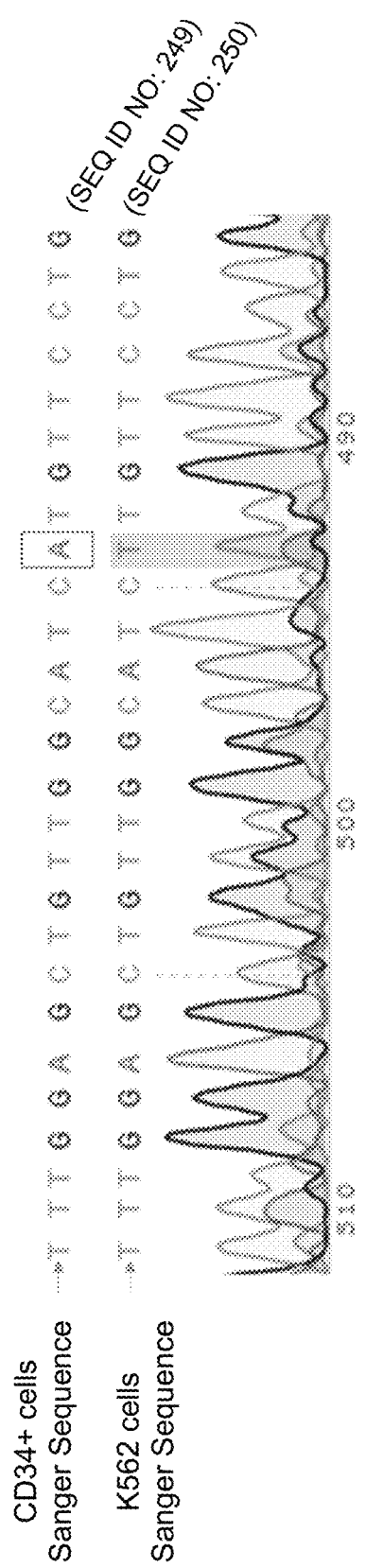
FIG. 2. A trace of a Sanger sequencing result showing a mutation in one target GSH site in K562 cells (SEQ ID NOs: 249 and 250).
Figure 3:
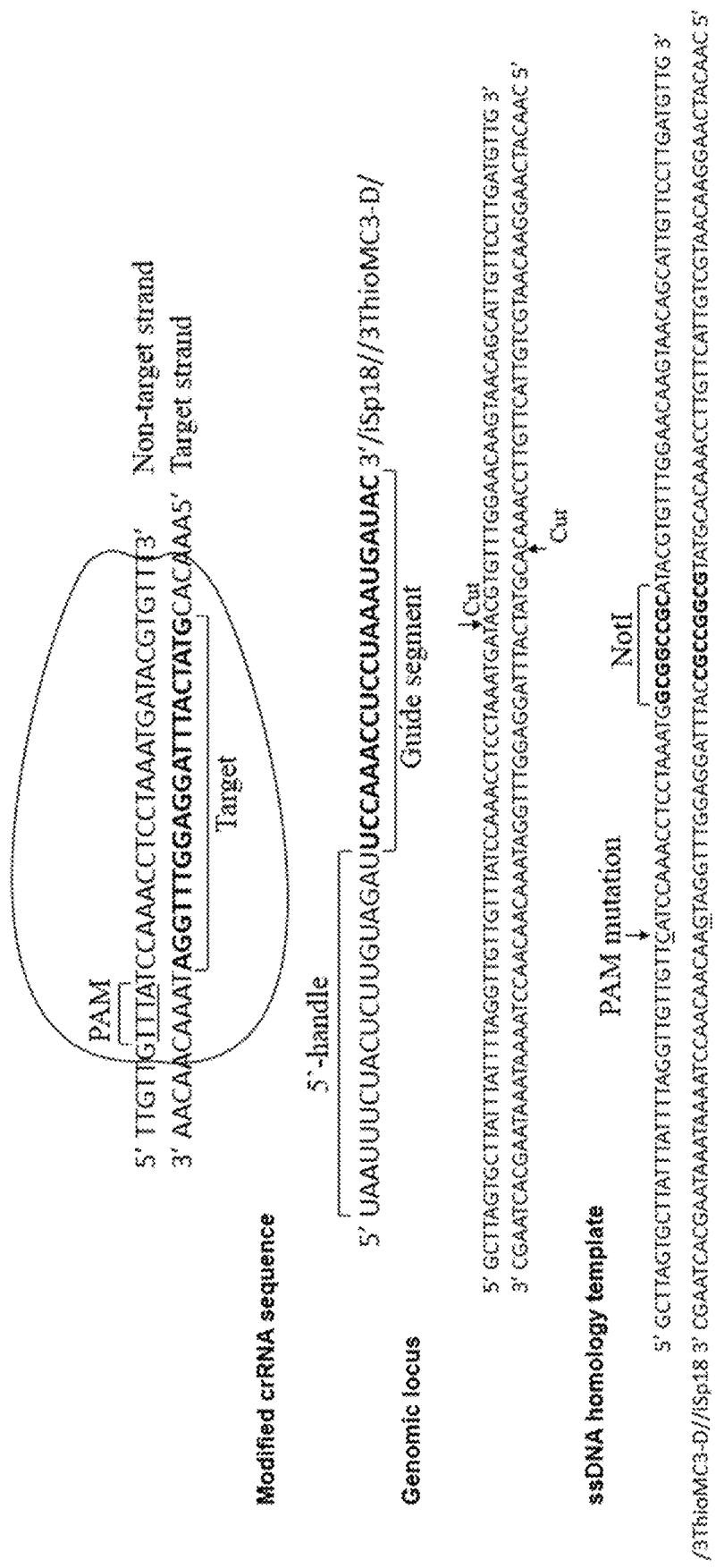
FIG. 3. Schematic showing the design and sequence of crRNA (SEQ ID NO: 253) and homology-directed repair template (also referred to herein as a homology template (HT or HDT)) (SEQ ID NOs: 256, 257) for a second GSH location (SEQ ID NOs: 251, 252, 254, 255) within human HSC and HSPC.
Figure 5:
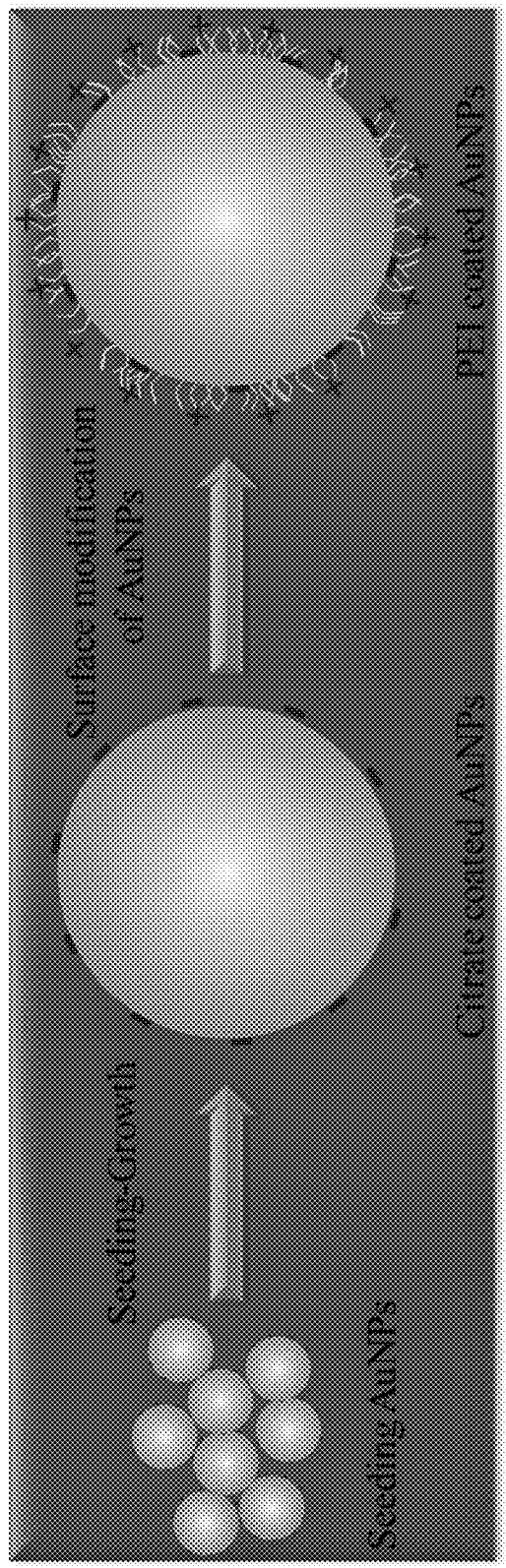
FIG. 5. Schematic of early production scheme for gold nanoparticles (AuNPs), a scalable, synthetic delivery scaffold with established in vivo compatibility.

In a particular exemplary embodiment, a Cpf1/crRNA gene editing system was designed to target the chr11: 67812349-67812375 genomic safe harbor (GSH) location (FIG. 1). Sanger sequencing results in K562 for this location spotted a A>T mutation in 15 bp after the PAM site (TTTG; FIG. 2) which resulted in lower cutting efficiency in this cell line compared to CD34+ cells. Also it has been shown that the cutting efficiency for the TTTA PAM site is higher than TTTG or TTTC. Therefore, another GSH location was identified in chromosome 11 (chr11: 67839126-67839150) with a TTTA PAM site which can increase cutting efficiency (FIG. 3). In addition, a SNP screen in this location did not identify any common SNP. Homology-directed repair templates (HT) were also designed. Synthesized HTs were 100 bp ssDNA bearing NotI restriction site for the assessment of HDR (FIGS. 1 and 3).

(III) Nanoparticles. As indicated previously, delivery methods of gene editing systems that do not rely on electroporation or viral vectors are needed. In addition to providing GSH and associated targeting gene editing components, the current disclosure also provides engineered nanoparticles that allow delivery of the gene editing components. The nanoparticles are engineered to include all components for targeted gene editing, for example, within a GSH. When a therapeutic use need only de-activate a problematic gene, the nanoparticles need only be associated with a targeting element and a cutting element (although other components may be included as necessary or helpful for a particular purpose). When a therapeutic use adds or corrects a gene, the nanoparticles are associated with a targeting element, a cutting element, and a donor template.

Particular embodiments utilize colloidal metal nanoparticles. A colloidal metal includes any water-insoluble metal particle or metallic compound dispersed in liquid water. A colloid metal can be a suspension of metal particles in aqueous solution. Any metal that can be made in colloidal form can be used, including gold, silver, copper, nickel, aluminum, zinc, calcium, platinum, palladium, and iron. In particular embodiments, gold nanoparticles are used, e.g., prepared from $HAuCl_4$. In particular embodiments, the nanoparticles are non-gold nanoparticles that are coated with gold to make gold-coated nanoparticles.

Methods for making colloidal metal nanoparticles, including gold colloidal nanoparticles from $HAuCl_4$, are known to those having ordinary skill in the art. For example, the methods described herein as well as those described elsewhere (e.g., US 2001/005581; 2003/0118657; and 2003/0053983) can be used to make nanoparticles.

In particular exemplary embodiments, AuNPs were synthesized in three different size ranges (15, 50, 100 nm) by an optimized Turkevich and seeding-growth methods (Shahbazi, et al., Nanomedicine (Lond), 2017. 12(16): p. 1961-1973; Shahbazi, et al., Nanotechnology, 2017. 28(2): p. 025103; Turkevich, et al. Discussions of the Faraday Society, 1951. 11(0): p. 55-75; Perrault & Chan, Journal of the American Chemical Society, 2009. 131(47): p. 17042-17043). In the first step, seed AuNPs of 15 nm were synthesized by bringing 100 mL of 0.25 mM gold (III) chloride trihydrate solution to the boiling point and adding 1 mL of 3.33% trisodium citrate dehydrate solution. Synthesis of nanoparticles was carried out in high stirring speeds over 10 min. Prepared nanoparticles were cooled down to 4° C. and used in the following growth step.

In order to prepare AuNPs in 50 nm and 100 nm size ranges, two different 100 mL of 0.25 mM gold (III) chloride trihydrate solutions were prepared and in mild stirring conditions 2440 µL and 304 µL of seed AuNPs were added separately to synthesize 50 nm and 100 nm AuNPs, respectively. To these solutions was added 1 mL of 15 mM trisodium citrate dehydrate solution and the mixture was brought to the highest stirring speed. Then, 1 mL of 25 mM hydroquinone solution was added and synthesis was continued over 30 min for 50 nm AuNPs and 5 h for 100 nm AuNPs. Finally, synthesized nanoparticles were purified by centrifuging at 5000×g and dispersing in ultra-pure water.

While AuNPs are particularly described, nanoparticles encompassed in the present disclosure may be provided in different forms, e.g., as solid nanoparticles (e.g., metal such as silver, gold, iron, titanium), non-metal, lipid-based solids, polymers, suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present disclosure.

Semi-solid and soft nanoparticles have been manufactured, and are within the scope of the present disclosure. A nanoparticle of a semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants.

A nanoparticle can include any suitable material, e.g., a biocompatible material. The biocompatible material can be a polymer. Suitable nanoparticle polymers include polystyrene, silicone rubber, polycarbonate, polyurethanes, polypropylenes, polymethylmethacrylate, polyvinyl chloride, polyesters, polyethers, and polyethylene. Examples of specific polymers include poly(caprolactone) (PCL), ethylene vinyl acetate polymer (EVA), poly(lactic acid) (PLA), poly (L-lactic acid) (PLLA), poly(glycolic acid) (PGA), poly (lactic acid-co-glycolic acid) (PLGA), poly(L-lactic acid-co-glycolic acid) (PLLGA), poly(D,L-lactide) (PDLA), poly (L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), poly anhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyethylenimine (PEI), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), trimethylene carbonate, and polyvinylpyrrolidone.

In particular embodiments, the nanoparticle is a lipid nanoparticle. A lipid nanoparticle can include one or more lipids, and one or more of the polymers listed above.

Lipidoid compounds are also particularly useful in the administration of gene editing system components. In particular embodiments, aminoalcohol lipidoid compounds are combined with gene editing system components to be delivered to a cell or a subject to form microparticles, nanoparticles, liposomes, or micelles. The gene editing system components to be delivered by the particles, liposomes, or micelles may be a polynucleotide, protein, peptide, or small molecule. Aminoalcohol lipidoid compounds may be combined with other aminoalcohol lipidoid compounds, polymers (synthetic or natural), surfactants, cholesterol, carbohydrates, proteins, lipids, etc. to form particles.

Figure 6:
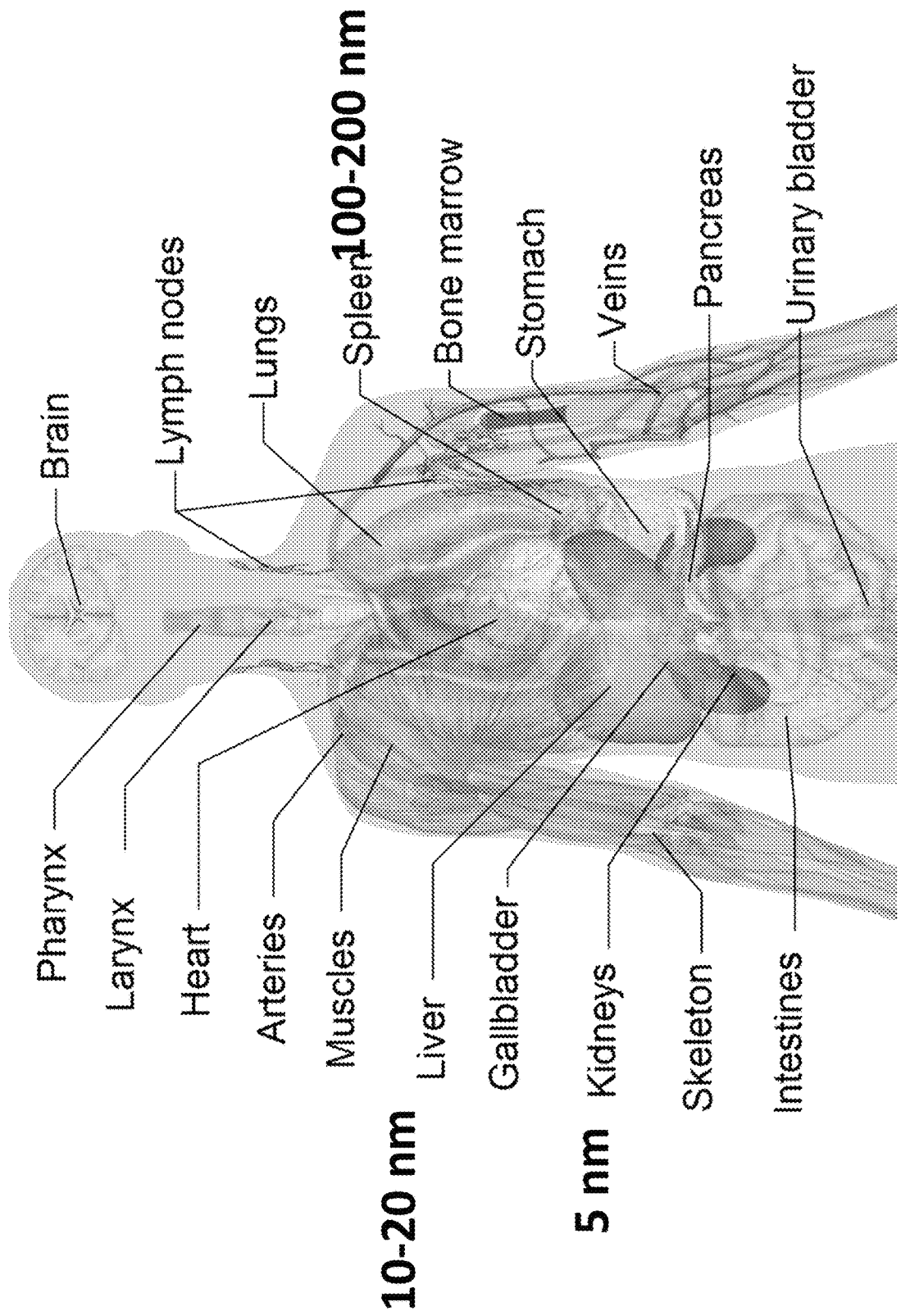
FIG. 6. AuNP size determines destination tissue/elimination pathway in humans.

As depicted in FIG. 6, the size of an AuNP can be selected to affect biodistribution within the human body. Nanoparticles suitable for use in the present disclosure can be any shape and can range in size from 5 nm-1000 nm in size, e.g., from 5 nm-10 nm, 5-50 nm, 5 nm-75 nm, 5 nm-40 nm, 10 nm-30, or 20 nm-30 nm. Nanoparticles can also have a size in the range of from 10 nm-15 nm, 15 nm-20 nm, 20 nm-25 nm, 25 nm-30 nm, 30 nm-35 nm, 35 nm-40 nm, 40 nm-45 nm, or 45 nm-50 nm, 50 nm-55 nm, 55 nm-60 nm, 60 nm-65 nm, 65 nm-70 nm, 70 nm-75 nm 75 nm-80 nm, 80 nm-85 nm, 85 nm-90 nm, 90 nm-95 nm, 95 nm-100 nm, 100 nm-105 nm, 105 nm-110 nm, 110 nm-115 nm, 115 nm-120 nm, 120 nm-125 nm, 125 nm-130 nm, 130 nm-135 nm, 135 nm-140 nm, 140 nm-145 nm, 145 nm-150 nm, 100 nm-500 nm, 100 nm-150 nm, 150 nm-200 nm, 200 nm-250 nm, 250 nm-300 nm, 300 nm-350 nm, 350 nm-400 nm, 400 nm-450 nm, or 450 nm-500 nm. In particular embodiments, nanoparticles greater than 550 nm are excluded. This is because particles or aggregrated particles of >600 nm are not amenable to cellular uptake.

Particular embodiments can also include nanoparticles associated with targeting molecules. Targeting molecules can be used to target the nanoparticle to a specific cell so that activity of the gene editing system can be spatially or temporally controlled. For example, the activity and destination of the gene editing system can be controlled by a targeting molecule that has binding affinity for a cell surface protein or other localized cellular component.

In particular embodiments, targeting molecules include antibodies or binding domains thereof that result in selective delivery of nanoparticles to selected cell types. In particular embodiments, selective delivery is exclusive to a selected cell population. In particular embodiments, at least 65%, 70%, 75%, 80%, 85%, 90%, 95% or 99% of administered nanoparticles are delivered to a selected cell population.

In particular embodiments, binding domains include cell marker ligands, receptor ligands, antibodies, peptides, peptide aptamers, nucleic acids, nucleic acid aptamers, spiegelmers or combinations thereof. Within the context of selected cell targeting ligands, binding domains include any substance that binds to another substance to form a complex capable of supporting selective delivery.

As indicated, "antibodies" are one example of binding domains and include whole antibodies or binding fragments of an antibody, e.g., Fv, Fab, Fab', F(ab')$_2$, Fc, and single chain Fv fragments (scFvs) or any biologically effective fragments of an immunoglobulin that bind specifically to a motif expressed by a selected cell type. Antibodies or antigen binding fragments include all or a portion of polyclonal antibodies, monoclonal antibodies, human antibodies, humanized antibodies, synthetic antibodies, chimeric antibodies, bispecific antibodies, mini bodies, and linear antibodies.

Antibodies from human origin or humanized antibodies have lowered or no immunogenicity in humans and have a lower number of non-immunogenic epitopes compared to non-human antibodies. Antibodies and their fragments will generally be selected to have a reduced level of antigenicity in human subjects.

In particular embodiments, HSCs are targeted for selective delivery of nanoparticles. In particular embodiments, HSCs are targeted for selective delivery with binding domains that selectively bind CD34 and CD90. In particular embodiments, HSC can be targeted for selective delivery with one or more binding domains that selectively bind known antigens expressed on the surface of HSCs and HSPCs: CD34, CD46, CD90, CD133, Sca-1 and/or CD117.

Mature T cells can be targeted for selective delivery with binding domains that selectively bind CD3. Activated T-cells can be targeted for selective delivery with binding domains that selectively bind 4-1BB (CD137), CD69, and/or CD25. T helper cells can be targeted for selective delivery with binding domains that selectively bind CD4. Cytotoxic T-cells can be targeted for selective delivery with binding domains that selectively bind CD8. "Central memory" T-cells (or "TCM") can be targeted for selective delivery with binding domains that selectively bind CD62L, CCR7, CD25, CD127, CD45RO, and/or CD95. "Effector memory" T-cell (or "TEM") can be targeted for selective delivery with binding domains that selectively bind granzyme B and/or perforin. Regulatory T cells ("TREG") can be targeted for selective delivery with binding domains that selectively bind CD25, CTLA-4, GITR, GARP and/or LAP. "Naive" T-cells can be targeted for selective delivery with binding domains that selectively bind CD62L, CCR7, CD28, CD127 and/or CD45RA.

Natural killer cells (also known as NK cells, K cells, and killer cells) can be targeted for selective delivery with binding domains that selectively bind CD8, CD16 and/or CD56.

Macrophages (and their precursors, monocytes) can be targeted for selective delivery with binding domains that selectively bind CD11b, F4/80; CD68; CD11c; IL-4Rα; and/or CD163.

Immature dendritic cells (i.e., pre-activation) can be targeted for selective delivery with binding domains that selectively bind: CD1a, CD1b, CD1c, CD1d, CD21, CD35, CD39, CD40, CD86, CD101, CD148, CD209, and/or DEC-205.

B cells can be targeted for selective delivery with binding domains that selectively bind CD5, CD19, CD20, CD21, CD22, CD35, CD40, CD52, and/or CD80.

Lymphocyte function-associated antigen 1 (LFA-1) is expressed by all T-cells, B-cells, and monocytes/macrophages. Accordingly, selected cell targeting ligands can bind LFA-1 to achieve selective delivery of nanoparticles to T-cells, B-cells, and monocytes/macrophages.

In particular embodiments, a targeting molecule can be responsive to, i.e. activated or inactivated by, an effector on or in the cell. In particular embodiments, other components within a sequence can include regulatory nucleotides such as a promoter element, a small interfering or hairpin RNA or a microRNA to control expression of another gene in the same cell, or a DNA barcode for cellular tracking.

Aptamers may be designed to facilitate selective delivery, including delivery across the cellular membrane, to intracellular compartments, or into the nucleus. Such a structure can include, either in addition to the one or more aptamer(s) or without such one or more aptamer(s), moiety(ies) so as to render the guide deliverable, inducible or responsive to (for example activatable or inactivatable by) a selected effector, for example responds to normal or pathological physiological conditions, including without limitation pH, hypoxia, $O_2$ concentration, temperature, protein concentration, enzymatic concentration, lipid structure, light exposure, mechanical disruption (e.g., ultrasound waves), magnetic fields, electric fields, or electromagnetic radiation. Methods of making aptamers and conjugating such aptamers to the surface of a nanoparticle are known in the art, see for example Huang et al. Anal. Chem., 2008, 80 (3), pp 567-572.

In particular embodiments, an RNA aptamer sequence has binding affinity for an aptamer ligand on or in the cell. In particular embodiments, the aptamer ligand is on the cell, for example so that it is at least partially available on the extra-cellular face or side of the cell membrane. For example, the aptamer ligand may be a cell-surface protein. The aptamer ligand may therefore be one part of a fusion protein, one other part of the fusion protein having a membrane anchor or membrane-spanning domain. In particular embodiments, the aptamer ligand is in the cell. For example, the aptamer ligand may be internalized within a cell, i.e. within (beyond) the cell membrane, for example in the cytoplasm, within an organelle (including mitochondria), within an endosome, or in the nucleus. In particular embodiments, an aptamer can include a donor template sequence, which can include an HDR template and a therapeutic nucleic acid sequence.

(IV) Conjugation of Active Components to Nanoparticles. As indicated, a variety of active components can be conjugated to the nanoparticles disclosed herein for targeted gene editing. For example, nucleic acids that are gene editing system components can be conjugated directly or indirectly, and covalently or noncovalently, to the surface of the nanoparticle. For example, a nucleic acid may be covalently bonded at one end of the nucleic acid to the surface of the nanoparticle.

Nucleic acids conjugated to the nanoparticle can have a length of from 10 nucleotides (nt)-1000 nt, e.g., 1 nt-25 nt, 25 nt-50 nt, 50 nt-100 nt, 100 nt-250 nt, 250 nt-500 nt, 500 nt-1000 nt or greater than 1000 nt. In particular embodiments, nucleic acids modified by conjugation to a linker do not exceed 50 nt or 40 nt in length.

When conjugated indirectly through, for example, an intervening linker, any type of molecule can be used as a linker. For example, a linker can be an aliphatic chain including at least two carbon atoms (e.g., 3, 4, 5, 6, 7, 8, 9, 10, 11, 12, 13, 14, or more carbon atoms), and can be substituted with one or more functional groups including a ketone, ether, ester, amide, alcohol, amine, urea, thiourea, sulfoxide, sulfone, sulfonamide, and/or disulfide.

In particular embodiments the linker includes a disulfide at the free end (e.g. the end not conjugated to the guide RNA) that couples the nanoparticle surface. In particular embodiments, the disulfide is a $C_2$-$C_{10}$ disulfide, that is it can be an aliphatic chain terminating in a disulfide that includes 2, 3, 4, 5, 6, 7, 8, 9, or 10 carbon atoms, although it is envisioned that longer aliphatic chains can be used. In particular embodiments, the disulfide is a 3 carbon disulfide (C3 S—S). Linkers can have either sulfhydryl groups (SH) or disulfide groups (S—S) or a different number of sulfur atoms. In particular embodiments, a thiol modification can be introduced without using a linker. In particular embodiments, a nuclease enzyme is delivered as a protein pre-conjugated with its guide RNA (a ribonucleoprotein (RNP) complex). In this formulation, the guide RNA molecule is bound to the nanoparticle and the nuclease enzyme, by default, can be also bound (see, for example, FIGS. 7B and 7D).

One advance disclosed herein is the ability to modify CRISPR components for linkage to a nanoparticle. This is because most of the modifications in CRISPR components can compromise cutting efficiency. For example, Li et al. (Engineering CRISPR-Cpf1 crRNAs and mRNAs to maximize genome editing efficiency. 2017. 1: p. 0066) indicated that the 5' end of Cpf1 crRNA is not safe for any modification because such modifications result in the abrogation of the crRNA binding to Cpf1 nuclease. Disclosed herein is a modification to the 3' end of crRNA that does not compromise cutting efficiency. In particular embodiments, in the first step of conjugation to a nanoparticle the 3' end of the crRNA is modified with an 18-atom hexa-ethyleneglycol spacer (18 spacer) and 3 carbon disulfide (C3 S—S) to attach the crRNA to the surface of AuNPs.

Based on the foregoing, in particular embodiments, for example when the nanoparticle includes gold, a linker can be any thiol-containing molecule. Reaction of a thiol group with Au results in a covalent sulfide (—S—) bond. AuNPs have high affinity to thiol (—SH) and dithiol (S—S) groups and semi-covalent bonds occur between the surface of AuNP and sulfur groups (Hakkinen, Nat Chem, 2012. 4(6): p. 443-455). In particular embodiments, thiol groups can be added to nucleic acids to facilitate attachment to the surface of AuNPs. This approach can improve nucleic acid uptake and stability (see, e.g., Mirkin, et al., A Nature, 1996. 382(6592): p. 607-609).

Figure 7A:
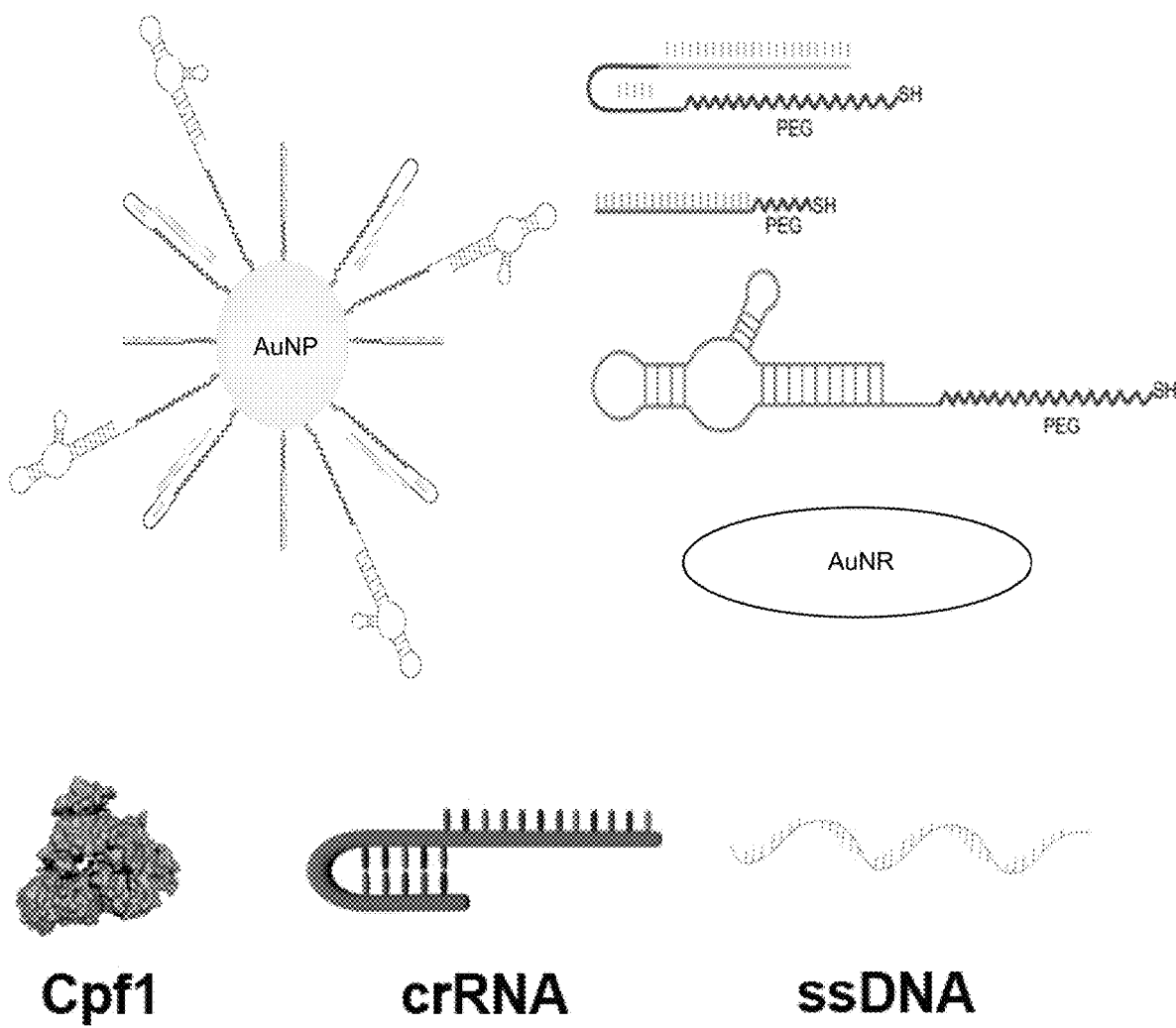
FIGS. 7A-7D. Schematics depicting an exemplary AuNP associated with all gene editing components required for gene addition and/or correction.
Figure 7B:
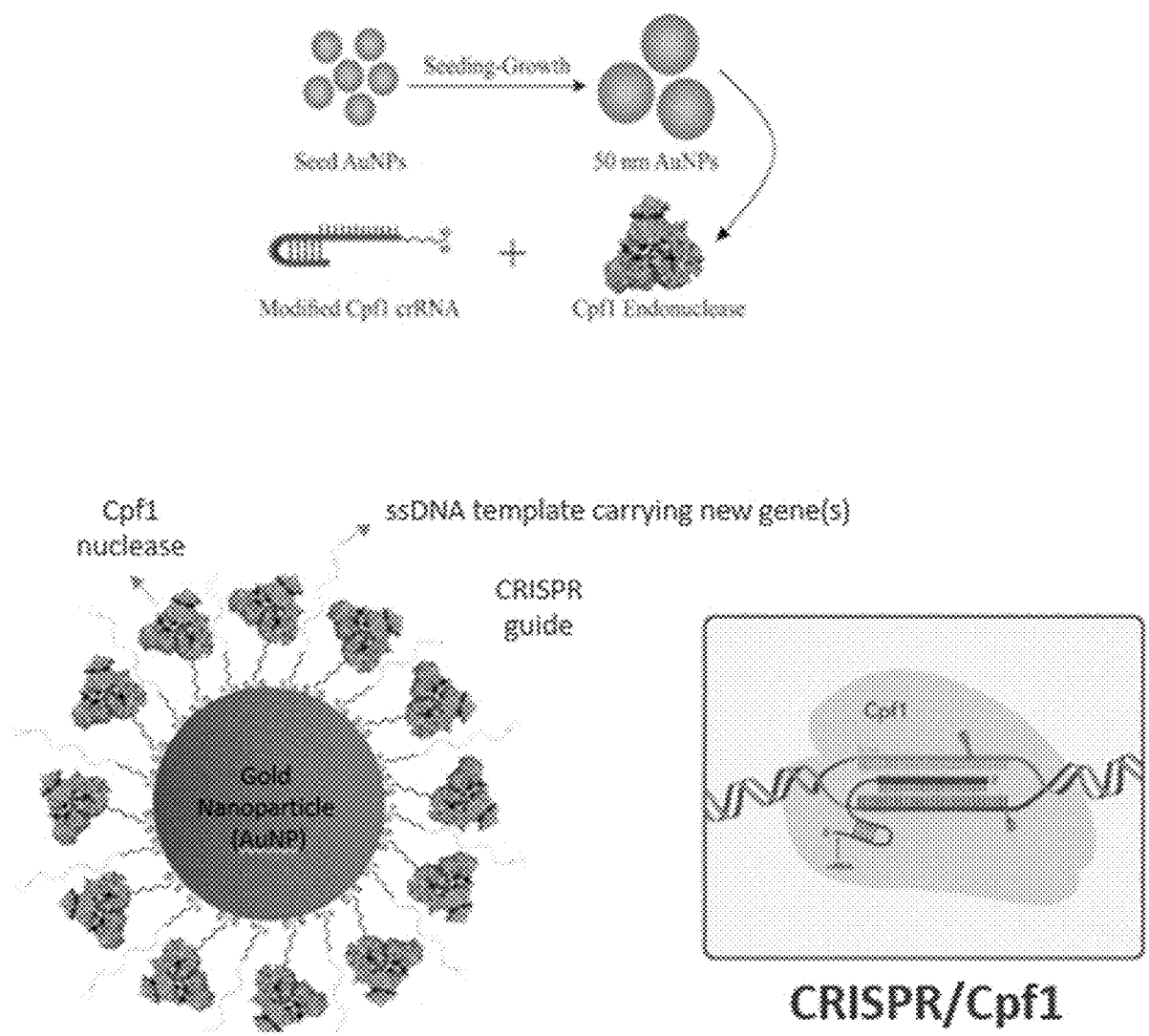
Figure 7C:
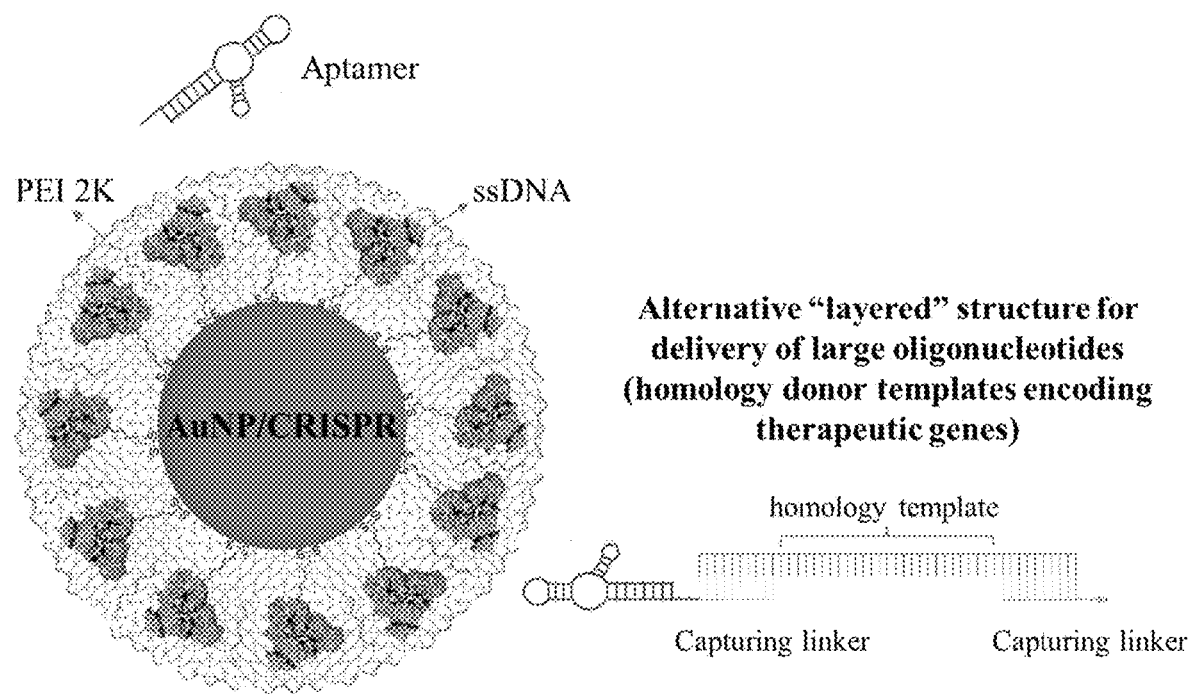
Figure 7D:
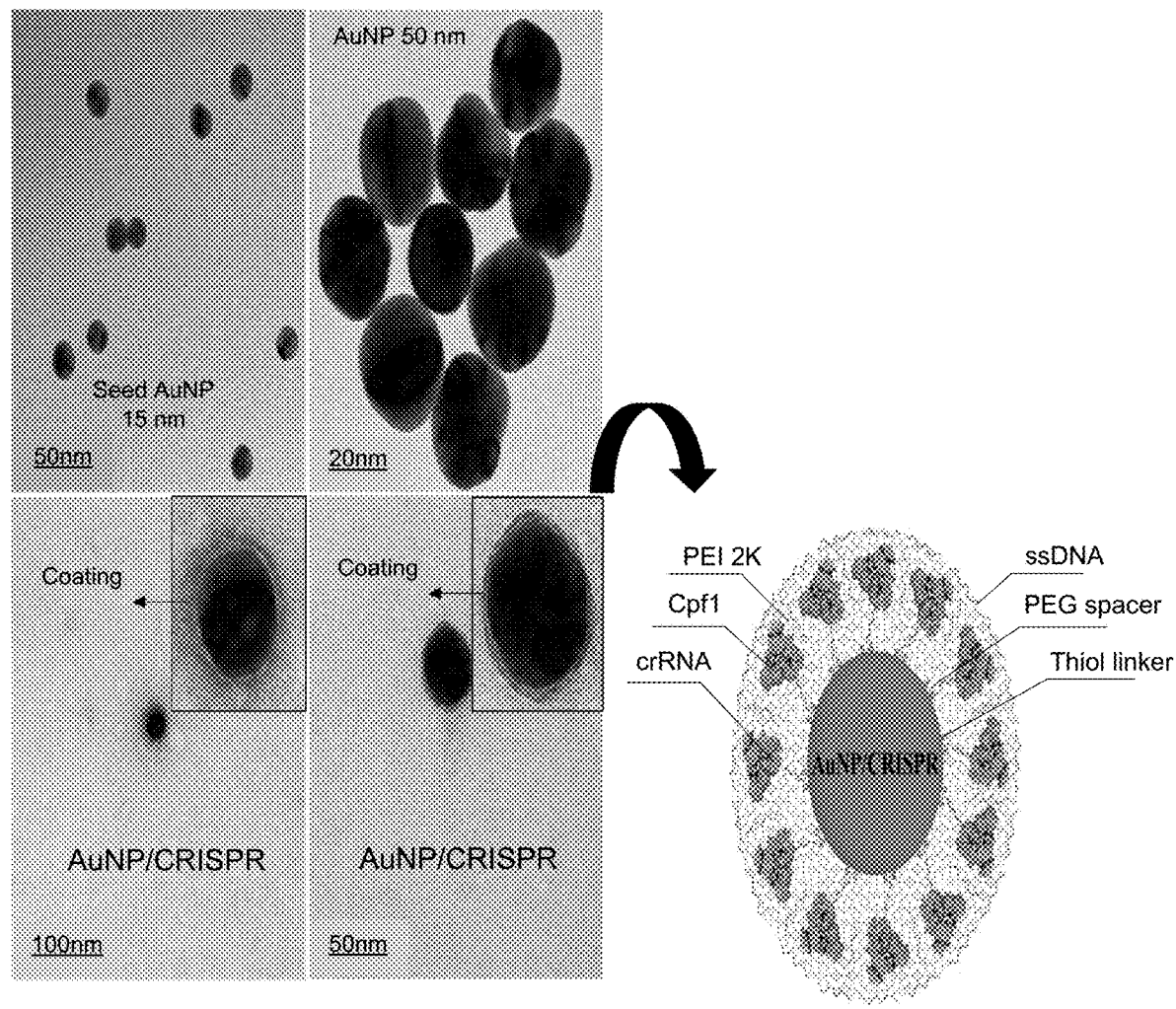
Figure 8:
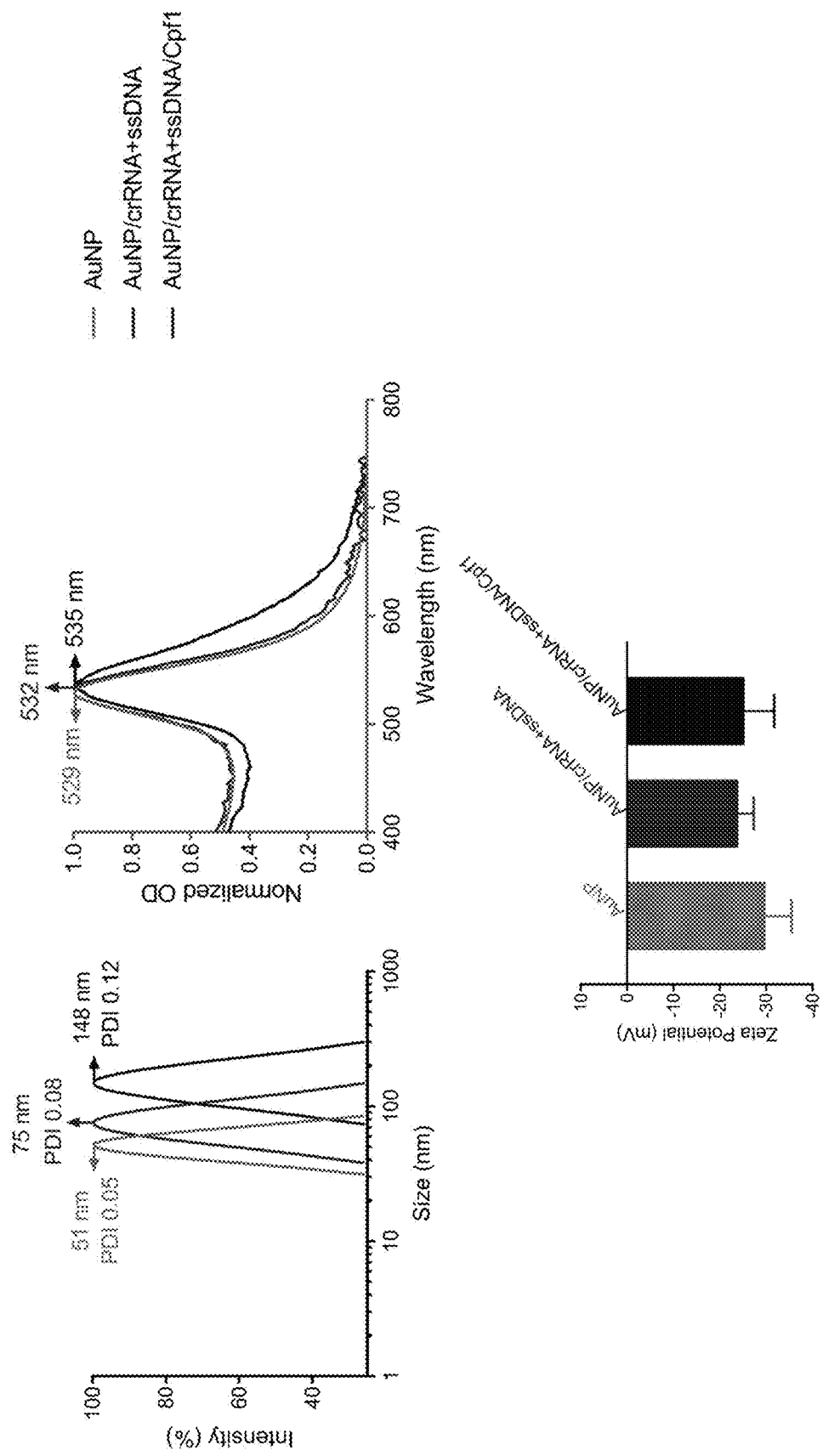
FIG. 8. Fully-loaded AuNPs are monodisperse and display good zeta potential.

Using an optimized two step method of seeding-growth, highly monodisperse AuNPs were synthesized in 3 different size ranges (15 nm, 50 nm, 100 nm) and conjugated with Cpf1 crRNA and endonuclease (FIGS. 7B, 7D, 100). Because of the strong electrostatic repulsion between the negatively charged surface and negatively charged crRNA it is difficult to attach the crRNA to the surface of AuNPs without, for example, the thiol modification. In particular embodiments, in the second step, after purification of the crRNA conjugated AuNPs, Cpf1 endonuclease is added and incubated with crRNA conjugated AuNPs to facilitate its binding to the 5' handle of the crRNA (Dong, et al., Nature, 2016. 532(7600): p. 522-526). The compact structure of the designed nanoformulation containing both crRNA and Cpf1 endonuclease results in a conformation which increases the stability against degrading agents and facilitates the uptake of the AuNP/CRISPR nanoformulation by cells owing to an overall neutral charge (i.e., zeta potential). While special relevance was given to optimizing the disclosed nanoformulation for CRISPR/Cpf1, the same concept may be applied to other CRISPR classes. Also, along with the crRNA and Cpf1 endonuclease, 18 spacer thiol modified single stranded DNA (ssDNA) can be attached to the surface of AuNPs to obtain a novel nanoformulation with the aim of being used in homology directed repair (HDR).

In particular embodiments, a spacer-thiol linker can be added to either of the Cpf1 or Cas9 proteins themselves or engineered variants of the foregoing (e.g., as described below), by addition of a cysteine residue on either the N- or C-terminus. The nuclease protein can then be added as a first layer on the gold nanoparticle surface. This spacer-thiol linker can increase the stability of the protein and increase cutting efficiency. In particular embodiments, an RNA complex is formed between crRNA and nuclease and then attached to the surface of gold nanoparticles through a spacer-thiol linker.

As indicated previously, adding gene-editing components of a bacterial origin as a first loading step can provide beneficial shielding of these components following administration to a subject with pre-existing immunity to the component. The shielding can be due to other gene-editing components (e.g., donor templates) and need not rely on a protective polymer shell. In particular embodiments, a polymer shell is excluded. In particular embodiments, the shielding may permit serial in vivo administration.

In particular embodiments, crRNAs can be added to AuNPs in different AuNP/crRNA w/w ratios (0.25, 0.5, 1, 1.5, 2, 3, 4, 5, 6) and mixed. Citrate buffer with the pH of 3 can be added to the mixture in 10 mM concentration to screen the negative repulsion between negatively charged crRNA and AuNP. After stirring for 5 min, nanoparticles can be centrifuged down and the unbound crRNA can be visualized by agarose gel electrophoresis. After determining the optimal conjugation concentration, 1 μL of 63 μM Cpf1 nuclease can be added to AuNP/crRNA solution and incubated for 20 min.

Importantly, the use of a citrate buffer provides significant advantages in manufacturing. Previous methods have relied on the use of NaCl to screen the negatively-charged nanoparticle surface and reduce repulsion of similarly negatively-charged DNA. However, NaCl can cause irreversible aggregation of gold nanoparticles, so it must be added gradually over time with incremental changes in concentration. Generally, NaCl must be added over a 48 hour time period to avoid aggregation. When citrate buffer is used with a pH of 3, this binding can happen with higher efficiency in less than 3 minutes. Zhang, et al. (2012). Journal of the American Chemical Society 134(17): 7266-7269 reducing the cost of goods and time in the GMP manufacturing facility.

Size and morphology of prepared AuNP/CRISPR nanoformulations can be characterized by imaging under transmission electron microscope (TEM). AuNPs (4 μL) can be added to copper grids and allowed to dry out overnight. Imaging is carried out at 120 kV.

CRISPR coating can be visualized by negative staining electron microscopy. AuNP/CRISPR nanoformulation can be stained with 0.7% uranyl formate and 2% uranyl acetate, respectively. Stained sample (4 μL) can be added to carbon-coated copper grid and incubated for 1 min and blotted with a piece of filter paper. After three washing cycles with 20 μl stain solution, 4 μl stain solution can be added to the grids and blotted and air dried.

Also, AuNP/CRISPR nanoformulations can be characterized by Nanodrop UV-visible spectrophotometer by analyzing the shifts in localized surface plasmon resonance (LSPR) peak of the AuNPs before and after conjugation with CRISPR components.

In particular embodiments, a nanoparticle is layered, such as during synthesis to include PEI or other positively charged polymer for increasing surface area and conjugating larger ssDNA or other molecules, such as targeting molecules and/or large donor templates (see, for example, FIG. 7C). This nanoformulation can be prepared in a layer by layer form and positively charged polymers (such as; PEI in different molecular weights and forms) can be used to coat the negatively charged surface of either gold nanoparticles or CRISPR coated gold nanoparticles to attach either gene editing components and other components (such as antibody binding domains). Layering essentially increases the surface area of the nanoparticle available for conjugating molecules such as large oligonucleotides with or without other proteins.

In particular embodiments, PEI can be added as a second layer and ssDNA can be added as a third layer. Alternatively, the conjugation steps can be changed by adding ssDNA as a second layer and PEI as a third layer. In particular embodiments, PEI, polymers, and ssDNA are not included as a first layer, as this layer can be reserved for RNP complexes coupled to linkers.

Figure 9A:
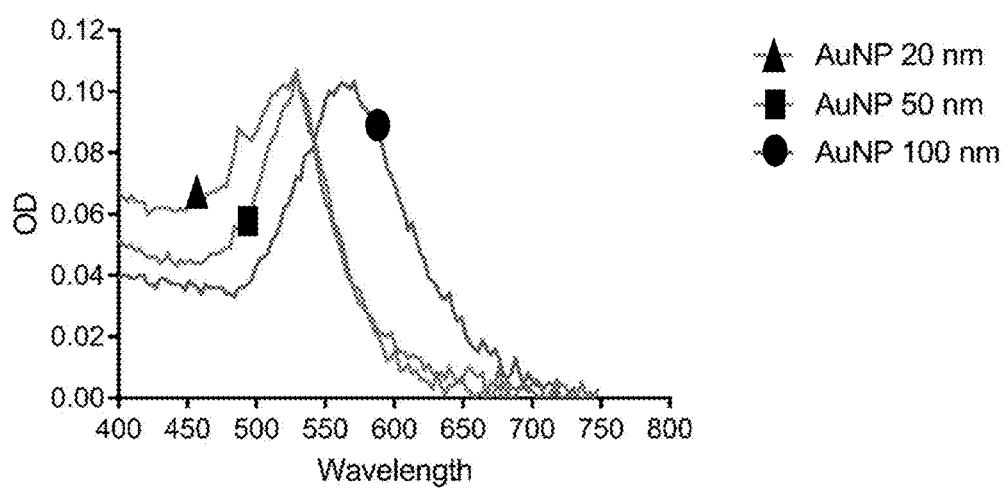
FIGS. 9A-9D. Graphs and digital images showing the characteristic properties of synthesized AuNPs and optimal loading concentrations.
Figure 9B:
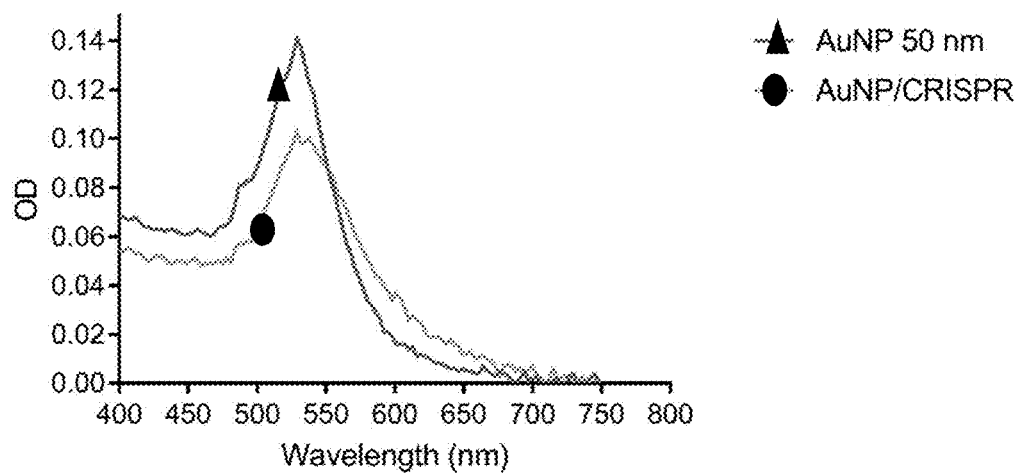

In particular embodiments, a multilayered nanoformulation of the disclosure has an average size of 25-30 nm and is highly monodisperse. Transmission electron microscope images (TEM) and localized surface plasmon resonance shifts (LSPR) of gold nanoparticles (AuNPs) showed a uniform surface coating without any aggregation (FIGS. 9A, 9B). Given the synthetic nature of the entire delivery system, all components can be assembled within a few hours, as opposed to previous approaches which required multiple days due to, for example, use of NaCl as a charge screen.

Figure 9C:
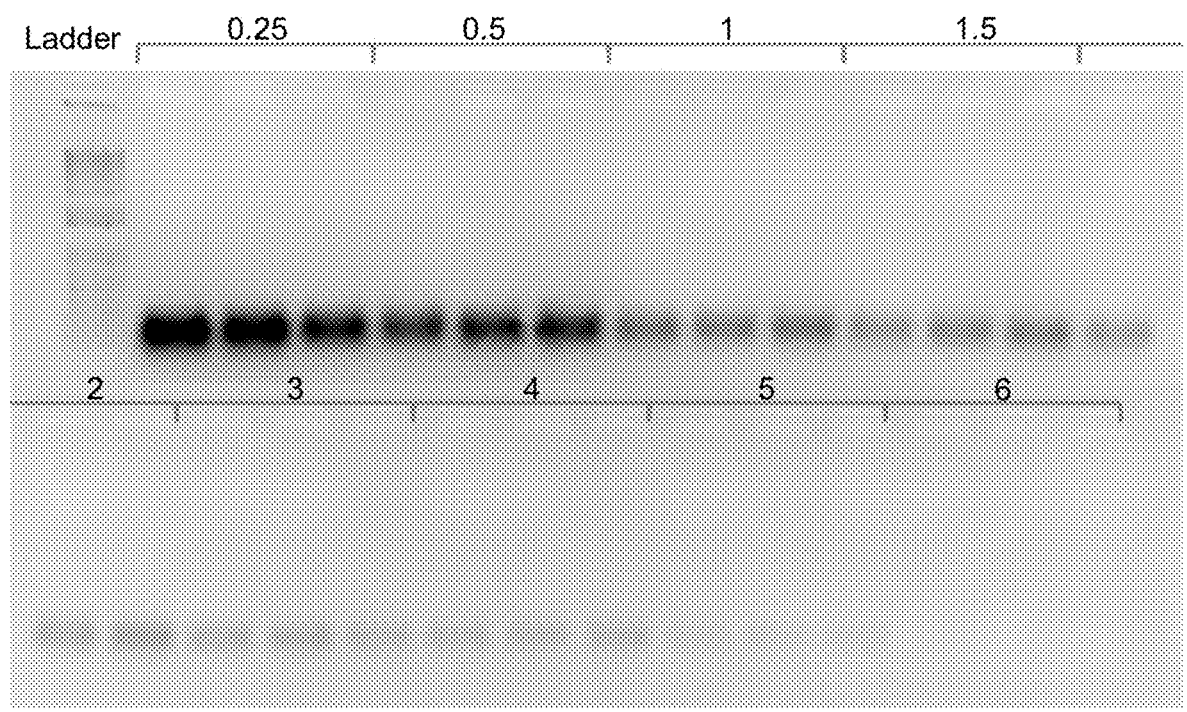
Figure 9D:
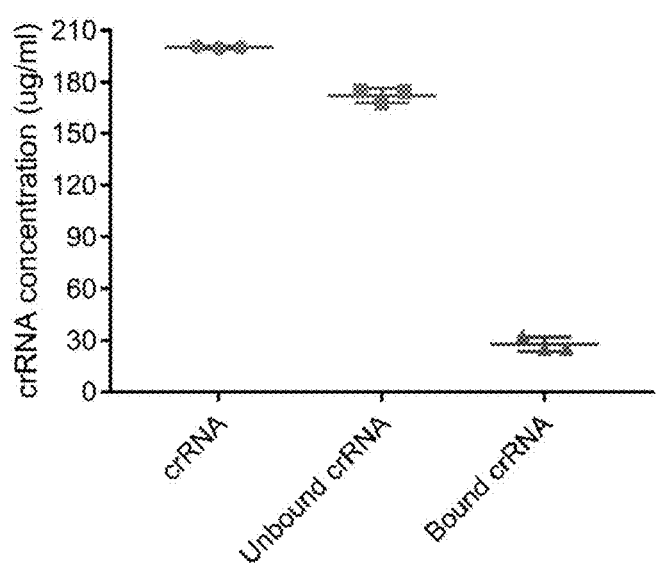
Figure 10B:
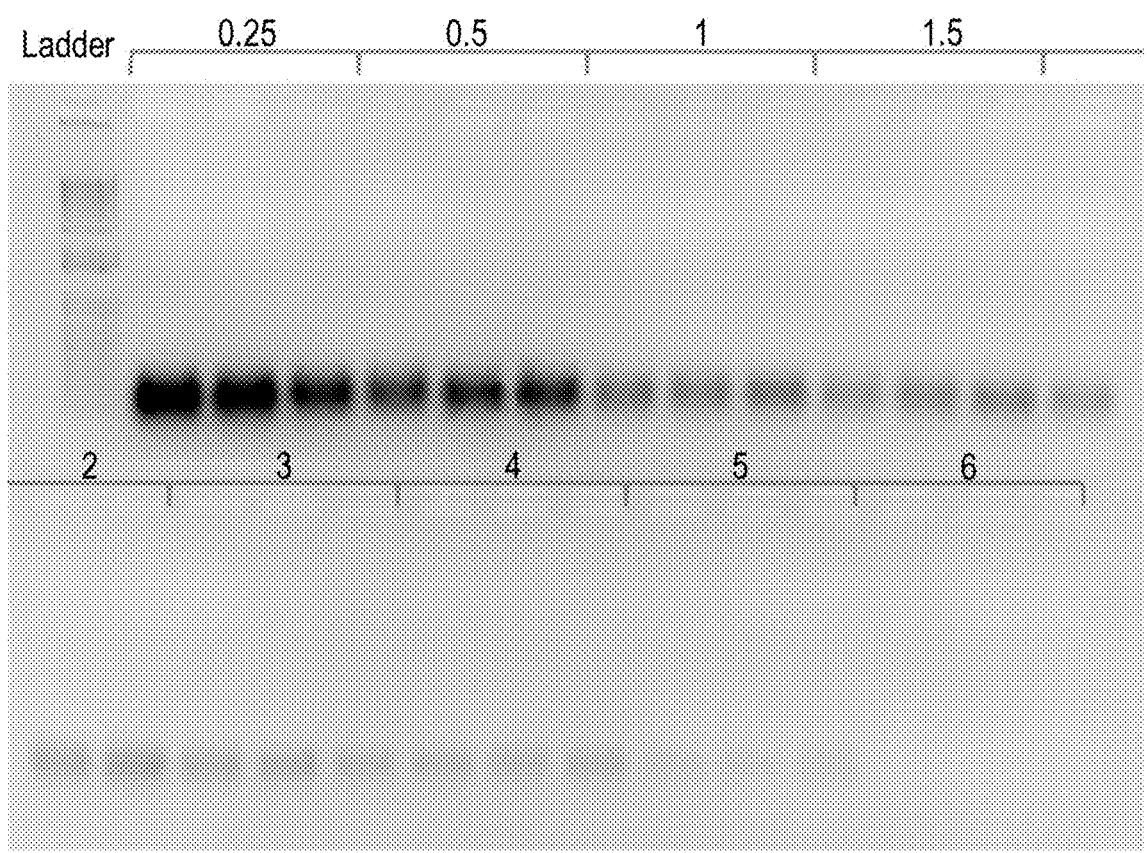
Figure 10C:
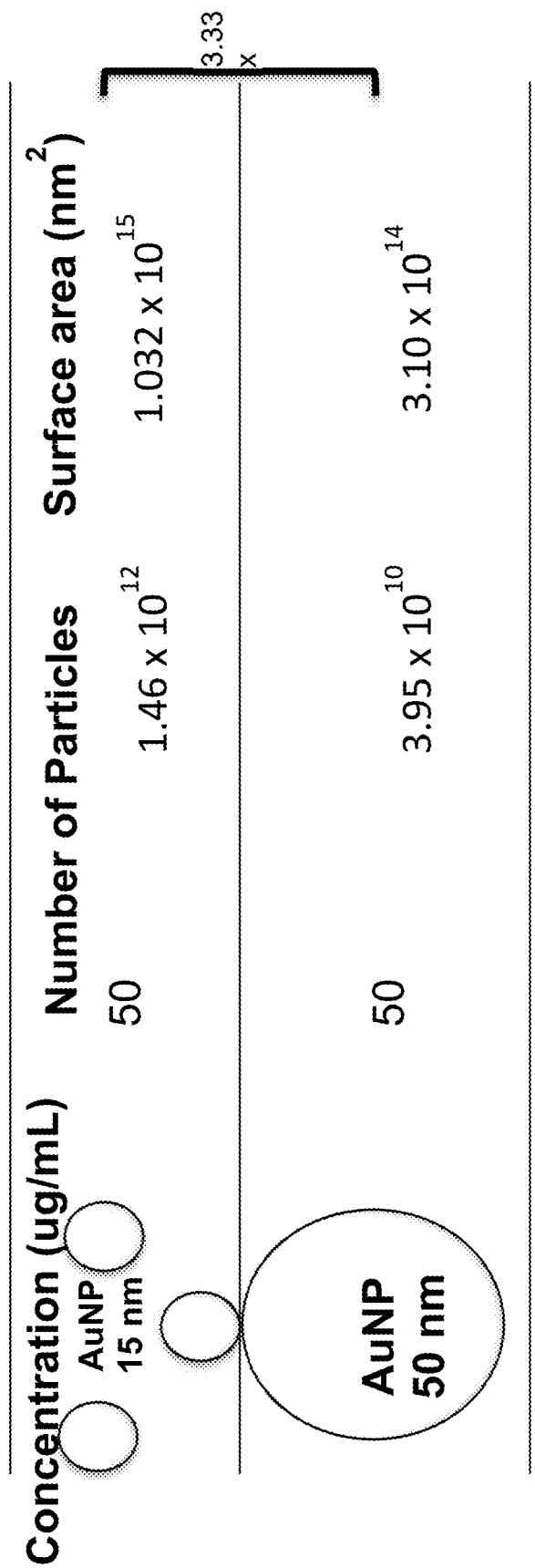
Figure 11A:
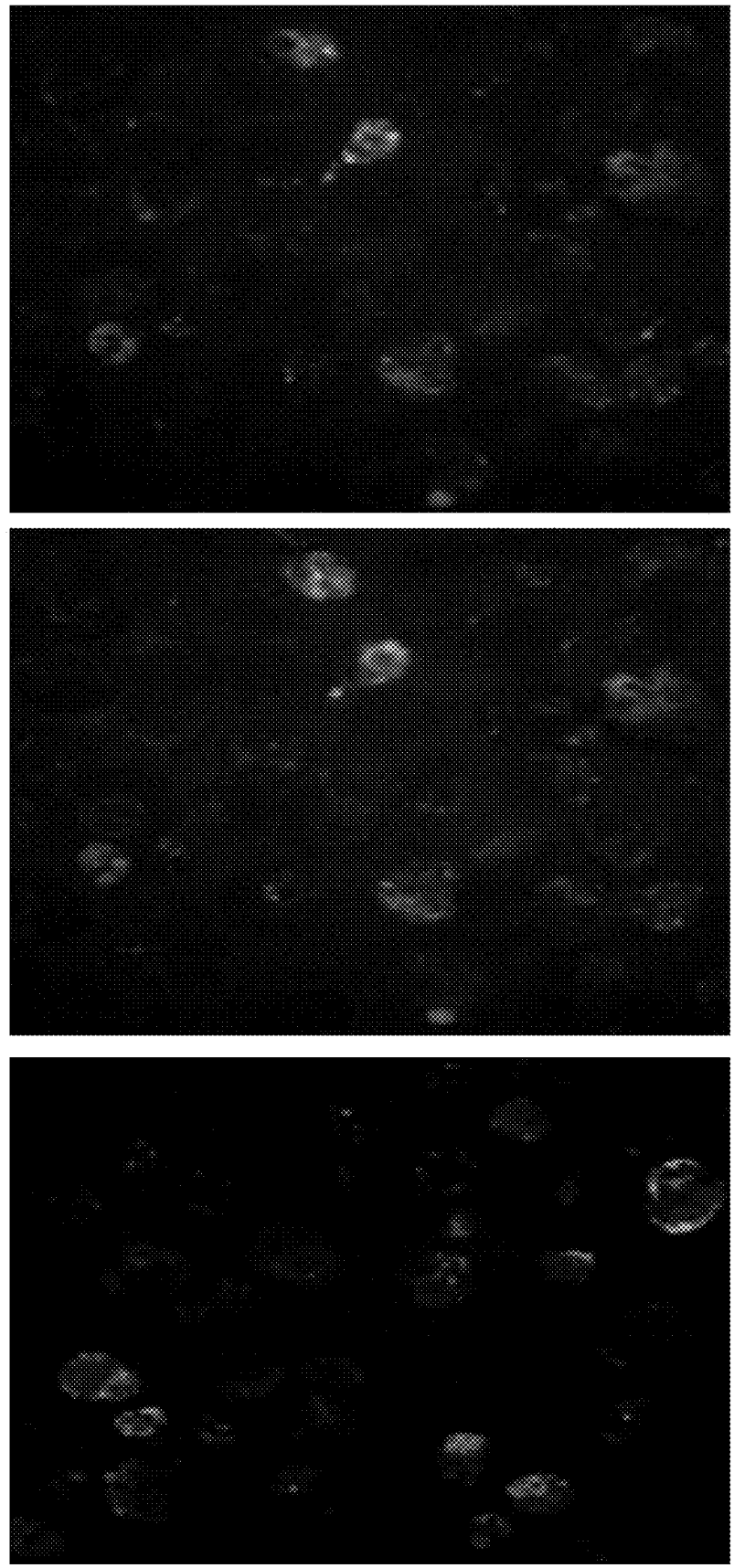
FIGS. 11A, 11B.
Figure 11B:
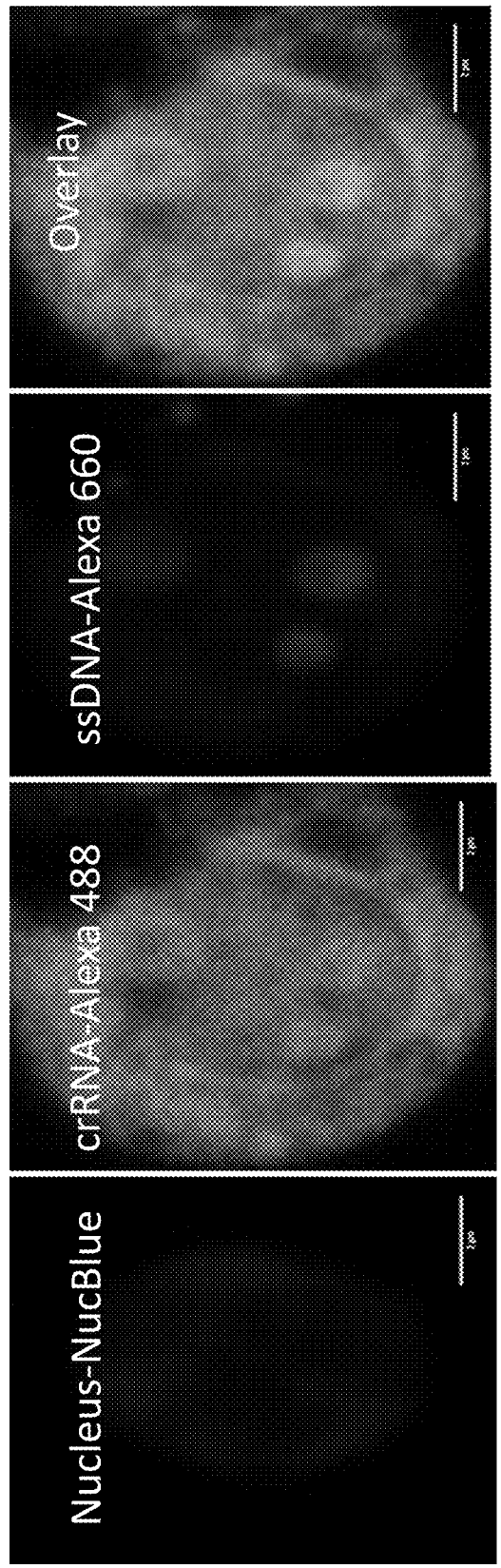

As shown in FIGS. 7D and 9A, synthesized nanoparticles were highly monodisperse and successful 4 nm coating without any aggregation was achieved which increased the size of the nanoparticles to 54 nm after coating for 50 nm AuNPs. Also, decrease in the intensity and red shifting of the localized surface plasmon (LSPR) of AuNPs showed the successful conjugation with CRISPR components without any aggregation (FIG. 9A). Also, oligonucleotide loading studies with the model 18 spacer C3 S—S modified ssDNA in different AuNP/ssDNA w/w ratios showed that the ratio of 6 is optimal to carry out the conjugation (FIG. 9C). Using this optimal loading ratio crRNA was loaded on the surface of AuNPs in 30 μg/mL concentration (FIG. 9D). These data help calculate the exact application dosage for gene editing studies.

The described approaches resulted in a highly potent, loaded, CRISPR nanoformulation capable of delivering both synthetic, non-chemically modified CRISPR Cpf1 or CRISPR Cas9 ribonucleoproteins along with a ssDNA homology template for insertion of new DNA, without the need for electroporation (FIG. 7D). In particular embodiments, the hydrodynamic size of a fully loaded AuNP is 150-190 nm, 160-185 nm, 170-180 nm or 176 nm.

(V) Gene Editing Efficiency. The optimal concentrations of crRNA, hAsCpf1 RNA and ssODN for electroporation were determined in K562 cells. The optimal concentration displays the highest viability and GFP expression. K562 cells were cultured in 24 well plates in $1\times10^5$ cells/well concentration. Iscove's Modified Dulbecco's Medium (IMDM) with 10% FBS and 1% PenStrep was used to culture the cells. CD34+ cells were cultured in 24 well plates in $5\times10^5$ cells/well concentration. Culture conditions for CD34+ cells were the same as K562 cells with required growth factors. AuNP/CRISPR nanoformulations were added in 25 nM concentration to the wells and editing efficiency was evaluated after 48 h incubation. Electroporation of the cells was performed with a Harvard Apparatus ECM 830 Square Wave Electroporation System using BTX Express Solution (USA). in 1 mm cuvettes in 250 V and 5 ms pulse duration. 1 mm BTX cuvettes with a 2 mm gap width were used to electroporate 1-3 million K562 cells at 250V for 5 milliseconds. Cells were resuspended in culture media and analyzed following electroporation.

Figure 12A:
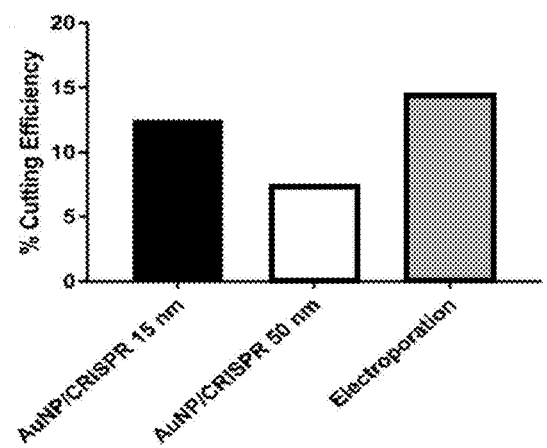
FIGS. 12A-12D. Graphs showing the gene cutting efficiency in K562 cells and CD34+ cells.
Figure 12B:
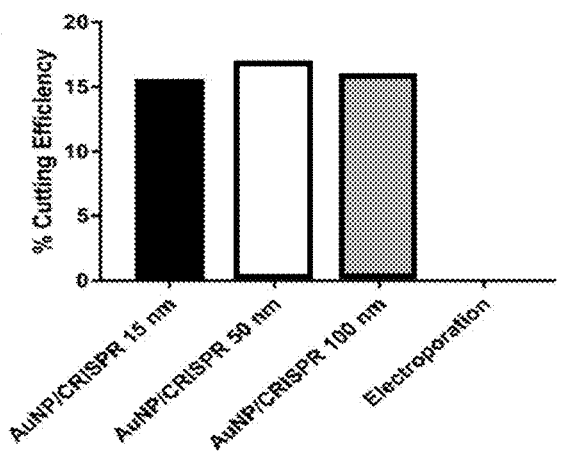
Figure 12C:
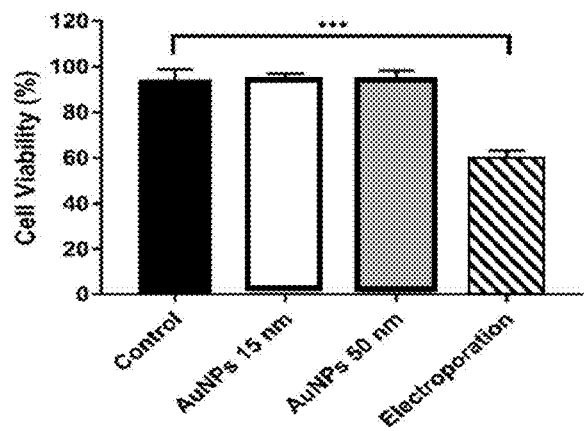
Figure 12D:
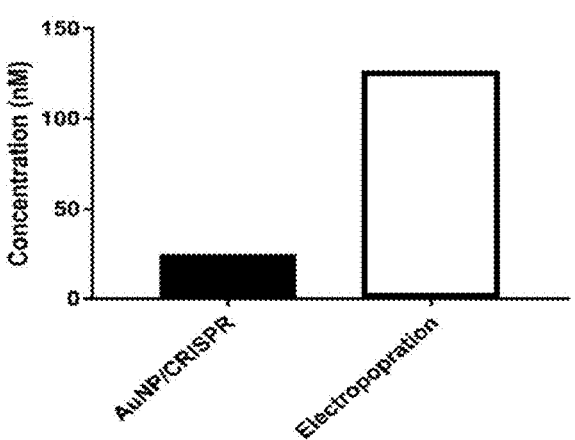
Figure 14:
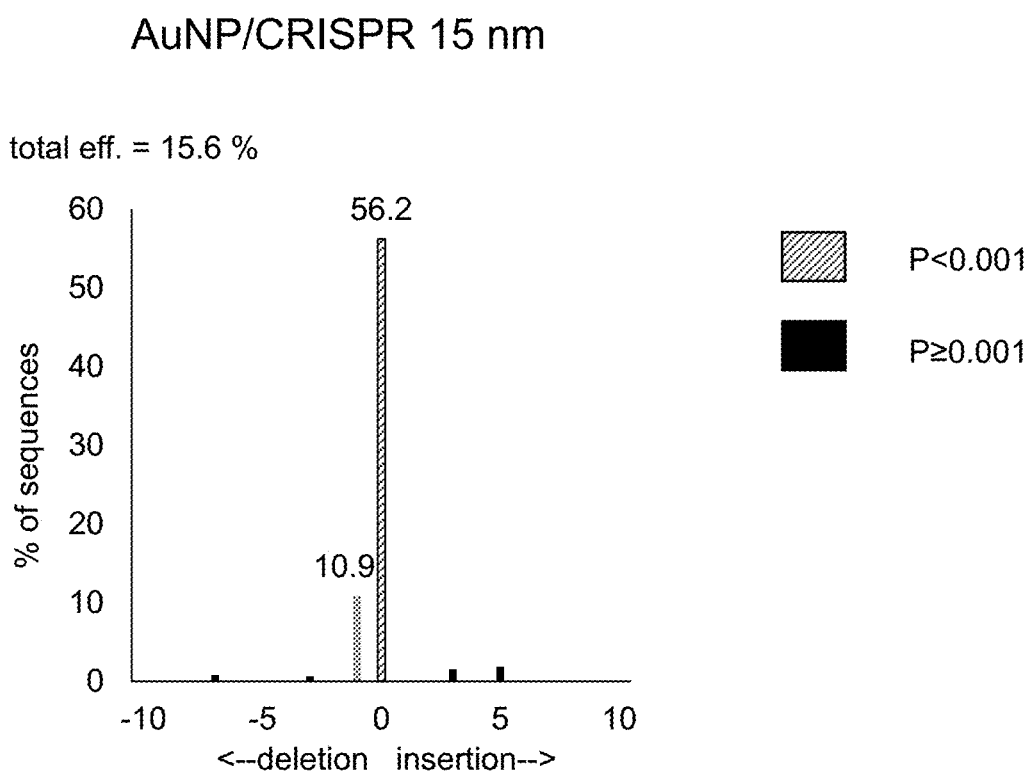
FIG. 14. TIDE assay results showing indels after editing with AuNP/CRISPR nanoformulations in CD34+ cells.
Figure 14:
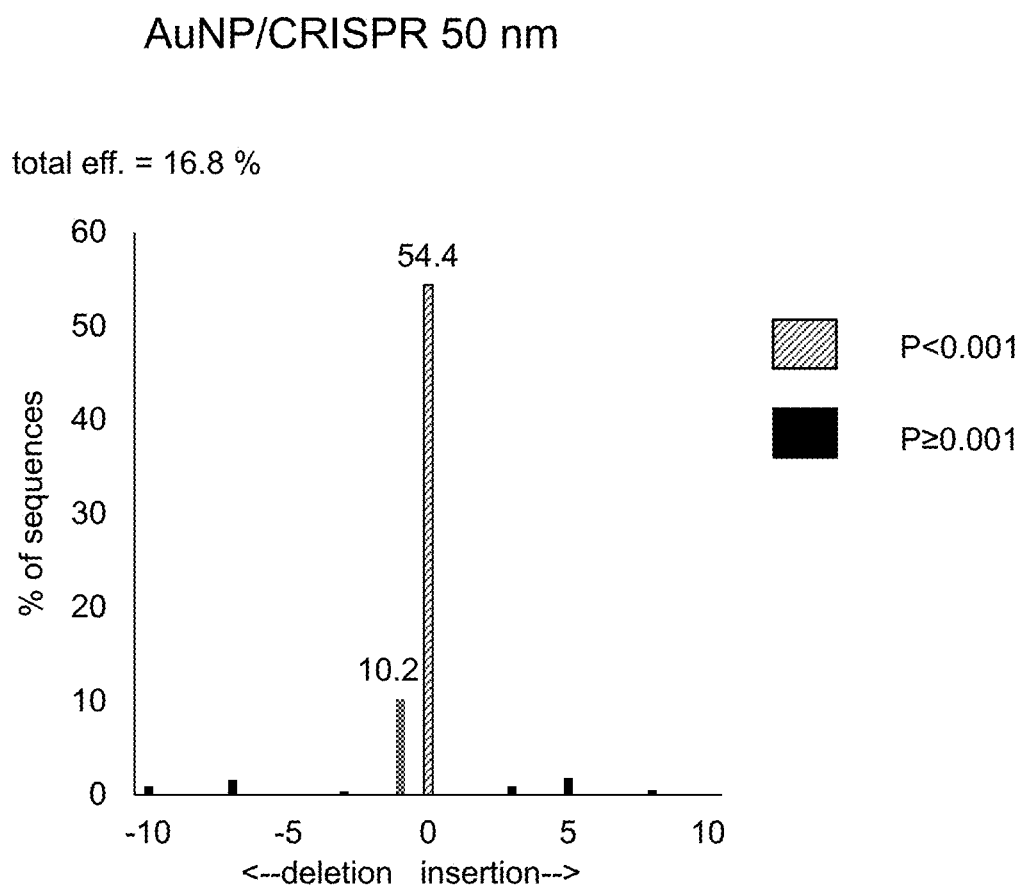
Figure 14:
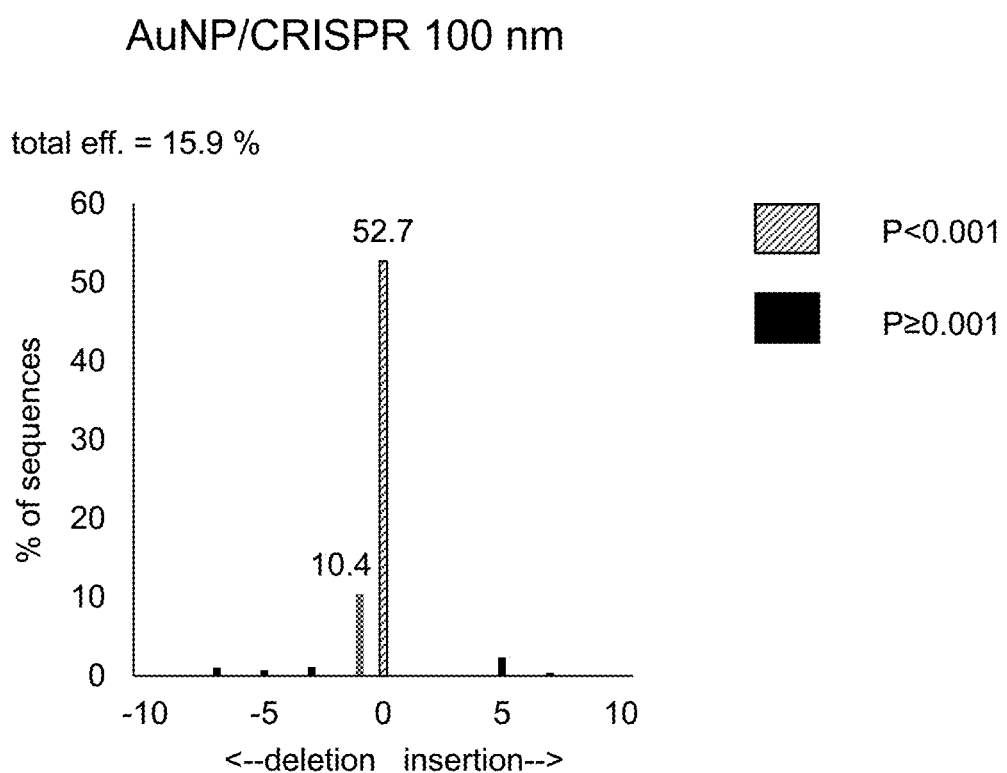
Figure 15A:
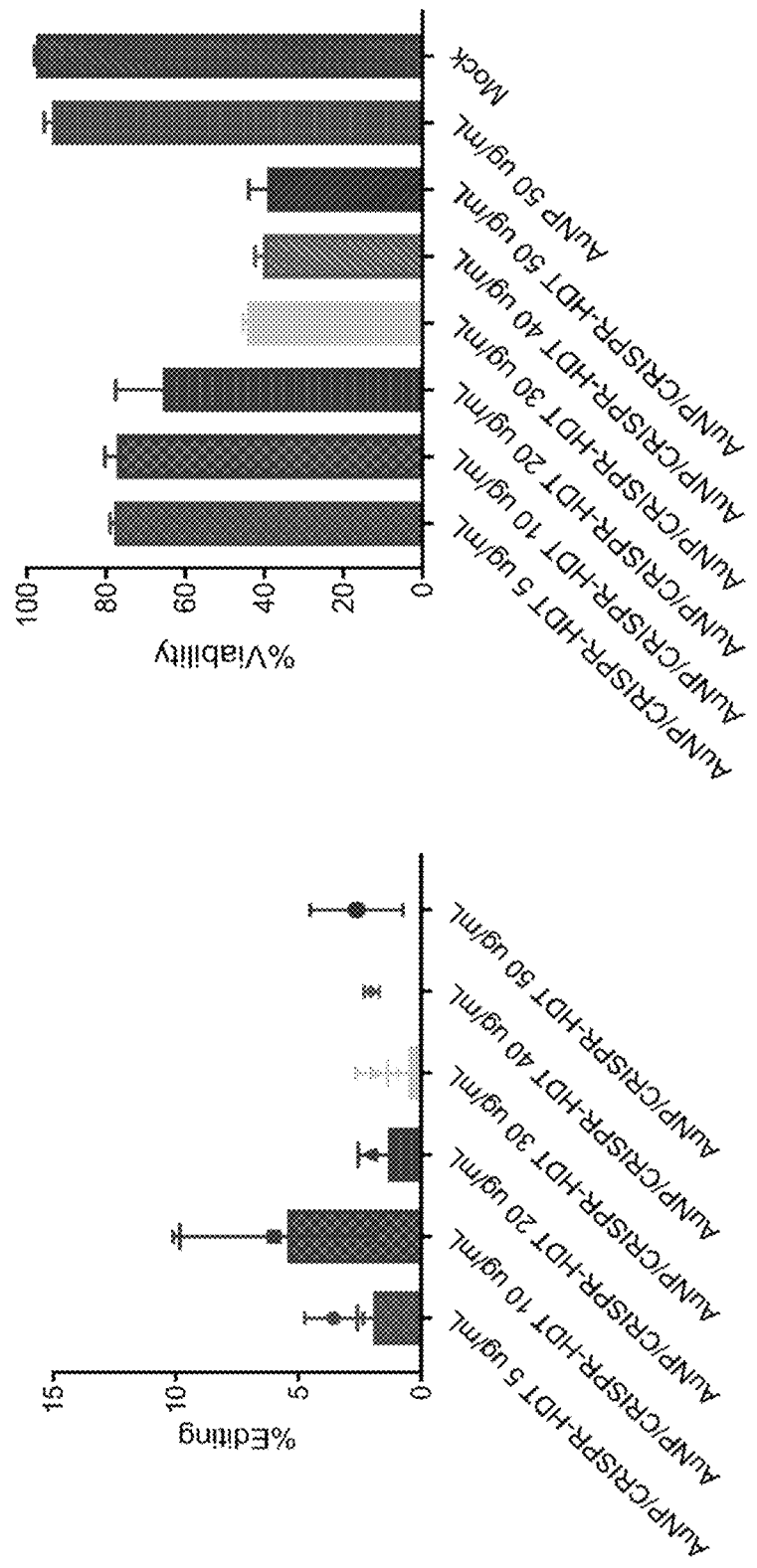
FIGS. 15A-15D.
Figure 15B:
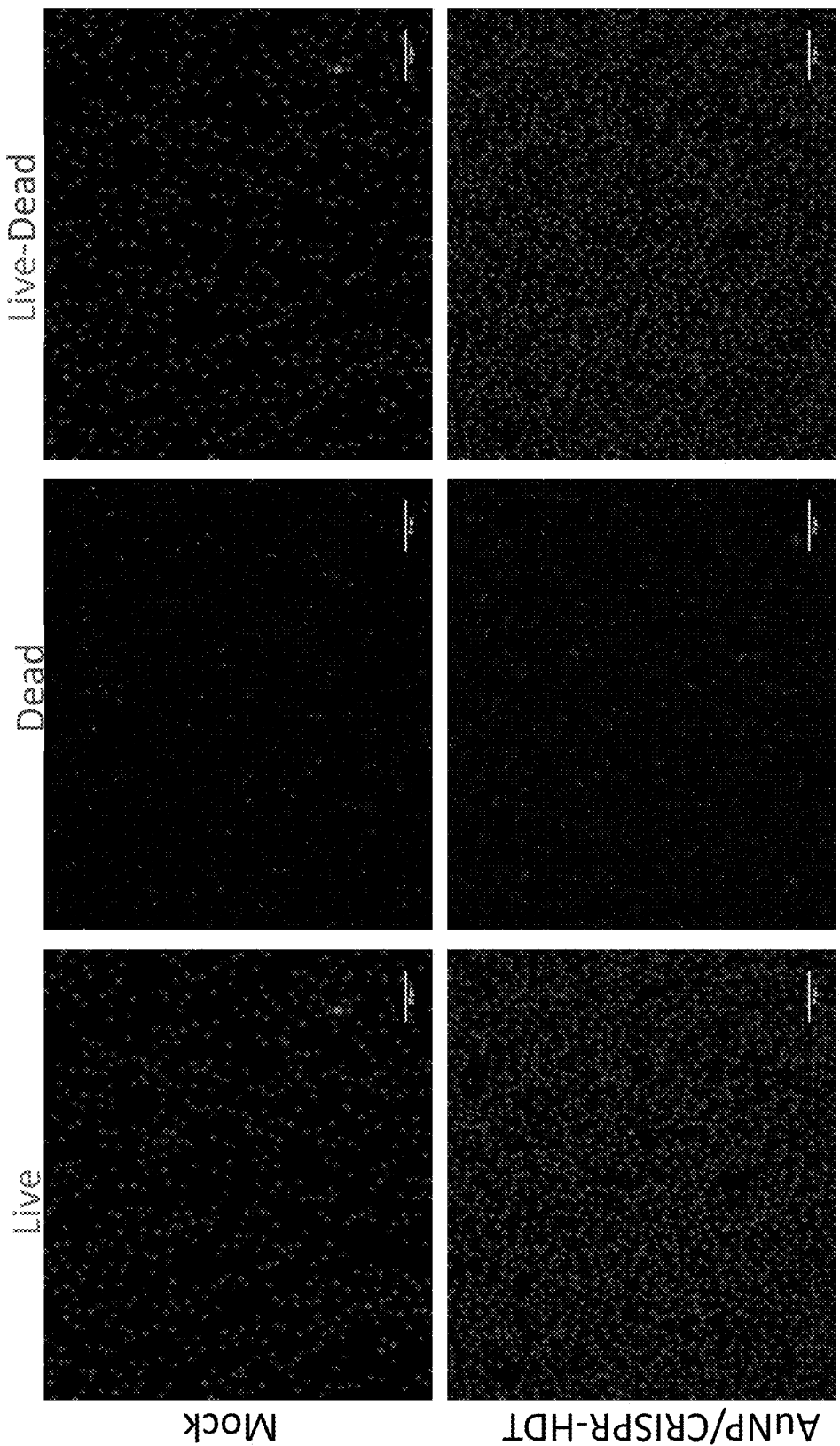
Figure 15C:
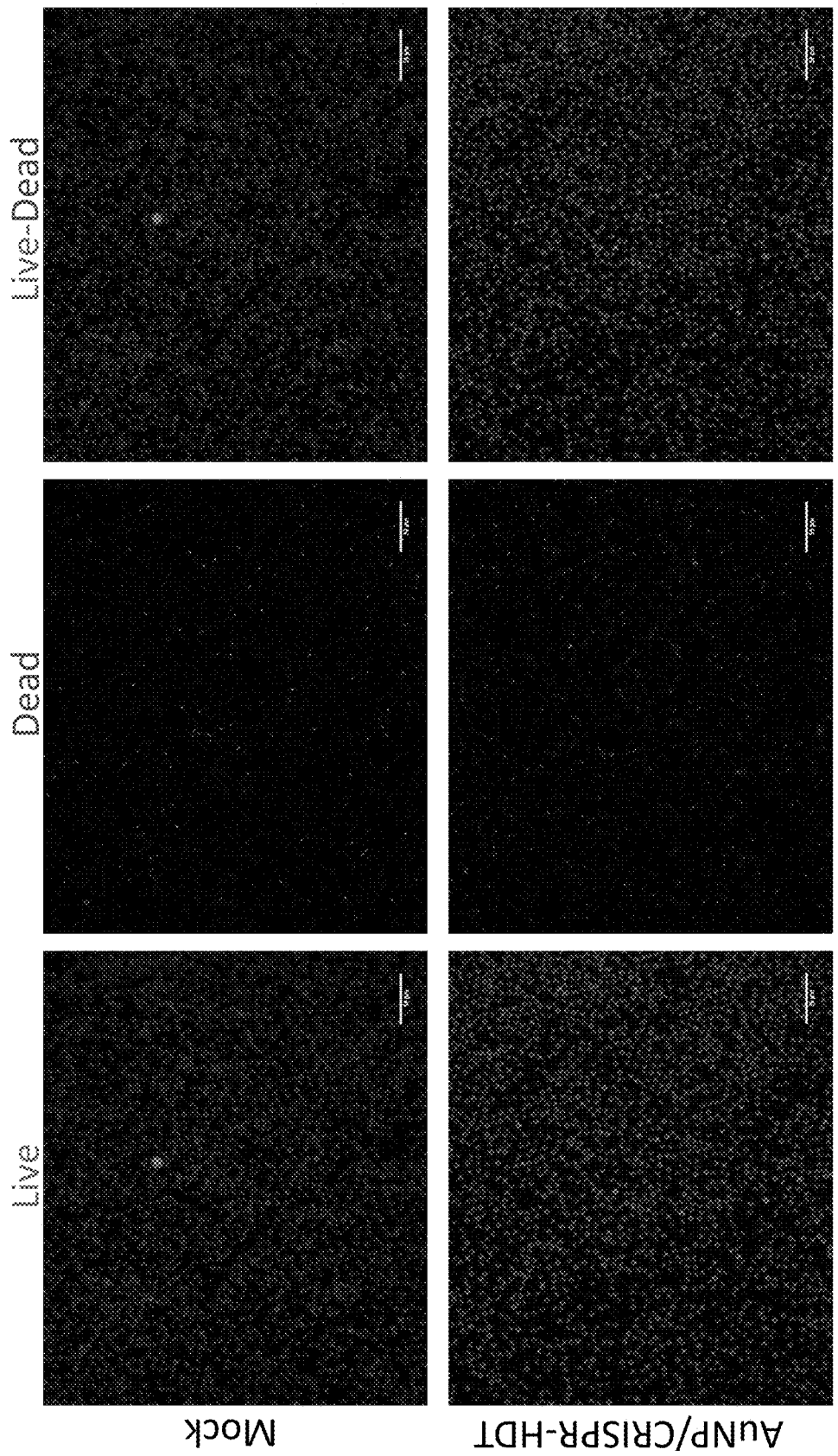
Figure 15D:
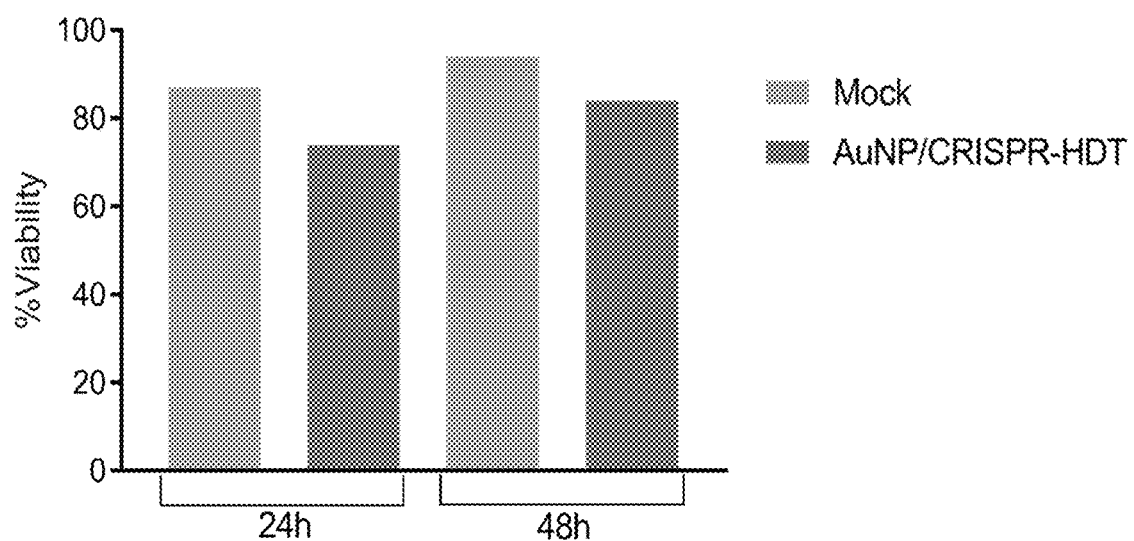

AuNP/CRISPR nanoformulations targeting the chr11: 67812349-67812375 location were able to successfully cut the target site in very low crRNA and Cpf1 endonuclease concentrations (25 nM) in comparison to electroporation method in which a higher amount of crRNA and Cpf1 was used (126 nM) (FIG. 12A) to achieve the same efficiency of cutting. Cutting efficiency for this site was low due to the A>T mutation 15 bp after the PAM site (FIG. 2). In the next test, the same location was targeted in primary CD34+ cells and it was shown that AuNP/CRISPR nanoformulations were able to target the site in a very low crRNA and Cpf1 endonuclease concentrations with very good cutting efficiency without raising any toxic effects (FIGS. 12B, 12C, and 14). Unfortunately, electroporation of the primary CD34+ cells adversely affected the viability of the cells and no cutting was seen for electroporated cells. Calculated concentration for AuNP/CRISPR nanoformulation was 5 fold lower than required concentration for electroporation method (FIG. 12D). As previously mentioned by Kim et al. (Nat Biotechnol, 2016. 34(8): p. 863-8), the rate of deletions to insertions was higher with the CRISPR Cpf1 gene editing system (FIG. 14).

Figure 16:
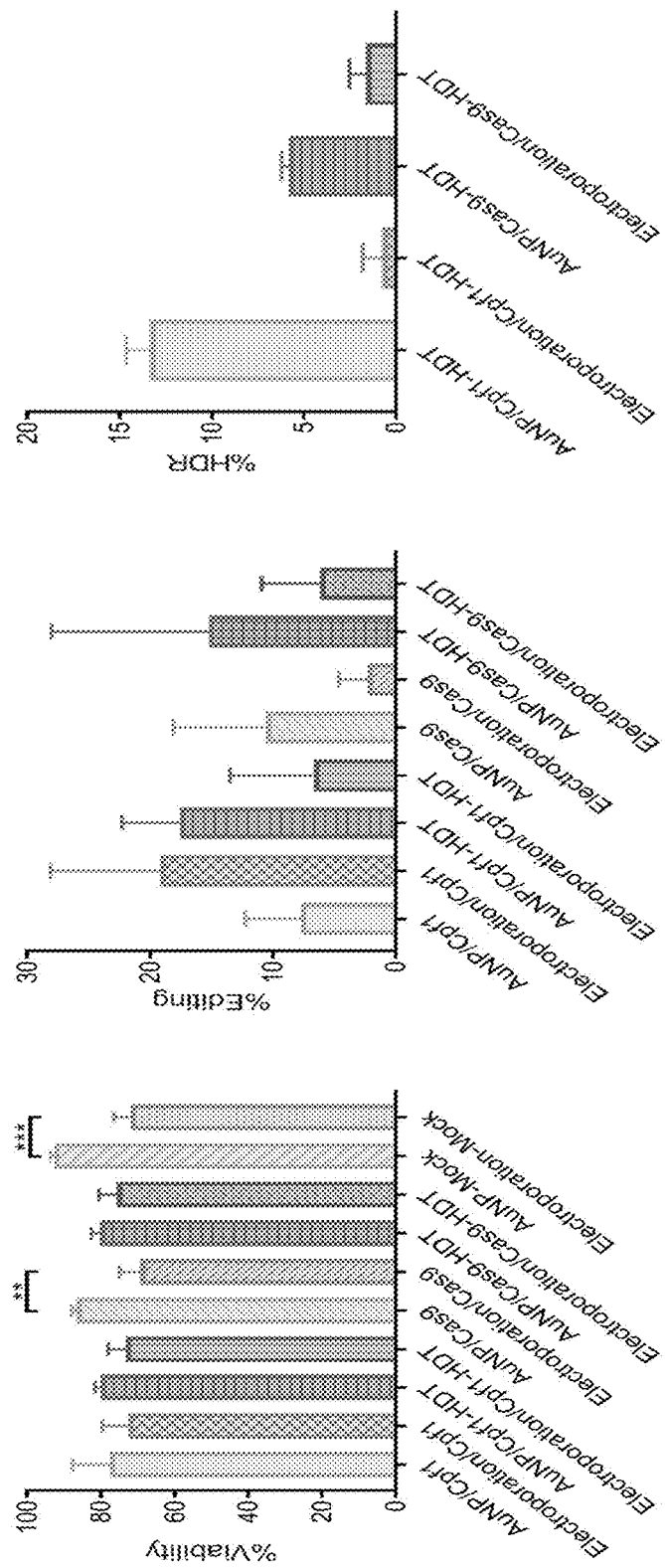
FIG. 16. The goal of the study leading to the data presented in FIG. 16 was to compare Cpf1 and Cas9 delivered by AuNP or electroporation, respectively. The same procedures were used as described in relation to FIG. 13, except that CD34+ cells were initially obtained from a different human donor. All formulation conditions were the same such that the only variables are Cpf1 vs. Cas9; AuNP vs. Electroporation; homology-directed repair template (HDT; ssODN) present vs. absent. Electroporation conditions: 1 mm electroporation cuvets; 125 mV; 5 ms. Editing analysis by TIDE. A CCR5 non-target sequence of CCR5 locus is depicted (SEQ ID NO: 263).
Figure 17A:
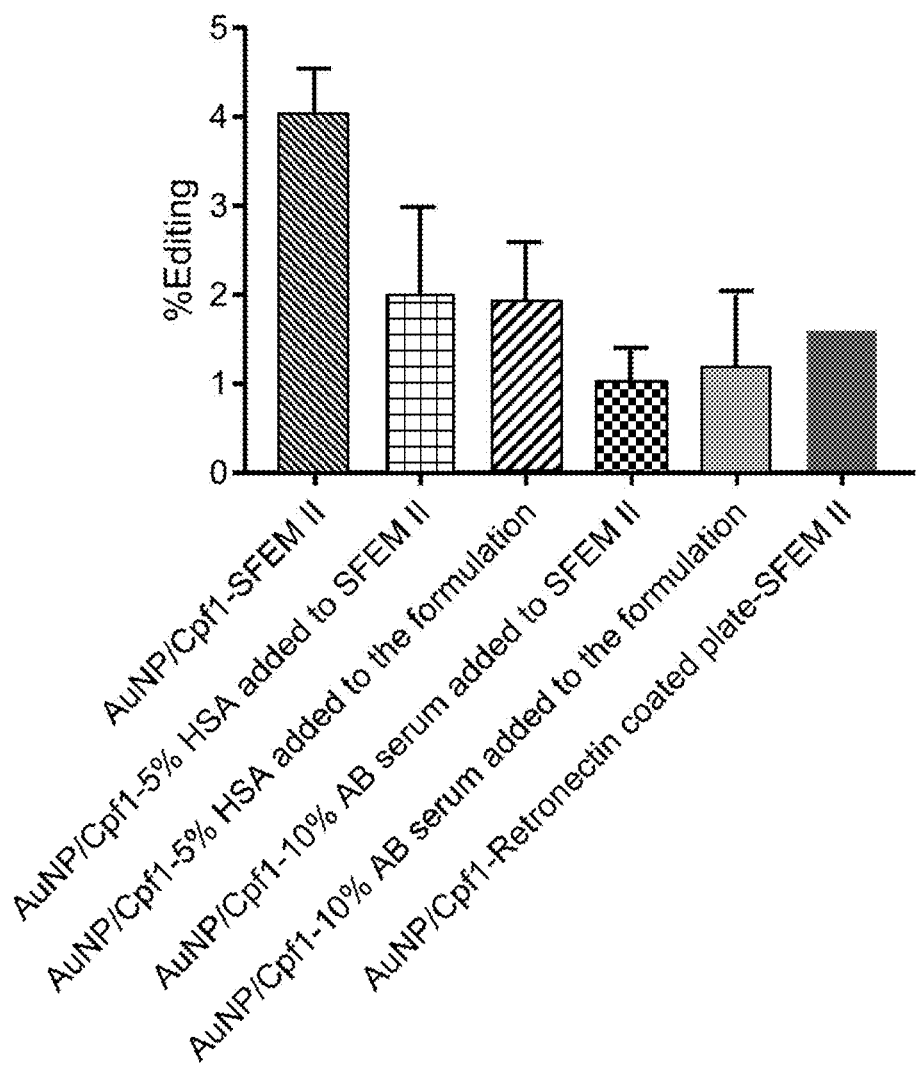
FIGS. 17A-17C. Serum-free, HSPC-supportive media conditions improve (17A) editing, (17B) HDR, and (17C) cell viability.
Figure 17B:
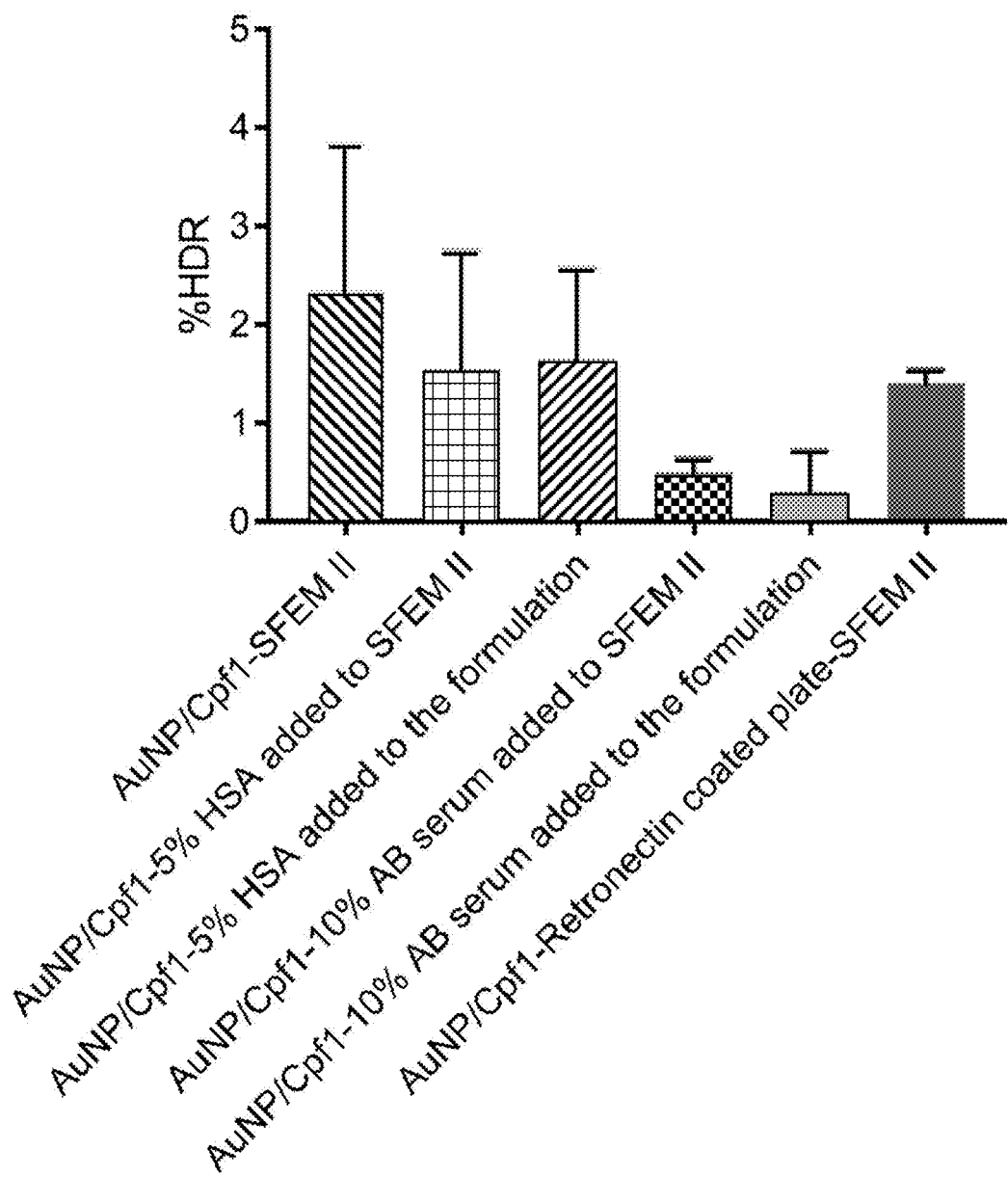
Figure 17C:
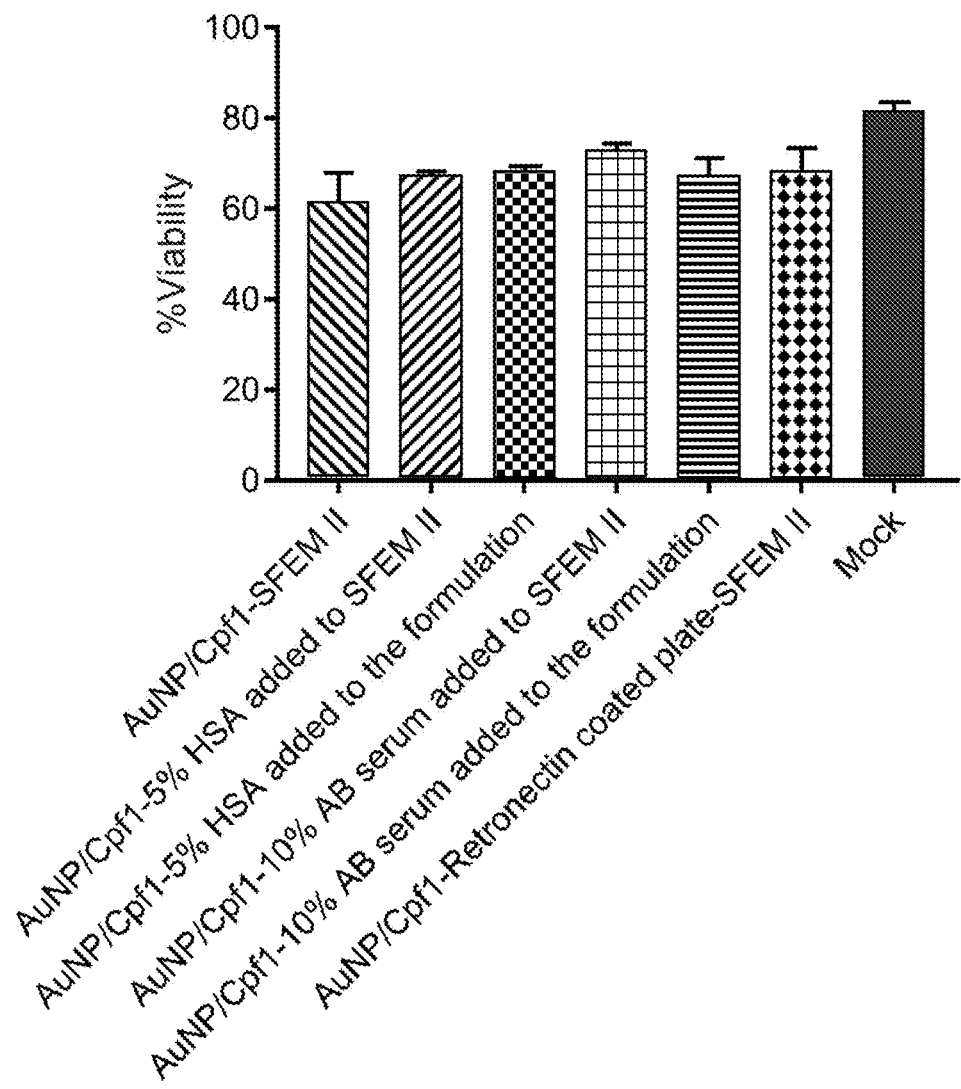
Figure 18B:
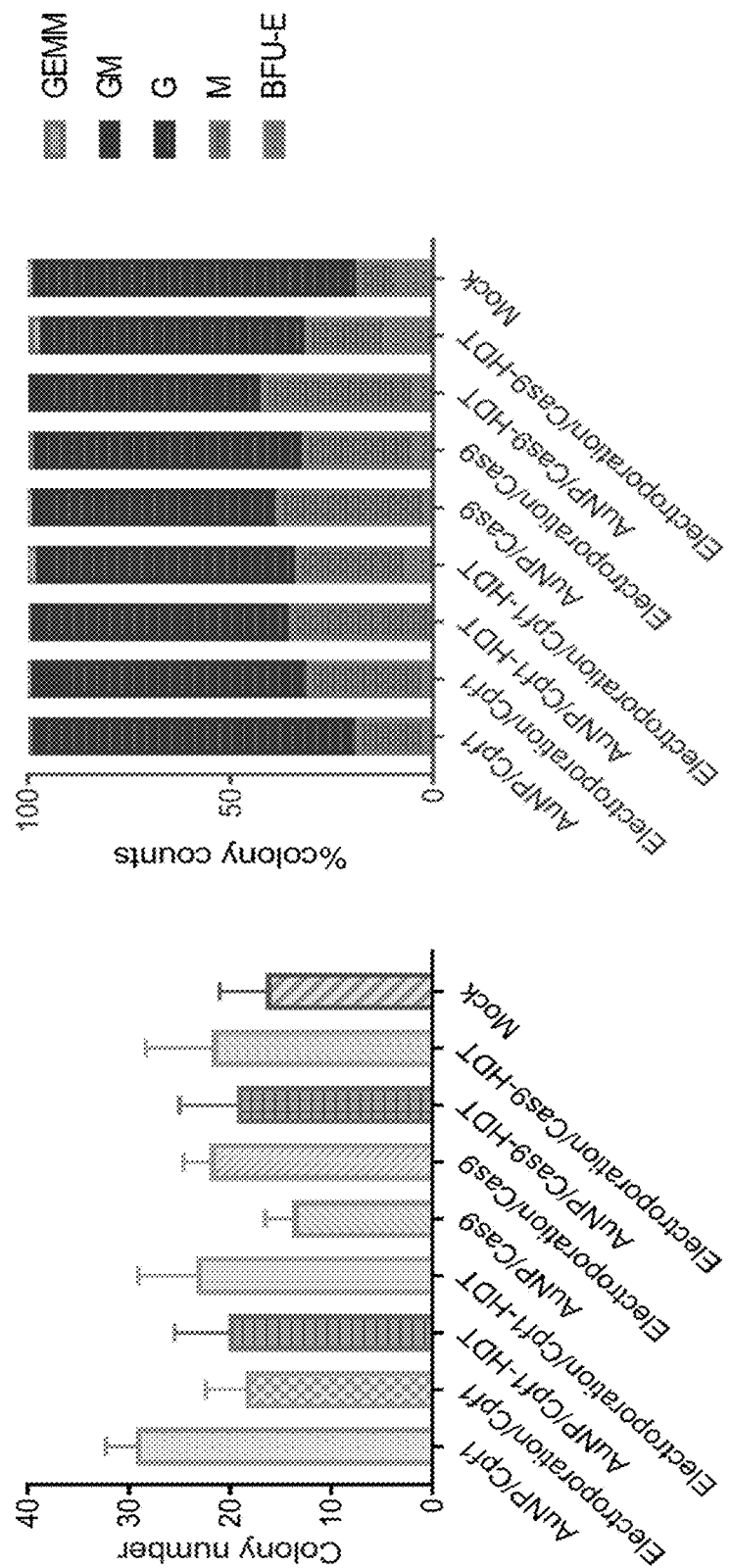
Figure 19:
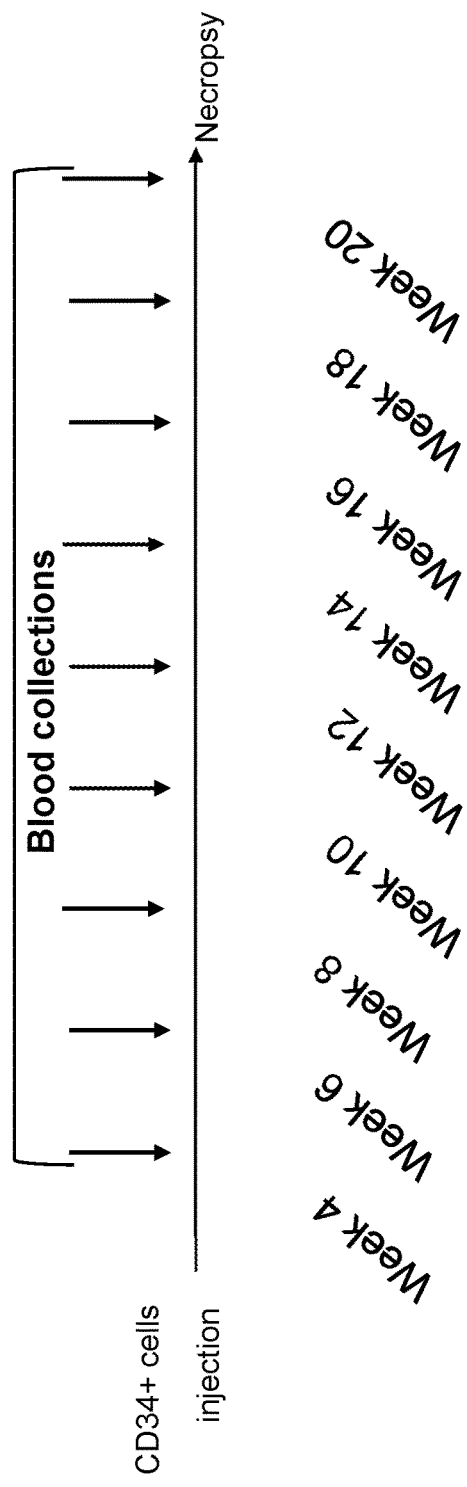
FIG. 19. AuNP-treated CD34+ cells engraft in vivo. Experimental notes and methodology. The same procedures were used as described in relation to FIG. 13, except that CD34+ cells were initially obtained from a different human donor. After 48 hours, cells were harvested, washed, and injected into sublethally irradiated adult (8-12 week) NSG mice. Cell reserves were used to assess plate colony assays and to isolate gDNA for PCR amplification and analysis.

As shown in FIG. 16, AuNP-mediated gene delivery improves Cas9 performance, however, Cpf1 is better for HDR. AuNP treated cells demonstrated higher viability compared to electroporated cells. For Cas9, AuNP mediated delivery improved total editing and HDR, relative to electroporation. For Cpf1 delivered without a homology-directed repair template (HDT), electroporation resulted in higher total gene editing (indels). This suggests that electroporation itself may impact the repair pathway used or the frequency of Cpf1 cutting at the target site. Addition of HDT to the Cpf1 formulation improved total editing and resulted in the highest HDR rates. Together, these data suggest that the fully-loaded formulation of AuNP+Cpf1/crRNA+HDT results in the highest rates of HDR with minimal indel formation. This is ideal for a number of target loci for gene editing.

Figure 13:
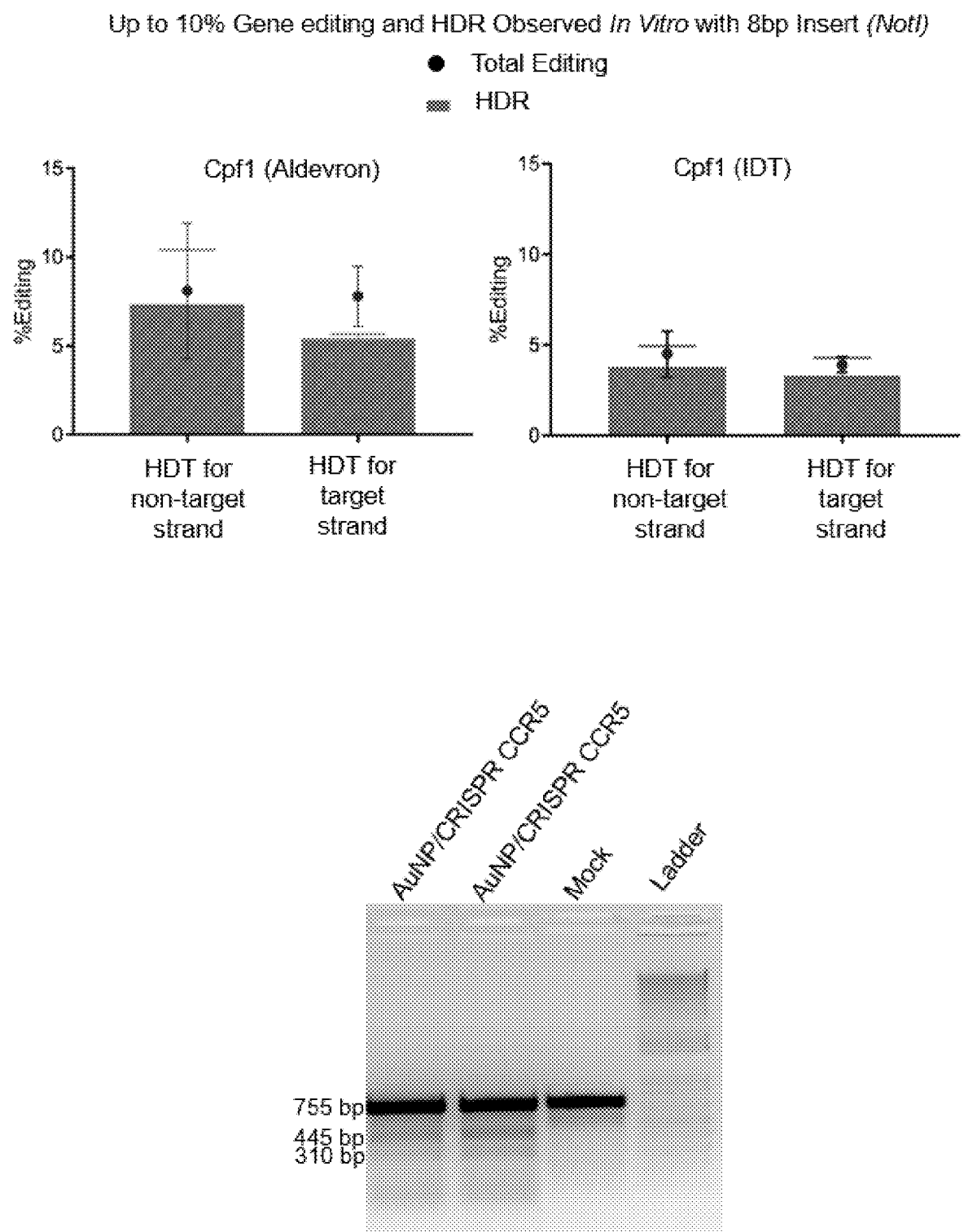
FIG. 13. Up to 10% gene editing and HDR was observed in vitro in primary CD34+ cells obtained from a G-CSF mobilized healthy adult donor. CD34+ cells were thawed using a rapid-thaw method and cultured overnight in Iscove's Modified Dulbecco's Medium (IMDM) containing 10% FBS and 1% Pen/Strep. The following morning, AuNPs were seeded and assembled as follows: seed; add crRNA with a PEG spacer to prevent electrostatic repulsions; add Cpf1 protein and allow RNPs to form; coat with 2K branched PEI and ssODN. In this example, there were no chemical modifications of crRNA other than terminal thiol additions to promote covalent bonding with the AuNP surface for attachment. SsODN was used as the homology-directed repair template (HDT), here a 8 bp insert using a NotI site flanked by 40 nt of homology (symmetric) to CCR5 target locus. Formulated AuNPs were added to cells and incubated for 48 hours with gentle plate mixing. After 48 hours, cells were harvested, washed, and gDNA was isolated for PCR amplification and analysis.
Figure 13:
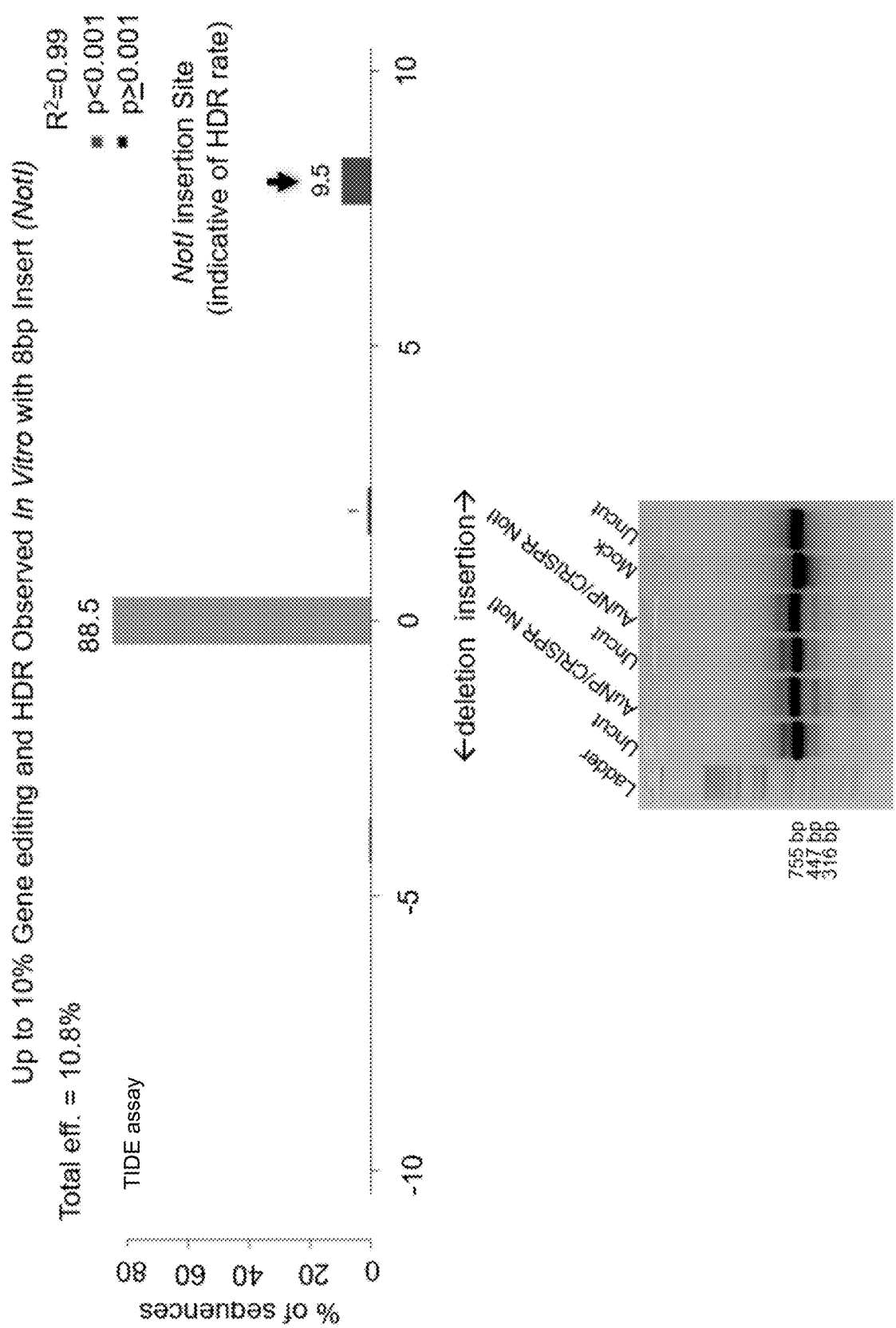
Figure 20A:
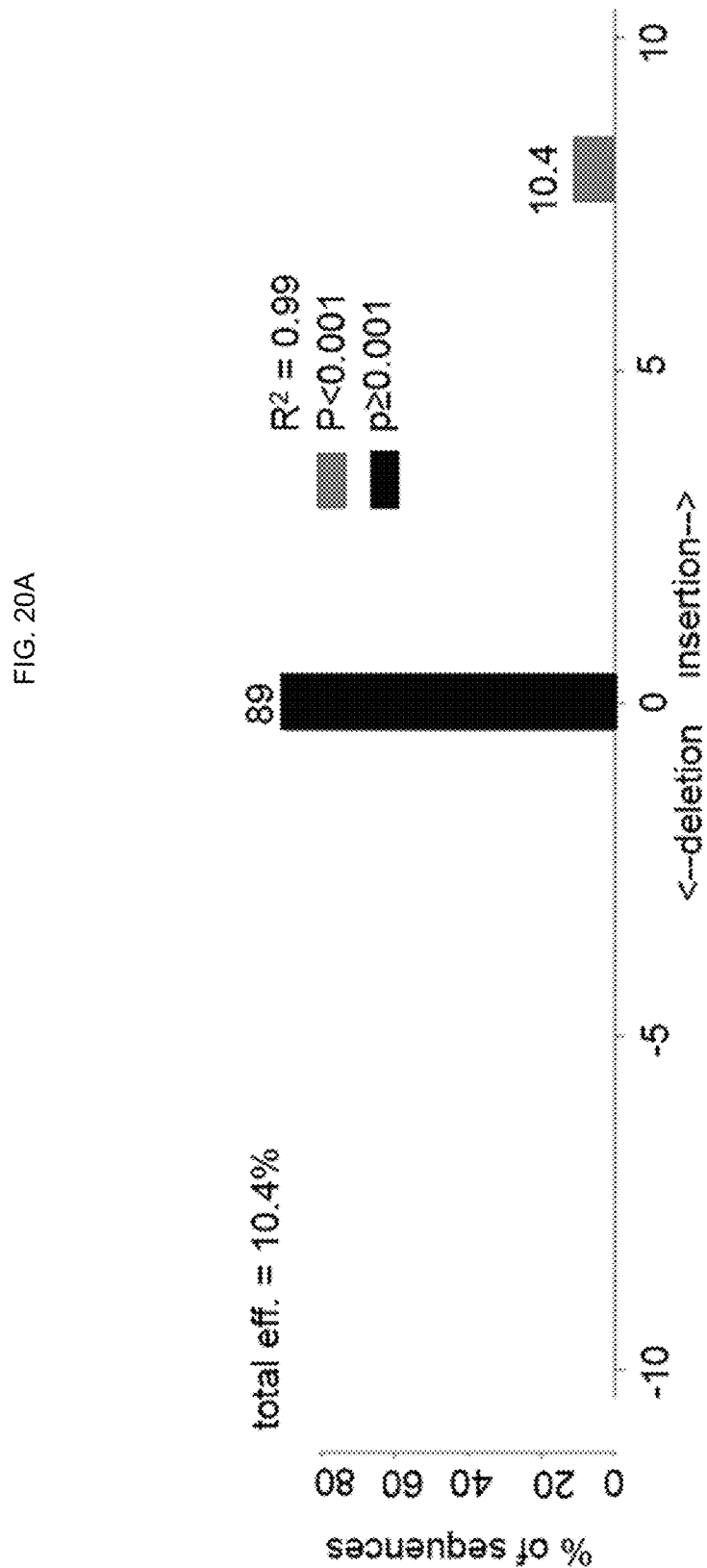
FIGS. 20A-20C. In vitro analysis of cells transplanted into NSG mice.
Figure 20B:
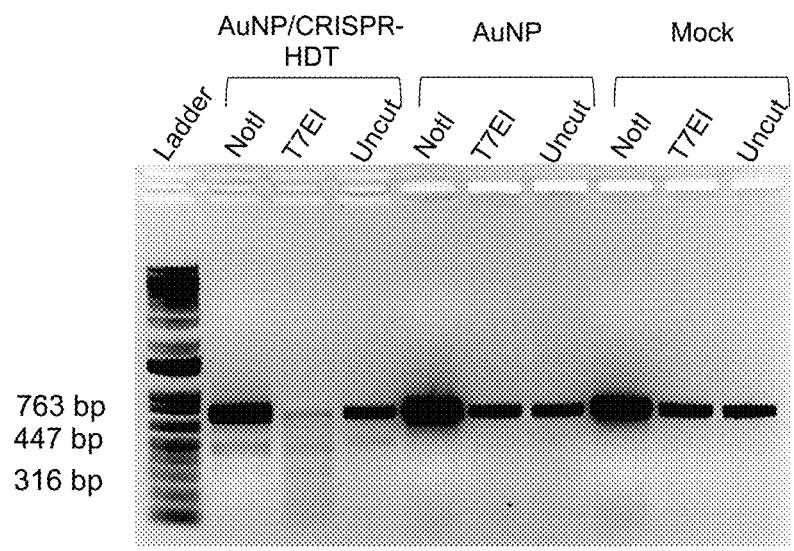
Figure 20C:
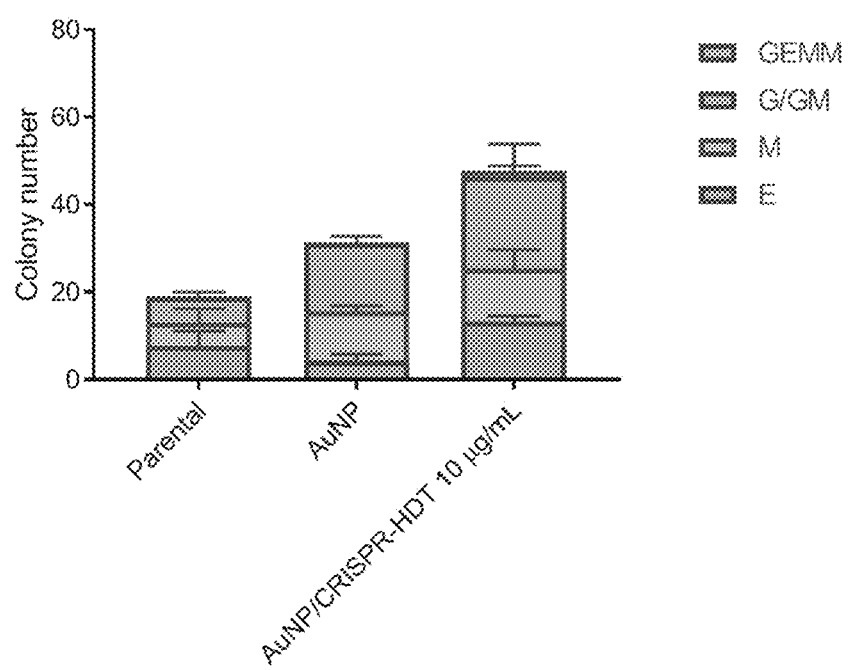
Figure 21A:
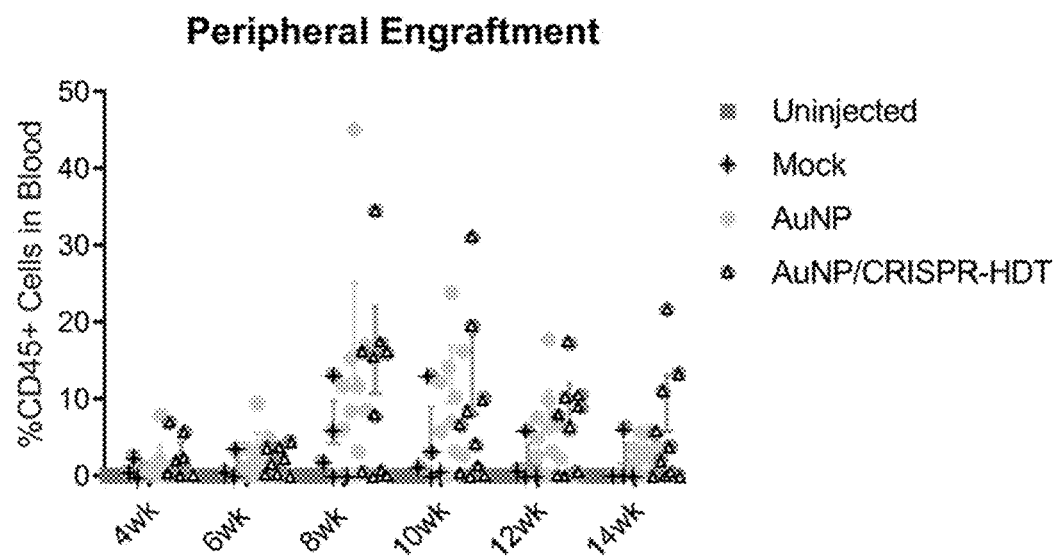
FIGS. 21A-21J. In vivo analysis of cells transplanted into NSG mice. AuNP-treated hCD34+ cells engraft better than mock-treated cells.
Figure 21B:
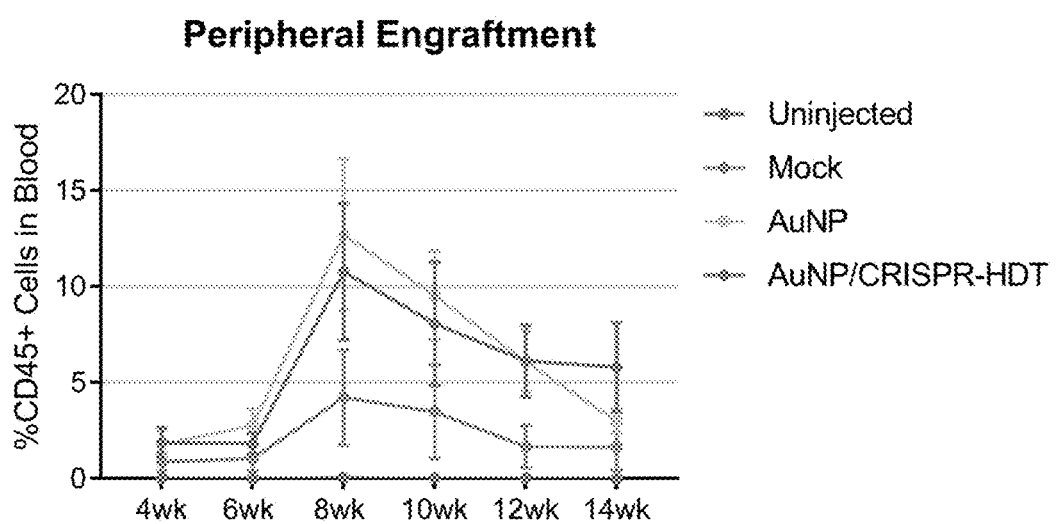
Figure 21C:
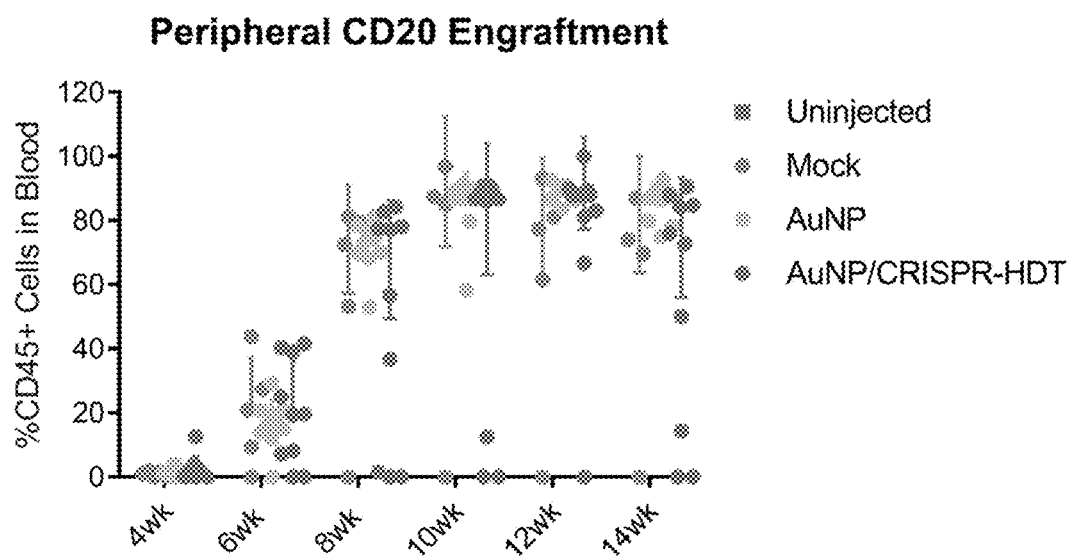
Figure 21D:
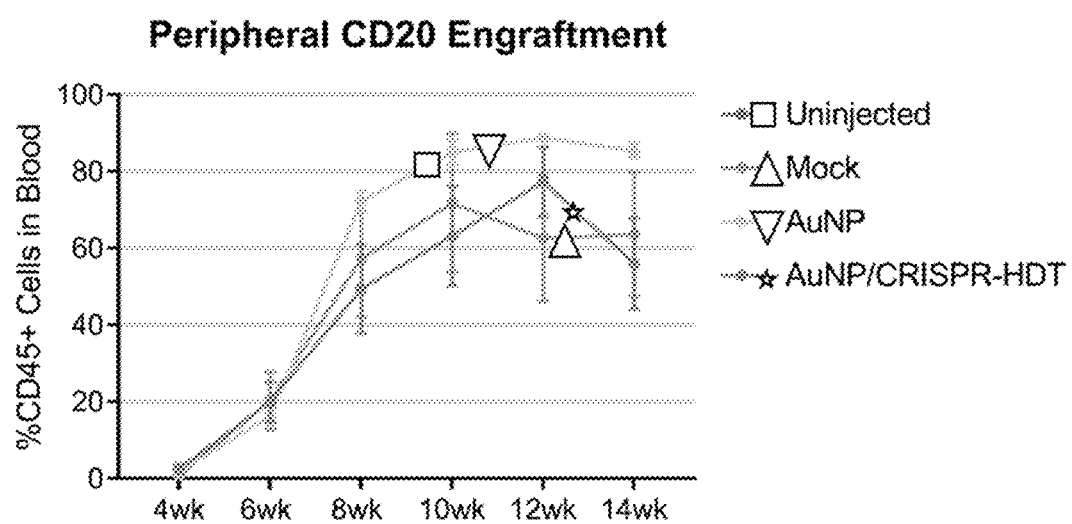
Figure 21E:
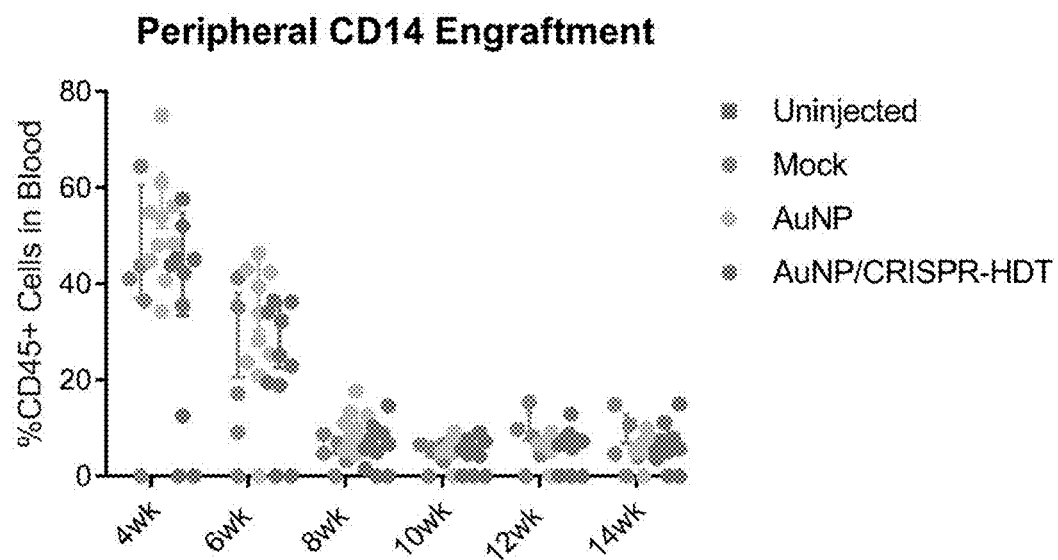
Figure 21F:
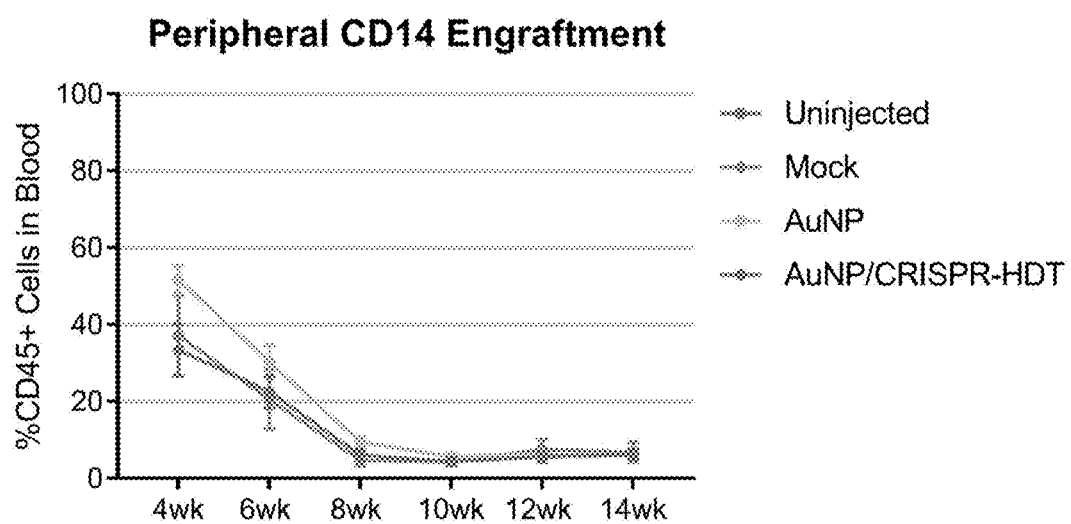
Figure 21G:
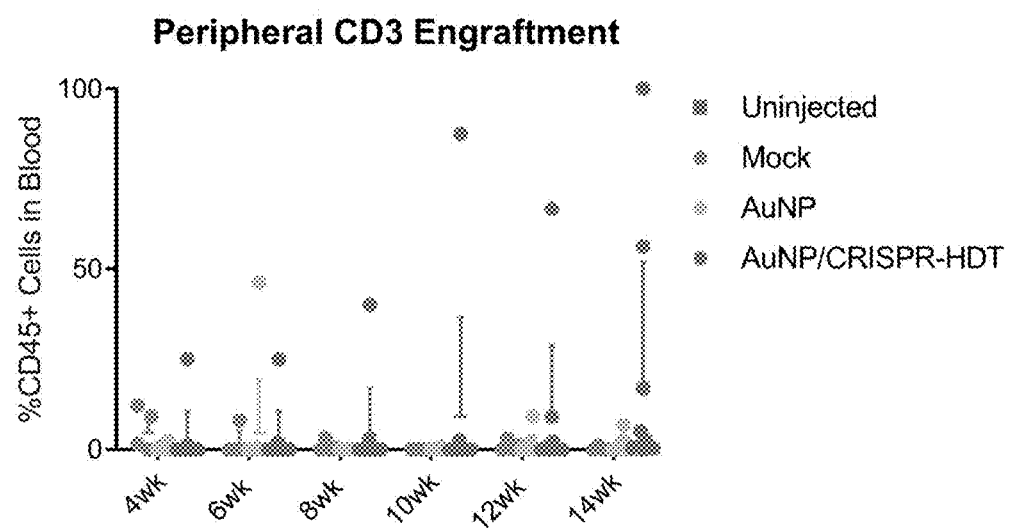
Figure 21H:
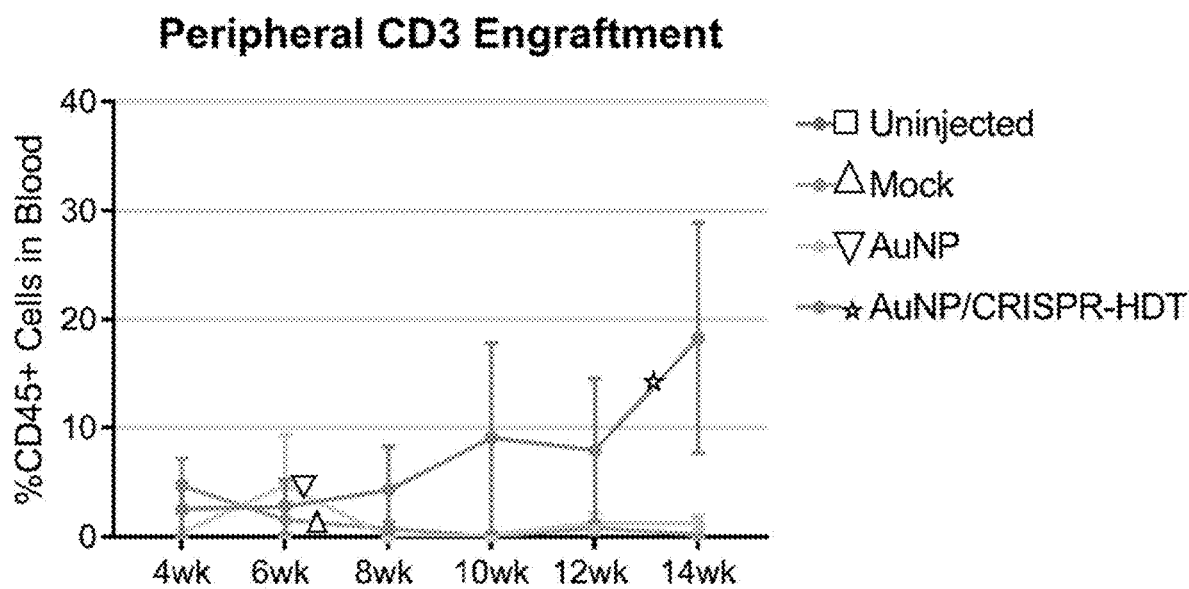
Figure 21I:
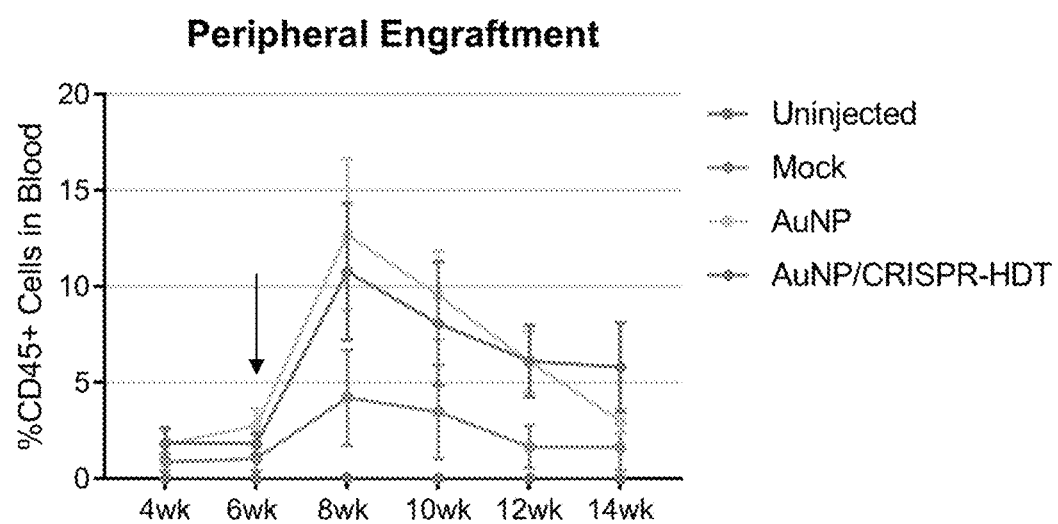
Figure 21J:
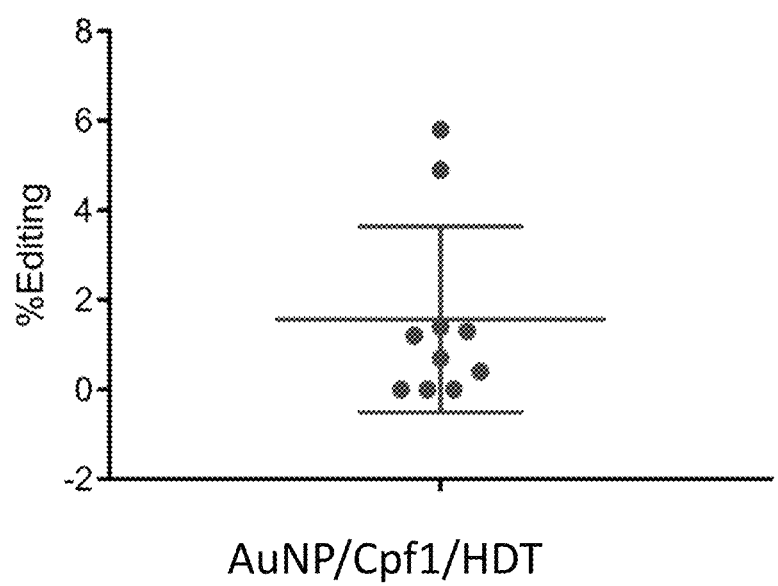
Figure 22:
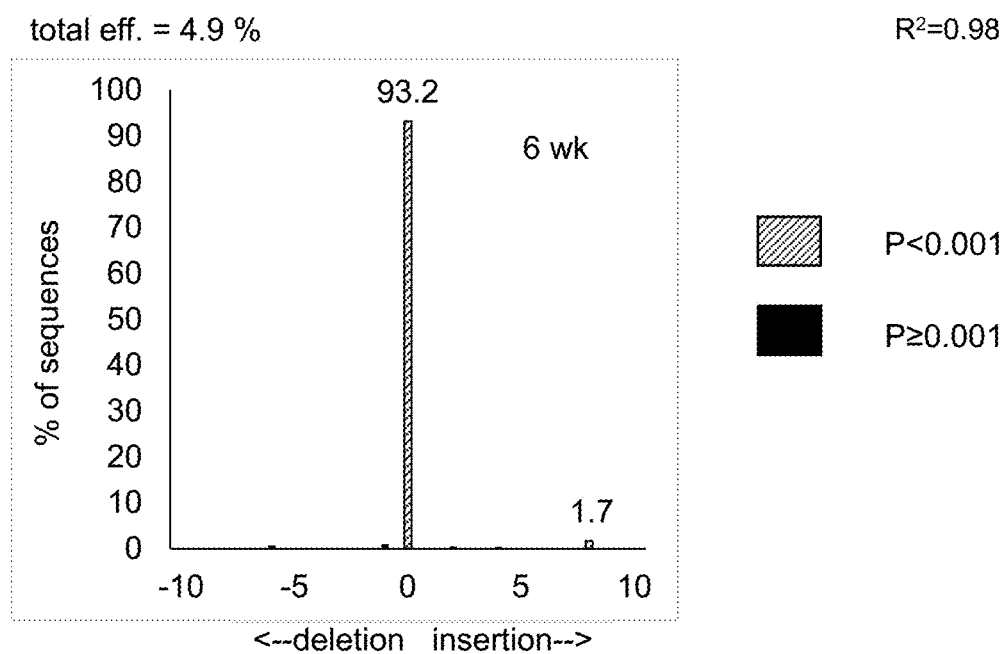
FIG. 22. Early post-transplant analysis suggests gene edited cell engraftment. Peripheral blood was collected for gDNA analysis at 6 weeks after transplant (arrow in FIG. 21I). Across all mice treated with fully-loaded AuNPs, 7/10 displayed detecable editing ranging from 0.5-6% by TIDE. In one mouse (5% total editing), 1.7% HDR was observed by TIDE analysis.

Confocal microscopy demonstrated that disclosed nanoformulations avoided lysosomal entrapment and successfully localized to the nucleus of $CD34^+$ primary hematopoietic cells from healthy donors. Knock-in frequencies of up to 10% were demonstrated using a NotI restriction enzyme template with homology arm lengths of ±40 nucleotides to a CCR5 locus without cytotoxicity. Designing template to the non-target DNA strand yielded a higher homology directed repair (HDR) efficiency (FIG. 13), with clear 447 bp and 316 bp cut bands following digestion with NotI and T7E1 enzymes (FIG. 20B). Direct comparison of Cpf1 and Cas9 nuclease activity at the same CCR5 target site demonstrated a Cpf1 bias for HDR and template knock-in over Cas9, which prferentially generated indels. Xenotransplantation of CRISPR Cpf1 nanoformulation-treated human $CD34^+$ cells into immune deficient mice demonstrated an early increased trend in engraftment compared to non-treated cells, suggesting an unkown benefit of nanoformulation-treated HSPCs. The frequency of CCR5 genetically modified cell engraftment was the same as observed in culture, with 10% of human cells displaying NotI template addition in vivo.

(VI) Nanoparticle Compositions and Cell Formulations. Nanoparticles disclosed herein can be formulated into compositions for administration to subjects.

In particular embodiments, blood cells can be obtained from a subject or donor and genetically modified (e.g., within a GSH) before administration to the subject to treat a condition. Common sources of appropriate blood cells include mobilized peripheral blood samples, bone marrow samples, and/or umbilical cord blood.

Exemplary carriers for nanoparticle compositions and/or cell formulations include saline, buffered saline, physiological saline, water, Hanks' solution, Ringer's solution, Nonnosol-R (Abbott Labs), Plasma-Lyte A® (Baxter Laboratories, Inc., Morton Grove, Ill.), glycerol, ethanol, and combinations thereof. In particular embodiments, nanoparticle compositions and/or cell formulations are administered to subjects as soon as reasonably possible following their initial formulation.

In particular embodiments, carriers can be supplemented with human serum albumin (HSA) or other human serum components or fetal bovine serum or other species serum components. In particular embodiments, a carrier for infusion includes buffered saline with 5% HSA or dextrose. Additional isotonic agents include polyhydric sugar alcohols including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent component adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Where necessary or beneficial, nanoparticle compositions and/or cell formulations can include a local anesthetic such as lidocaine to ease pain at a site of injection.

Therapeutically effective amounts of nanoparticles within a composition can include at least 0.1% w/v or w/w particles; at least 1% w/v or w/w particles; at least 10% w/v or w/w particles; at least 20% w/v or w/w particles; at least 30% w/v or w/w particles; at least 40% w/v or w/w particles; at least 50% w/v or w/w particles; at least 60% w/v or w/w particles; at least 70% w/v or w/w particles; at least 80% w/v or w/w particles; at least 90% w/v or w/w particles; at least 95% w/v or w/w particles; or at least 99% w/v or w/w particles.

Therapeutically effective amounts of cells within cell-based formulations can be greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$ cells.

The nanoparticle compositions and/or cell formulations disclosed herein can be prepared for administration by, for example, injection, infusion, perfusion, or lavage.

In particular embodiments, it can be necessary or beneficial to freeze dry a nanoparticle composition and/or to cryopreserve a cell-based formulation. Such techniques are well known to those of ordinary skill in the art.

(VII) Exemplary Methods of Use. Hematopoietic stem cells (HSC) are stem cells that can give rise to all blood cell types such as the white blood cells of the immune system (e.g., virus-fighting T cells and antibody-producing B cells) and red blood cells. The therapeutic administration of HSC can be used to treat a variety of adverse conditions including immune deficiency diseases, blood disorders, malignant cancers, infections, and radiation exposure (e.g., cancer treatment, accidental, or attack-based). As examples, more than 80 primary immune deficiency diseases are recognized by the World Health Organization. These diseases are characterized by an intrinsic defect in the immune system in which, in some cases, the body is unable to produce any or enough antibodies against infection. In other cases, cellular defenses to fight infection fail to work properly. Typically, primary immune deficiencies are inherited disorders.

Examples of diseases that can be treated using the nanoparticle compositions or cell formulations of the disclosure include a monogenetic blood disorder, hemophilia, Grave's Disease, rheumatoid arthritis, pernicious anemia, Multiple Sclerosis (MS), inflammatory bowel disease, systemic lupus erythematosus (SLE), Wiskott-Aldrich syndrome (WAS), chronic granulomatous disease (CGD), Battens disease, adrenoleukodystrophy (ALD) or metachromatic leukodystrophy (MLD), muscular dystrophy, pulmonary aveolar proteinosis (PAP), pyruvate kinase deficiency, Shwachmann-Diamond-Blackfan anemia, dyskeratosis congenita, cystic fibrosis, Parkinson's disease, Alzheimer's disease, amyotrophic lateral sclerosis (Lou Gehrig's disease), acute lymphoblastic leukemia (ALL), acute myelogenous leukemia (AML), agnogenic myeloid metaplasia, amegakaryocytosis/congenital thrombocytopenia, ataxia telangiectasia, β-thalassemia major, CLL, chronic myelogenous leukemia (CML), chronic myelomonocytic leukemia, common variable immune deficiency (CVID), complement disorders, congenital (X-linked) agammaglobulinemia, familial erythrophagocytic lymphohistiocytosis, Hodgkin's lymphoma, Hurler's syndrome, hyper IgM, IgG subclass deficiency, juvenile myelomonocytic leukemia, mucopolysaccharidoses, multiple myeloma, myelodysplasia, non-Hodgkin's lymphoma, paroxysmal nocturnal hemoglobinuria (PNH), primary immunodeficiency diseases with antibody deficiency, pure red cell aplasia, refractory anemia, selective IgA deficiency, severe aplastic anemia, SCD, and/or specific antibody deficiency.

Particular embodiments include treatment of bacterial and/or parasitic infections. One exemplary parasite includes malaria-causing *Plasmodium*.

The compositions and formulations disclosed herein can be used for treating subjects (humans, veterinary animals (dogs, cats, reptiles, birds, etc.), livestock (horses, cattle, goats, pigs, chickens, etc.), and research animals (monkeys, rats, mice, fish, etc.). In particular embodiments, subjects are human patients. Nanoparticles described herein can be customized for any target while GSH sites are specific to humans and non-human primates.

Treating subjects includes delivering therapeutically effective amounts. Therapeutically effective amounts include those that provide effective amounts, prophylactic treatments, and/or therapeutic treatments.

An "effective amount" is the amount of a formulation necessary to result in a desired physiological change in a subject. Effective amounts are often administered for research purposes.

Assay for HSPC functionality. The most robust assay for HSPC functionality is the ability to reconstitute hematopoiesis in a conditioned recipient. In particular embodiments, human HSPC are xenotransplanted following electroporation of an optimal CRISPR/Cpf1 pair and ssODN combination into sub-lethally irradiated neonatal NOD/SCIDgamma$^{null}$ (NSG) mice. The hematology, engraftment and persistence of GFP$^+$ cells is then monitored by flow cytometry across blood cell lineages and time for 20 weeks after transplant. Genomic DNA (gDNA) is also isolated from blood, BM and spleen of transplanted animals at the time of necropsy for DNA barcode sequencing to determine the number of clones contributing to GFP$^+$ cell hematopoiesis observed in vivo. Animals receiving HSPC modified with CRISPR/Cpf1 and ssODN are monitored for GFP$^+$ cells by flow cytometry across blood cell lineages and time. Genomic DNA (gDNA) is isolated from blood, BM and spleen of transplanted animals at the time of necropsy for DNA barcode sequencing to determine the number of clones contributing to GFP+ cell hematopoiesis observed in vivo, in addition to more thorough evaluation of indel formation and persistence.

A "prophylactic treatment" includes a treatment administered to a subject who does not display signs or symptoms of a condition to be treated or displays only early signs or symptoms of the condition to be treated such that treatment is administered for the purpose of diminishing, preventing, or decreasing the risk of developing the condition. Thus, a prophylactic treatment functions as a preventative treatment against a condition.

A "therapeutic treatment" includes a treatment administered to a subject who displays symptoms or signs of a condition and is administered to the subject for the purpose of reducing the severity or progression of the condition.

The actual dose and amount of a therapeutic composition or formulation administered to a particular subject can be determined by a physician, veterinarian, or researcher taking into account parameters such as physical and physiological factors including target; body weight; type of condition; severity of condition; upcoming relevant events, when known; previous or concurrent therapeutic interventions; idiopathy of the subject; and route of administration, for example. In addition, in vitro and in vivo assays can optionally be employed to help identify optimal dosage ranges.

Therapeutically effective amounts can be administered through any appropriate administration route such as by, injection, infusion, perfusion, or lavage.

In particular embodiments, methods of the present disclosure can restore BM function in a subject in need thereof. In particular embodiments, restoring BM function can include improving BM repopulation with gene corrected cells as compared to a subject in need thereof not administered a therapy described herein. Improving BM repopulation with gene corrected cells can include increasing the percentage of cells that are gene corrected. In particular embodiments, the cells are selected from white blood cells and BM derived cells. In particular embodiments, the percentage of cells that are gene corrected can be measured using an assay selected from quantitative real time PCR and flow cytometry.

In particular embodiments, methods of the present disclosure can normalize primary and secondary antibody responses to immunization in a subject in need thereof. Normalizing primary and secondary antibody responses to immunization can include restoring B-cell and/or T-cell cytokine signaling programs functioning in class switching and memory response to an antigen. Normalizing primary and secondary antibody responses to immunization can be measured by a bacteriophage immunization assay. In particular embodiments, restoration of B-cell and/or T-cell cytokine signaling programs can be assayed after immunization with the T-cell dependent neoantigen bacteriophage φX174. In particular embodiments, normalizing primary and secondary antibody responses to immunization can include increasing the level of IgA, IgM, and/or IgG in a subject in need thereof to a level comparable to a reference level derived from a control population. In particular embodiments, normalizing primary and secondary antibody responses to immunization can include increasing the level of IgA, IgM, and/or IgG in a subject in need thereof to a level greater than that of a subject in need thereof not administered a gene therapy described herein. The level of IgA, IgM, and/or IgG can be measured by, for example, an immunoglobulin test. In particular embodiments, the immunoglobulin test includes antibodies binding IgG, IgA, IgM, kappa light chain, lambda light chain, and/or heavy chain. In particular embodiments, the immunoglobulin test includes serum protein electrophoresis, immunoelectrophoresis, radial immunodiffusion, nephelometry and turbidimetry. Commercially available immunoglobulin test kits include MININEPH™ (Binding site, Birmingham, UK), and immunoglobulin test systems from Dako (Denmark) and Dade Behring (Marburg, Germany). In particular embodiments, a sample that can be used to measure immunoglobulin levels includes a blood sample, a plasma sample, a cerebrospinal fluid sample, and a urine sample.

In particular embodiments, methods of the present disclosure can improve the kinetics and/or clonal diversity of lymphocyte reconstitution in a subject in need thereof. In particular embodiments, improving the kinetics of lymphocyte reconstitution can include increasing the number of circulating T lymphocytes to within a range of a reference level derived from a control population. In particular embodiments, improving the kinetics of lymphocyte reconstitution can include increasing the absolute CD3+ lymphocyte count to within a range of a reference level derived from a control population. A range of a reference level can be a range of values observed in or exhibited by normal (i.e., non-immuno-compromised) subjects for a given parameter. In particular embodiments, improving the kinetics of lymphocyte reconstitution can include reducing the time required to reach normal lymphocyte counts as compared to a subject in need thereof not administered a therapy described herein. In particular embodiments, improving the kinetics of lymphocyte reconstitution can include increasing the frequency of gene corrected lymphocytes as compared to a subject in need thereof not administered a therapy described herein. In particular embodiments, improving the kinetics of lymphocyte reconstitution can include increasing diversity of clonal repertoire of gene corrected lymphocytes in the subject as compared to a subject in need thereof not administered a gene therapy described herein.

In particular embodiments, methods of the present disclosure can restore T-cell mediated immune responses in a subject in need thereof. Restoration of T-cell mediated immune responses can include restoring thymic output and/or restoring normal T lymphocyte development.

In particular embodiments, restoring thymic output can include restoring the frequency of CD3+ T cells expressing CD45RA in PB to a level comparable to that of a reference level derived from a control population. In particular embodiments, restoring thymic output can include restoring the number of T cell receptor excision circles (TRECs) per $10^6$ maturing T cells to a level comparable to that of a reference level derived from a control population. The number of TRECs per $10^6$ maturing T cells can be determined as described in Kennedy D R et al. (2011) Vet Immunol Immunopathol 142: 36-48.

In particular embodiments, restoring normal T lymphocyte development includes restoring the ratio of CD4+ cells: CD8+ cells to 2. In particular embodiments, restoring normal T lymphocyte development includes detecting the presence of αβ TCR in circulating T-lymphocytes. The presence of αβ TCR in circulating T-lymphocytes can be detected, for example, by flow cytometry using antibodies that bind an α and/or β chain of a TCR. In particular embodiments, restoring normal T lymphocyte development includes detecting the presence of a diverse TCR repertoire comparable to that of a reference level derived from a control population. TCR diversity can be assessed by TCRVβ spectratyping, which analyzes genetic rearrangement of the variable region of the TCRβ gene. Robust, normal spectratype profiles can be characterized by a Gaussian distribution of fragments sized across 17 families of TCRVβ segments. In particular embodiments, restoring normal T lymphocyte development includes restoring T-cell specific signaling pathways. Restoration of T-cell specific signaling pathways can be assessed by lymphocyte proliferation following exposure to the T cell mitogen phytohemagglutinin (PHA). In particular embodiments, restoring normal T lymphocyte development includes restoring white blood cell count, neutrophil cell count, monocyte cell count, lymphocyte cell count, and/or platelet cell count to a level comparable to a reference level derived from a control population.

In particular embodiments, a therapeutically effective treatment induces or increases production of hemoglobin; induces or increases production of beta-globin, or alpha-globin; and/or increases the availability of oxygen to cells in the body.

In particular embodiments, a therapeutically effective treatment increases blood cell counts, improves blood cell function, and/or increases oxygenation of cells.

In particular embodiments, a therapeutically effective treatment increases the production of coagulation/clotting factor VIII or coagulation/clotting factor IX, causes the production of normal versions of coagulation factor VIII or coagulation factor IX, reduces the production of antibodies to coagulation/clotting factor VIII or coagulation/clotting factor IX, and/or causes the proper formation of blood clots.

In particular embodiments, a therapeutically effective treatment causes the degradation of mucopolysaccharides in lysosomes, reduces, eliminates, prevents, or delays the swelling in various organs, including the head (exp. Macrosephaly), the liver, spleen, tongue, or vocal cords; reduces fluid in the brain; reduces heart valve abnormalities; prevents or dilates narrowing airways, reduces or prevent upper respiratory conditions like infections and sleep apnea; and/or reduces, eliminates, prevents, or delays the destruction of neurons and/or the symptoms associated with the destruction of neurons.

In particular embodiments, therapeutically effective amounts may provide function to immune and other blood cells, reduce or eliminate an immune-mediated condition; and/or reduce or eliminate a symptom of the immune-mediated condition.

In particular embodiments, particular methods of use include in the treatment of conditions where corrected cells have a selective advantage over non-corrected cells. For example, in FA and SCID, corrected cells have an advantage and only transducing the therapeutic gene into a "few" HSPCs is sufficient for therapeutic efficacy.

Additional methods of treatment can be found in International Patent Application PCT/US2016/014378, filed Jan. 21, 2016 and U.S. Provisional Application Nos. 62/351,761, filed Jun. 17, 2016 and 62/428,994, filed Jan. 1, 2016, each of which is specifically incorporated herein in their entirety.

(VIII) Reference Levels Derived from Control Populations. Obtained values for parameters associated with a therapy described herein can be compared to a reference level derived from a control population, and this comparison can indicate whether a therapy described herein is effective for a subject in need thereof. Reference levels can be obtained from one or more relevant datasets from a control population. A "dataset" as used herein is a set of numerical values resulting from evaluation of a sample (or population of samples) under a desired condition. The values of the dataset can be obtained, for example, by experimentally obtaining measures from a sample and constructing a dataset from these measurements. As is understood by one of ordinary skill in the art, the reference level can be based on e.g., any mathematical or statistical formula useful and known in the art for arriving at a meaningful aggregate reference level from a collection of individual data points; e.g., mean, median, median of the mean, etc. Alternatively, a reference level or dataset to create a reference level can be obtained from a service provider such as a laboratory, or from a database or a server on which the dataset has been stored.

A reference level from a dataset can be derived from previous measures derived from a control population. A "control population" is any grouping of subjects or samples of like specified characteristics. The grouping could be according to, for example, clinical parameters, clinical assessments, therapeutic regimens, disease status, severity of condition, etc. In particular embodiments, the grouping is based on age range (e.g., 0-2 years) and non-immunocompromised status. In particular embodiments, a normal control population includes individuals that are age-matched to a test subject and non-immune compromised. In particular embodiments, age-matched includes, e.g., 0-6 months old; 0-1 year old; 0-2 years old; 0-3 years old; 10-15 years old, as is clinically relevant under the circumstances. In particular embodiments, a control population can include those that have an immune deficiency and have not been administered a therapeutically effective amount In particular embodiments, the relevant reference level for values of a particular parameter associated with a therapy described herein is obtained based on the value of a particular corresponding parameter associated with a therapy in a control population to determine whether a therapy disclosed herein has been therapeutically effective for a subject in need thereof.

In particular embodiments, conclusions are drawn based on whether a sample value is statistically significantly different or not statistically significantly different from a reference level. A measure is not statistically significantly different if the difference is within a level that would be expected to occur based on chance alone. In contrast, a statistically significant difference or increase is one that is greater than what would be expected to occur by chance alone. Statistical significance or lack thereof can be determined by any of various methods well-known in the art. An example of a commonly used measure of statistical significance is the p-value. The p-value represents the probability of obtaining a given result equivalent to a particular data point, where the data point is the result of random chance alone. A result is often considered significant (not random chance) at a p-value less than or equal to 0.05. In particular embodiments, a sample value is "comparable to" a reference level derived from a normal control population if the sample value and the reference level are not statistically significantly different.

(IX) Kits. The disclosure also provides kits containing any one or more of the elements disclosed in the methods and compositions herein. In particular embodiments, a kit can include guide RNA and a nuclease capable of cutting a target sequence in a blood cell GSH and an HDR template. Elements may be provided individually or in combinations, and may be provided in any suitable container, such as a vial, a bottle, a bag or a tube. In some embodiments, the kit includes instructions in one or more languages, for example in more than one language.

In particular embodiments, a kit includes one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g., in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from 7 to 10. In some embodiments, the kit includes a homologous recombination template polynucleotide.

Exemplary Embodiments: a gene editing sequence to target a genomic safe harbor disclosed herein (see, e.g., FIG. 1, 3, 4); a nanoparticle conjugated to gene editing sequences disclosed herein (see, e.g., FIG. 1, 3, 4); a CRISPR gene editing sequence modified at the 3' end.

1. A method of genetically modifying a cell at a target sequence within chromosome 11 including SEQ ID NOs. 1-194, 197-208, 210, 213, 242, 245, 251, or 254 including: contacting the cell with a targeting element, a cutting element, and a homology-directed repair template wherein the contacting results in (i) cutting within the target sequence; and (ii) homology-directed repair (HDR).
2. The method of embodiment 1, wherein the targeting element, the cutting element and the homology-directed repair template are part of a CRISPR gene editing system, a meganuclease gene editing system, a zinc finger nuclease (ZFN) gene editing system, or a transcription activator-like effector-based nuclease (TALEN) gene editing system.
3. The method of embodiment 1 or 2, wherein the targeting element is crRNA that hybridizes to one of SEQ ID NOs. 1-194, 197-208, 210, 213, 242, 245, 251, or 254.
4. The method of any of embodiments 1-3, wherein the cutting element is Cpf1 or Cas 9.
5. The method of embodiment 4, wherein the Cpf1 or Cas9 includes a sequence selected from SEQ ID NOs: 215-241.
6. The method of embodiment 4, wherein the Cpf1 is a variant of a Cpf1 selected from SEQ ID NOs: 216-227, or 229-241.
7. The method of any of embodiments 1-6, wherein the homology-directed repair template includes homology arms to the target sequence, and wherein the homology-directed repair template is part of a donor template further including a therapeutic gene that results in expression of a therapeutic gene product.
8. The method of embodiment 7, wherein the therapeutic gene or therapeutic gene product is selected from skeletal protein 4.1, glycophorin, p55, the Duffy allele, globin family genes; WAS; phox; dystrophin; pyruvate kinase; CLN3; ABCD1; arylsulfatase A; SFTPB; SFTPC; NLX2.1; ABCA3; GATA1; ribosomal protein genes; TERT; TERC; DKC1; TINF2; CFTR; LRRK2; PARK2; PARK7; PINK1; SNCA; PSEN1; PSEN2; APP; SOD1; TDP43; FUS; ubiquilin 2; C9ORF72, α2β1; αvβ3; αvβ5; αvβ63; BOB/GPR15; Bonzo/STRL-33/TYMSTR; CCR2; CCR3; CCR5; CCR8; CD4; CD46; CD55; CXCR4; aminopeptidase-N; HHV-7; ICAM; ICAM-1; PRR2/HveB; HveA; α-dystroglycan; LDLR/α2MR/LRP; PVR; PRR1/HveC, laminin receptor, 101F6, 123F2, 53BP2, abl, ABLI, ADP, aFGF, APC, ApoAI, ApoAIV, ApoE, ATM, BAI-1, BDNF, Beta*(BLU), bFGF, BLC1, BLC6, BRCA1, BRCA2, CBFA1, CBL, C-CAM, CFTR, CNTF, COX-1, CSFIR, CTS-1, cytosine deaminase, DBCCR-1, DCC, Dp, DPC-4, E1A, E2F, EBRB2, erb, ERBA, ERBB, ETS1, ETS2, ETV6, Fab, FancA, FancB, FancC, FancD1, FancD2, FancE, FancF, FancG, FancI, FancJ, FancL, FancM, FancN, FancO, FancP, FancQ, FancR, FancS, FancT, FancU, FancV, and FancW, FCC, FGF, FGR, FHIT, fms, FOX, FUS 1, FUS1, FYN, G-CSF, GDAIF, Gene 21, Gene 26, GM-CSF, GMF, gsp, HCR, HIC-1, HRAS, hst, IGF, IL-1, IL-2, IL-3, IL-4, IL-5, IL-6, IL-7, IL-8, IL-9, IL-10, IL-11 IL-12, ING1, interferon α, interferon β, interferon γ, IRF-1, JUN, KRAS, LCK, LUCA-1, LUCA-2, LYN, MADH4, MADR2, MCC, mda7, MDM2, MEN-I, MEN-II, MLL, MMAC1, MYB, MYC, MYCL1, MYCN, neu, NF-1, NF-2, NGF, NOEY1, NOEY2, NRAS, NT3, NT5, OVCA1, p16, p21, p27, p53, p57, p73, p300, PGS, PIM1, PL6, PML, PTEN, raf, Rap1A, ras, Rb, RB1, RET, rks-3, ScFv, scFV ras, SEM A3, SRC, TAL1, TCL3, TFPI, thrombospondin, thymidine kinase, TNF, TP53, trk, T-VEC, VEGF, VHL, WT1, WT-1, YES, zac1, iduronidase, IDS, GNS, HGSNAT, SGSH, NAGLU, GUSB, GALNS, GLB1, ARSB, HYAL1, F8, F9, HBB, CYB5R3, γC, JAK3, IL7RA, RAG1, RAG2, DCLRE1C, PRKDC, LIG4, NHEJ1, CD3D, CD3E, CD3Z, CD3G, PTPRC, ZAP70, LCK, AK2, ADA, PNP, WHN, CHD7, ORAI1, STIM1, CORO1A, CIITA, RFXANK, RFX5, RFXAP, RMRP, DKC1, TERT, TINF2, DCLRE1B, and SLC46A1.

9. The method of embodiment 7 or 8, wherein the homology arms are 40 nucleotides (nt)-1000 nt.
10. The method of any of embodiments 1-9, wherein the targeting element and the cutting element are separate molecules or are part of a single dual-purpose molecule.
11. The method of any of embodiments 1-10, wherein the targeting element and the cutting element are coupled to a nanoparticle.
12. The method of embodiment 11, wherein the nanoparticle includes a gold nanoparticle.
13. The method of any of embodiments 1-12 wherein the targeting element and/or the cutting element are conjugated to a spacer.
14. The method of embodiment 13 wherein the spacer includes a thiol modification.
15. The method of embodiment 14 wherein the thiol modification is covalently linked to the surface of the nanoparticle.
16. The method of any of embodiments 13-15 wherein the targeting element includes a 3' end and a 5' end, and wherein the 3' end is conjugated to the spacer.
17. The method of any of embodiments 11-16 wherein the nanoparticle is associated with at least two layers wherein the first layer includes the targeting element and the second layer includes a donor template including a therapeutic gene and homology-directed repair templates; and wherein at least a portion of the second layer is farther from the surface of the nanoparticle than the first layer.
18. The method of any of embodiments 11-17, wherein the nanoparticle is coupled to a targeting molecule.
19. The method of embodiment 18, wherein the targeting molecule includes a CD34 binding domain or a CD90 binding domain.
20. The method of any of embodiments 1-19, wherein the cell includes a hematopoietic stem cell (HSC), a hematopoietic progenitor cell (HPC), a hematopoietic stem and progenitor cell (HSPC), a T cell, a natural killer (NK) cell, a B cell, a macrophage, a monocyte, a mesenchymal stem cell (MSC), a white blood cell (WBC), a mononuclear cell (MNC), a endothelial cell (EC), a stromal cell, and/or a bone marrow fibroblast.
21. The method of embodiment 20, wherein the blood cell includes a CD34$^+$CD45RA$^-$CD90$^+$ HSC.

22. The method of embodiment 20 or 21, wherein the blood cell is a human blood cell.
23. The method of any of embodiments 1-22, wherein the cutting results in a staggered DNA double strand break with a 2-4-nt 5' overhangs.
24. The method of any of embodiments 1-23 utilizing at least one of the following target sequence crRNA pairs: (i) target: SEQ ID NO: 132/crRNA: SEQ ID NO: 195; (ii) target: SEQ ID NO: 108/crRNA: SEQ ID NO: 196; (iii) target: SEQ ID NO: 203/crRNA: SEQ ID NO: 209; (iv) target: SEQ ID NO: 210/crRNA: SEQ ID NO: 211; (v) target: SEQ ID NO: 242/crRNA: SEQ ID NO: 244; and (vi) target: SEQ ID NO: 251/crRNA: SEQ ID NO: 253.
25. A nanoparticle associated with at least two active layers wherein the first layer includes a DNA targeting element and a cutting element and wherein the second layer includes a donor template including a therapeutic gene and homology-directed repair templates; and wherein at least portions of the second layer are farther from the surface of the nanoparticle than the first layer.
26. The nanoparticle of embodiment 24 wherein the targeting element hybridizes to one of SEQ ID NOs. 1-194, 197-208, 210, 212, 213, 242, 245, 251, 254, 258, or 263.
27. The nanoparticle of embodiment 25 or 26, wherein the DNA targeting element is crRNA with a 3' end and a 5' end, wherein the 3' end is conjugated to a spacer.
28. The nanoparticle of any of embodiments 25-27 wherein the DNA targeting element is crRNA with a 3' end and a 5' end, wherein the 5' end is conjugated to the cutting element.
29. The nanoparticle of embodiment 27 or 28 wherein the spacer includes a thiol modification that is covalently linked to the surface of the nanoparticle.
30. The nanoparticle of any of embodiments 25-29 wherein the cutting element is Cpf1 or Cas 9.
31. The nanoparticle of any of embodiments 27-30, wherein the crRNA includes SEQ ID NOs: 195, 196, 209, 211, 244, 253, 260, or 264.
32. The nanoparticle of embodiments 30 or 31, wherein the Cpf1 or Cas9 includes a sequence selected from SEQ ID NOs: 215-241.
33. The nanoparticle of any of embodiments 30-32, wherein the Cpf1 includes a variant of a Cpf1 selected from SEQ ID NOs: 216-227, or 229-241.
34. The nanoparticle of any of embodiments 25-33, wherein the nanoparticle is a gold nanoparticle.
35. The nanoparticle of any of embodiments 25-34, wherein the nanoparticle is coupled to a targeting molecule.
36. The nanoparticle of embodiment 35, wherein the targeting molecule includes a CD34 binding domain or a CD90 binding domain.
37. A therapeutic formulation including a nanoparticle of any of embodiments 24-35.
38. A cell genetically-modifed by a method of any of embodiments 1-24 or a nanoparticle of any of embodiments 25-36.
39. The cell of embodiment 38, wherein the cell is a hematopoietic stem cell (HSC), a hematopoietic progenitor cell (HPC), a hematopoietic stem and progenitor cell (HSPC), a T cell, a natural killer (NK) cell, a B cell, a macrophage, a monocyte, a mesenchymal stem cell (MSC), a white blood cell (WBC), a mononuclear cell (MNC), a endothelial cell (EC), a stromal cell, and/or a bone marrow fibroblast.
40. The cell of embodiment 38 or 39, wherein the cell is a $CD34^{+}CD45RA^{-}CD90^{+}$ HSC.
41. The cell of any of embodiments 38-40, wherein the cell is a human blood cell.
42. A therapeutic formulation including a cell of any of embodiments 38-41.
43. A method of providing a therapeutic nucleic acid sequence to a patient in need thereof including administering a therapeutic formulation of embodiment 37 and/or 42, to the patient thereby providing a therapeutic nucleic acid sequence to the patient.

Variants of protein and/or nucleic acid sequences disclosed herein can also be used. Variants include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein and nucleic acid sequences described or disclosed herein wherein the variant exhibits substantially similar or improved biological function.

"% sequence identity" refers to a relationship between two or more sequences, as determined by comparing the sequences. In the art, "identity" also means the degree of sequence relatedness between protein and nucleic acid sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. "Default values" will mean any set of values or parameters, which originally load with the software when first initialized.

In particular embodiments, variant proteins include conservative amino acid substitutions. In particular embodiments, a conservative amino acid substitution may not substantially change the structural characteristics of the reference sequence (e.g., a replacement amino acid should not tend to break a helix that occurs in the reference sequence, or disrupt other types of secondary structure that characterizes the reference sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden & J. Tooze, eds., Garland Publishing, New York, N.Y. (1991)); and Thornton et al., Nature, 354:105 (1991).

In particular embodiments, a "conservative substitution" involves a substitution found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gln); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

As indicated previously, in particular embodiments, variants include engineered Cpf1s. For example, US 2018/0030425 describes engineered Cpf1 nucleases from *Lachnospiraceae bacterium* ND2006 and *Acidaminococcus* sp. BV3L6 with altered and improved target specificity. Particular variants include *Lachnospiraceae bacterium* ND2006 of SEQ ID NO: 232, e.g., at least including amino acids 19-1246 of SEQ ID NO: 232, with mutations (i.e., replacement of the native amino acid with a different amino acid, e.g., alanine, glycine, or serine), at one or more of the following positions: S203, N274, N278, K290, K367, K532, K609, K915, Q962, K963, K966, K1002, and/or S1003 of SEQ ID NO: 232 (or at positions analogous thereto, e.g., S185, N256, N260, K272, K349, K514, K591, K897, Q944, K945, K948, K984, and/or S985 of SEQ ID NO: 233). SEQ ID NO: 233 is identical to SEQ ID NO: 232 but lacks the first 18 amino acids. Particular Cpf1 variants can also include *Acidaminococcus* sp. BV3L6 Cpf1 (AsCpf1) of SEQ ID NO: 230, e.g., at least comprising amino acids 1-1307 of SEQ ID NO: 230, with mutations (i.e., replacement of the native amino acid with a different amino acid, e.g., alanine, glycine, or serine (except where the native amino acid is serine)), at one or more of the following positions: N178, S186, N278, N282, R301, T315, S376, N515, K523, K524, K603, K965, Q1013, Q1014, and/or K1054 of SEQ ID NO: 230. In particular embodiments, engineered Cpf1 variants include eCfp1.

Other Cpf1 variants include Cpf1 homologs and orthologs of the Cpf1 polypeptides disclosed in Zetsche et al. (2015) Cell 163: 759-771 as well as the Cpf1 polypeptides disclosed in U.S. 2016/0208243. Examples of Cpf1 sequences include SEQ ID NOs: 216-227 and 229-241 disclosed herein.

Other engineered Cpf1 variants are known to those of ordinary skill in the art and included within the scope of the current disclosure (see, e.g., WO/2017/184768).

Exemplary Manufacturing Embodiment.

| Parameter | Disclosed Embodiment |
|---|---|
| Size of AuNP Core | 15 nm |
| AuNP Synthesis Method | Turkevich (1951) |
| Starting solution | 0.25 mM chloroauric acid (HAuCl$_4$) |
| 1st synthesis step | Bring above solution to boiling point and reduce by adding 3.33% sodium citrate (Na3C6H5O7) while stirring vigorously (700 rpm) under a reflux system |
| 2nd synthesis step | Reduce by adding 3.33% sodium citrate (Na$_3$C$_6$H$_5$O$_7$) while stirring vigorously (700 rpm) under a reflux system |
| Cleanup step | Wash AuNPs 3X |
| Initial Resuspension | Rnase free molecular grade water (H$_2$O) |
| First Loading Step | 10 micrograms/mL AuNP added to crRNA (Cpf1/Cas12a) or crRNA + tracrRNA (Cas9)solution at a weight/weight ratio of 0.5 |
| Second Loading Step | 10 mM Citrate buffer (pH 3.0) added and mixed for 5 min. Nanoconjugates are centrifuged at 20000 × g for 20 minutes at room temperature and re-dispersed in 0.9% sodium choloride. |
| Third Loading Step | Add nuclease protein (Cpf1/Cas12a or Cas9) to nanoconjugate solution at a weight/weight ratio of 0.6 |
| Fourth Loading Step | Add 0.005% branched polyethylenimine (2000 MW) and mix by pipetting. |
| Fifth Loading Step | Add single stranded DNA template (ssODN) to nanoconjugates in a weight to weight ratio of 1.0 |
| Final Resuspension | RNase free water |
| Guide RNA Loaded | Guide RNA (crRNA) with the following modifications: For Cpf1 (Cas12a): 1. 3' 18-atom oligo ethylene glycol (OEG) spacer (iSp18) 2. 3' terminal thiol For Cas9: (unmodified tracrRNA) 1. 5' 18-atom oligo ethylene glycol (OEG) spacer (iSp18) 2. 5' terminal thiol |
| Nuclease Loaded | Cpf1 (Cas12a), Cas9, or Mega-TAL |
| ssODN Loaded | Unmodified homology-directed template with symmetric or asymmetric homolgy arms of any length, up to a total of 3 kilobases in total |
| Final actual size of fully loaded AuNP | 25-30 nm |
| Final hydrodynamic size of fully loaded AuNP | 176 nm |

Example 1. Synthesizing Gold Nanoparticle Cores. Gold nanoparticles (AuNPs) of 15 nm size range were synthesized by Turkevich's method with slight modification. Turkevich, et al., (1951). Discussions of the Faraday Society 11(0): 55-75.). 0.25 mM Chlorauric acid solution was brought to the boiling point and reduced by adding 3.33% sodium citrate solution and stirred vigorously under reflux system for 10 min. Synthesized nanoparticles were washed three times and re-dispersed in highly pure water.

Cpf1 and Cas9 Guide RNA Structures. Single Cpf1 guide RNA was ordered from commercial source, Integrated DNA Technologies; IDT), with two custom modifications on the 3' end. The first modification included an 18-atom oligo ethylene glycol (OEG) spacer (iSp18), and the second modification included a thiol modification. The OEG spacer (e.g. polyethylene glycol (PEG) or hexaethylene glycol (HEG), etc.), was at a ratio of 1 per oligonucleotide and served to prevent electrostatic repulsion between oligonucleotides. While an 18-atom spacer was used, other lengths are also appropriate. The thiol modification was also added at a ratio of 1 per oligonucleotide and served as the basis for covalent interactions to bind the oligonucleotide to the surface of the gold nanoparticle.

```
                                    (SEQ ID NO: 260)
5'-/AltR1/rUrA rArUrU rUrCrU rArCrU rCrUrU rGrUrA rGrArU rCrArC rCrCrG rArUrC rCrArC rUrGrG rGrGrA rGrCrA /iSp18//3ThioMC3-D/-3'
```

For cas9, a two-part guide system including tracrRNA and crRNA was used. crRNA for Cas9 was ordered from IDT with the same 18 spacer-thiol modifications as above, but on the 5' end.

```
                                    (SEQ ID NO: 264)
5'-/5ThioMC6-D//iSp18/rCrA rCrCrC rGrArU rCrCrA rCrUrG rGrGrG rArGrC rGrUrU rUrUrA rGrArG rCrUrA rUrGrC rU/AltR2/-3'
```

The accompanying tracrRNA was unmodified.

Preparing the AuNP/CRISPR Nanoformulation. crRNAs with 18 spacer-thiol modifications were used. AuNPs in 10 μg/mL concentration was added to crRNA solution in AuNP/crRNA w/w ratio of 0.5. Following that, citrate buffer with the pH of 3 was added in 10 mM concentration and mixed for 5 min. Prepared AuNP/crRNA nanoconjugates were centrifuged down and re-dispersed in PBS. Then, Cpf1 nuclease was added in AuNP/Cpf1 w/w ratio of 0.6. Polyethylenimine (PEI) of 2000 MW was added in 0.005% concentration and mixed thoroughly. In the final step, ssDNA template was added in the AuNP/ssDNA w/w ratio of 1.

Prophetic Example 1. The translational relevance of the pigtail macaque (*M. nemestrina*) model in terms of cross-reactivity of human reagents and scale has been previously established. This model has served as an important step in clinical translation of HSPC gene therapy. For example, this model has been used to critically evaluate the hematologic potential and safety of LV gene modified and CCR5 edited HSPC, and to track the fate and persistence of these cells in vivo over years. Optimal crRNA pairs identified as above are paired with an optimal nanoparticle delivery strategy identified as above to gene modify autologous HSPC from three nonhuman primates for autologous transplantation after myeloablative, total body irradiation. Safety and feasibility is assessed by measuring product fitness in vitro and in vivo.

In more detail, autologous transplant is performed for CD34$^+$CD90$^+$CD45RA$^-$HSPC after nanoparticle-mediated CRISPR/Cpf1 GSH editing and reporter transgene insertion. Three juvenile pigtail macaques are primed with recombinant human granulocyte colony stimulating factor (GCS-F; 100 mcg/kg/day×4 days) and stem cell factor (SCF; 50 mcg/kg/day×4 days) as subcutaneous injections. Bone marrow is harvested into heparin on the 4$^{th}$ day of priming. The leukocytes are isolated by ammonium chloride lysis and are labeled with IgM monoclonal antibody 12-8 (CD34$^+$) at 4° C. for 30 minutes, washed, and incubated with rat monoclonal anti-mouse IgM microbeads for 30 minutes at 4° C., washed, and then immunoselected. All additional selection procedures will be conducted as described above. The optimal nanoparticle formulation and treatment protocol identified as above is used to accomplish GSH gene editing and targeted GFP transgene insertion. During ex vivo HSPC manipulation monkeys receive myeloablative total body irradiation (1020cGy) as four fractionated doses over 2 days from a linear accelerator. Gene modified HSPC are formulated in PlasmaLyte and autologous serum for intravenous re-infusion 24 hours after the last irradiation dose is delivered. Animals receive supportive care as needed (transfusions, intravenous fluids, etc.).

Gene modified HSPC products will be tested for viability, in vitro colony-forming capacity (CFC), sterility, mycoplasma, endotoxin, cell phenotype, indel formation and transgene expression. All test protocols to be applied are approved for use in phase I clinical trials of autologous cell therapy. Safety is determined by the ability to generate autologous nanoparticle-treated cells which are considered suitable for infusion (i.e., sterile, mycoplasma-free, low endotoxin, >70% viable). Feasibility is determined by the viable cell yield throughout the process and the success of GSH editing and reporter transgene insertion at scale. The target cell dose at infusion is ≥125,000 CD34$^+$CD90$^+$CD45RA$^-$ cells per kilogram of body weight based on our preliminary data.

Safety in vivo is measured by hematologic recovery kinetics and supportive care needs after transplant, as well as clonality of engrafted gene edited cells. Peripheral blood is collected daily from each transplanted animal and analyzed by an automated hematology analyzer until hematologic recovery is observed. Recovery is defined as an absolute neutrophil count >500/mcL and platelets >50,000/mcL for 3 consecutive measurements with an increasing trend observed in both parameters. After hematologic recovery, peripheral blood is collected at least twice per month. Flow cytometry is performed regularly to monitor engraftment levels of nanoparticle-treated cells which express reporter transgene (GFP), as well as lineage markers to determine the extent of multi-lineage reconstitution. Genomic DNA (gDNA) is extracted from these samples and subjected to analysis by Surveyor and DNA barcode and GSH locus sequencing as described above. For DNA barcode sequencing, a single round of PCR amplification is performed and resulting reactions are submitted for sequencing using the Illumina MiSeq platform. Sequence reads are subjected to bioinformatics processing to identify unique barcode events and relative clonal contributions as a measure of clone abundance. Clones are mapped as a function of time and contribution. For GSH locus sequencing the primers corresponding to the optimal crRNA pair identified above are used to sequence the GSH locus. The frequency of engrafted cells containing indels versus reporter transgene cassettes is determined.

This study establishes the scaled protocol for nanoparticle-mediated GSH editing and targeted reporter gene insertion. This protocol serves as the basis for evaluating clinically therapeutic transgene delivery across many disease targets. The results of this study provide the basis for evaluation of strategies for improving gene edited HSPC engraftment and differentiation in this clinically relevant and translational large animal model.

Prophetic Example 2. Validate optimal GSH locus for gene editing in CD34$^+$CD45RA$^-$CD90$^+$ cells. Healthy donor bone marrow (BM) aspirates are obtained from a commercial provider or under an IRB Protocol. Mobilized peripheral blood products (mAPH) are obtained from healthy donors post granulocyte-colony stimulating factor (G-CSF) administration and leukapheresis collection. For BM, red blood cells are depleted by hetastarch sedimentation, and CD34$^+$ cells are immune-selected. For mAPH a standard immunoselection of CD34$^+$ cells is performed. Resulting CD34-enriched products from both HSPC sources are stained with antibodies specific to CD90 and CD45RA and the target HSPC population (CD90⁺CD45RA⁻) is collected by fluorescence-activated cell sorting as previously described [Radtke et al., Sci. Transl. Med. 2017; 9 (414).].

CD34+CD45RA-CD90+ cells are targeted with multiple CRISPR/Cpf1 nucleases designed for a candidate GSH identified. Specificity and function is evaluated in vitro and in vivo to identify the optimal GSH locus. Chemically modified mRNA is used to increase intracellular stability, while homology arms and phosphorothioate modification is incorporated into the ssODN to improve HDR efficiency.

Cells are suspended in StemSpan media containing recombinant human growth factors stem cell factor (SCF), thrombopoietin (TPO) and fms-like tyrosine kinase 3 ligand (flt3-L) and incubated at 30° C. for 24 hours. Media is changed the following day and cultures will be prepared for subsequent analysis and infusion. Viability is monitored by flow cytometry and/or trypan blue staining.

At least three methods can be applied to determine the efficiency and specificity of gene addition. First, flow cytometry can be used to assess GFP and/or therapeutic gene expression. This shows the frequency of cells with cassette incorporation and GFP/therapeutic gene expression/function. Second, the Surveyor assay (Ran et al. Cell. 2013; 154(6): 1380-1389) is used to determine the frequency of indels versus transgene insertion at the target locus. Briefly, cells are pelleted and DNA extracted and purified. Resulting DNA is quantified and subjected to PCR using primers designed to the locus targeted by the specific CRISPR/Cpf1 nuclease pair. Appropriate mismatch-containing controls are PCR amplified. Following PCR, products are denatured and re-annealed to form heteroduplexes, which are subsequently treated with Surveyor enzyme and analyzed by gel electrophoresis. Imaging and densitometry are then used to calculate an editing efficiency for each locus. Finally, BLISS is applied to identify off-target DSBs (Yan et al. Nat Commun 2017; 8: 15058). Cells are first transferred to glass slides by cytospinning, followed by permeabilization and fixation. In situ DSBs are polished and ligated to synthetic oligonucleotides containing a unique sample barcode and multiplex identifier, followed by an RA5 Illumina sequencing adaptor and T7 promoter. DNA is then purified and subjected to sonication followed by in vitro transcription and prepared as a library for Illumina-based sequencing. This permits identification of genomic locations of off-target DSBs and quantitation of DSB frequency as the number of reads corresponding to a specific genomic location for a given number of cells immobilized onto the original slide. Following these analyses, the optimal CRISPR/Cpf1 pair and ssODN combination is identified for further analysis in vivo, for example as described below. The optimal combination demonstrates the highest efficiency of barcoded transgene insertion at the desired locus with minimal toxicity in vitro and the lowest frequency of off-target DSB formation across donors and HSPC sources (BM and mAPH).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in gene editing at a targeted GSH site.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Particular embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

What is claimed is:

1. A method of genetically modifying a cell through homology-directed repair (HDR) within a genomic safe harbor loci wherein the method comprises:

contacting the cell with a gold nanoparticle (AuNP) comprising at least two active layers wherein the first layer comprises
a crRNA with a 3' end and a 5' end,
wherein the 3' end is conjugated to a spacer with a thiol modification, and the 5' end is conjugated to a nuclease to form a crRNA-nuclease ribonucleoprotein (RNP) complex, and
wherein the thiol modification is covalently linked to the surface of a gold core of the AuNP
and wherein the second layer comprises
a donor template comprising a therapeutic gene and HDR templates and wherein the second layer is farther from the surface of the gold core than the first layer and wherein the crRNA-nuclease RNP complex binds a PAM-site within human (h) chromosome (chr) 11 at positions 67681215-67741765, 67691162-67691186, 67723825-67723849, 67805337-67845629, 67812349-67812375, 67812443-67812469, 67839126-67839150, or 67895738-67941098 or hchr3 at positions 46373915-46373939 and results in cutting of the DNA at the PAM of the PAM-site thereby genetically modifying the cell through HDR within the genomic safe harbor loci.

2. The method of claim 1, wherein the cell is a hematopoietic stem cell (HSC), a hematopoietic progenitor cell (HPC), a hematopoietic stem and progenitor cell (HSPC), a T cell, a natural killer (NK) cell, a B cell, a macrophage, a monocyte, a mesenchymal stem cell (MSC), a white blood cell (WBC), a mononuclear cell (MNC), a endothelial cell (EC), a stromal cell, and/or a bone marrow fibroblast.

3. A nanoparticle (NP) comprising a metallic core associated with two active NP layers wherein the first NP layer comprises
a crRNA with a 3' end and a 5' end,
wherein the 3' end is conjugated to a spacer with a thiol modification, and the 5' end is conjugated to a nuclease to form a crRNA-nuclease ribonucleoprotein (RNP) complex,
wherein the thiol modification is covalently linked to the surface of the metallic NP core and
wherein the crRNA-nuclease RNP complex binds a target PAM-site within human (h) chromosome (chr) 11 at positions 67681215-67741765; 67691162-67691186; 67723825-67723849; 67805337-67845629; 67812349-67812375; 67812443-67812469; 67839126-67839150; or 67895738-67941098 or hchr3 at positions 46373915-46373939 and results in cutting of the DNA at the PAM of the PAM-site;
and wherein the second NP layer comprises a donor template comprising a therapeutic gene and homology-directed repair templates; and wherein the second NP layer is farther from the surface of the metallic core than the first NP layer.

4. The NP of claim 3, wherein the metallic core is less than 20 nm in diameter.

5. The NP of claim 3, wherein the metallic core is gold.

6. The NP of claim 3, further comprising a positively-charged polymer coating.

7. The NP of claim 6, wherein the positively-charged polymer coating surrounds the RNP complex and contacts the surface of the metallic core.

8. The NP of claim 6, wherein the positively-charged polymer has a molecular weight of less than 2500 daltons.

9. The NP of claim 6, wherein the positively-charged polymer coating comprises polyethyleneimine with a molecular weight of 2000 daltons.

10. The NP of claim 3, wherein
the target site is hchr11: 67723825-67723849 and has the sequence as set forth in SEQ ID NO: 132,
the target site is hchr11:67691162-67691186 and has the sequence as set forth in SEQ ID NO: 108,
the target site is hchr11:67812349-67812375 and has the sequence as set forth in SEQ ID NO: 203,
the target site is hchr11:67839126-67839150 and has the sequence as set forth in SEQ ID NO: 210, or
the target site is hchr3:46373915-46373939 and has the sequence as set forth in SEQ ID NO: 212.

11. The NP of claim 3, wherein the crRNA comprises:
SEQ ID NO: 195 or a sequence with at least 98% identity to SEQ ID NO: 195 that binds within Hchr11: 67723825-67723849;
SEQ ID NO: 196 or a sequence with at least 98% identity to SEQ ID NO: 196 that binds within Hchr11: 67691162-67691186,
SEQ ID NO: 209 or a sequence with at least 98% identity to SEQ ID NO: 209 that binds within Hchr11: 67812349-67812375,
SEQ ID NO: 211 or a sequence with at least 98% identity to SEQ ID NO: 211 that binds within hchr11: 67839126-67839150, or
SEQ ID NO: 260 or a sequence with at least 98% identity to SEQ ID NO: 260 that binds within hchr3:46373915-46373939.

12. The NP of claim 3, wherein the nuclease is Cpf1 or Cas9.

13. The NP of claim 3, wherein the nuclease is Cpf1 and has a sequence as set forth in SEQ ID NOs: 229-241 or is encoded by a sequence as set forth in SEQ ID NOs: 216-227.

14. The NP of claim 3, wherein the NP is coupled to a targeting molecule through a linkage with the nuclease.

15. The NP of claim 14, wherein the targeting molecule comprises a CD34 binding domain or a CD90 binding domain.

16. The NP of claim 3, wherein the therapeutic gene comprises or encodes skeletal protein 4.1, glycophorin, p55, the Duffy allele, globin family genes; WAS; phox; dystrophin; pyruvate kinase; CLN3; ABCD1; arylsulfatase A; SFTPB; SFTPC; NLX2.1; ABCA3; GATA1; ribosomal protein genes; TERT; TERC; DKC1; TINF2; CFTR; LRRK2; PARK2; PARK7; PINK1; SNCA; PSEN1; PSEN2; APP; SOD1; TDP43; FUS; ubiquilin 2; C9ORF72, α2β1; αvβ3; αvβ5; αvβ63; BOB/GPR15; Bonzo/STRL-33/TYMSTR; CCR2; CCR3; CCR5; CCR8; CD4; CD46; CD55; CXCR4; aminopeptidase-N; HHV-7; ICAM; ICAM-1; PRR2/HveB; HveA; α-dystroglycan; LDLR/α2MR/LRP; PVR; PRR1/

HveC, laminin receptor, 101F6, 123F2, 53BP2, abl, ABLI, ADP, aFGF, APC, ApoAl, ApoAlV, ApoE, ATM, BAI-1, BDNF, Beta*(BLU), bFGF, BLC1, BLC6, BRCA1, BRCA2, CBFA1, CBL, C-CAM, CFTR, CNTF, COX-1, CSFIR, CTS-1, cytosine deaminase, DBCCR-1, DCC, Dp, DPC-4, E1A, E2F, EBRB2, erb, ERBA, ERBB, ETS1, ETS2, ETV6, Fab, FancA, FancB, FancC, FancD1, FancD2, FancE, FancF, FancG, Fancl, FancJ, FancL, FancM, FancN, FancO, FancP, FancQ, FancR, FancS, FancT, FancU, FancV, and FancW, FCC, FGF, FGR, FHIT, fms, FOX, FUS 1, FUS1, FYN, G-CSF, GDAIF, Gene 21, Gene 26, GM-CSF, GMF, gsp, HCR, HIC-1, HRAS, hst, IGF, IL-1, IL-2, IL-3, IL-4, IL-5, IL-6, IL-7, IL-8, IL-9, IL-10, IL-11 IL-12, ING1, interferon α, interferon β, interferon y, IRF-1, JUN, KRAS, LCK, LUCA-1, LUCA-2, LYN, MADH4, MADR2, MCC, mda7, MDM2, MEN-I, MEN-II, MLL, MMAC1, MYB, MYC, MYCL1, MYCN, neu, NF-1, NF-2, NGF, NOEY1, NOEY2, NRAS, NT3, NTS, OVCA1, p16, p21, p27, p53, p57, p73, p300, PGS, PIM1, PL6, PML, PTEN, raf, Rap1A, ras, Rb, RB1, RET, rks-3, ScFv, scFV ras, SEM A3, SRC, TALI, TCL3, TFPI, thrombospondin, thymidine kinase, TNF, TP53, trk, T-VEC, VEGF, VHL, WT1, WT-1, YES, zac1, iduronidase, IDS, GNS, HGSNAT, SGSH, NAGLU, GUSB, GALNS, GLB1, ARSB, HYAL1, F8, F9, HBB, CYB5R3, γC, JAK3, IL7RA, RAG1, RAG2, DCLRE1C, PRKDC, LIG4, NHEJ1, CD3D, CD3E, CD3Z, CD3G, PTPRC, ZAP70, LCK, AK2, ADA, PNP, WHN, CHD7, ORAI1, STIM1, CORO1A, CIITA, RFXANK, RFX5, RFXAP, RMRP, DKC1, TERT, TINF2, DCLRE1B, and SLC46A1.

17. A cell genetically-modifed by a method of claim 1.

18. The cell of claim 17, wherein the cell is a hematopoietic stem cell (HSC), a hematopoietic progenitor cell (HPC), a hematopoietic stem and progenitor cell (HSPC), a T cell, a natural killer (NK) cell, a B cell, a macrophage, a monocyte, a mesenchymal stem cell (MSC), a white blood cell (WBC), a mononuclear cell (MNC), a endothelial cell (EC), a stromal cell, and/or a bone marrow fibroblast.

19. The cell of claim 17, wherein the cell is a CD34$^+$CD45RA$^-$CD90$^+$HSC.

20. The cell of claim 17, wherein the cell is a human blood cell.

* * * * *

```
                        SEQUENCE LISTING

<160> NUMBER OF SEQ ID NOS: 264

<210> SEQ ID NO 1
<211> LENGTH: 25
<212> TYPE: DNA
<213> ORGANISM: Homo sapiens

<400> SEQUENCE: 1
tttaaaaaaa gtcttcataa taaaa                                          25

<210> SEQ ID NO 2
<211> LENGTH: 25
<212> TYPE: DNA
<213> ORGANISM: Homo sapiens

<400> SEQUENCE: 2
tttacttctg tgcacccata gactc                                          25

<210> SEQ ID NO 3
<211> LENGTH: 25
<212> TYPE: DNA
<213> ORGANISM: Homo sapiens

<400> SEQUENCE: 3
tttaactctg ccatgggtgc cagga                                          25

<210> SEQ ID NO 4
<211> LENGTH: 25
<212> TYPE: DNA
<213> ORGANISM: Homo sapiens

<400> SEQUENCE: 4
tttagccact gtgagaaaca gttta                                          25
```

```
<210> SEQ ID NO 5
<211> LENGTH: 25
<212> TYPE: DNA
<213> ORGANISM: Homo sapiens

<400> SEQUENCE: 5
tttataaggc taagtagtat tctat                                              25

<210> SEQ ID NO 6
<211> LENGTH: 25
<212> TYPE: DNA
<213> ORGANISM: Homo sapiens

<400> SEQUENCE: 6
tttatccact aattgttgat gggca                                              25

<210> SEQ ID NO 7
<211> LENGTH: 25
<212> TYPE: DNA
<213> ORGANISM: Homo sapiens

<400> SEQUENCE: 7
tttattttct ttttggtaag aagga                                              25

<210> SEQ ID NO 8
<211> LENGTH: 25
<212> TYPE: DNA
<213> ORGANISM: Homo sapiens

<400> SEQUENCE: 8
tttaaaataa tcgtcattct ttttg                                              25

<210> SEQ ID NO 9
<211> LENGTH: 25
<212> TYPE: DNA
<213> ORGANISM: Homo sapiens

<400> SEQUENCE: 9
tttatattaa tccttgtatg tctga                                              25

<210> SEQ ID NO 10
<211> LENGTH: 25
<212> TYPE: DNA
<213> ORGANISM: Homo sapiens

<400> SEQUENCE: 10
tttaaatgga taagttaggc tgggc                                              25

<210> SEQ ID NO 11
<211> LENGTH: 25
<212> TYPE: DNA
<213> ORGANISM: Homo sapiens

<400> SEQUENCE: 11
tttacacaaa ctgtacttgt aggta                                              25

<210> SEQ ID NO 12
<211> LENGTH: 25
<212> TYPE: DNA
<213> ORGANISM: Homo sapiens

<400> SEQUENCE: 12
tttagtgagg aaaaactaca tttat                                              25
```

```
<210> SEQ ID NO 13
<211> LENGTH: 25
<212> TYPE: DNA
<213> ORGANISM: Homo sapiens

<400> SEQUENCE: 13
tttaaaaagg gaaaattagg gagaa                                          25

<210> SEQ ID NO 14
<211> LENGTH: 25
<212> TYPE: DNA
<213> ORGANISM: Homo sapiens

<400> SEQUENCE: 14
tttactaaat gacctcttcg ccaaa                                          25

<210> SEQ ID NO 15
<211> LENGTH: 25
<212> TYPE: DNA
<213> ORGANISM: Homo sapiens

<400> SEQUENCE: 15
tttagtgata tgaaaagaac catgc                                          25

<210> SEQ ID NO 16
<211> LENGTH: 25
<212> TYPE: DNA
<213> ORGANISM: Homo sapiens

<400> SEQUENCE: 16
tttaaatttt ccagtgtctc agtgt                                          25

<210> SEQ ID NO 17
<211> LENGTH: 25
<212> TYPE: DNA
<213> ORGANISM: Homo sapiens

<400> SEQUENCE: 17
tttaagcctg aaaacctaaa aaatg                                          25

<210> SEQ ID NO 18
<211> LENGTH: 25
<212> TYPE: DNA
<213> ORGANISM: Homo sapiens

<400> SEQUENCE: 18
tttaaaaatt agctgcgttg gtggt                                          25

<210> SEQ ID NO 19
<211> LENGTH: 25
<212> TYPE: DNA
<213> ORGANISM: Homo sapiens

<400> SEQUENCE: 19
tttagctgct ttaaaatgtg aactc                                          25

<210> SEQ ID NO 20
<211> LENGTH: 25
<212> TYPE: DNA
<213> ORGANISM: Homo sapiens

<400> SEQUENCE: 20
tttaatctca agtcacttct ctagg                                          25
```

```
<210> SEQ ID NO 21
<211> LENGTH: 25
<212> TYPE: DNA
<213> ORGANISM: Homo sapiens

<400> SEQUENCE: 21
tttaaacgct cgttagatca ctgga                                      25

<210> SEQ ID NO 22
<211> LENGTH: 25
<212> TYPE: DNA
<213> ORGANISM: Homo sapiens

<400> SEQUENCE: 22
tttaaggcag gaatcagggt gccat                                      25

<210> SEQ ID NO 23
<211> LENGTH: 25
<212> TYPE: DNA
<213> ORGANISM: Homo sapiens

<400> SEQUENCE: 23
tttaaaaaaa tcccaggtga cccta                                      25

<210> SEQ ID NO 24
<211> LENGTH: 25
<212> TYPE: DNA
<213> ORGANISM: Homo sapiens

<400> SEQUENCE: 24
tttaatcttg cagggacagg aagga                                      25

<210> SEQ ID NO 25
<211> LENGTH: 25
<212> TYPE: DNA
<213> ORGANISM: Homo sapiens

<400> SEQUENCE: 25
tttaaaatgt gaactccaaa tcagg                                      25

<210> SEQ ID NO 26
<211> LENGTH: 25
<212> TYPE: DNA
<213> ORGANISM: Homo sapiens

<400> SEQUENCE: 26
tttattattt cgttgttttt cctct                                      25

<210> SEQ ID NO 27
<211> LENGTH: 25
<212> TYPE: DNA
<213> ORGANISM: Homo sapiens

<400> SEQUENCE: 27
tttatcttgg tgtttgaact cggat                                      25

<210> SEQ ID NO 28
<211> LENGTH: 25
<212> TYPE: DNA
<213> ORGANISM: Homo sapiens

<400> SEQUENCE: 28
```
tttactgccc atttagctgc tttaa                                25

<210> SEQ ID NO 29
<211> LENGTH: 25
<212> TYPE: DNA
<213> ORGANISM: Homo sapiens

<400> SEQUENCE: 29
tttaacttga ttaccttata gtcaa                                25

<210> SEQ ID NO 30
<211> LENGTH: 25
<212> TYPE: DNA
<213> ORGANISM: Homo sapiens

<400> SEQUENCE: 30
tttatatatt taacttctgt atttt                                25

<210> SEQ ID NO 31
<211> LENGTH: 25
<212> TYPE: DNA
<213> ORGANISM: Homo sapiens

<400> SEQUENCE: 31
tttatctgct atagctaaca aattt                                25

<210> SEQ ID NO 32
<211> LENGTH: 25
<212> TYPE: DNA
<213> ORGANISM: Homo sapiens

<400> SEQUENCE: 32
tttaacttct gtattttcta aaact                                25

<210> SEQ ID NO 33
<211> LENGTH: 25
<212> TYPE: DNA
<213> ORGANISM: Homo sapiens

<400> SEQUENCE: 33
tttataacac accagcatca gttac                                25

<210> SEQ ID NO 34
<211> LENGTH: 25
<212> TYPE: DNA
<213> ORGANISM: Homo sapiens

<400> SEQUENCE: 34
tttattatct ttcctgtttt ctaat                                25

<210> SEQ ID NO 35
<211> LENGTH: 25
<212> TYPE: DNA
<213> ORGANISM: Homo sapiens

<400> SEQUENCE: 35
tttaatatta acatttgcta atttc                                25

<210> SEQ ID NO 36
<211> LENGTH: 25
<212> TYPE: DNA
<213> ORGANISM: Homo sapiens

<400> SEQUENCE: 36
tttaaaaggc cagatgtcaa ttcag        25

<210> SEQ ID NO 37
<211> LENGTH: 25
<212> TYPE: DNA
<213> ORGANISM: Homo sapiens

<400> SEQUENCE: 37
tttatgcaga tagatatata ttttt        25

<210> SEQ ID NO 38
<211> LENGTH: 25
<212> TYPE: DNA
<213> ORGANISM: Homo sapiens

<400> SEQUENCE: 38
tttaatcact ggatcatgga cctaa        25

<210> SEQ ID NO 39
<211> LENGTH: 25
<212> TYPE: DNA
<213> ORGANISM: Homo sapiens

<400> SEQUENCE: 39
tttagtgttt cttagaaact taaca        25

<210> SEQ ID NO 40
<211> LENGTH: 25
<212> TYPE: DNA
<213> ORGANISM: Homo sapiens

<400> SEQUENCE: 40
tttacagcag tgccattcac aatgg        25

<210> SEQ ID NO 41
<211> LENGTH: 25
<212> TYPE: DNA
<213> ORGANISM: Homo sapiens

<400> SEQUENCE: 41
tttataggcc caggtctaga tctgg        25

<210> SEQ ID NO 42
<211> LENGTH: 25
<212> TYPE: DNA
<213> ORGANISM: Homo sapiens

<400> SEQUENCE: 42
tttagcccta tcttatccat atgga        25

<210> SEQ ID NO 43
<211> LENGTH: 25
<212> TYPE: DNA
<213> ORGANISM: Homo sapiens

<400> SEQUENCE: 43
tttatgtcta gtacttaggg cagta        25

<210> SEQ ID NO 44
<211> LENGTH: 25
<212> TYPE: DNA
<213> ORGANISM: Homo sapiens

```
<400> SEQUENCE: 44
tttacaatta attgtagttc tttga                                        25

<210> SEQ ID NO 45
<211> LENGTH: 25
<212> TYPE: DNA
<213> ORGANISM: Homo sapiens

<400> SEQUENCE: 45
tttattttct tagatttact ctgta                                        25

<210> SEQ ID NO 46
<211> LENGTH: 25
<212> TYPE: DNA
<213> ORGANISM: Homo sapiens

<400> SEQUENCE: 46
tttaaaaact gggtttacaa ataaa                                        25

<210> SEQ ID NO 47
<211> LENGTH: 25
<212> TYPE: DNA
<213> ORGANISM: Homo sapiens

<400> SEQUENCE: 47
tttaaacatt ttgactgtag ccatt                                        25

<210> SEQ ID NO 48
<211> LENGTH: 25
<212> TYPE: DNA
<213> ORGANISM: Homo sapiens

<400> SEQUENCE: 48
tttatgactg tttcatgtgt gctca                                        25

<210> SEQ ID NO 49
<211> LENGTH: 25
<212> TYPE: DNA
<213> ORGANISM: Homo sapiens

<400> SEQUENCE: 49
tttataacct cacctttggc tttta                                        25

<210> SEQ ID NO 50
<211> LENGTH: 25
<212> TYPE: DNA
<213> ORGANISM: Homo sapiens

<400> SEQUENCE: 50
tttagaagtc catataaggg gatgc                                        25

<210> SEQ ID NO 51
<211> LENGTH: 25
<212> TYPE: DNA
<213> ORGANISM: Homo sapiens

<400> SEQUENCE: 51
tttactgtta attagtcctt gctta                                        25

<210> SEQ ID NO 52
<211> LENGTH: 25
<212> TYPE: DNA
<213> ORGANISM: Homo sapiens
```

```
<400> SEQUENCE: 52
tttatctatg aacctcatag gtcct                                      25

<210> SEQ ID NO 53
<211> LENGTH: 25
<212> TYPE: DNA
<213> ORGANISM: Homo sapiens

<400> SEQUENCE: 53
tttactatag ttaattggaa cactt                                      25

<210> SEQ ID NO 54
<211> LENGTH: 25
<212> TYPE: DNA
<213> ORGANISM: Homo sapiens

<400> SEQUENCE: 54
tttaacgtta aatctctttc taaca                                      25

<210> SEQ ID NO 55
<211> LENGTH: 25
<212> TYPE: DNA
<213> ORGANISM: Homo sapiens

<400> SEQUENCE: 55
tttatctcct ttaaattccc atgtt                                      25

<210> SEQ ID NO 56
<211> LENGTH: 25
<212> TYPE: DNA
<213> ORGANISM: Homo sapiens

<400> SEQUENCE: 56
tttagtccaa ataaagcaac aatac                                      25

<210> SEQ ID NO 57
<211> LENGTH: 25
<212> TYPE: DNA
<213> ORGANISM: Homo sapiens

<400> SEQUENCE: 57
tttatccatt cccaaccaca aagaa                                      25

<210> SEQ ID NO 58
<211> LENGTH: 25
<212> TYPE: DNA
<213> ORGANISM: Homo sapiens

<400> SEQUENCE: 58
tttaatttct ccacttgatt aactt                                      25

<210> SEQ ID NO 59
<211> LENGTH: 25
<212> TYPE: DNA
<213> ORGANISM: Homo sapiens

<400> SEQUENCE: 59
tttagccaaa ggacatgcct aaaat                                      25

<210> SEQ ID NO 60
<211> LENGTH: 25
<212> TYPE: DNA
```

```
<213> ORGANISM: Homo sapiens

<400> SEQUENCE: 60
tttaggaatt aataaaaatt gtata                                    25

<210> SEQ ID NO 61
<211> LENGTH: 25
<212> TYPE: DNA
<213> ORGANISM: Homo sapiens

<400> SEQUENCE: 61
tttaatgcat ccataaacag aactg                                    25

<210> SEQ ID NO 62
<211> LENGTH: 25
<212> TYPE: DNA
<213> ORGANISM: Homo sapiens

<400> SEQUENCE: 62
tttagggtgg ttctcctggg atttt                                    25

<210> SEQ ID NO 63
<211> LENGTH: 25
<212> TYPE: DNA
<213> ORGANISM: Homo sapiens

<400> SEQUENCE: 63 tttatcccatt acgcatgagg tccct                                   25

<210> SEQ ID NO 64
<211> LENGTH: 25
<212> TYPE: DNA
<213> ORGANISM: Homo sapiens

<400> SEQUENCE: 64
tttacacaag caacaccagc tgcag                                    25

<210> SEQ ID NO 65
<211> LENGTH: 25
<212> TYPE: DNA
<213> ORGANISM: Homo sapiens

<400> SEQUENCE: 65
tttaaatact tgacaaaaaa gattg                                    25

<210> SEQ ID NO 66
<211> LENGTH: 25
<212> TYPE: DNA
<213> ORGANISM: Homo sapiens

<400> SEQUENCE: 66
tttaaagggg gtctctacta aatct                                    25

<210> SEQ ID NO 67
<211> LENGTH: 25
<212> TYPE: DNA
<213> ORGANISM: Homo sapiens

<400> SEQUENCE: 67
tttaatcttt atctgaccta aattt                                    25

<210> SEQ ID NO 68
<211> LENGTH: 25
```

```
<212> TYPE: DNA
<213> ORGANISM: Homo sapiens

<400> SEQUENCE: 68
tttataaaga aattccgcaa gaact                                              25

<210> SEQ ID NO 69
<211> LENGTH: 25
<212> TYPE: DNA
<213> ORGANISM: Homo sapiens

<400> SEQUENCE: 69
tttatgattt aaggggaag ctttg                                               25

<210> SEQ ID NO 70
<211> LENGTH: 25
<212> TYPE: DNA
<213> ORGANISM: Homo sapiens

<400> SEQUENCE: 70
tttaatgctt tcaacatcga ttgct                                              25

<210> SEQ ID NO 71
<211> LENGTH: 25
<212> TYPE: DNA
<213> ORGANISM: Homo sapiens

<400> SEQUENCE: 71
tttacggaga ggatacaaag atcct                                              25

<210> SEQ ID NO 72
<211> LENGTH: 25
<212> TYPE: DNA
<213> ORGANISM: Homo sapiens

<400> SEQUENCE: 72
tttaagatct tcctataatt atagc                                              25

<210> SEQ ID NO 73
<211> LENGTH: 25
<212> TYPE: DNA
<213> ORGANISM: Homo sapiens

<400> SEQUENCE: 73
tttaattttt gttggagtct tttct                                              25

<210> SEQ ID NO 74
<211> LENGTH: 25
<212> TYPE: DNA
<213> ORGANISM: Homo sapiens

<400> SEQUENCE: 74 tttattttt aaaaccagaa cattt                                               25

<210> SEQ ID NO 75
<211> LENGTH: 25
<212> TYPE: DNA
<213> ORGANISM: Homo sapiens

<400> SEQUENCE: 75
tttagttctc ttttatact ccaaa                                               25

<210> SEQ ID NO 76
```

<210> SEQ ID NO 77
<211> LENGTH: 25
<212> TYPE: DNA
<213> ORGANISM: Homo sapiens

<400> SEQUENCE: 76
tttactaaga atagtgtagg ggtta                                  25

<210> SEQ ID NO 77
<211> LENGTH: 25
<212> TYPE: DNA
<213> ORGANISM: Homo sapiens

<400> SEQUENCE: 77 tttactatttt cccatcttat gtata                                 25

<210> SEQ ID NO 78
<211> LENGTH: 25
<212> TYPE: DNA
<213> ORGANISM: Homo sapiens

<400> SEQUENCE: 78
tttagcaggt gtcttgatcc ccctt                                  25

<210> SEQ ID NO 79
<211> LENGTH: 25
<212> TYPE: DNA
<213> ORGANISM: Homo sapiens

<400> SEQUENCE: 79 tttatttttct agtccccctt tgatc                                 25

<210> SEQ ID NO 80
<211> LENGTH: 25
<212> TYPE: DNA
<213> ORGANISM: Homo sapiens

<400> SEQUENCE: 80
tttaaaatca tcttattgtt tacaa                                  25

<210> SEQ ID NO 81
<211> LENGTH: 25
<212> TYPE: DNA
<213> ORGANISM: Homo sapiens

<400> SEQUENCE: 81
tttagagaga tatattttcc tctag                                  25

<210> SEQ ID NO 82
<211> LENGTH: 25
<212> TYPE: DNA
<213> ORGANISM: Homo sapiens

<400> SEQUENCE: 82
tttaaaagtg gtcacaagtg gggga                                  25

<210> SEQ ID NO 83
<211> LENGTH: 25
<212> TYPE: DNA
<213> ORGANISM: Homo sapiens

<400> SEQUENCE: 83
tttactagaa acctttccca tattg                                  25

```
<210> SEQ ID NO 84
<211> LENGTH: 25
<212> TYPE: DNA
<213> ORGANISM: Homo sapiens

<400> SEQUENCE: 84
tttattgctc tgtaacagat tacca                                    25

<210> SEQ ID NO 85
<211> LENGTH: 25
<212> TYPE: DNA
<213> ORGANISM: Homo sapiens

<400> SEQUENCE: 85
tttaccagcc atcttagaac aaatt                                    25

<210> SEQ ID NO 86
<211> LENGTH: 25
<212> TYPE: DNA
<213> ORGANISM: Homo sapiens

<400> SEQUENCE: 86
tttacagaat tcgctttccc tttaa                                    25

<210> SEQ ID NO 87
<211> LENGTH: 25
<212> TYPE: DNA
<213> ORGANISM: Homo sapiens

<400> SEQUENCE: 87
tttattaagc taaacctagg tacaa                                    25

<210> SEQ ID NO 88
<211> LENGTH: 25
<212> TYPE: DNA
<213> ORGANISM: Homo sapiens

<400> SEQUENCE: 88
tttaggatca ccttaacttg gtgag                                    25

<210> SEQ ID NO 89
<211> LENGTH: 25
<212> TYPE: DNA
<213> ORGANISM: Homo sapiens

<400> SEQUENCE: 89
tttactattt ccectggagt cttta                                    25

<210> SEQ ID NO 90
<211> LENGTH: 25
<212> TYPE: DNA
<213> ORGANISM: Homo sapiens

<400> SEQUENCE: 90
tttaataagt cttttgatta caggc                                    25

<210> SEQ ID NO 91
<211> LENGTH: 25
<212> TYPE: DNA
<213> ORGANISM: Homo sapiens

<400> SEQUENCE: 91
tttactctgt agcttttaa aatca                                     25
```

-continued

<210> SEQ ID NO 92
<211> LENGTH: 25
<212> TYPE: DNA
<213> ORGANISM: Homo sapiens

<400> SEQUENCE: 92
tttacttctt ttaagatctt cctat                                 25

<210> SEQ ID NO 93
<211> LENGTH: 25
<212> TYPE: DNA
<213> ORGANISM: Homo sapiens

<400> SEQUENCE: 93
tttactttgc tctgtgaaca gagtt                                 25

<210> SEQ ID NO 94
<211> LENGTH: 25
<212> TYPE: DNA
<213> ORGANISM: Homo sapiens

<400> SEQUENCE: 94
tttaattcct gtttcatttt cccat                                 25

<210> SEQ ID NO 95
<211> LENGTH: 25
<212> TYPE: DNA
<213> ORGANISM: Homo sapiens

<400> SEQUENCE: 95
tttagggcgt gactgtgaat aactc                                 25

<210> SEQ ID NO 96
<211> LENGTH: 25
<212> TYPE: DNA
<213> ORGANISM: Homo sapiens

<400> SEQUENCE: 96
tttattcaat ttctcctaag tctgc                                 25

<210> SEQ ID NO 97
<211> LENGTH: 25
<212> TYPE: DNA
<213> ORGANISM: Homo sapiens

<400> SEQUENCE: 97
tttaaaaata tttagcaact gggac                                 25

<210> SEQ ID NO 98
<211> LENGTH: 25
<212> TYPE: DNA
<213> ORGANISM: Homo sapiens

<400> SEQUENCE: 98
tttacgttcc cagatcgtat ttctt                                 25

<210> SEQ ID NO 99
<211> LENGTH: 25
<212> TYPE: DNA
<213> ORGANISM: Homo sapiens

<400> SEQUENCE: 99
tttagttcat ggcaagcaag tcatt                                 25

<210> SEQ ID NO 100
<211> LENGTH: 25
<212> TYPE: DNA
<213> ORGANISM: Homo sapiens

<400> SEQUENCE: 100
tttaggccac caattggggg cattt                                    25

<210> SEQ ID NO 101
<211> LENGTH: 25
<212> TYPE: DNA
<213> ORGANISM: Homo sapiens

<400> SEQUENCE: 101
tttaccaacc atcactgcca tcgtc                                    25

<210> SEQ ID NO 102
<211> LENGTH: 25
<212> TYPE: DNA
<213> ORGANISM: Homo sapiens

<400> SEQUENCE: 102
tttaacccca gaaactgtta attcc                                    25

<210> SEQ ID NO 103
<211> LENGTH: 25
<212> TYPE: DNA
<213> ORGANISM: Homo sapiens

<400> SEQUENCE: 103
tttatagtta tttacagaat tcgct                                    25

<210> SEQ ID NO 104
<211> LENGTH: 25
<212> TYPE: DNA
<213> ORGANISM: Homo sapiens

<400> SEQUENCE: 104
tttatttgtg caacaatggg gaatt                                    25

<210> SEQ ID NO 105
<211> LENGTH: 25
<212> TYPE: DNA
<213> ORGANISM: Homo sapiens

<400> SEQUENCE: 105
tttaataaag caataggaag acgtt                                    25

<210> SEQ ID NO 106
<211> LENGTH: 25
<212> TYPE: DNA
<213> ORGANISM: Homo sapiens

<400> SEQUENCE: 106
tttaagtcac aggggtgtag accct                                    25

<210> SEQ ID NO 107
<211> LENGTH: 25
<212> TYPE: DNA
<213> ORGANISM: Homo sapiens

<400> SEQUENCE: 107
tttagtgacc accctactct attgt 25

<210> SEQ ID NO 108
<211> LENGTH: 25
<212> TYPE: DNA
<213> ORGANISM: Homo sapiens

<400> SEQUENCE: 108
tttaatagaa tagcctcata tttta 25

<210> SEQ ID NO 109
<211> LENGTH: 25
<212> TYPE: DNA
<213> ORGANISM: Homo sapiens

<400> SEQUENCE: 109
tttaaccact cccactccca attac 25

<210> SEQ ID NO 110
<211> LENGTH: 25
<212> TYPE: DNA
<213> ORGANISM: Homo sapiens

<400> SEQUENCE: 110
tttagatgga actagcattc cacaa 25

<210> SEQ ID NO 111
<211> LENGTH: 25
<212> TYPE: DNA
<213> ORGANISM: Homo sapiens

<400> SEQUENCE: 111
tttaaaagta gcagcttaag ccaga 25

<210> SEQ ID NO 112
<211> LENGTH: 25
<212> TYPE: DNA
<213> ORGANISM: Homo sapiens

<400> SEQUENCE: 112
tttagttaat ttcttatata agagc 25

<210> SEQ ID NO 113
<211> LENGTH: 25
<212> TYPE: DNA
<213> ORGANISM: Homo sapiens

<400> SEQUENCE: 113
tttaaggtag atctgtgcag gggga 25

<210> SEQ ID NO 114
<211> LENGTH: 25
<212> TYPE: DNA
<213> ORGANISM: Homo sapiens

<400> SEQUENCE: 114
tttactcctc ccgaagagga tggat 25

<210> SEQ ID NO 115
<211> LENGTH: 25
<212> TYPE: DNA
<213> ORGANISM: Homo sapiens

<400> SEQUENCE: 115
tttaacatag atattgaagt cagag                                          25

<210> SEQ ID NO 116
<211> LENGTH: 25
<212> TYPE: DNA
<213> ORGANISM: Homo sapiens

<400> SEQUENCE: 116
tttatcatat tactattttg ccagt                                          25

<210> SEQ ID NO 117
<211> LENGTH: 25
<212> TYPE: DNA
<213> ORGANISM: Homo sapiens

<400> SEQUENCE: 117
tttagttaca tgattttaa gagtt                                           25

<210> SEQ ID NO 118
<211> LENGTH: 25
<212> TYPE: DNA
<213> ORGANISM: Homo sapiens

<400> SEQUENCE: 118
tttacctggt tctgtaaata tttta                                          25

<210> SEQ ID NO 119
<211> LENGTH: 25
<212> TYPE: DNA
<213> ORGANISM: Homo sapiens

<400> SEQUENCE: 119
tttattatgt gagtgataaa tttga                                          25

<210> SEQ ID NO 120
<211> LENGTH: 25
<212> TYPE: DNA
<213> ORGANISM: Homo sapiens

<400> SEQUENCE: 120
tttacacccc ccacccccga ggcct                                          25

<210> SEQ ID NO 121
<211> LENGTH: 25
<212> TYPE: DNA
<213> ORGANISM: Homo sapiens

<400> SEQUENCE: 121
tttaactgaa catgtgttgg aggaa                                          25

<210> SEQ ID NO 122
<211> LENGTH: 25
<212> TYPE: DNA
<213> ORGANISM: Homo sapiens

<400> SEQUENCE: 122
tttaatttat ctatgaacct catag                                          25

<210> SEQ ID NO 123
<211> LENGTH: 25
<212> TYPE: DNA
<213> ORGANISM: Homo sapiens

```
<400> SEQUENCE: 123
tttatttttt tatttttttaa aacca                                    25

<210> SEQ ID NO 124
<211> LENGTH: 25
<212> TYPE: DNA
<213> ORGANISM: Homo sapiens

<400> SEQUENCE: 124
tttatccttt ttactcctcc cgaag                                     25

<210> SEQ ID NO 125
<211> LENGTH: 25
<212> TYPE: DNA
<213> ORGANISM: Homo sapiens

<400> SEQUENCE: 125
tttaaacttt tttaaatagg taaag                                     25

<210> SEQ ID NO 126
<211> LENGTH: 25
<212> TYPE: DNA
<213> ORGANISM: Homo sapiens

<400> SEQUENCE: 126 tttaatttttt aataaagcaa tagga                                    25

<210> SEQ ID NO 127
<211> LENGTH: 25
<212> TYPE: DNA
<213> ORGANISM: Homo sapiens

<400> SEQUENCE: 127
tttacatata gttttttgagc cttttt                                   25

<210> SEQ ID NO 128
<211> LENGTH: 25
<212> TYPE: DNA
<213> ORGANISM: Homo sapiens

<400> SEQUENCE: 128
tttaaaagtt ttaccagcca tctta                                     25

<210> SEQ ID NO 129
<211> LENGTH: 25
<212> TYPE: DNA
<213> ORGANISM: Homo sapiens

<400> SEQUENCE: 129
tttatttggg ctatttgcca aacag                                     25

<210> SEQ ID NO 130
<211> LENGTH: 25
<212> TYPE: DNA
<213> ORGANISM: Homo sapiens

<400> SEQUENCE: 130
tttaactatg gttcctttaa atcag                                     25

<210> SEQ ID NO 131
<211> LENGTH: 25
<212> TYPE: DNA
<213> ORGANISM: Homo sapiens
```

```
<400> SEQUENCE: 131
tttataaggg gacaatccaa catct                                          25

<210> SEQ ID NO 132
<211> LENGTH: 25
<212> TYPE: DNA
<213> ORGANISM: Homo sapiens

<400> SEQUENCE: 132
tttattcgga cccgtgctac aactt                                          25

<210> SEQ ID NO 133
<211> LENGTH: 25
<212> TYPE: DNA
<213> ORGANISM: Homo sapiens

<400> SEQUENCE: 133
tttattatcc attttaactt gatta                                          25

<210> SEQ ID NO 134
<211> LENGTH: 25
<212> TYPE: DNA
<213> ORGANISM: Homo sapiens

<400> SEQUENCE: 134
tttatcagtt gtccaatttg tggtg                                          25

<210> SEQ ID NO 135
<211> LENGTH: 25
<212> TYPE: DNA
<213> ORGANISM: Homo sapiens

<400> SEQUENCE: 135
tttaaattcc catgttgcaa cccta                                          25

<210> SEQ ID NO 136
<211> LENGTH: 25
<212> TYPE: DNA
<213> ORGANISM: Homo sapiens

<400> SEQUENCE: 136
tttaataatt tttctactta tactt                                          25

<210> SEQ ID NO 137
<211> LENGTH: 25
<212> TYPE: DNA
<213> ORGANISM: Homo sapiens

<400> SEQUENCE: 137
tttacccagt gggtaaaatg atcta                                          25

<210> SEQ ID NO 138
<211> LENGTH: 25
<212> TYPE: DNA
<213> ORGANISM: Homo sapiens

<400> SEQUENCE: 138
tttaggtgta tgatactttt agtgc                                          25

<210> SEQ ID NO 139
<211> LENGTH: 25
<212> TYPE: DNA
```

```
<213> ORGANISM: Homo sapiens

<400> SEQUENCE: 139
tttaggttct acatattgaa gcttt                                              25

<210> SEQ ID NO 140
<211> LENGTH: 25
<212> TYPE: DNA
<213> ORGANISM: Homo sapiens

<400> SEQUENCE: 140
tttaagttct tgtttggttc ggggc                                              25

<210> SEQ ID NO 141
<211> LENGTH: 25
<212> TYPE: DNA
<213> ORGANISM: Homo sapiens

<400> SEQUENCE: 141
tttattcatc acaacaggta agtcc                                              25

<210> SEQ ID NO 142
<211> LENGTH: 25
<212> TYPE: DNA
<213> ORGANISM: Homo sapiens

<400> SEQUENCE: 142
tttaaaggat aaagaataat atagg                                              25

<210> SEQ ID NO 143
<211> LENGTH: 25
<212> TYPE: DNA
<213> ORGANISM: Homo sapiens

<400> SEQUENCE: 143
tttattttca catccacagc tccta                                              25

<210> SEQ ID NO 144
<211> LENGTH: 25
<212> TYPE: DNA
<213> ORGANISM: Homo sapiens

<400> SEQUENCE: 144
tttagtcccc gcatcgtgtg ggggg                                              25

<210> SEQ ID NO 145
<211> LENGTH: 25
<212> TYPE: DNA
<213> ORGANISM: Homo sapiens

<400> SEQUENCE: 145
tttatttaga tggaactagc attcc                                              25

<210> SEQ ID NO 146
<211> LENGTH: 25
<212> TYPE: DNA
<213> ORGANISM: Homo sapiens

<400> SEQUENCE: 146
tttatctgca cttattaaat ggcct                                              25

<210> SEQ ID NO 147
<211> LENGTH: 25
```

```
<212> TYPE: DNA
<213> ORGANISM: Homo sapiens

<400> SEQUENCE: 147
tttatccttg gacataatta aagaa                                              25

<210> SEQ ID NO 148
<211> LENGTH: 25
<212> TYPE: DNA
<213> ORGANISM: Homo sapiens

<400> SEQUENCE: 148
tttaacagtg gctttagttc tcttt                                              25

<210> SEQ ID NO 149
<211> LENGTH: 25
<212> TYPE: DNA
<213> ORGANISM: Homo sapiens

<400> SEQUENCE: 149
tttagtacag cagcctgaac tgact                                              25

<210> SEQ ID NO 150
<211> LENGTH: 25
<212> TYPE: DNA
<213> ORGANISM: Homo sapiens

<400> SEQUENCE: 150
tttaaaacga cctggtctcc cgcat                                              25

<210> SEQ ID NO 151
<211> LENGTH: 25
<212> TYPE: DNA
<213> ORGANISM: Homo sapiens

<400> SEQUENCE: 151
tttactctgt gacaatatat tctat                                              25

<210> SEQ ID NO 152
<211> LENGTH: 25
<212> TYPE: DNA
<213> ORGANISM: Homo sapiens

<400> SEQUENCE: 152
tttatactcc aaacttcaga cccag                                              25

<210> SEQ ID NO 153
<211> LENGTH: 25
<212> TYPE: DNA
<213> ORGANISM: Homo sapiens

<400> SEQUENCE: 153
tttaaattta gttttttat tatct                                               25

<210> SEQ ID NO 154
<211> LENGTH: 25
<212> TYPE: DNA
<213> ORGANISM: Homo sapiens

<400> SEQUENCE: 154
tttaaatagg taaaggcagg gagga                                              25

<210> SEQ ID NO 155
```

-continued

```
<211> LENGTH: 25
<212> TYPE: DNA
<213> ORGANISM: Homo sapiens

<400> SEQUENCE: 155
tttaactcct cttttctttt ctgga                                          25

<210> SEQ ID NO 156
<211> LENGTH: 25
<212> TYPE: DNA
<213> ORGANISM: Homo sapiens

<400> SEQUENCE: 156
tttaatttgg gaatattggg ttaat                                          25

<210> SEQ ID NO 157
<211> LENGTH: 25
<212> TYPE: DNA
<213> ORGANISM: Homo sapiens

<400> SEQUENCE: 157
tttagagtca gtatagatgg ttttt                                          25

<210> SEQ ID NO 158
<211> LENGTH: 25
<212> TYPE: DNA
<213> ORGANISM: Homo sapiens

<400> SEQUENCE: 158
tttatgctgg gaaccggagg gctgg                                          25

<210> SEQ ID NO 159
<211> LENGTH: 25
<212> TYPE: DNA
<213> ORGANISM: Homo sapiens

<400> SEQUENCE: 159
tttaaaagaa aagttaggtt ggtgt                                          25

<210> SEQ ID NO 160
<211> LENGTH: 25
<212> TYPE: DNA
<213> ORGANISM: Homo sapiens

<400> SEQUENCE: 160
tttatgttgt acatgccaca aaaaa                                          25

<210> SEQ ID NO 161
<211> LENGTH: 25
<212> TYPE: DNA
<213> ORGANISM: Homo sapiens

<400> SEQUENCE: 161
tttagtaatg tctggccaac tgtga                                          25

<210> SEQ ID NO 162
<211> LENGTH: 25
<212> TYPE: DNA
<213> ORGANISM: Homo sapiens

<400> SEQUENCE: 162
tttatttctt gttgggagga tgagg                                          25
```

```
<210> SEQ ID NO 163
<211> LENGTH: 25
<212> TYPE: DNA
<213> ORGANISM: Homo sapiens

<400> SEQUENCE: 163
tttaattaag gctttgactg catta                                              25

<210> SEQ ID NO 164
<211> LENGTH: 25
<212> TYPE: DNA
<213> ORGANISM: Homo sapiens

<400> SEQUENCE: 164
tttacactct tcactcgctt tgtcc                                              25

<210> SEQ ID NO 165
<211> LENGTH: 25
<212> TYPE: DNA
<213> ORGANISM: Homo sapiens

<400> SEQUENCE: 165
tttaagagtt tgatttatcc ttttt                                              25

<210> SEQ ID NO 166
<211> LENGTH: 25
<212> TYPE: DNA
<213> ORGANISM: Homo sapiens

<400> SEQUENCE: 166
tttagctatt tgttatggca gcaac                                              25

<210> SEQ ID NO 167
<211> LENGTH: 25
<212> TYPE: DNA
<213> ORGANISM: Homo sapiens

<400> SEQUENCE: 167
tttattatct ttccaatact ttaac                                              25

<210> SEQ ID NO 168
<211> LENGTH: 25
<212> TYPE: DNA
<213> ORGANISM: Homo sapiens

<400> SEQUENCE: 168
tttaaggctt gtttatttgt gtttt                                              25

<210> SEQ ID NO 169
<211> LENGTH: 25
<212> TYPE: DNA
<213> ORGANISM: Homo sapiens

<400> SEQUENCE: 169
tttatctggt ccccgaggca gtgca                                              25

<210> SEQ ID NO 170
<211> LENGTH: 25
<212> TYPE: DNA
<213> ORGANISM: Homo sapiens

<400> SEQUENCE: 170
tttaaagaag gatatttaga attttt                                             25
```

```
<210> SEQ ID NO 171
<211> LENGTH: 25
<212> TYPE: DNA
<213> ORGANISM: Homo sapiens

<400> SEQUENCE: 171
tttaaaggta ggcctcaaaa agaac                                   25

<210> SEQ ID NO 172
<211> LENGTH: 25
<212> TYPE: DNA
<213> ORGANISM: Homo sapiens

<400> SEQUENCE: 172
tttatttgtt cttttaattt atcta                                   25

<210> SEQ ID NO 173
<211> LENGTH: 25
<212> TYPE: DNA
<213> ORGANISM: Homo sapiens

<400> SEQUENCE: 173
tttatctgac ctaaattttg accaa                                   25

<210> SEQ ID NO 174
<211> LENGTH: 25
<212> TYPE: DNA
<213> ORGANISM: Homo sapiens

<400> SEQUENCE: 174
tttaggctcc tgggattcac aagaa                                   25

<210> SEQ ID NO 175
<211> LENGTH: 25
<212> TYPE: DNA
<213> ORGANISM: Homo sapiens

<400> SEQUENCE: 175
tttactggca aactgggagg agaga                                   25

<210> SEQ ID NO 176
<211> LENGTH: 25
<212> TYPE: DNA
<213> ORGANISM: Homo sapiens

<400> SEQUENCE: 176
tttaacctta acgtgcttga ggttt                                   25

<210> SEQ ID NO 177
<211> LENGTH: 25
<212> TYPE: DNA
<213> ORGANISM: Homo sapiens

<400> SEQUENCE: 177
tttatttcta tattttgagg acatg                                   25

<210> SEQ ID NO 178
<211> LENGTH: 25
<212> TYPE: DNA
<213> ORGANISM: Homo sapiens

<400> SEQUENCE: 178
tttagaattt ttaggctcct gggat                                   25
```

```
<210> SEQ ID NO 179
<211> LENGTH: 25
<212> TYPE: DNA
<213> ORGANISM: Homo sapiens

<400> SEQUENCE: 179
tttatgattt gctgccagaa cattt                                    25

<210> SEQ ID NO 180
<211> LENGTH: 25
<212> TYPE: DNA
<213> ORGANISM: Homo sapiens

<400> SEQUENCE: 180
tttattgatt ttttaaattt tctaa                                    25

<210> SEQ ID NO 181
<211> LENGTH: 25
<212> TYPE: DNA
<213> ORGANISM: Homo sapiens

<400> SEQUENCE: 181
tttatcccac tgcgggtcct gagca                                    25

<210> SEQ ID NO 182
<211> LENGTH: 25
<212> TYPE: DNA
<213> ORGANISM: Homo sapiens

<400> SEQUENCE: 182
tttataattt ccatgctttt tcagt                                    25

<210> SEQ ID NO 183
<211> LENGTH: 25
<212> TYPE: DNA
<213> ORGANISM: Homo sapiens

<400> SEQUENCE: 183
tttatctgta attctgcaga ccctc                                    25

<210> SEQ ID NO 184
<211> LENGTH: 25
<212> TYPE: DNA
<213> ORGANISM: Homo sapiens

<400> SEQUENCE: 184
tttaaagggg aagctttgaa gagga                                    25

<210> SEQ ID NO 185
<211> LENGTH: 25
<212> TYPE: DNA
<213> ORGANISM: Homo sapiens

<400> SEQUENCE: 185
tttacctgcc ggtagtcctt ggtcc                                    25

<210> SEQ ID NO 186
<211> LENGTH: 25
<212> TYPE: DNA
<213> ORGANISM: Homo sapiens

<400> SEQUENCE: 186
```

```
tttaccaatg tgttctaagt tttca                                              25

<210> SEQ ID NO 187
<211> LENGTH: 25
<212> TYPE: DNA
<213> ORGANISM: Homo sapiens

<400> SEQUENCE: 187
tttaaaaaaa taaatactga ccttg                                              25

<210> SEQ ID NO 188
<211> LENGTH: 25
<212> TYPE: DNA
<213> ORGANISM: Homo sapiens

<400> SEQUENCE: 188
tttatcttgt aggtggttaa gaact                                              25

<210> SEQ ID NO 189
<211> LENGTH: 25
<212> TYPE: DNA
<213> ORGANISM: Homo sapiens

<400> SEQUENCE: 189
tttatttctt ttcacgaatt gctgg                                              25

<210> SEQ ID NO 190
<211> LENGTH: 25
<212> TYPE: DNA
<213> ORGANISM: Homo sapiens

<400> SEQUENCE: 190
tttatgtggt gttcagagcc ccagg                                              25

<210> SEQ ID NO 191
<211> LENGTH: 25
<212> TYPE: DNA
<213> ORGANISM: Homo sapiens

<400> SEQUENCE: 191
tttatcggtg ttattgatga tcatt                                              25

<210> SEQ ID NO 192
<211> LENGTH: 25
<212> TYPE: DNA
<213> ORGANISM: Homo sapiens

<400> SEQUENCE: 192
tttattttat ttcttgttgg gagga                                              25

<210> SEQ ID NO 193
<211> LENGTH: 25
<212> TYPE: DNA
<213> ORGANISM: Homo sapiens

<400> SEQUENCE: 193
tttaaattgg ctataaatct ttgac                                              25

<210> SEQ ID NO 194
<211> LENGTH: 25
<212> TYPE: DNA
<213> ORGANISM: Homo sapiens

<400> SEQUENCE: 194
```

```
tttaccttta ctgttaatta gtcct                                           25
```

<210> SEQ ID NO 195
<211> LENGTH: 41
<212> TYPE: RNA
<213> ORGANISM: Artificial Sequence
<220> FEATURE:
<223> OTHER INFORMATION: crRNA for SEQ ID NO: 132

<400> SEQUENCE: 195

```
uaauuucuac ucuuguagau uucggacccg ugcuacaacu u                         41
```

<210> SEQ ID NO 196
<211> LENGTH: 41
<212> TYPE: RNA
<213> ORGANISM: Artificial Sequence
<220> FEATURE:
<223> OTHER INFORMATION: crRNA for Cpf1 target site of SEQ ID NO: 108

<400> SEQUENCE: 196

```
uaauuucuac ucuuguagau auagaauagc cucauauuuu a                         41
```

<210> SEQ ID NO 197
<211> LENGTH: 27
<212> TYPE: DNA
<213> ORGANISM: Homo sapiens

<400> SEQUENCE: 197

```
tttgtgtccc cgttttggtt ggtaaac                                         27
```

<210> SEQ ID NO 198
<211> LENGTH: 27
<212> TYPE: DNA
<213> ORGANISM: Homo sapiens

<400> SEQUENCE: 198

```
tttaaaaatc aataccgata ataatga                                         27
```

<210> SEQ ID NO 199
<211> LENGTH: 27
<212> TYPE: DNA
<213> ORGANISM: Homo sapiens

<400> SEQUENCE: 199

```
tttcttaata tgaatattaa tatcggt                                         27
```

<210> SEQ ID NO 200
<211> LENGTH: 27
<212> TYPE: DNA
<213> ORGANISM: Homo sapiens

<400> SEQUENCE: 200

```
tttccgtatc tggaaggggc atcttgg                                         27
```

<210> SEQ ID NO 201
<211> LENGTH: 27
<212> TYPE: DNA
<213> ORGANISM: Homo sapiens

<400> SEQUENCE: 201

```
tttccttagg accggaagga ttacagc                                         27
```

<210> SEQ ID NO 202

```
<211> LENGTH: 27
<212> TYPE: DNA
<213> ORGANISM: Homo sapiens

<400> SEQUENCE: 202
tttgcctaaa aggcactatg tcaaatg                                              27

<210> SEQ ID NO 203
<211> LENGTH: 27
<212> TYPE: DNA
<213> ORGANISM: Homo sapiens

<400> SEQUENCE: 203
tttggagctg ttggcatcat gttcctg                                              27

<210> SEQ ID NO 204
<211> LENGTH: 27
<212> TYPE: DNA
<213> ORGANISM: Homo sapiens

<400> SEQUENCE: 204
tttgattctt ttctatctca ggacaga                                              27

<210> SEQ ID NO 205
<211> LENGTH: 27
<212> TYPE: DNA
<213> ORGANISM: Homo sapiens

<400> SEQUENCE: 205
tttatagaca tcccacactg tagttct                                              27

<210> SEQ ID NO 206
<211> LENGTH: 27
<212> TYPE: DNA
<213> ORGANISM: Homo sapiens

<400> SEQUENCE: 206
tttattaatt tgagaaccaa cataagg                                              27

<210> SEQ ID NO 207
<211> LENGTH: 27
<212> TYPE: DNA
<213> ORGANISM: Homo sapiens

<400> SEQUENCE: 207
tttattttct ttttggtaag aaggaac                                              27

<210> SEQ ID NO 208
<211> LENGTH: 27
<212> TYPE: DNA
<213> ORGANISM: Homo sapiens

<400> SEQUENCE: 208
tttcacacac acacacacac acacaca                                              27

<210> SEQ ID NO 209
<211> LENGTH: 43
<212> TYPE: RNA
<213> ORGANISM: Artificial Sequence
<220> FEATURE:
<223> OTHER INFORMATION: crRNA for Cpf1 target site of SEQ ID NO: 203

<400> SEQUENCE: 209
uaauuucuac ucuguagau gagcuguugg caucaugul uc cug                           43
```

<210> SEQ ID NO 210
<211> LENGTH: 25
<212> TYPE: DNA
<213> ORGANISM: Homo sapiens

<400> SEQUENCE: 210
tttatccaaa cctcctaaat gatac                                          25

<210> SEQ ID NO 211
<211> LENGTH: 41
<212> TYPE: RNA
<213> ORGANISM: Artificial Sequence
<220> FEATURE:
<223> OTHER INFORMATION: crRNA for Cpf1 target site of SEQ ID NO: 210

<400> SEQUENCE: 211
uaauuucuac ucuuguagau uccaaaccuc cuaaaugaua c                        41

<210> SEQ ID NO 212
<211> LENGTH: 25
<212> TYPE: DNA
<213> ORGANISM: Homo sapiens

<400> SEQUENCE: 212
tttacacccg atccactggg gagca                                          25

<210> SEQ ID NO 213
<211> LENGTH: 27
<212> TYPE: DNA
<213> ORGANISM: Homo sapiens

<400> SEQUENCE: 213
tttttgattc ttttctatct caggaca                                        27

<210> SEQ ID NO 214
<211> LENGTH: 511
<212> TYPE: DNA
<213> ORGANISM: Homo sapiens

<400> SEQUENCE: 214
ggggttgggg ttgcgccttt tccaaggcag ccctgggttt gcgcagggac gcggctgctc    60
tgggcgtggt tccgggaaac gcagcggcgc cgaccctggg tctcgcacat tcttcacgtc   120
cgttcgcagc gtcacccgga tcttcgccgc taccttgtg ggccccccgg cgacgcttcc    180
tgctccgccc ctaagtcggg aaggttcctt gcggttcgcg gcgtgccgga cgtgacaaac   240
ggaagccgca cgtctcacta gtaccctcgc agacggacag cgccagggag caatggcagc   300
gcgccgaccg cgatgggctg tggccaatag cggctgctca gcggggcgcg ccgagagcag   360
cggccgggaa ggggcggtgc gggaggcggg gtgtggggcg gtagtgtggg ccctgttcct   420
gcccgcgcgc tgttccgcat tctgcaagcc tccggagcgc acgtcggcag tcggctccct   480
cgttgaccga atcaccgacc tctctcccca g                                  511

<210> SEQ ID NO 215
<211> LENGTH: 4107
<212> TYPE: DNA
<213> ORGANISM: Streptococcus pyogenes

<400> SEQUENCE: 215
atggataaga aatactcaat aggcttagat atcggcacaa atagcgtcgg atgggcggtg    60

-continued

```
atcactgatg aatataaggt tccgtctaaa aagttcaagg ttctgggaaa tacagaccgc      120
cacagtatca aaaaaaatct tatagggct cttttatttg acagtggaga gacagcggaa      180
gcgactcgtc tcaaacggac agctcgtaga aggtatacac gtcggaagaa tcgtatttgt      240
tatctacagg agattttttc aaatgagatg gcgaaagtag atgatagttt ctttcatcga      300
cttgaagagt cttttttggt ggaagaagac aagaagcatg aacgtcatcc tattttgga      360 aatatagtag atgaagttgc ttatcatgag aaatatccaa ctatctatca tctgcgaaaa      420
aaattggtag attctactga taaagcggat ttgcgcttaa tctatttggc cttagcgcat      480
atgattaagt ttcgtggtca ttttttgatt gagggagatt taaatcctga taatagtgat      540
gtggacaaac tatttatcca gttggtacaa acctacaatc aattatttga agaaaaccct      600
attaacgcaa gtggagtaga tgctaaagcg attctttctg cacgattgag taaatcaaga      660
cgattagaaa atctcattgc tcagctcccc ggtgagaaga aaaatggctt atttgggaat      720
ctcattgctt tgtcattggg tttgaccct aatttttaaat caaattttga tttggcagaa      780
gatgctaaat tacagctttc aaaagatact tacgatgatg atttagataa tttattggcg      840
caaattggag atcaatatgc tgatttgttt ttggcagcta agaatttatc agatgctatt      900
ttactttcag atatcctaag agtaaatact gaaataacta aggctcccct atcagcttca      960
atgattaaac gctacgatga acatcatcaa gacttgactc ttttaaaagc tttagttcga     1020
caacaacttc cagaaaagta taagaaatc ttttttgatc aatcaaaaaa cggatatgca      1080
ggttatattg atgggggagc tagccaagaa gaatttata aatttatcaa accaatttta      1140
gaaaaaatgg atggtactga ggaattattg gtgaaactaa atcgtgaaga tttgctgcgc      1200
aagcaacgga cctttgacaa cggctctatt ccccatcaaa ttcacttggg tgagctgcat      1260
gctattttga agacaagaa agacttttat ccatttttaa aagacaatcg tgagaagatt      1320
gaaaaaatct tgacttttcg aattccttat tatgttggtc cattggcgcg tggcaatagt      1380
cgttttgcat ggatgactcg gaagtctgaa gaaacaatta ccccatggaa ttttgaagaa     1440
gttgtcgata aaggtgcttc agctcaatca tttattgaac gcatgacaaa ctttgataaa      1500
aatcttccaa atgaaaaagt actaccaaaa catagttttgc tttatgagta ttttacggtt      1560
tataacgaat tgacaaaggt caaatatgtt actgaaggaa tgcgaaaacc agcatttctt      1620
tcaggtgaac agaagaaagc cattgttgat ttactcttca aaacaaatcg aaaagtaacc      1680
gttaagcaat taaagaaga ttatttcaaa aaaatagaat gttttgatag tgttgaaatt      1740
tcaggagttg aagatagatt taatgcttca ttaggtacct accatgattt gctaaaaatt      1800
attaaagata aagatttttt ggataatgaa gaaatgaag atatcttaga ggatattgtt      1860
ttaacattga ccttatttga agataggag atgattgagg aaagacttaa acatatgct      1920 cacctctttg atgataaggt gatgaaacag cttaaacgtc gccgttatac tggttgggga      1980
cgtttgtctc gaaaattgat taatggtatt agggataagc aatctggcaa acaatatta      2040 gatttttttga aatcagatgg ttttgccaat cgcaatttta tgcagctgat ccatgatgat      2100
agtttgacat ttaaagaaga cattcaaaaa gcacaagtgt ctggacaagg cgatagttta      2160
catgaacata ttgcaaattt agctggtagc cctgctatta aaaaggtat tttacagact      2220 gtaaaagttg ttgatgaatt ggtcaaagta atggggcggc ataagccaga aaatatcgtt      2280
attgaaatgg cacgtgaaaa tcagacaact caaaagggcc agaaaaattc gcgagagcgt      2340
atgaaacgaa tcgaagaagg tatcaaagaa ttaggaagtc agattcttaa agagcatcct      2400
gttgaaaata ctcaattgca aaatgaaaag ctctatctct attatctcca aaatggaaga     2460
```

```
gacatgtatg tggaccaaga attagatatt aatcgtttaa gtgattatga tgtcgatcac    2520
attgttccac aaagtttcct taaagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taaacttatt cgagaggtta agtgattac cttaaaatct     2880 aaattagttt ctgacttccg aaaagatttc caattctata agtacgtga gattaacaat     2940 taccatcatg cccatgatgc gtatctaaat gccgtcgttg gaactgcttt gattaagaaa    3000
tatccaaaac ttgaatcgga gtttgtctat ggtgattata agtttatga tgttcgtaaa     3060 atgattgcta agtctgagca agaaataggc aaagcaaccg caaatatttt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aaagggaaat cgaagaagtt aaaatccgtt    3480
aaagagttac tagggatcac aattatgaaa agaagttcct ttgaaaaaaa tccgattgac    3540 ttttttagaag ctaaaggata taaggaagtt aaaaaagact taatcattaa actacctaaa   3600 tatagtctt  ttgagttaga aaacggtcgt aacggatgc tggctagtgc cggagaatta     3660
caaaaaggaa atgagctggc tctgccaagc aaatatgtga atttttata tttagctagt     3720 cattatgaaa agttgaaggg tagtccagaa gataacgaac aaaaacaatt gtttgtggag    3780
cagcataagc attatttaga tgagattatt gagcaaatca gtgaattttc taagcgtgtt    3840
attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta acgatatac gtctacaaaa     4020 gaagttttag atgccactct tatccatcaa tccatcactg gtctttatga aacacgcatt    4080
gatttgagtc agctaggagg tgactga                                        4107
```

<210> SEQ ID NO 216
<211> LENGTH: 3903
<212> TYPE: DNA
<213> ORGANISM: Francisella tularensis

<400> SEQUENCE: 216

```
atgtcaattt atcaagaatt tgttaataaa tatagtttaa gtaaaactct aagatttgag      60
ttaatcccac agggtaaaac acttgaaaac ataaaagcaa gaggtttgat tttagatgat    120
gagaaaagag ctaaagacta caaaaaggct aaacaaataa ttgataaata tcatcagttt    180
tttatagagg agatattaag ttcggtttgt attagcgaag attttattaca aaactattct    240 gatgtttatt ttaaacttaa aaagagtgat gatgataatc tacaaaaaga ttttaaaagt    300 gcaaagagata cgataaagaa acaaatatct gaatatataa aggactcaga gaaatttaag    360
aatttgttta atcaaaacct tatcgatgct aaaaaagggc aagagtcaga tttaattcta    420
```

```
tggctaaagc aatctaagga taatggtata gaactatttta aagccaatag tgatatcaca    480
gatatagatg aggcgttaga aataatcaaa tcttttaaag gttggacaac ttattttaag    540
ggttttcatg aaaatagaaa aaatgtttat agtagcaatg atattcctac atctattatt    600
tataggatag tagatgataa tttgcctaaa tttctagaaa ataaagctaa gtatgagagt    660
ttaaaagaca aagctccaga agctataaac tatgaacaaa ttaaaaaaga tttggcagaa    720 gagctaaccct tgatattga ctacaaaaca tctgaagtta atcaaagagt tttttcactt    780
gatgaagttt ttgagatagc aaactttaat aattatctaa atcaaagtgg tattactaaa    840
tttaatacta ttattggtgg taaatttgta aatggtgaaa atacaaagag aaaaggtata    900
aatgaatata taaatctata ctcacagcaa ataaatgata aacactcaa aaaatataaa     960 atgagtgttt tatttaagca aattttaagt gatacagaat ctaaatcttt tgtaattgat   1020
aagttagaag atgatagtga tgtagttaca acgatgcaaa gttttttatga gcaaatagca   1080 gcttttaaaa cagtagaaga aaaatctatt aaagaaacac tatctttatt atttgatgat   1140
ttaaaagctc aaaaacttga tttgagtaaa atttattttta aaaatgataa atctcttact   1200
gatctatcac aacaagtttt tgatgattat agtgttattg gtacagcggt actagaatat   1260
ataactcaac aaatagcacc taaaaatctt gataaccta gtaagaaaga gcaagaatta    1320
atagccaaaa aaactgaaaa agcaaaatac ttatctctag aaactataaa gcttgcctta   1380 gaagaatttta ataagcatag agatatagat aaacagtgta ggtttgaaga atacttgca    1440 aactttgcgg ctattccgat gatatttgat gaaatagctc aaaacaaaga caatttggca   1500
cagatatcta tcaaatatca aaatcaaggt aaaaaagacc tacttcaagc tagtgcggaa   1560
gatgatgtta aagctatcaa ggatctttta gatcaaacta ataatctctt acataaacta   1620
aaaatatttc atattagtca gtcagaagat aaggcaaata ttttagacaa ggatgagcat   1680
ttttatctag tatttgagga gtgctacttt gagctagcga atatagtgcc tctttataac   1740
aaaattagaa actatataac tcaaaagcca tatagtgatg agaaattaa gctcaattttt   1800 gagaactcga ctttggctaa tggttgggat aaaaataaag agcctgacaa tacggcaatt   1860
ttatttatca aagatgataa atattatctg ggtgtgatga ataagaaaaa taacaaaata   1920
tttgatgata aagctatcaa agaaaataaa ggcgagggtt ataaaaaaat tgtttataaa   1980
cttttacctg gcgcaaataa aatgttacct aaggttttct tttctgctaa atctataaaa   2040
ttttataatc ctagtgaaga tatacttaga ataagaaatc attccacaca tacaaaaaat   2100
ggtagtcctc aaaaaggata tgaaaaattt gagtttaata ttgaagattg ccgaaaattt   2160
atagattttt ataaacagtc tataagtaag catccggagt ggaaagattt tggatttaga   2220
ttttctgata ctcaaagata taattctata gatgaatttt atagagaagt tgaaaatcaa   2280
ggctacaaac taacttttga aaatatatca gagagctata ttgatagcgt agttaatcag   2340
ggtaaattgt acctattcca aatctataat aaagatttt cagcttatag caaagggcga   2400
ccaaatctac atactttata ttggaaagcg ctgtttgatg agagaaatct tcaagatgtg   2460
gtttataagc taaatggtga ggcagagctt tttatcgta acaatcaat acctaaaaaa    2520 atcactcacc cagctaaaga ggcaaatagc t aataaaaaca aagataatcc taaaaaagag   2580
agtgtttttg aatatgattt aatcaaagat aaacgcttta ctgaagataa gttttctttt    2640
cactgtccta ttcaatcaa ttttaaatct agtggagcta ataagtttaa tgatgaaatc    2700 aattttattgc taaaagaaaa agcaaatgat gttcatatat taagtataga tagaggtgaa   2760
agacatttag cttactatac tttggtagat ggtaaaggca atatcatcaa acaagatact   2820
```

```
ttcaacatca ttggtaatga tagaatgaaa acaaactacc atgataagct tgctgcaata      2880
gagaaagata gggattcagc taggaaagac tggaaaaaga taaataacat caaagagatg      2940
aaagagggct atctatctca ggtagttcat gaaatagcta agctagttat agagtataat      3000
gctattgtgg tttttgagga tttaaatttt ggatttaaaa gagggcgttt caaggtagag      3060
aagcaggtct atcaaaagtt agaaaaaatg ctaattgaga aactaaacta tctagttttc      3120
aaagataatg agtttgataa aactggggga gtgcttagag cttatcagct aacagcacct      3180
tttgagactt ttaaaaagat gggtaaacaa acaggtatta tctactatgt accagctggt      3240
tttacttcaa aaatttgtcc tgtaactggt tttgtaaatc agttatatcc taagtatgaa      3300
agtgtcagca atctcaaga gttctttagt aagtttgaca agatttgtta taaccttgat      3360
aagggctatt tgagtttag ttttgattat aaaaactttg gtgacaaggc tgccaaaggc      3420
aagtggacta tagctagctt tgggagtaga ttgattaact ttagaaattc agataaaaat      3480
cataattggg atactcgaga gtttatcca actaaagagt tggagaaatt gctaaaagat      3540
tattctatcg aatatgggca tggcgaatgt atcaaagcag ctatttgcgg tgagagcgac      3600
aaaaagtttt ttgctaagct aactagtgtc ctaaatacta tcttacaaat gcgtaactca      3660
aaaacaggta ctgagttaga ttatctaatt tcaccagtag cagatgtaaa tggcaatttc      3720
tttgattcgc gacaggcgcc aaaaaatatg cctcaagatg ctgatgccaa tggtgcttat      3780
catattgggc taaaggtct gatgctacta ggtaggatca aaaataatca agagggcaaa      3840
aaactcaatt tggttatcaa aaatgaagag tattttgagt tcgtgcagaa taggaataac      3900
taa                                                                  3903

<210> SEQ ID NO 217
<211> LENGTH: 3921
<212> TYPE: DNA
<213> ORGANISM: Acidaminococcus sp. BV3L6

<400> SEQUENCE: 217
atgacacagt tcgagggctt taccaacctg tatcaggtga gcaagacact gcggtttgag       60
ctgatcccac agggcaagac cctgaagcac atccaggagc agggcttcat cgaggaggac      120
aaggcccgca tgatcactac aaggagctg aagcccatca tcgatcggat ctacaagacc      180
tatgccgacc agtgcctgca gctggtgcag ctggattggg agaacctgag cgccgccatc      240
gactcctata gaaaggagaa aaccgaggag acaaggaacg ccctgatcga ggagcaggcc      300
acatatcgca tgccatcca cgactactc atcggccgga cagacaacct gaccgatgcc      360
atcaataaga gacacgccga gatctacaag ggcctgttca aggccgagct gtttaatggc      420
aaggtgctga agcagctggg caccgtgacc acaaccgagc acgagaacgc cctgctgcgg      480
agcttcgaca gtttacaac ctacttctcc ggcttttatg agaacaggaa gaacgtgttc      540
agcgccgagg atatcagcac agccatccca caccgcatcg tgcaggacaa cttccccaag      600
tttaaggaga attgtcacat cttcacacgc ctgatcaccg ccgtgcccag cctgcgggag      660
cactttgaga acgtgaagaa ggccatcggc atcttcgtga gcacctccat cgaggaggtg      720
ttttcctccc ttttttataa ccagctgctg acacagaccc agatcgacct gtataaccag      780
ctgctgggag gaatctctcg ggaggcaggc accgagaaga tcaagggcct gaacgaggtg      840
ctgaatctgg ccatccagaa gaatgatgag acagccccaca tcatcgcctc cctgccacac      900
agattcatcc ccctgtttaa gcagatcctg tccgatagga cacccctgtc tttcatcctg      960
```

-continued

```
gaggagttta agagcgacga ggaagtgatc cagtccttct gcaagtacaa gacactgctg      1020
agaaacgaga acgtgctgga gacagccgag gccctgttta acgagctgaa cagcatcgac      1080
ctgacacaca tcttcatcag ccacaagaag ctggagacaa tcagcagcgc cctgtgcgac      1140
cactgggata cactgaggaa tgccctgtat gagcggagaa tctccgagct gacaggcaag      1200
atcaccaagt ctgccaagga gaaggtgcag cgcagcctga agcacgagga tatcaacctg      1260
caggagatca tctctgccgc aggcaaggag ctgagcgagg ccttcaagca gaaaaccagc      1320
gagatcctgt cccacgcaca cgccgccctg gatcagccac tgcctacaac cctgaagaag      1380
caggaggaga aggagatcct gaagtctcag ctggacagcc tgctgggcct gtaccacctg      1440
ctggactggt ttgccgtgga tgagtccaac gaggtggacc ccgagttctc tgcccggctg      1500
accggcatca agctggagat ggagccttct ctgagcttct acaacaaggc cagaaattat      1560
gccaccaaga agccctactc cgtggagaag ttcaagctga actttcagat gcctacactg      1620
gcctctggct gggacgtgaa taaggagaag aacaatggcg ccatcctgtt tgtgaagaac      1680
ggcctgtact atctgggcat catgccaaag cagaagggca ggtataaggc cctgagcttc      1740
gagcccacag agaaaaccag cgagggcttt gataagatgt actatgacta cttccctgat      1800
gccgccaaga tgatcccaaa gtgcagcacc cagctgaagg ccgtgacagc ccactttcag      1860
acccacacaa cccccatcct gctgtccaac aatttcatcg agcctctgga gatcacaaag      1920
gagatctacg acctgaacaa tcctgagaag gagccaaaga gtttcagac agcctacgcc      1980 aagaaaaccg gcgaccagaa gggctacaga gaggccctgt gcaagtggat cgacttcaca      2040
agggattttc tgtccaagta taccaagaca acctctatcg atctgtctag cctgcggcca      2100
tcctctcagt ataaggacct gggcgagtac tatgccgagc tgaatcccct gctgtaccac      2160
atcagcttcc agagaatcgc cgagaaggag atcatggatg ccgtggagac aggcaagctg      2220
tacctgttcc agatctataa caaggacttt gccaagggcc accacggcaa gcctaatctg      2280
cacacactgt attggaccgg cctgtttttc tccagagaacc tggccaagac aagcatcaag      2340
ctgaatggcc aggccgagct gttctaccgc cctaagtcca ggatgaagag gatggcacac      2400
cggctgggag agaagatgct gaacaagaag ctgaaggatc agaaaacccc aatccccgac      2460
accctgtacc aggagctgta cgactatgtg aatcacagac tgtcccacga cctgtctgat      2520
gaggccaggg ccctgctgcc caacgtgatc accaaggagg tgtctcacga gatcatcaag      2580
gataggcgct ttaccagcga caagttcttt ttccacgtgc ctatcacact gaactatcag      2640
gccgccaatt cccccatcta agttcaaccag agggtgaatg cctacctgaa ggagcacccc      2700
gagacaccta tcatcggcat cgatcggggc gagagaaacc tgatctatat cacagtgatc      2760
gactccaccg gcaagatcct ggagcagcgg agcctgaaca ccatccagca gtttgattac      2820
cagaagaagc tggacaacag ggagaaggag agggtggcag caaggcaggc ctggtctgtg      2880
gtgggcacaa tcaaggatct gaagcagggc tatctgagcc aggtcatcca cgagatcgtg      2940
gacctgatga tccactacca ggccgtggtg gtgctggaga acctgaattt cggctttaag      3000
agcaagagga ccggcatcgc cgagaaggcc gtgtaccagc agttcgagaa gatgctgatc      3060
gataagctga attgcctggt gctgaaggac tatccagcag agaaagtggg aggcgtgctg      3120
aacccatacc agctgacaga ccagttcacc tcctttgcca gatgggcac ccagtctggc      3180 ttcctgtttt acgtgcctgc cccatataca tctaagatcg atcccctgac cggcttcgtg      3240
gaccccttcg tgtggaaaac catcaagaat cacgagagcc gcaagcactt cctgagggc      3300 ttcgactttc tgcactacga cgtgaaaacc ggcgacttca tcctgcactt taagatgaac      3360
```

-continued

```
agaaatctgt ccttccagag gggcctgccc ggctttatgc ctgcatggga tatcgtgttc    3420
gagaagaacg agacacagtt tgacgccaag ggcacccctt tcatcgccgg caagagaatc    3480
gtgccagtga tcgagaatca cagattcacc ggcagatacc gggacctgta tcctgccaac    3540
gagctgatcg ccctgctgga ggagaagggc atcgtgttca gggatggctc caacatcctg    3600
ccaaagctgc tggagaatga cgattctcac gccatcgaca ccatggtggc cctgatccgc    3660
agcgtgctgc agatgcggaa ctccaatgcc gccacaggcg aggactatat caacagcccc    3720
gtgcgcgatc tgaatggcgt gtgcttcgac tcccggtttc agaacccaga gtggcccatg    3780
gacgccgatg ccaatggcgc ctaccacatc gccctgaagg ccagctgct gctgaatcac    3840 ctgaaggaga gcaaggatct gaagctgcag aacggcatct ccaatcagga ctggctggcc    3900
tacatccagg agctgcgcaa c                                              3921
```

<210> SEQ ID NO 218
<211> LENGTH: 3699
<212> TYPE: DNA
<213> ORGANISM: Lachnospiraceae bacterium MC2017

<400> SEQUENCE: 218

```
atggattacg gcaacggcca gtttgagcgg agagccccc tgaccaagac aatcaccctg     60
cgcctgaagc ctatcggcga gacacgggag acaatccgcg agcagaagct gctggagcag    120
gacgccgcct tcagaaagct ggtggagaca gtgacccta tcgtggacga ttgtatcagg     180
aagatcgccg ataacgccct gtgccacttt ggcaccgagt atgacttcag ctgtctgggc    240
aacgccatct ctaagaatga cagcaaggcc atcaagaagg acagagaa ggtggagaag      300 ctgctggcca aggtgctgac cgagaatctg ccagatggcc tgcgcaaggt gaacgacatc    360
aattccgccg ccttttatcca ggatacactg acctcttcg tgcaggacga tgccgacaag    420
cgggtgctga tccaggagct gaagggcaag accgtgctga tgcagcggtt cctgaccaca    480
cggatcacag ccctgaccgt gtggctgccc gacagagtgt tcgagaactt taatatcttc    540
atcgagaacg ccgagaagat gagaatcctg ctggactccc ctctgaatga aagatcatg     600 aagtttgacc cagatgccga gcagtacgcc tctctggagt tctatggcca gtgcctgtct    660
cagaaggaca tcgatagcta caacctgatc atctccggca tctatgccga cgatgaggtg    720
aagaaccctg gcatcaatga atcgtgaag gagtacaatc agcagatccg gggcgacaag    780
gatgagtccc cactgcccaa gctgaagaag ctgcacaagc agatcctgat gccagtggag    840
aaggccttct ttgtgcgcgt gctgtctaac gacagcgatg cccggagcat cctggagaag    900
atcctgaagg acacagagat gctgccctcc aagatcatcg aggccatgaa ggaggcagat    960
gcaggcgaca tcgccgtgta cggcagccgg ctgcacgagc tgagccacgt gatctacggc   1020
gatcacggca gctgtccca gatcatctat gacaaggagt ccaagaggat ctctgagctg   1080
atggagacac tgtctccaaa ggagcgcaag gagagcaaga gcggctgga gggcctggag    1140 gagcacatca gaaagtctac atacaccttc gacgagctga acaggtatgc cgagaagaat    1200
gtgatggcag catacatcgc agcagtggag gagtcttgtg ccgagatcat gagaaaggag    1260
aaggatctga ggaccctgct gagcaaggag gacgtgaaga tccggggcaa cagacacaat    1320
acactgatcg tgaagaacta ctttaatgcc tggaccgtgt tccggaacct gatcagaatc    1380
ctgaggcgca gtccgaggc cgagatcgac tctgacttct acgatgtgct ggacgattcc    1440
gtggaggtgc tgtctctgac atacaagggc gagaatctgt gccgcagcta tatcaccaag    1500
```

```
aagatcggct ccgacctgaa gcccgagatc gccacatacg gcagcgccct gaggcctaac      1560
agccgctggt ggtccccagg agagaagttt aatgtgaagt ccacaccat cgtgcggaga      1620 gatggccggc tgtactattt catcctgccc aagggcgcca agcctgtgga gctggaggac    1680
atggatggcg acatcgagtg tctgcagatg agaaagatcc ctaacccaac aatctttctg   1740
cccaagctgg tgttcaagga ccctgaggcc ttctttaggg ataatccaga ggccgacgag   1800
ttcgtgtttc tgagcggcat gaaggccccc gtgacaatca ccagagagac atacgaggcc  1860
tacaggtata agctgtatac cgtgggcaag ctgcgcgatg gcgaggtgtc cgaagaggag 1920
tacaagcggg ccctgctgca ggtgctgacc gcctacaagg agtttctgga gaacagaatg 1980
atctatgccg acctgaattt cggctttaag gatctggagg agtataagga cagctccgag 2040
tttatcaagc aggtggagac acacaacacc ttcatgtgct gggccaaggt gtctagctcc    2100
cagctggacg atctggtgaa gtctggcaac ggcctgctgt tcgagatctg gagcgagcgc   2160
ctggagtcct actataagta cggcaatgag aaggtgctgc ggggctatga gggcgtgctg   2220
ctgagcatcc tgaaggatga gaacctggtg tccatgcgga ccctgctgaa cagccggccc 2280
atgctggtgt accggccaaa ggagtctagc aagcctatgg tggtgcaccg ggatggcagc  2340
agagtggtgg acaggtttga taaggacggc aagtacatcc cccctgaggt gcacgacgag 2400
ctgtatcgct tctttaacaa tctgctgatc aaggagaagc tgggcgagaa ggcccggaag  2460
atcctggaca caagaaggt gaaggtgaag gtgctggaga gcgagagagt gaagtggtcc   2520
aagttctacg atgagcagtt tgccgtgacc ttcagcgtga agaagaacgc cgattgtctg   2580
gacaccacaa aggacctgaa tgccgaagtg atggagcagt atagcgagtc caacagactg   2640
atcctgatca ggaataccac agatatcctg tactatctgg tgctggacaa gaatggcaag  2700
gtgctgaagc agagatccct gaacatcatc aatgacggcg ccaggatgt ggactggaag   2760 gagaggttcc gccaggtgac aaaggataga acgagggct acaatgagtg ggattattcc   2820
aggacctcta cgacctgaa ggaggtgtac ctgaattatg ccctgaagga gatcgccgag  2880
gccgtgatcg agtacaacgc catcctgatc atcgagaaga tgtctaatgc ctttaaggac  2940
aagtatagct tcctggacga cgtgaccttc aagggcttcg agacaaagct gctggccaag  3000
ctgagcgatc tgcactttag gggcatcaag gacggcgagc catgttcctt cacaaacccc  3060
ctgcagctgt gccagaacga ttctaataag atcctgcagg acggcgtgat ctttatggtg   3120
ccaaattcta tgacacggag cctggacccc gacaccggct tcatctttgc catcaacgac   3180
cacaatatca ggaccaagaa ggccaagctg aactttctga gcaagttcga tcagctgaag   3240
gtgtcctctg agggctgcct gatcatgaag tacagcggcg attccctgcc tacacacaac  3300
accgacaatc gcgtgtggaa ctgctgttgc aatcacccaa tcacaaacta tgaccgggag 3360
acaaagaagg tggagttcat cgaggagccc gtggaggagc tgtcccgcgt gctggaggag  3420
aatggcatcg agacagacac cgagctgaac aagctgaatg agcgggagaa cgtgcctggc  3480
aaggtggtgg atgccatcta ctctctggtg ctgaattatc tgcgcggcac agtgagcgga 3540
gtggcaggac agagggccgt gtactatagc cctgtgaccg gcaagaagta cgatatctcc  3600
tttatccagg ccatgaacct gaataggaag tgtgactact ataggatcgg ctccaaggag  3660 agggagagt ggaccgattt cgtggcccag ctgatcaac                           3699
```

<210> SEQ ID NO 219
<211> LENGTH: 3684
<212> TYPE: DNA
<213> ORGANISM: Lachnospiraceae bacterium ND2006

<400> SEQUENCE: 219

```
atgagcaagc tggagaagtt tacaaactgc tactccctgt ctaagaccct gaggttcaag      60
gccatccctg tgggcaagac ccaggagaac atcgacaata gcggctgct ggtggaggac      120
gagaagagag ccgaggatta aagggcgtg aagaagctgc tggatcgcta ctatctgtct      180
tttatcaacg acgtgctgca cagcatcaag ctgaagaatc tgaacaatta catcagcctg      240
ttccggaaga aaccagaac cgagaaggag aataaggagc tggagaacct ggagatcaat      300
ctgcggaagg agatcgccaa ggccttcaag ggcaacgagg ctacaagtc cctgtttaag      360
aaggatatca tcgagacaat cctgccagag ttcctggacg ataaggacga gatcgccctg      420
gtgaacagct tcaatggctt taccacagcc ttcaccggct ctttgataa cagagagaat      480
atgttttccg aggaggccaa gagcacatcc atcgccttca ggtgtatcaa cgagaatctg      540
acccgctaca tctctaatat ggacatcttc gagaaggtgg acgccatctt tgataagcac      600
gaggtgcagg agatcaagga gaagatcctg aacagcgact atgatgtgga ggatttctt      660
gagggcgagt tctttaactt tgtgctgaca caggagggca tcgacgtgta taacgccatc      720
atcgcggct tcgtgaccga gagcggcgag aagatcaagg gcctgaacga gtacatcaac      780
ctgtataatc agaaaaccaa gcagaagctg cctaagttta gccactgta taagcaggtg      840
ctgagcgatc gggagtctct gagcttctac ggcgagggca atacatccga tgaggaggtg      900
ctggaggtgt ttagaaacac cctgaacaag aacagcgaga tcttcagctc catcaagaag      960
ctggagaagc tgttcaagaa ttttgacgag tactctagcg ccggcatctt tgtgaagaac      1020
ggccccgcca tcagcacaat ctccaaggat atcttcggcg agtggaacgt gatccgggac      1080
aagtggaatg ccgagtatga cgatatccac ctgaagaaga aggccgtggt gaccgagaag      1140
tacgaggacg atcggagaaa gtccttcaag aagatcggct ccttttctct ggagcagctg      1200
caggagtacg ccgacgccga tctgtctgtg gtggagaagc tgaaggagat catcatccag      1260
aaggtggatg agatctacaa ggtgtatggc tcctctgaga agctgttcga cgccgatttt      1320
gtgctggaga gagcctgaa gaagaacgac gccgtggtgg ccatcatgaa ggacctgctg      1380
gattctgtga gagcttcga gaattacatc aaggccttct tggcgaggg caaggagaca      1440
aacagggacg agtccttcta tggcgatttt gtgctggcct acgacatcct gctgaaggtg      1500
gaccacatct acgatgccat ccgcaattat gtgacccaga gccctactc taaggataag      1560
ttcaagctgt attttcagaa ccctcagttc atgggcggct gggacaagga taaggagaca      1620
gactatcggg ccaccatcct gagatacggc tccaagtact atctggccat catggataag      1680
aagtacgcca agtgcctgca gaagatcgac aaggacgatg tgaacggcaa ttacgagaag      1740
atcaactata gctgctgcc cggccctaat aagatgctgc caaaggtgtt cttttctaag      1800
aagtggatgg cctactataa ccccagcgag gacatccaga gatctacaa gaatggcaca      1860
ttcaagaagg gcgatatgtt taacctgaat gactgtcaca gctgatcga cttctttaag      1920
gatagcatct cccggtatcc aaagtggtcc aatgcctacg atttcaactt ttctgagaca      1980
gagaagtata aggacatcgc cggcttttac agagaggtgg aggagcaggg ctataaggtg      2040
agcttcgagt ctgccagcaa gaaggaggtg gataagctgg tggaggaggg caagctgtat      2100
atgttccaga tctataacaa ggactttttcc gataagtctc acggcacacc caatctgcac      2160
accatgtact tcaagctgct gtttgacgag aacaatcacg acagatcag gctgagcgga      2220
ggagcagagc tgttcatgag gcgcgcctcc ctgaagaagg aggagctggt ggtgcaccca      2280
```

```
gccaactccc ctatcgccaa caagaatcca gataatccca agaaaaccac aaccctgtcc     2340
tacgacgtgt ataaggataa gaggttttct gaggaccagt acgagctgca catcccaatc     2400
gccatcaata agtgcccaa gaacatcttc aagatcaata cagaggtgcg cgtgctgctg      2460
aagcacgacg ataaccccta tgtgatcggc atcgataggg gcgagcgcaa tctgctgtat     2520
atcgtggtgg tggacggcaa gggcaacatc gtggagcagt attccctgaa cgagatcatc     2580
aacaacttca acggcatcag gatcaagaca gattaccact ctctgctgga caagaaggag    2640
aaggagaggt tcgaggcccg ccagaactgg acctccatcg agaatatcaa ggagctgaag     2700
gccggctata tctctcaggt ggtgcacaag atctgcgagc tggtggagaa gtacgatgcc     2760
gtgatcgccc tggaggacct gaactctggc tttaagaata gccgcgtgaa ggtggagaag    2820
caggtgtatc agaagttcga gaagatgctg atcgataagc tgaactacat ggtggacaag    2880
aagtctaatc cttgtgcaac aggcggcgcc ctgaagggct atcagatcac caataagttc    2940
gagagcttta gtccatgtc tacccagaac ggcttcatct tttacatccc tgcctggctg     3000
acatccaaga tcgatccatc taccggcttt gtgaacctgc tgaaaaccaa gtataccagc    3060
atcgccgatt ccaagaagtt catcagctcc tttgacagga tcatgtacgt gcccgaggag    3120
gatctgttcg agtttgccct ggactataag aacttctctc gcacagacgc cgattacatc     3180
aagaagtgga agctgtactc ctacggcaac cggatcagaa tcttccggaa tcctaagaag    3240
aacaacgtgt tcgactggga ggaggtgtgc ctgaccagcg cctataagga gctgttcaac    3300
aagtacggca tcaattatca gcagggcgat atcagagccc tgctgtgcga gcagtccgac    3360 aaggcccttct actctagctt tatggcccctg atgagcctga tgctgcagat gcggaacagc   3420
atcacaggcc gcaccgacgt ggattttctg atcagccctg tgaagaactc cgacggcatc    3480
ttctacgata gccggaacta tgaggcccag gagaatgcca tcctgccaaa gaacgccgac    3540
gccaatggcg cctataacat cgccagaaag gtgctgtggg ccatcggcca gttcaagaag    3600
gccgaggacg agaagctgga taaggtgaag atcgccatct ctaacaagga gtggctggag    3660
tacgcccaga ccagcgtgaa gcac                                           3684
```

<210> SEQ ID NO 220
<211> LENGTH: 3900
<212> TYPE: DNA
<213> ORGANISM: Francisella tularensis subsp. Novicida U112

<400> SEQUENCE: 220

```
atgagcatct accaggagtt cgtcaacaag tattcactga gtaagacact gcggttcgag       60
ctgatcccac agggcaagac actggagaac atcaaggccc gaggcctgat tctggacgat      120
gagaagcggg caaagactat aagaaagcc aagcagatca ttgataaata ccaccagttc        180
tttatcgagg aaattctgag ctccgtgtgc atcagtgagg atctgctgca gaattactca       240
gacgtgtact tcaagctgaa gaagagcgac gatgacaacc tgcagaagga cttcaagtcc       300
gccaaggaca ccatcaagaa acagattagc gagtacatca aggactccga aaagtttaaa      360
aatctgttca ccagaatct gatcgatgct aagaaaggcc aggagtccga cctgatcctg       420
tggctgaaac agtctaagga caatgggatt gaactgttca aggctaactc cgatatcact       480
gatattgacg aggcactgga aatcatcaag agcttcaagg gatggaccac atactttaaa     540
ggcttccacg agaaccgcaa gaacgtgtac tccagcaacg acattcctac ctccatcatc      600
taccgaatcg tcgatgacaa tctgccaaag ttcctggaga caaggccaa atatgaatct      660 ctgaaggaca agctcccga ggcaattaat tacgaacaga tcaagaaaga tctggctgag      720
```

```
gaactgacat tcgatatcga ctataagact agcgaggtga accagagggt ctttccctg    780 gacgaggtgt ttgaaatcgc caatttcaac aattacctga accagtccgg cattactaaa    840
ttcaatacca tcattggcgg gaagtttgtg aacggggaga ataccaagcg caagggaatt    900
aacgaataca tcaatctgta tagccagcag atcaacgaca aaactctgaa gaatacaag     960 atgtctgtgc tgttcaaaca gatcctgagt gataccgagt ccaagtcttt tgtcattgat   1020
aaactggaag atgactcaga cgtggtcact accatgcaga gcttttatga gcagatcgcc   1080
gctttcaaga cagtggagga aaaatctatt aaggaaactc tgagtctgct gttcgatgac   1140
ctgaaagccc agaagctgga cctgagtaag atctacttca aaaacgataa gagtctgaca   1200
gacctgtcac agcaggtgtt tgatgactat ccgtgattg ggaccgccgt cctggagtac    1260
attacacagc agatcgctcc aaagaacctg gataatccct ctaagaaaga gcaggaactg   1320
atcgctaaga aaccgagaa ggcaaaatat ctgagtctgg aaacaattaa gctggcactg    1380
gaggagttca acaagcacag ggatattgac aaacagtgcc gctttgagga aatcctggcc   1440
aacttcgcag ccatccccat gattttgat gagatcgccc agaacaaaga caatctggct    1500
cagatcagta ttaagtacca gaaccagggc aagaaagacc tgctgcaggc ttcagcagaa   1560
gatgacgtga aagccatcaa ggatctgctg gaccagacca caatctgct gcacaagctg     1620 aaaatcttcc atattagtca gtcagaggat aaggctaata tcctggataa agacgaacac   1680
ttctacctgg tgttcgagga atgttacttc gagctggcaa acattgtccc cctgtataac   1740
aagattagga actacatcac acagaagcct tactctgacg agaagtttaa actgaacttc   1800
gaaaatagta ccctggccaa cgggtgggat aagaacaagg agcctgacaa cacagctatc   1860
ctgttcatca aggatgacaa gtactatctg ggagtgatga ataagaaaaa caataagatc   1920
ttcgatgaca aagccattaa ggagaacaaa ggggaaggat acaagaaaat cgtgtataag   1980
ctgctgcccg cgcaaataa gatgctgcct aaggtgttct tcagcgccaa gagtatcaaa   2040
ttctacaacc catccgagga catcctgcgg attagaaatc actcaacaca tactaagaac   2100
gggagccccc agaagggata tgagaaattt gagttcaaca tcgaggattg caggaagttt   2160
attgacttct acaagcagag catctccaaa caccctgaat ggaaggattt tggcttccgg   2220
ttttccgaca cacagagata taactctatc gacgagttct accgcgaggt ggaaaatcag   2280
gggtataagc tgacttttga gaacatttct gaaagttaca tcgacagcgt ggtcaatcag   2340
ggaaagctgt acctgttcca gatctataac aaagattttt cagcatacag caagggcaga   2400
ccaaacctgc atacactgta ctggaaggcc ctgttcgatg agaggaatct gcaggacgtg   2460
gtctataaac tgaacggaga ggccgaactg ttttaccgga agcagtctat tcctaagaaa   2520
atcactcacc cagctaagga ggccatcgct aacaagaaca aggacaatcc taagaaagag   2580
agcgtgttcg aatacgatct gattaaggac aagcggttca ccgaagataa gttctttttc   2640
cattgtccaa tcaccattaa cttcaagtca gcggcgcta acaagttcaa cgacgagatc    2700
aatctgctgc tgaaggaaaa agcaaacgat gtgcacatcc tgagcattga ccgaggagag   2760
cggcatctgg cctactatac cctggtggat ggcaaaggga atatcattaa gcaggataca   2820
ttcaacatca ttggcaatga ccggatgaaa accaactacc acgataaact ggctgcaatc   2880
gagaaggata gagactcagc taggaaggac tggaagaaaa tcaacaacat taaggagatg   2940
aaggaaggct atctgagcca ggtggtccat gagattgcaa agctggtcat cgaatacaat   3000
gccattgtgg tgttcgagga tctgaacttc ggctttaaga gggggcgctt taaggtggaa   3060
```

```
aaacaggtct atcagaagct ggagaaaatg ctgatcgaaa agctgaatta cctggtgttt    3120
aaagataacg agttcgacaa gaccggaggc gtcctgagag cctaccagct gacagctccc    3180
tttgaaactt tcaagaaaat gggaaaacag acaggcatca tctactatgt gccagccgga    3240
ttcacttcca agatctgccc cgtgaccggc tttgtcaacc agctgtaccc taaatatgag    3300
tcagtgagca agtcccagga atttttcagc aagttcgata agatctgtta taatctggac    3360 aagggg tact tcgagttttc cttcgattac aagaacttcg gcgacaaggc cgctaagggg    3420
aaatggacca ttgcctcctt cggatctcgc ctgatcaact ttcgaaattc cgataaaaac    3480
cacaattggg acactaggga ggtgtaccca accaaggagc tggaaaagct gctgaaagac    3540
tactctatcg agtatggaca tggcgaatgc atcaaggcag ccatctgtgg cgagagtgat    3600
aagaaatttt tcgccaagct gacctcagtg ctgaatacaa tcctgcagat gcggaactca    3660
aagaccggga cagaactgga ctatctgatt agccccgtgg ctgatgtcaa cggaaacttc    3720
ttcgacagca gacaggcacc caaaaatatg cctcaggatg cagacgccaa cggggcctac    3780
cacatcgggc tgaagggact gatgctgctg ggccggatca agaacaatca ggaggggaag    3840
aagctgaacc tggtcattaa gaacgaggaa tacttcgagt ttgtccagaa tagaaataac    3900
```

<210> SEQ ID NO 221
<211> LENGTH: 4431
<212> TYPE: DNA
<213> ORGANISM: Peregrinibacteria bacterium GW2011_GWA_33_10

<400> SEQUENCE: 221

```
atgtccaact tctttaagaa tttcaccaac ctgtatgagc tgtccaagac actgaggttt      60
gagctgaagc ccgtgggcga caccctgaca acatgaagg accacctgga gtacgatgag     120
aagctgcaga ccttcctgaa ggatcagaat atcgacgatg cctatcaggc cctgaagcct     180
cagttcgacg agatccacga ggagtttatc acagattctc tggagagcaa gaaggccaag     240
gagatcgact tctccgagta cctggatctg tttcaggaga agaaggagct gaacgactct     300
gagaagaagc tgcgcaacaa gatcggcgag acattcaaca aggccggcga gaagtggaag     360
aaggagaagt accctcagta tgagtggaag aagggctcca agatcgccaa tggcgccgac     420
atcctgtctt gccaggatat gctgcagttt atcaagtata agaacccaga ggatgagaag     480
atcaagaatt acatcgacga tacactgaag ggcttcttta cctatttcgg cggctttaat     540
cagaacaggg ccaactacta tgagacaaag aaggaggcct ccaccgcagt ggcaacaagg     600
atcgtgcacg agaacctgcc aaagttctgt gacaatgtga tccagtttaa gcacatcatc     660
aagcggaaga aggatggcac cgtggagaaa accgagagaa agaccgagta cctgaacgcc     720
taccagtatc tgaagaacaa taacaagatc acacagatca aggacgccga gacagagaag     780
atgatcgagt ctacacccat cgccgagaag atcttcgacg tgtactactt cagcagctgc     840
ctgagccaga agcagatcga ggagtacaac cggatcatcg gccactataa tctgctgatc     900
aacctgtata accaggccaa gagatctgag gcaagcacc tgagcgccaa cgagaagaag     960
tataaggacc tgcctaagtt caagaccctg tataagcaga tcggctgcgg caagaagaag    1020
gacctgtttt acacaatcaa gtgtgatacc gaggaggagg ccaataagtc ccggaacgag    1080
ggcaaggagt cccactctgt ggaggagatc atcaacaagg cccaggaggc catcaataag    1140
tacttcaagt ctaataacga ctgtgagaat atcaacaccg tgcccgactt catcaactat    1200
atcctgacaa aggagaatta cgagggcgtg tattggagca aggccgccat gaacaccatc    1260
tccgacaagt acttcgccaa ttatcacgac ctgcaggata gactgaagga ggccaaggtg    1320
```

```
tttcagaagg ccgataagaa gtccgaggac gatatcaaga tcccagaggc catcgagctg    1380
tctggcctgt tcggcgtgct ggacagcctg gccgattggc agaccacact gtttaagtct    1440
agcatcctga gcaacgagga caagctgaag atcatcacag attcccagac ccctctgag     1500 gccctgctga agatgatctt caatgacatc gagaagaaca tggagtcctt tctgaaggag    1560
acaaacgata tcatcaccct gaagaagtat aagggcaata aggagggcac cgagaagatc    1620
aagcagtggt tcgactatac actggccatc aaccggatgc tgaagtactt tctggtgaag    1680
gagaataaga tcaagggcaa ctccctggat accaatatct ctgaggccct gaaaaccctg    1740
atctacagcg acgatgccga gtggttcaag tggtacgacg ccctgagaaa ctatctgacc    1800
cagaagcctc aggatgaggc caaggagaat aagctgaagc tgaatttcga caacccatct    1860
ctggccggcg ctgggatgt gaacaaggag tgcagcaatt tttgcgtgat cctgaaggac     1920
aagaacgaga agaagtacct ggccatcatg aagaagggcg agaataccct gttccagaag    1980
gagtggacag agggccgggg caagaacctg acaaagaagt ctaatccact gttcgagatc    2040
aataactgcg agatcctgag caagatggag tatgactttt gggccgacgt gagcaagatg    2100
atccccaagt gtagcaccca gctgaaggcc gtggtgaacc acttcaagca gtccgacaat    2160
gagttcatct ttcctatcgg ctacaaggtg acaagcggcg agaagtttag ggaggagtgc    2220
aagatctcca gcaggacttt cgagctgaat aacaaggtgt taataagaa cgagctgagc     2280 gtgaccgcca tgcgctacga tctgtcctct acacaggaga agcagtatat caaggccttc    2340
cagaaggagt actgggagct gctgtttaag caggagaagc gggacaccaa gctgacaaat    2400
aacgagatct tcaacgagtg gatcaatttt tgcaacaaga gtatagcga gctgctgtcc     2460 tgggagagaa agtacaagga tgccctgacc aattggatca acttctgtaa gtactttctg    2520
agcaagtatc ccaagaccac actgttcaac tactcttta aggagagcga gaattataac     2580
tccctggacg agttctaccg ggacgtggat atctgttctt acaagctgaa tatcaacacc    2640
acaatcaata gagcatcct ggatagactg gtggaggagg gcaagctgta cctgtttgag     2700
atcaagaatc aggacagcaa cgatggcaag tccatcggcc acaagaataa cctgcacacc    2760
atctactgga acgccatctt cgagaatttt gacaacaggc taagctgaa tggcgaggcc     2820 gagatcttct atcgcaaggc catctccaag gataagctgg gcatcgtgaa gggcaagaaa    2880
accaagaacg gcaccgagat catcaagaat tacagattca gcaaggagaa gtttatcctg    2940
cacgtgccaa tcaccctgaa cttctgctcc aataacgagt atgtgaatga catcgtgaac    3000
acaaagttct acaattttc caacctgcac tttctgggca tcgataggg cgagaagcac     3060 ctggcctact attctctggt gaataagaac ggcgagatcg tggaccaggg cacactgaac    3120
ctgcctttca ccgacaagga tggcaatcag cgcagcatca gaaggagaa gtactttat     3180 aacaagcagg aggacaagtg ggaggccaag gaggtggatt gttggaatta taacgacctg    3240
ctggatgcca tggcctctaa ccgggacatg gccagaaaga attggcagag atcggcacc     3300 atcaaggagg ccaagaacgg ctacgtgagc ctggtcatca ggaagatcgc cgatctggcc    3360
gtgaataacg agcgccccgc cttcatcgtg ctggaggacc tgaatacagg ctttaagcgg    3420
tccagacaga agatcgataa gagcgtgtac cagaagttcg agctggccct ggccaagaag    3480
ctgaactttc tggtggacaa gaatgccaag cgcgatgaga tcggctcccc tacaaaggcc    3540
ctgcagctga cccccctgt gaataactac ggcgacattg agaacaagaa gcaggccggc    3600
atcatgctgt atacccgggc caattatacc tctcagacag atccagccac aggctggaga    3660
```

| | |
|---|---|
| aagaccatct atctgaaggc cggccccgag gagacaacat acaagaagga cggcaagatc | 3720 |
| aagaacaaga gcgtgaagga ccagatcatc gagacattca ccgatatcgg ctttgacggc | 3780 |
| aaggattact atttcgagta cgacaagggc gagtttgtgg atgagaaaac cggcgagatc | 3840 |
| aagcccaaga gtggcggct gtactccggc gagaatggca agtccctgga caggttccgc | 3900 |
| ggagagaggg agaaggataa gtatgagtgg aagatcgaca agatcgatat cgtgaagatc | 3960 |
| ctggacgatc tgttcgtgaa ttttgacaag aacatcagcc tgctgaagca gctgaaggag | 4020 |
| ggcgtggagc tgacccggaa taacgagcac ggcacaggcg agtccctgag attcgccatc | 4080 |
| aacctgatcc agcagatccg gaataccggc aataacgaga gagacaacga tttcatcctg | 4140 |
| tccccagtga gggacgagaa tggcaagcac tttgactctc gcgagtactg ggataaggag | 4200 |
| acaaagggcg agaagatcag catgcccagc tccggcgatg ccaatggcgc cttcaacatc | 4260 |
| gcccggaagg gcatcatcat gaacgcccac atcctggcca atagcgactc caaggatctg | 4320 |
| tccctgttcg tgtctgacga ggagtgggat ctgcacctga ataacaagac cgagtggaag | 4380 |
| aagcagctga acatctttc tagcaggaag gccatggcca agcgcaagaa g | 4431 |

<210> SEQ ID NO 222
<211> LENGTH: 4056
<212> TYPE: DNA
<213> ORGANISM: Parcubacteria bacterium GWC2011_GWC2_44_17

<400> SEQUENCE: 222

| | |
|---|---|
| atggagaaca tcttcgacca gtttatcggc aagtacagcc tgtccaagac cctgagattc | 60 |
| gagctgaagc ccgtgggcaa gacagaggac ttcctgaaga tcaacaaggt gtttgagaag | 120 |
| gatcagacca tcgacgatag ctacaatcag gccaagttct attttgattc cctgcaccag | 180 |
| aagtttatcg acgccgccct ggcctccgat aagacatccg agctgtcttt ccagaacttt | 240 |
| gccgacgtgc tggagaagca gaataagatc atcctggata agaagagaga gatgggcgcc | 300 |
| ctgaggaagc gcgacaagaa cgccgtgggc atcgataggc tgcagaagga gatcaatgac | 360 |
| gccgaggata tcatccagaa ggagaaggag aagatctaca aggacgtgcg caccctgttc | 420 |
| gataacgagg ccgagtcttg gaaaacctac tatcaggagc gggaggtgga cggcaagaag | 480 |
| atcaccttca gcaaggccga cctgaagcag aagggcgccg atttctgac agccgccggc | 540 |
| atcctgaagg tgctgaagta tgagttcccc gaggagaagg agaaggagtt tcaggccaag | 600 |
| aaccagccct ccctgttcgt ggaggagaag gagaatcctg ccagaagag gtacatcttc | 660 |
| gactcttttg ataagttcgc cggctatctg accaagtttc agcagacaaa gaagaatctg | 720 |
| tacgcagcag acggcaccag cacagcagtg gccacccgca tcgccgataa ctttatcatc | 780 |
| ttccaccaga ataccaaggt gttccgggac aagtacaaga acaatcacac agacctgggc | 840 |
| ttcgatgagg agaacatctt tgagatcgag aggtataaga attgcctgct gcagcgcgag | 900 |
| atcgagcaca tcaagaatga aatagctac aacaagatca tcggccggat caataagaag | 960 |
| atcaaggagt atcgggacca gaaggccaag gataccaagc tgacaaagtc cgacttccct | 1020 |
| ttctttaaga acctggataa gcagatcctg ggcgaggtgg agaaggagaa gcagctgatc | 1080 |
| gagaaaaccc gggagaaaac cgaggaggac gtgctgatcg agcggttcaa ggagttcatc | 1140 |
| gagaacaatg aggagaggtt caccgccgcc aagaagctga tgaatgcctt ctgtaacggc | 1200 |
| gagtttgagt ccgagtacga gggcatctat ctgaagaata aggccatcaa cacaatctcc | 1260 |
| cggagatggt tcgtgtctga cagagatttt gagctgaagc tgcctcagca gaagtccaag | 1320 |
| aacaagtctg agaagaatga gccaaaggtg aagaagttca tctccatcgc cgagatcaag | 1380 |

```
aacgccgtgg aggagctgga cggcgatatc tttaaggccg tgttctacga caagaagatc    1440
atcgcccagg gcggctctaa gctggagcag ttcctggtca tctggaagta cgagtttgag    1500
tatctgttcc gggacatcga gagagagaac ggcgagaagc tgctgggcta tgatagctgc    1560
ctgaagatcg ccaagcagct gggcatcttc ccacaggaga aggaggcccg cgagaaggca    1620
accgccgtga tcaagaatta cgccgacgcc ggcctgggca tcttccagat gatgaagtat    1680
tttctctgg acgataagga tcggaagaac accccggcc agctgagcac aaatttctac      1740
gccgagtatg acggctacta caaggatttc gagtttatca agtactacaa cgagtttagg    1800
aacttcatca ccaagaagcc tttcgacgag gataagatca agctgaactt tgagaatggc    1860
gccctgctga agggctggga cgagaacaag gagtacgatt tcatgggcgt gatcctgaag    1920
aaggagggcc gcctgtatct gggcatcatg cacaagaacc accggaagct gtttcagtcc    1980
atgggcaatg ccaagggcga caacgccaat agataccaga agatgatcta taagcagatc    2040
gccgacgcct ctaaggatgt gcccaggctg ctgctgacca gcaagaaggc catggagaag    2100
ttcaagcctt cccaggagat cctgagaatc aagaaggaga aaaccttcaa gcgggagagc    2160
aagaactttt ccctgagaga tctgcacgcc ctgatcgagt actataggaa ctgcatccct    2220
cagtacagca attggtcctt ttatgacttc cagtttcagg ataccggcaa gtaccagaat    2280
atcaaggagt tcacagacga tgtgcagaag tacggctata gatctccttt cgcgacatc     2340
gacgatgagt atatcaatca ggccctgaac gagggcaaga tgtacctgtt cgaggtggtg    2400
aacaaggata tctataacac caagaatggc tccaagaatc tgcacacact gtactttgag    2460
cacatcctgt ctgccgagaa cctgaatgac ccagtgttca gctgtctgg catggccgag     2520
atctttcagc ggcagcccag cgtgaacgaa agagagaaga tcaccacaca gaagaatcag    2580
tgtatcctgg acaagggcga tagagcctac aagtataggc gctacaccga agagaagatc    2640
atgttccaca tgagcctggt gctgaacaca ggcaagggcg agatcaagca ggtgcagttt    2700
aataagatca tcaaccagag gatcagctcc tctgacaacg agatgagggt gaatgtgatc    2760
ggcatcgatc gcggcgagaa gaacctgctg tactatagcg tggtgaagca gaatggcgag    2820
atcatcgagc aggcctccct gaacgagatc aatggcgtga actaccggga caagctgatc    2880
gagagggaga aggagcgcct gaagaaccgg cagagctgga agcctgtggt gaagatcaag    2940
gatctgaaga agggctacat ctcccacgtg atccacaaga tctgccagct gatcgagaag    3000
tattctgcca tcgtggtgct ggaggacctg aatatgagat tcaagcagat caggggagga    3060
atcgagcgga gcgtgtacca gcagttcgag aaggccctga tcgataagct gggctatctg    3120
gtgtttaagg acaacaggga tctgagggca ccaggaggcg tgctgaatgg ctaccagctg    3180
tctgcccct ttgtgagctt cgagaagatg cgcaagcaga ccggcatcct gttctacaca     3240
caggccgagt ataccagcaa gacagaccca atcaccggct tcggaagaa cgtgtatatc     3300
tctaatagcg cctccctgga taagatcaag gaggccgtga agaagttcga cgccatcggc    3360
tgggatggca aggagcagtc ttacttcttt aagtacaacc cttacaacct ggccgacgag    3420
aagtataaga actctaccgt gagcaaggag tgggccatct tgccagcgc cccaagaatc     3480
cggagacaga agggcgagga cggctactgg aagtatgata gggtgaaagt gaatgaggag    3540
ttcgagaagc tgctgaaggt ctggaatttt gtgaacccaa aggccacaga tatcaagcag    3600
gagatcatca gaaggagaa ggcaggcgac ctgcagggag agaaggagct ggatggccgg     3660
ctgagaaact tttggcactc tttcatctac ctgtttaacc tggtgctgga gctgcgcaat    3720
```

| | |
|---|---|
| tctttcagcc tgcagatcaa gatcaaggca ggagaagtga tcgcagtgga cgagggcgtg | 3780 |
| gacttcatcg ccagcccagt gaagcccttc tttaccacac ccaaccctta catccctcc | 3840 |
| aacctgtgct ggctggccgt ggagaatgca gacgcaaacg gagcctataa tatcgccagg | 3900 |
| aagggcgtga tgatcctgaa gaagatccgc gagcacgcca agaaggaccc cgagttcaag | 3960 |
| aagctgccaa acctgtttat cagcaatgca gagtgggacg aggcagcccg ggattggggc | 4020 |
| aagtacgcag gcaccacagc cctgaacctg gaccac | 4056 |

<210> SEQ ID NO 223
<211> LENGTH: 3618
<212> TYPE: DNA
<213> ORGANISM: Lachnospiraceae bacterium MA2020

<400> SEQUENCE: 223

| | |
|---|---|
| atgtactatg agtccctgac caagcagtac cccgtgtcta agacaatccg gaatgagctg | 60 |
| atccctatcg gcaagacact ggataacatc cgccagaaca atatcctgga gagcgacgtg | 120 |
| aagcggaagc agaactacga gcacgtgaag ggcatcctgg atgagtatca caagcagctg | 180 |
| atcaacgagg ccctggacaa ttgcacctg ccatccctga gatcgccgc cgagatctac | 240 |
| ctgaagaatc agaaggaggt gtctgacaga gaggatttca acaagacaca ggacctgctg | 300 |
| aggaaggagt ggtggagaa gctgaaggcc cacgagaact ttaccaagat cggcaagaag | 360 |
| gacatcctgg atctgctgga gaagctgcct tccatctctg aggacgatta caatgccctg | 420 |
| gagagcttcc gcaactttta cacctatttc acatcctaca caaggtgcg ggagaatctg | 480 |
| tattctgata aggagaagag ctccacagtg gcctacagac tgatcaacga gaatttccca | 540 |
| aagtttctgg acaatgtgaa gagctatagg tttgtgaaaa ccgcaggcat cctggcagat | 600 |
| ggcctgggag aggaggagca ggactccctg ttcatcgtgg acattcaa caagaccctg | 660 |
| acacaggacg gcatcgatac ctacaattct caagtgggca agatcaactc tagcatcaat | 720 |
| ctgtataacc agaagaatca gaaggccaat ggcttcagaa gatcccccaa gatgaagatg | 780 |
| ctgtataagc agatcctgtc cgatagggag gagtctttca tcgacgagtt tcagagcgat | 840 |
| gaggtgctga tcgacaacgt ggagtcttat ggcagcgtgc tgatcgagtc tctgaagtcc | 900 |
| tctaaggtga gcgccttctt tgatgccctg agagagtcta agggcaagaa cgtgtacgtg | 960 |
| aagaatgacc tggccaagac agccatgagc aacatcgtgt tcgagaattg gaggaccttt | 1020 |
| gacgatctgc tgaaccagga gtacgacctg ccaacgaga acaagaagaa ggacgataag | 1080 |
| tatttcgaga gcgccagaa ggagctgaag aagaataaga gctactccct ggagcacctg | 1140 |
| tgcaacctgt ccgaggattc ttgtaacctg atcgagaatt atatccacca gatctccgac | 1200 |
| gatatcgaga atatcatcat caacaatgag acattcctgc gcatcgtgat caatgagcac | 1260 |
| gacaggtccc gcaagctggc caagaaccgg aaggccgtga aggccatcaa ggactttctg | 1320 |
| gattctatca aggtgctgga gcgggagctg aagctgatca cagctccgg ccaggagctg | 1380 |
| gagaaggatc tgatcgtgta ctctgcccac gaggagctgc tggtggagct gaagcaggtg | 1440 |
| gacagcctgt ataacatgac cagaaattat ctgacaaaga agcctttctc taccgagaag | 1500 |
| gtgaagctga actttaatcg cagcacactg ctgaacggct gggatcggaa taaggagaca | 1560 |
| gacaacctgg gcgtgctgct gctgaaggac ggcaagtact atctgggcat catgaacaca | 1620 |
| agcgccaata aggccttcgt gaatccccct gtggccaaga ccgagaaggt gtttaagaag | 1680 |
| gtggattaca agctgctgcc agtgcccaac cagatgctgc caaaggtgtt ctttgccaag | 1740 |
| agcaatatcg acttctataa ccccctctagc gagatctact ccaattataa gaagggcacc | 1800 |

```
cacaagaagg gcaatatgtt ttccctggag gattgtcaca acctgatcga cttctttaag    1860
gagtctatca gcaagcacga ggactggagc aagttcggct ttaagttcag cgatacagcc    1920
tcctacaacg acatctccga gttctatcgc gaggtggaga agcagggcta caagctgacc    1980
tatacagaca tcgatgagac atacatcaat gatctgatcg agcggaacga gctgtacctg    2040
ttccagatct ataataagga ctttagcatg tactccaagg gcaagctgaa cctgcacaca    2100
ctgtatttca tgatgctgtt tgatcagcgc aatatcgacg acgtggtgta taagctgaac    2160
ggagaggcag aggtgttcta taggccagcc tccatctctg aggacgagct gatcatccac    2220
aaggccggcg aggagatcaa gaacaagaat cctaaccggg ccagaaccaa ggagacaagc    2280
accttcagct acgacatcgt gaaggataag cggtatagca aggataagtt taccctgcac    2340
atccccatca caatgaactt cggcgtggat gaggtgaagc ggttcaacga cgccgtgaac    2400
agcgccatcc ggatcgatga gaatgtgaac gtgatcggca tcgaccgggg cgagagaaat    2460
ctgctgtacg tggtggtcat cgactctaag ggcaacatcc tggagcagat ctccctgaac    2520
tctatcatca ataaggagta cgacatcgag acagattatc acgcactgct ggatgagagg    2580
gagggcggca gagataaggc ccggaaggac tggaacaccg tggagaatat cagggacctg    2640
aaggccggct acctgagcca ggtggtgaac gtggtggcca agctggtgct gaagtataat    2700
gccatcatct gcctggagga cctgaacttt ggcttcaaga gggccgcca gaaggtggag    2760 aagcaggtgt accagaagtt cgagaagatg ctgatcgata agctgaatta cctggtcatc    2820
gacaagagcc gcgagcagac atcccctaag gagctgggag gcgccctgaa cgcactgcag    2880
ctgacctcta gttcaagag ctttaaggag ctgggcaagc agtccggcgt gatctactat    2940
gtgcctgcct acctgacctc taagatcgat ccaaccacag gcttcgccaa tctgtttat    3000 atgaagtgtg agaacgtgga gaagtccaag agattctttg acggctttga tttcatcagg    3060
ttcaacgccc tggagaacgt gttcgagttc ggctttgact accggagctt cacccagagg    3120
gcctgcggca tcaattccaa gtggaccgtg tgcaccaacg gcgagcgcat catcaagtat    3180
cggaatccag ataagaacaa tatgttcgac gagaaggtgg tggtggtgac cgatgagatg    3240
aagaacctgt ttgagcagta caagatcccc tatgaggatg gcagaaatgt gaaggacatg    3300
atcatcagca acgaggaggc cgagttctac cggagactgt ataggctgct gcagcagacc    3360
ctgcagatga gaaacagcac ctccgacggc acaagggatt acatcatctc ccctgtgaag    3420
aataagagag aggcctactt caacagcgag ctgtccgacg gctctgtgcc aaaggacgcc    3480
gatgccaacg gcgcctacaa tatcgccaga aagggcctgt gggtgctgga gcagatcagg    3540
cagaagagcg agggcgagaa gatcaatctg gccatgacca acgccgagtg gctggagtat    3600
gcccagacac acctgctg                                                 3618
```

<210> SEQ ID NO 224
<211> LENGTH: 3714
<212> TYPE: DNA
<213> ORGANISM: Candidatus Methanoplasma termitum

<400> SEQUENCE: 224

```
atgaacaatt acgacgagtt caccaagctg tatcctatcc agaaaaccat ccggtttgag     60
ctgaagccac agggcagaac catggagcac ctggagacat tcaacttctt tgaggaggac    120
cgggatagag ccgagaagta taagatcctg aaggaggcca tcgacgagta ccacaagaag    180
tttatcgatg agcacctgac caatatgtcc ctggattgga actctctgaa gcagatcagc    240
```

```
gagaagtact ataagagcag ggaggagaag acaagaagg tgttcctgtc cgagcagaag      300
aggatgcgcc aggagatcgt gtctgagttt aagaaggacg atcgcttcaa ggacctgttt      360
tccaagaagc tgttctctga gctgctgaag gaggagatct acaagaaggg caaccaccag      420
gagatcgacg ccctgaagag cttcgataag ttttccggct atttcatcgg cctgcacgag      480
aataggaaga acatgtactc cgacggcgat gagatcaccg ccatctccaa tcgcatcgtg      540
aatgagaact tccccaagtt tctggataac ctgcagaagt accaggaggc caggaagaag      600
tatcctgagt ggatcatcaa ggccgagagc gccctggtgg cccacaatat caagatggac      660
gaggtgttct ccctggagta ctttaataag gtgctgaacc aggagggcat ccagcggtac      720
aacctggccc tgggcggcta tgtgaccaag agcggcgaga agatgatggg cctgaatgat      780
gccctgaacc tggcccacca gtccgagaag agctccaagg gcagaatcca catgacccc      840 ctgttcaagc agatcctgtc cgagaaggag tccttctctt catccccga cgtgtttaca      900 gaggattctc agctgctgcc tagcatcggc ggcttctttg cccagatcga aatgacaag      960 gatggcaaca tcttcgaccg ggccctggag ctgatctcta gctacgccga gtatgatacc     1020
gagcggatct atatcagaca ggccgacatc aatagagtgt ccaacgtgat ctttggagag     1080
tggggcaccc tgggaggcct gatgagggag tacaaggccg actctatcaa tgatatcaac     1140
ctggagcgca catgcaagaa ggtggacaag tggctggatt ctaaggagtt tgccctgagc     1200
gatgtgctgg aggccatcaa ggaccggc aacaatgacg ccttcaacga gtatatctcc     1260
aagatgcgga cagccagaga aagatcgat gccgcccgca aggagatgaa gttcatcagc     1320
gagaagatct ccggcgatga ggagtctatc cacatcatca agaccctgct ggacagcgtg     1380
cagcagttcc tgcacttctt taatctgttt aaggcaaggc aggacatccc actggatgga     1440
gccttctacg ccgagtttga cgaggtgcac agcaagctgt tgccatcgt gcccctgtat     1500 aacaaggtgc ggaactatct gaccaagaac aatctgaaca caaagaagat caagctgaat     1560
ttcaagaacc ctacactggc caatggctgg gaccagaaca aggtgtacga ttatgcctcc     1620
ctgatctttc tgcgggacgg caattactat ctgggcatca tcaatcctaa gagaaagaag     1680
aacatcaagt cgagcaggg ctctggcaac ggcccttct accggaagat ggtgtataag     1740
cagatccccg ccctaataa gaacctgcca agagtgttcc tgacctccac aaagggcaag     1800
aaggagtata gccctctaa ggagatcatc gagggctacg aggccgacaa gcacatcagg     1860
ggcgataagt tcgacctgga tttttgtcac aagctgatcg atttctttaa ggagtccatc     1920
gagaagcaca aggactggtc taagttcaac ttctacttca gcccaaccga gagctatggc     1980
gacatctctg agttctacct ggatgtggag aagcagggct atcgcatgca ctttgagaat     2040
atcagcgccg agacaatcga cgagtatgtg gagaagggcg atctgtttct gttccagatc     2100
tacaacaagg attttgtgaa ggccgccacc ggcaagaagg acatgcacac aatctactgg     2160
aatgccgcct tcagccccga gaacctgcag gacgtggtgg tgaagctgaa cggcgaggcc     2220
gagctgtttt atagggacaa gtccgatatc aaggagatcg tgcaccgcga gggcgagatc     2280
ctggtgaata ggacctacaa cggccgcaca ccagtgcccg acaagatcca caagaagctg     2340
accgattatc acaatggccg gacaaaggac ctgggcgagg ccaaggagta cctggataag     2400
gtgagatact tcaaggccca ctatgacatc accaaggatc ggagatacct gaacgacaag     2460
atctatttcc acgtgcctct gaccctgaac ttcaaggcca acggcaagaa gaatctgaac     2520
aagatggtca tcgagaagtt cctgtccgat gagaaggccc acatcatcgg catcgacagg     2580
ggcgagcgca atctgctgta ctattccatc atcgacaggt ctggcaagat catcgatcag     2640
```

```
cagagcctga atgtgatcga cggctttgat tatcgggaga agctgaacca gagagagatc   2700
gagatgaagg atgcccgcca gtcttggaac gccatcggca agatcaagga cctgaaggag   2760
ggctacctga gcaaggccgt gcacgagatc accaagatgg ccatccagta taatgccatc   2820
gtggtcatgg aggagctgaa ctacggcttc aagcggggcc ggttcaaggt ggagaagcag   2880
atctatcaga gttcgagaa tatgctgatc gataagatga actacctggt gtttaaggac   2940
gcacctgatg agtccccagg aggcgtgctg aatgcctacc agctgacaaa cccactggag   3000
tctttcgcca agctgggcaa gcagaccggc atcctgtttt acgtgccagc cgcctataca   3060
tccaagatcg accccaccac aggcttcgtg aatctgttta cacctcctc taagacaaac   3120 gcccaggagc ggaaggagtt cctgcagaag tttgagagca tctcctattc tgccaaggat   3180
ggcggcatct tgccttcgc ctttgactac agaaagttcg gcaccagcaa gacagatcac   3240
aagaacgtgt ggaccgccta tacaaacggc gagaggatgc gctacatcaa ggagaagaag   3300
cggaatgagc tgtttgaccc ttctaaggag atcaaggagg ccctgaccag ctccggcatc   3360
aagtacgatg gcggccagaa catcctgcca gacatcctga ggagcaacaa taacggcctg   3420
atctacacaa tgtattctag cttcatcgcc gccatccaga tgcgcgtgta cgacggcaag   3480
gaggattata tcatcagccc catcaagaac tccaagggcg agttctttag gaccgacccc   3540
aagaggcgcg agctgcctat cgacgccgat gccaatggcg cctacaacat cgccctgagg   3600
ggagagctga caatgagggc aatcgcagag aagttcgacc ctgatagcga aagatggcc   3660 aagctggagc tgaagcacaa ggattggttc gagtttatgc agaccagagg cgac          3714

<210> SEQ ID NO 225
<211> LENGTH: 3846
<212> TYPE: DNA
<213> ORGANISM: Eubacterium eligens

<400> SEQUENCE: 225
atgaacggca ataggtccat cgtgtaccgc gagttcgtgg gcgtgatccc cgtggccaag     60
accctgagga tgagctgcg ccctgtgggc cacacacagg agcacatcat ccagaacggc    120
ctgatccagg aggacgagct gcggcaggag aagagcaccg agctgaagaa catcatggac    180
gattactata gagagtacat cgataagtct ctgagcggcg tgaccgacct ggacttcacc    240
ctgctgttcg agctgatgaa cctggtgcag agctcccccct ccaaggacaa taagaaggcc    300
ctggagaagg agcagtctaa gatgagggag cagatctgca cccacctgca gtccgactct    360
aactacaaga atatctttaa cgccaagctg ctgaaggaga tcctgcctga tttcatcaag    420
aactacaatc agtatgacgt gaaggataag gccggcaagc tggagacact ggccctgttt    480
aatggcttca gcacatactt taccgacttc tttgagaaga ggaagaacgt gttcaccaag    540
gaggccgtga gcacatccat cgcctaccgc atcgtgcacg agaactccct gatcttcctg    600
gccaatatga cctcttataa agagatcagc gagaaggccc tggatgagat cgaagtgatc    660
gagaagaaca atcaggacaa gatgggcgat tgggagctga atcagatctt taaccctgac    720
ttctacaata tggtgctgat ccagtccggc atcgacttct acaacgagat ctgcggcgtg    780
gtgaatgccc acatgaacct gtactgtcag cagaccaaga acaattataa cctgttcaag    840
atgcggaagc tgcacaagca gatcctggcc tacaccagca ccagcttcga ggtgcccaag    900
atgttcgagg acgatatgag cgtgtataac gccgtgaacg ccttcatcga cgagacagag    960
aagggcaaca tcatcggcaa gctgaaggat atcgtgaata agtacgacga gctggatgag   1020
```

```
aagagaatct atatcagcaa ggacttttac gagacactga gctgcttcat gtccggcaac    1080
tggaatctga tcacaggctg cgtggagaac ttctacgatg agaacatcca cgccaagggc    1140
aagtccaagg aggagaaggt gaagaaggcc gtgaaggagg acaagtacaa gtctatcaat    1200
gacgtgaacg atctggtgga gaagtatatc gatgagaagg agaggaatga gttcaagaac    1260
agcaatgcca agcagtacat ccgcgagatc tccaacatca tcaccgacac agagacagcc    1320
cacctggagt atgacgatca catctctctg atcgagagcg aggagaaggc cgacgagatg    1380
aagaagcggc tggatatgta tatgaacatg taccactggg ccaaggcctt tatcgtggac    1440
gaggtgctgg acagagatga gatgttctac agcgatatcg acgatatcta taatatcctg    1500
gagaacatcg tgccactgta taatcgggtg agaaaactacg tgacccagaa gccctacaac    1560
```

```
gaggacaatg agatcaacta cgccgacggc cacgatatca ggatcgatat ggagaagatg    3480
gacgaggata agaagagcga gttctttgcc cagctgctga gcctgtataa gctgaccgtg    3540
cagatgcgca attcctatac agaggccgag gagcaggaga acggcatctc ttacgacaag    3600
atcatcagcc ctgtgatcaa tgatgagggc gagttctttg actccgataa ctataaggag    3660
tctgacgata aggagtgcaa gatgccaaag gacgccgatg ccaacggcgc ctactgtatc    3720
gccctgaagg gcctgtatga ggtgctgaag atcaagagcg agtggaccga ggacggcttt    3780
gataggaatt gcctgaagct gccacacgca gagtggctgg acttcatcca gaacaagcgg    3840
tacgag                                                              3846

<210> SEQ ID NO 226
<211> LENGTH: 4119
<212> TYPE: DNA
<213> ORGANISM: Moraxella bovoculi 237

<400> SEQUENCE: 226
atgctgttcc aggactttac ccacctgtat ccactgtcca agacagtgag atttgagctg      60
aagcccatcg ataggaccct ggagcacatc acgccaaga acttcctgtc tcaggacgag     120
acaatggccg atatgcacca aaggtgaaa gtgatcctgg acgattacca ccgcgacttc     180
atcgccgata tgatgggcga ggtgaagctg accaagctgg ccgagttcta tgacgtgtac     240
ctgaagtttc ggaagaaccc aaaggacgat gagctgcaga agcagctgaa ggatctgcag     300
gccgtgctga aaaggagat cgtgaagccc atcggcaatg cggcaagta taaggccggc     360 tacgacaggc tgttcggcgc caagctgttt aaggacggca aggagctggg cgatctggcc     420
aagttcgtga tcgcacagga gggagagagc tccccaaagc tggcccacct ggcccacttc     480
gagaagtttt ccacctattt cacaggcttt cacgataacc ggaagaatat gtattctgac     540
gaggataagc acaccgccat cgcctaccgc ctgatccacg agaacctgcc ccggtttatc     600
gacaatctgc agatcctgac cacaatcaag cagaagcact ctgccctgta cgatcagatc     660
atcaacgagc tgaccgccag cggcctggac gtgtctctgg ccagccacct ggatggctat     720
cacaagctgc tgacacagga gggcatcacc gcctacaata cactgctggg aggaatctcc     780
ggagaggcag gctctcctaa gatccagggc atcaacgagc tgatcaattc tcaccacaac     840
cagcactgcc acaagagcga gagaatcgcc aagctgaggc cactgcacaa gcagatcctg     900
tccgacggca tgagcgtgtc cttcctgccc tctaagtttg ccgacgatag cgagatgtgc     960
caggccgtga cgagttcta tgccactac gccgacgtgt cgccaaggt gcagagcctg    1020 ttcgacggct tgacgatca ccagaaggat ggcatctacg tggagcacaa gaacctgaat    1080
gagctgtcca gcaggccctt cggcgacttt gcactgctgg acgcgtgct ggacggatac    1140 tatgtggatg tggtgaatcc agagttcaac gagcggtttg ccaaggccaa gaccgacaat    1200
gccaaggcca agctgacaaa ggagaaggat aagttcatca agggcgtgca ctccctggcc    1260
tctctggagc aggccatcga gcactatacc gcaaggcacg acgatgagag cgtgcaggca    1320
ggcaagctgg gacagtactt caagcacggc ctggccggag tggacaaccc catccagaag    1380
atccacaaca atcacagcac catcaagggc tttctggaga gggagcgccc tgcaggagag    1440 agagcctgc caaagatcaa gtccggcaag aatcctgaga tgacacagct gaggcagctg    1500
aaggagctgc tggataacgc cctgaatgtg gcccacttcg ccaagctgct gaccacaaag    1560
accacactgg acaatcagga tggcaacttc tatggcgagt ttggcgtgct gtacgacgag    1620
```

```
ctggccaaga tccccaccct gtataacaag gtgagagatt acctgagcca gaagcctttc    1680
tccaccgaga agtacaagct gaactttggc aatccaacac tgctgaatgg ctgggacctg    1740
aacaaggaga aggataattt cggcgtgatc ctgcagaagg acggctgcta ctatctggcc    1800
ctgctggaca aggcccacaa gaaggtgttt gataacgccc taatacagg caagagcatc     1860
tatcagaaga tgatctataa gtacctggag gtgaggaagc agttccccaa ggtgttcttt    1920
tccaaggagg ccatcgccat caactaccac ccttctaagg agctggtgga gatcaaggac    1980
aagggccggc agagatccga cgatgagcgc ctgaagctgt atcggtttat cctggagtgt    2040
ctgaagatcc accctaagta cgataagaag ttcgagggcg ccatcggcga catccagctg    2100
tttaagaagg ataagaaggg cagagaggtg ccaatcagcg agaaggacct gttcgataag    2160
atcaacggca tcttttctag caagcctaag ctggagatgg aggacttctt tatcggcgag    2220
ttcaagaggt ataacccaag ccaggacctg gtggatcagt ataatatcta caagaagatc    2280
gactccaacg ataatcgcaa gaaggagaat ttctacaaca atcaccccaa gtttaagaag    2340
gatctggtgc ggtactatta cgagtctatg tgcaagcacg aggagtggga ggagagcttc    2400
gagttttcca agaagctgca ggacatcggc tgttacgtgg atgtgaacga gctgtttacc    2460
gagatcgaga cacggagact gaattataag atctccttct gcaacatcaa tgccgactac    2520
atcgatgagc tggtggagca gggccagctg tatctgttcc agatctacaa caaggacttt    2580
tccccaaagg cccacggcaa gcccaatctg cacaccctgt acttcaaggc cctgttttct    2640
gaggacaacc tggccgatcc tatctataag ctgaatggcg aggcccagat cttctacaga    2700
aaggcctccc tggacatgaa cgagacaaca atccacaggg ccggcgaggt gctggagaac    2760
aagaatcccg ataatcctaa gaagagacag ttcgtgtacg acatcatcaa ggataagagg    2820
tacacacagg acaagttcat gctgcacgtg ccaatcacca tgaactttgg cgtgcagggc    2880
atgacaatca aggagttcaa taagaaggtg aaccagtcta tccagcagta tgacgaggtg    2940
aacgtgatcg gcatcgatcg gggcgagaga cacctgctgt acctgaccgt gatcaatagc    3000
aagggcgaga tcctggagca gtgttccctg aacgacatca ccacagcctc tgccaatggc    3060
acacagatga ccacacctta ccacaagatc ctggataaga gggagatcga gcgcctgaac    3120
gcccgggtgg gatggggcga gatcgagaca atcaaggagc tgaagtctgg ctatctgagc    3180
cacgtggtgc accagatcag ccagctgatg ctgaagtaca acgccatcgt ggtgctggag    3240
gacctgaatt tcggctttaa gaggggccgc tttaaggtgg agaagcagat ctatcagaac    3300
ttcgagaatg ccctgatcaa gaagctgaac cacctggtgc tgaaggacaa ggccgacgat    3360
gagatcggct cttacaagaa tgccctgcag ctgaccaaca atttcacaga tctgaagagc    3420
atcggcaagc agaccggctt cctgttttat gtgcccgcct ggaacacctc taagatcgac    3480
cctgagacag gctttgtgga tctgctgaag ccaagatacg agaacatcgc ccagagccag    3540
gccttctttg gcaagttcga caagatctgc tataatgccg acaaggatta cttcgagttt    3600
cacatcgact acgccaagtt taccgataag gccaagaata gccgcagat ctggacaatc    3660
tgttcccacg gcgacaagcg gtacgtgtac gataagacag ccaaccagaa taagggcgcc    3720
gccaagggca tcaacgtgaa tgatgagctg aagtccctgt cgcccgcca ccacatcaac    3780
gagaagcagc ccaacctggt catggacatc tgccagaaca atgataagga gtttcacaag    3840
tctctgatgt acctgctgaa aaccctgctg gccctgcgt acagcaacgc ctcctctgac    3900
gaggatttca tcctgtcccc cgtggcaaac gacgagggcg tgttctttaa tagcgccctg    3960
gccgacgata cacagcctca gaatgccgat gccaacggcg cctaccacat cgccctgaag    4020
```

-continued

```
ggcctgtggc tgctgaatga gctgaagaac tccgacgatc tgaacaaggt gaagctggcc      4080
atcgacaatc agacctggct gaatttcgcc cagaacagg                             4119

<210> SEQ ID NO 227
<211> LENGTH: 3969
<212> TYPE: DNA
<213> ORGANISM: Prevotella disiens

<400> SEQUENCE: 227
atggagaact atcaggagtt caccaacctg tttcagctga ataagacact gagattcgag        60
ctgaagccca tcggcaagac ctgcgagctg ctggaggagg gcaagatctt cgccagcggc       120
tcctttctgg agaaggacaa ggtgagggcc gataacgtga gctacgtgaa gaaggagatc       180
gacaagaagc acaagatctt tatcgaggag acactgagct ccttctctat cagcaacgat       240
ctgctgaagc agtactttga ctgctataat gagctgaagg ccttcaagaa ggactgtaag       300
agcgatgagg aggaggtgaa gaaaaccgcc ctgcgcaaca gtgtacctc catccagagg       360 gccatgcgcg aggccatctc tcaggccttt ctgaagagcc cccagaagaa gctgctggcc       420
atcaagaacc tgatcgagaa cgtgttcaag gccgacgaga atgtgcagca cttctccgag       480
tttaccagct atttctccgg cttttgagaca acagagaga atttctactc tgacgaggag       540
aagtccacat ctatcgccta taggctggtg cacgataacc tgcctatctt catcaagaac       600
atctacatct tcgagaagct gaaggagcag ttcgacgcca agaccctgag cgagatcttc       660
gagaactaca gctgtatgt ggccggctct agcctggatg aggtgttctc cctggagtac       720
tttaacaata ccctgacaca aagggcatc gacaactata atgccgtgat cggcaagatc       780
gtgaaggagg ataagcagga gatccagggc ctgaacgagc acatcaacct gtataatcag       840
aagcacaagg accggagact gcccttcttt atctccctga gaagcagat cctgtccgat       900 cgggaggccc tgtcttggct gcctgacatg ttcaagaatg attctgaagt gatcaaggcc       960
ctgaagggct tctacatcga ggacggcttt gagaacaatg tgctgacacc tctggccacc      1020
ctgctgtcct ctctggataa gtacaacctg aatggcatct ttatccgcaa caatgaggcc      1080
ctgagctccc tgtcccagaa cgtgtatcgg aattttttcta cgacgaggc catcgatgcc      1140 aacgccgagc tgcagacctt caacaattac gagctgatcg ccaatgccct gcgcgccaag      1200
atcaagaagg agacaaagca gggccggaag tctttcgaga gtacgagga gtatatcgat      1260 aagaaggtga aggccatcga cagcctgtcc atccaggaga tcaacgagct ggtggagaat      1320
tacgtgagcg agtttaactc taatagcggc aacatgccaa gaaggtgga ggactacttc      1380 agcctgatga ggaagggcga cttcggctcc aacgatctga tcgaaaatat caagaccaag      1440
ctgagcgccg cagagaagct gctgggcaca aagtaccagg acagccaa ggacatcttc      1500 aagaaggatg agaactccaa gctgatcaag gagctgctgg acgccaccaa gcagttccag      1560
cactttatca gccactgct gggcacaggc gaggaggcag atcgggacct ggtgttctac      1620
ggcgattttc tgcccctgta tgagaagttt gaggagctga ccctgctgta taacaaggtg      1680
cggaatagac tgacacagaa gcccctattc aaggacaaga tccgcctgtg cttcaacaag      1740
cctaagctga tgacaggctg ggtggattcc aagaccgaga agtctgacaa cggcacacag      1800
tacggcggct atctgttccg gaagaagaat gagatcggcg agtacgatta ttttctgggc      1860
atctctagca aggcccagct gttcagaaag aacgaggccg tgatcggcga ctacgagagg      1920
ctggattact atcagccaaa ggccaatacc atctacggct gcctatga gggcgagaac      1980
```

-continued

```
agctacaagg aggacaagaa gcggctgaac aaagtgatca tcgcctatat cgagcagatc    2040
aagcagacaa acatcaagaa gtctatcatc gagtccatct ctaagtatcc taatatcagc    2100
gacgatgaca aggtgacccc atcctctctg ctggagaaga tcaagaaggt gtctatcgac    2160
agctacaacg gcatcctgtc cttcaagtct tttcagagcg tgaacaagga agtgatcgat    2220
aacctgctga aaaccatcag cccctgaag aacaaggccg agtttctgga cctgatcaat    2280
aaggattatc agatcttcac cgaggtgcag gccgtgatcg acgagatctg caagcagaaa    2340
accttcatct actttccaat ctccaacgtg gagctggaga aggagatggg cgataaggac    2400
aagcccctgt gcctgttcca gatcagcaat aaggatctgt ccttcgccaa gacctttagc    2460
gccaacctgc ggaagaagag aggcgccgag aatctgcaca caatgctgtt taaggccctg    2520
atggagggca accaggataa tctgacctg ggctctggcg ccatcttcta cagagccaag    2580
agcctggacg gcaacaagcc cacacaccct gccaatgagg ccatcaagtg taggaacgtg    2640
gccaataagg ataaggtgtc cctgttcacc tacgacatct ataagaacag gcgctacatg    2700
gagaataagt tcctgtttca cctgagcatc gtgcagaact ataaggccgc caatgactcc    2760
gcccagctga cagctccgc caccgagtat atcagaaagg ccgatgacct gcacatcatc    2820
ggcatcgata ggggcgagcg caatctgctg tactattccg tgatcgatat gaagggcaac    2880
atcgtggagc aggactctct gaatatcatc aggaacaatg acctggagac agattaccac    2940
gacctgctgg ataagaggga gaaggagcgc aaggccaacc ggcagaattg ggaggccgtg    3000
gagggcatca aggacctgaa gaagggctac ctgagccagg ccgtgcacca gatcgcccag    3060
ctgatgctga agtataacgc catcatcgcc ctggaggatc tgggccagat gtttgtgacc    3120
cgcggccaga gatcgagaa ggccgtgtac cagcagttcg agaagagcct ggtggataag    3180
ctgtcctacc tggtggacaa gaagcggcct tataatgagc tgggcggcat cctgaaggcc    3240
taccagctgg cctctagcat caccaagaac aattctgaca gcagaacgg cttcctgttt    3300 tatgtgccag cctggaatac aagcaagatc gatcccgtga ccggctttac agacctgctg    3360
cggcccaagg ccatgaccat caaggaggcc caggacttct ttggcgcctt cgataacatc    3420
tcttacaatg acaagggcta tttcgagttt gagacaaact acgacaagtt taagatcaga    3480
atgaagagcg cccagaccag gtggacaatc tgcaccttcg caatcggat caagagaaag    3540 aaggataaga actactggaa ttatgaggag gtggagctga ccgaggagtt caagaagctg    3600
tttaaggaca gcaacatcga ttacgagaac tgtaatctga aggaggagat ccagaacaag    3660
gacaatcgca agttctttga tgacctgatc aagctgctgc agctgacact gcagatgcgg    3720
aactccgatg acaagggcaa tgattatatc atctctcctg tggccaacgc cgagggccag    3780
ttctttgact cccgcaatgg cgataagaag ctgccactgg atgcagacgc aaacggagcc    3840
tacaatatcg cccgcaaggg cctgtggaac atccggcaga tcaagcagac caagaacgac    3900
aagaagctga atctgagcat ctcctctaca gagtggctgg atttcgtgcg ggagaagcct    3960
tacctgaag                                                            3969
```

<210> SEQ ID NO 228
<211> LENGTH: 1368
<212> TYPE: PRT
<213> ORGANISM: Streptococcus pyogenes

<400> SEQUENCE: 228

```
Met Asp Lys Lys Tyr Ser Ile Gly Leu Asp Ile Gly Thr Asn Ser Val
1               5                   10                  15
```

```
Gly Trp Ala Val Ile Thr Asp Glu Tyr Lys Val Pro Ser Lys Lys Phe
                20                  25                  30
Lys Val Leu Gly Asn Thr Asp Arg His Ser Ile Lys Lys Asn Leu Ile
         35                  40                  45
Gly Ala Leu Leu Phe Asp Ser Gly Glu Thr Ala Glu Ala Thr Arg Leu
 50                  55                  60
Lys Arg Thr Ala Arg Arg Arg Tyr Thr Arg Arg Lys Asn Arg Ile Cys
 65                  70                  75                  80
Tyr Leu Gln Glu Ile Phe Ser Asn Glu Met Ala Lys Val Asp Asp Ser
                 85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
                115                 120                 125
His Glu Lys Tyr Pro Thr Ile Tyr His Leu Arg Lys Lys Leu Val Asp
        130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
            275                 280                 285
Leu Phe Leu Ala Ala Lys Asn Leu Ser Asp Ala Ile Leu Leu Ser Asp
 290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
```

```
            435                 440                 445
Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
850                 855                 860
```

```
Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260
```

-continued

```
His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 229
<211> LENGTH: 1300
<212> TYPE: PRT
<213> ORGANISM: Francisella tularensis

<400> SEQUENCE: 229

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270
```

```
Leu Asn Gln Ser Gly Ile Thr Lys Phe Asn Thr Ile Ile Gly Gly Lys
            275                 280                 285

Phe Val Asn Gly Glu Asn Thr Lys Arg Lys Gly Ile Asn Glu Tyr Ile
290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
                340                 345                 350

Gln Ser Phe Tyr Glu Gln Ile Ala Ala Phe Lys Thr Val Glu Glu Lys
            355                 360                 365

Ser Ile Lys Glu Thr Leu Ser Leu Leu Phe Asp Leu Lys Ala Gln
370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Thr Glu Lys Ala
            435                 440                 445

Lys Tyr Leu Ser Leu Glu Thr Ile Lys Leu Ala Leu Glu Glu Phe Asn
            450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
                500                 505                 510

Asp Leu Leu Gln Ala Ser Ala Glu Asp Asp Val Lys Ala Ile Lys Asp
            515                 520                 525

Leu Leu Asp Gln Thr Asn Asn Leu Leu His Lys Leu Lys Ile Phe His
            530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
                580                 585                 590

Asp Glu Lys Phe Lys Leu Asn Phe Glu Asn Ser Thr Leu Ala Asn Gly
            595                 600                 605

Trp Asp Lys Asn Lys Glu Pro Asp Asn Thr Ala Ile Leu Phe Ile Lys
610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
            675                 680                 685
```

```
Leu Arg Ile Arg Asn His Ser Thr His Thr Lys Asn Gly Ser Pro Gln
690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
                740                 745                 750

Phe Tyr Arg Glu Val Glu Asn Gln Gly Tyr Lys Leu Thr Phe Glu Asn
            755                 760                 765

Ile Ser Glu Ser Tyr Ile Asp Ser Val Val Asn Gln Gly Lys Leu Tyr
770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
                820                 825                 830

Arg Lys Gln Ser Ile Pro Lys Lys Ile Thr His Pro Ala Lys Glu Ala
            835                 840                 845

Ile Ala Asn Lys Asn Lys Asp Asn Pro Lys Lys Glu Ser Val Phe Glu
850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
                900                 905                 910

Ile Leu Ser Ile Asp Arg Gly Glu Arg His Leu Ala Tyr Tyr Thr Leu
            915                 920                 925

Val Asp Gly Lys Gly Asn Ile Ile Lys Gln Asp Thr Phe Asn Ile Ile
930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
                980                 985                 990

Ala Lys Leu Val Ile Glu Tyr Asn Ala Ile Val Val Phe Glu Asp Leu
            995                 1000                1005

Asn Phe Gly Phe Lys Arg Gly Arg Phe Lys Val Glu Lys Gln Val
    1010                1015                1020

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
```

```
                        1100                1105                1110

Lys Ile Cys Tyr Asn Leu Asp Lys Gly Tyr Phe Glu Phe Ser Phe
                    1115                1120                1125

Asp Tyr Lys Asn Phe Gly Asp Lys Ala Ala Lys Gly Lys Trp Thr
                    1130                1135                1140

Ile Ala Ser Phe Gly Ser Arg Leu Ile Asn Phe Arg Asn Ser Asp
                    1145                1150                1155

Lys Asn His Asn Trp Asp Thr Arg Glu Val Tyr Pro Thr Lys Glu
                    1160                1165                1170

Leu Glu Lys Leu Leu Lys Asp Tyr Ser Ile Glu Tyr Gly His Gly
                    1175                1180                1185

Glu Cys Ile Lys Ala Ala Ile Cys Gly Glu Ser Asp Lys Lys Phe
                    1190                1195                1200

Phe Ala Lys Leu Thr Ser Val Leu Asn Thr Ile Leu Gln Met Arg
                    1205                1210                1215

Asn Ser Lys Thr Gly Thr Glu Leu Asp Tyr Leu Ile Ser Pro Val
                    1220                1225                1230

Ala Asp Val Asn Gly Asn Phe Phe Asp Ser Arg Gln Ala Pro Lys
                    1235                1240                1245

Asn Met Pro Gln Asp Ala Asp Ala Asn Gly Ala Tyr His Ile Gly
                    1250                1255                1260

Leu Lys Gly Leu Met Leu Leu Gly Arg Ile Lys Asn Asn Gln Glu
                    1265                1270                1275

Gly Lys Lys Leu Asn Leu Val Ile Lys Asn Glu Glu Tyr Phe Glu
                    1280                1285                1290

Phe Val Gln Asn Arg Asn Asn
                    1295                1300

<210> SEQ ID NO 230
            <211> LENGTH: 1307
            <212> TYPE: PRT
            <213> ORGANISM: Acidaminococcus sp. BV3L6

<400> SEQUENCE: 230

Met Thr Gln Phe Glu Gly Phe Thr Asn Leu Tyr Gln Val Ser Lys Thr
            1               5                   10                  15

Leu Arg Phe Glu Leu Ile Pro Gln Gly Lys Thr Leu Lys His Ile Gln
                        20                  25                  30

Glu Gln Gly Phe Ile Glu Glu Asp Lys Ala Arg Asn Asp His Tyr Lys
                    35                  40                  45

Glu Leu Lys Pro Ile Ile Asp Arg Ile Tyr Lys Thr Tyr Ala Asp Gln
                50                  55                  60

Cys Leu Gln Leu Val Gln Leu Asp Trp Glu Asn Leu Ser Ala Ala Ile
            65                  70                  75                  80

Asp Ser Tyr Arg Lys Glu Lys Thr Glu Glu Thr Arg Asn Ala Leu Ile
                            85                  90                  95

Glu Glu Gln Ala Thr Tyr Arg Asn Ala Ile His Asp Tyr Phe Ile Gly
                        100                 105                 110

Arg Thr Asp Asn Leu Thr Asp Ala Ile Asn Lys Arg His Ala Glu Ile
                    115                 120                 125

Tyr Lys Gly Leu Phe Lys Ala Glu Leu Phe Asn Gly Lys Val Leu Lys
                130                 135                 140

Gln Leu Gly Thr Val Thr Thr Thr Glu His Glu Asn Ala Leu Leu Arg
            145                 150                 155                 160
```

-continued

```
Ser Phe Asp Lys Phe Thr Thr Tyr Phe Ser Gly Phe Tyr Glu Asn Arg
            165                 170                 175
Lys Asn Val Phe Ser Ala Glu Asp Ile Ser Thr Ala Ile Pro His Arg
        180                 185                 190
Ile Val Gln Asp Asn Phe Pro Lys Phe Lys Glu Asn Cys His Ile Phe
            195                 200                 205
Thr Arg Leu Ile Thr Ala Val Pro Ser Leu Arg Glu His Phe Glu Asn
        210                 215                 220
Val Lys Lys Ala Ile Gly Ile Phe Val Ser Thr Ser Ile Glu Glu Val
225                 230                 235                 240
Phe Ser Phe Pro Phe Tyr Asn Gln Leu Leu Thr Gln Thr Gln Ile Asp
            245                 250                 255
Leu Tyr Asn Gln Leu Leu Gly Gly Ile Ser Arg Glu Ala Gly Thr Glu
        260                 265                 270
Lys Ile Lys Gly Leu Asn Glu Val Leu Asn Leu Ala Ile Gln Lys Asn
        275                 280                 285
Asp Glu Thr Ala His Ile Ile Ala Ser Leu Pro His Arg Phe Ile Pro
    290                 295                 300
Leu Phe Lys Gln Ile Leu Ser Asp Arg Asn Thr Leu Ser Phe Ile Leu
305                 310                 315                 320
Glu Glu Phe Lys Ser Asp Glu Val Ile Gln Ser Phe Cys Lys Tyr
                325                 330                 335
Lys Thr Leu Leu Arg Asn Glu Asn Val Leu Glu Thr Ala Glu Ala Leu
            340                 345                 350
Phe Asn Glu Leu Asn Ser Ile Asp Leu Thr His Ile Phe Ile Ser His
        355                 360                 365
Lys Lys Leu Glu Thr Ile Ser Ser Ala Leu Cys Asp His Trp Asp Thr
    370                 375                 380
Leu Arg Asn Ala Leu Tyr Glu Arg Arg Ile Ser Glu Leu Thr Gly Lys
385                 390                 395                 400
Ile Thr Lys Ser Ala Lys Glu Lys Val Gln Arg Ser Leu Lys His Glu
            405                 410                 415
Asp Ile Asn Leu Gln Glu Ile Ile Ser Ala Ala Gly Lys Glu Leu Ser
        420                 425                 430
Glu Ala Phe Lys Gln Lys Thr Ser Glu Ile Leu Ser His Ala His Ala
        435                 440                 445
Ala Leu Asp Gln Pro Leu Pro Thr Thr Leu Lys Lys Gln Glu Glu Lys
    450                 455                 460
Glu Ile Leu Lys Ser Gln Leu Asp Ser Leu Leu Gly Leu Tyr His Leu
465                 470                 475                 480
Leu Asp Trp Phe Ala Val Asp Glu Ser Asn Glu Val Asp Pro Glu Phe
            485                 490                 495
Ser Ala Arg Leu Thr Gly Ile Lys Leu Glu Met Glu Pro Ser Leu Ser
        500                 505                 510
Phe Tyr Asn Lys Ala Arg Asn Tyr Ala Thr Lys Lys Pro Tyr Ser Val
        515                 520                 525
Glu Lys Phe Lys Leu Asn Phe Gln Met Pro Thr Leu Ala Ser Gly Trp
    530                 535                 540
Asp Val Asn Lys Glu Lys Asn Asn Gly Ala Ile Leu Phe Val Lys Asn
545                 550                 555                 560
Gly Leu Tyr Tyr Leu Gly Ile Met Pro Lys Gln Lys Gly Arg Tyr Lys
            565                 570                 575
Ala Leu Ser Phe Glu Pro Thr Glu Lys Thr Ser Glu Gly Phe Asp Lys
```

```
                580                 585                 590
Met Tyr Tyr Asp Tyr Phe Pro Asp Ala Ala Lys Met Ile Pro Lys Cys
                    595                 600                 605

Ser Thr Gln Leu Lys Ala Val Thr Ala His Phe Gln Thr His Thr Thr
            610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
            675                 680                 685

Lys Thr Thr Ser Ile Asp Leu Ser Ser Leu Arg Pro Ser Ser Gln Tyr
            690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
            835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys Ser Lys Arg Thr Gly Ile Ala Glu
            995                1000                1005
```

```
Lys Ala Val Tyr Gln Gln Phe Glu Lys Met Leu Ile Asp Lys Leu
        1010                1015                1020

Asn Cys Leu Val Leu Lys Asp Tyr Pro Ala Glu Lys Val Gly Gly
        1025                1030                1035

Val Leu Asn Pro Tyr Gln Leu Thr Asp Gln Phe Thr Ser Phe Ala
        1040                1045                1050

Lys Met Gly Thr Gln Ser Gly Phe Leu Phe Tyr Val Pro Ala Pro
        1055                1060                1065

Tyr Thr Ser Lys Ile Asp Pro Leu Thr Gly Phe Val Asp Pro Phe
        1070                1075                1080

Val Trp Lys Thr Ile Lys Asn His Glu Ser Arg Lys His Phe Leu
        1085                1090                1095

Glu Gly Phe Asp Phe Leu His Tyr Asp Val Lys Thr Gly Asp Phe
        1100                1105                1110

Ile Leu His Phe Lys Met Asn Arg Asn Leu Ser Phe Gln Arg Gly
        1115                1120                1125

Leu Pro Gly Phe Met Pro Ala Trp Asp Ile Val Phe Glu Lys Asn
        1130                1135                1140

Glu Thr Gln Phe Asp Ala Lys Gly Thr Pro Phe Ile Ala Gly Lys
        1145                1150                1155

Arg Ile Val Pro Val Ile Glu Asn His Arg Phe Thr Gly Arg Tyr
        1160                1165                1170

Arg Asp Leu Tyr Pro Ala Asn Glu Leu Ile Ala Leu Leu Glu Glu
        1175                1180                1185

Lys Gly Ile Val Phe Arg Asp Gly Ser Asn Ile Leu Pro Lys Leu
        1190                1195                1200

Leu Glu Asn Asp Asp Ser His Ala Ile Asp Thr Met Val Ala Leu
        1205                1210                1215

Ile Arg Ser Val Leu Gln Met Arg Asn Ser Asn Ala Ala Thr Gly
        1220                1225                1230

Glu Asp Tyr Ile Asn Ser Pro Val Arg Asp Leu Asn Gly Val Cys
        1235                1240                1245

Phe Asp Ser Arg Phe Gln Asn Pro Glu Trp Pro Met Asp Ala Asp
        1250                1255                1260

Ala Asn Gly Ala Tyr His Ile Ala Leu Lys Gly Gln Leu Leu Leu
        1265                1270                1275

Asn His Leu Lys Glu Ser Lys Asp Leu Lys Leu Gln Asn Gly Ile
        1280                1285                1290

Ser Asn Gln Asp Trp Leu Ala Tyr Ile Gln Glu Leu Arg Asn
        1295                1300                1305

<210> SEQ ID NO 231
<211> LENGTH: 1233
<212> TYPE: PRT
<213> ORGANISM: Lachnospiraceae bacterium MC2017

<400> SEQUENCE: 231

Met Asp Tyr Gly Asn Gly Gln Phe Glu Arg Arg Ala Pro Leu Thr Lys
1               5                   10                  15

Thr Ile Thr Leu Arg Leu Lys Pro Ile Gly Glu Thr Arg Glu Thr Ile
                20                  25                  30

Arg Glu Gln Lys Leu Leu Glu Gln Asp Ala Ala Phe Arg Lys Leu Val
            35                  40                  45

Glu Thr Val Thr Pro Ile Val Asp Asp Cys Ile Arg Lys Ile Ala Asp
```

```
            50                  55                  60
Asn Ala Leu Cys His Phe Gly Thr Glu Tyr Asp Phe Ser Cys Leu Gly
 65                  70                  75                  80

Asn Ala Ile Ser Lys Asn Asp Ser Lys Ala Ile Lys Lys Glu Thr Glu
                 85                  90                  95

Lys Val Glu Lys Leu Leu Ala Lys Val Leu Thr Glu Asn Leu Pro Asp
            100                 105                 110

Gly Leu Arg Lys Val Asn Asp Ile Asn Ser Ala Ala Phe Ile Gln Asp
            115                 120                 125

Thr Leu Thr Ser Phe Val Gln Asp Asp Ala Asp Lys Arg Val Leu Ile
            130                 135                 140

Gln Glu Leu Lys Gly Lys Thr Val Leu Met Gln Arg Phe Leu Thr Thr
145                 150                 155                 160

Arg Ile Thr Ala Leu Thr Val Trp Leu Pro Asp Arg Val Phe Glu Asn
                165                 170                 175

Phe Asn Ile Phe Ile Glu Asn Ala Glu Lys Met Arg Ile Leu Leu Asp
                180                 185                 190

Ser Pro Leu Asn Glu Lys Ile Met Lys Phe Asp Pro Asp Ala Glu Gln
                195                 200                 205

Tyr Ala Ser Leu Glu Phe Tyr Gly Gln Cys Leu Ser Gln Lys Asp Ile
210                 215                 220

Asp Ser Tyr Asn Leu Ile Ile Ser Gly Ile Tyr Ala Asp Asp Glu Val
225                 230                 235                 240

Lys Asn Pro Gly Ile Asn Glu Ile Val Lys Glu Tyr Asn Gln Gln Ile
                245                 250                 255

Arg Gly Asp Lys Asp Glu Ser Pro Leu Pro Lys Leu Lys Lys Leu His
                260                 265                 270

Lys Gln Ile Leu Met Pro Val Glu Lys Ala Phe Phe Val Arg Val Leu
                275                 280                 285

Ser Asn Asp Ser Asp Ala Arg Ser Ile Leu Glu Lys Ile Leu Lys Asp
                290                 295                 300

Thr Glu Met Leu Pro Ser Lys Ile Ile Glu Ala Met Lys Glu Ala Asp
305                 310                 315                 320

Ala Gly Asp Ile Ala Val Tyr Gly Ser Arg Leu His Glu Leu Ser His
                325                 330                 335

Val Ile Tyr Gly Asp His Gly Lys Leu Ser Gln Ile Ile Tyr Asp Lys
                340                 345                 350

Glu Ser Lys Arg Ile Ser Glu Leu Met Glu Thr Leu Ser Pro Lys Glu
                355                 360                 365

Arg Lys Glu Ser Lys Lys Arg Leu Glu Gly Leu Glu Glu His Ile Arg
                370                 375                 380

Lys Ser Thr Tyr Thr Phe Asp Glu Leu Asn Arg Tyr Ala Glu Lys Asn
385                 390                 395                 400

Val Met Ala Ala Tyr Ile Ala Ala Val Glu Glu Ser Cys Ala Glu Ile
                405                 410                 415

Met Arg Lys Glu Lys Asp Leu Arg Thr Leu Leu Ser Lys Glu Asp Val
                420                 425                 430

Lys Ile Arg Gly Asn Arg His Asn Thr Leu Ile Val Lys Asn Tyr Phe
                435                 440                 445

Asn Ala Trp Thr Val Phe Arg Asn Leu Ile Arg Ile Leu Arg Arg Lys
                450                 455                 460

Ser Glu Ala Glu Ile Asp Ser Asp Phe Tyr Asp Val Leu Asp Asp Ser
465                 470                 475                 480
```

```
Val Glu Val Leu Ser Leu Thr Tyr Lys Gly Glu Asn Leu Cys Arg Ser
                485                 490                 495

Tyr Ile Thr Lys Lys Ile Gly Ser Asp Leu Lys Pro Glu Ile Ala Thr
                500                 505                 510

Tyr Gly Ser Ala Leu Arg Pro Asn Ser Arg Trp Trp Ser Pro Gly Glu
            515                 520                 525

Lys Phe Asn Val Lys Phe His Thr Ile Val Arg Arg Asp Gly Arg Leu
        530                 535                 540

Tyr Tyr Phe Ile Leu Pro Lys Gly Ala Lys Pro Val Glu Leu Glu Asp
545                 550                 555                 560

Met Asp Gly Asp Ile Glu Cys Leu Gln Met Arg Lys Ile Pro Asn Pro
                565                 570                 575

Thr Ile Phe Leu Pro Lys Leu Val Phe Lys Asp Pro Glu Ala Phe Phe
                580                 585                 590

Arg Asp Asn Pro Glu Ala Asp Glu Phe Val Phe Leu Ser Gly Met Lys
                595                 600                 605

Ala Pro Val Thr Ile Thr Arg Glu Thr Tyr Glu Ala Tyr Arg Tyr Lys
            610                 615                 620

Leu Tyr Thr Val Gly Lys Leu Arg Asp Gly Glu Val Ser Glu Glu Glu
625                 630                 635                 640

Tyr Lys Arg Ala Leu Leu Gln Val Leu Thr Ala Tyr Lys Glu Phe Leu
                645                 650                 655

Glu Asn Arg Met Ile Tyr Ala Asp Leu Asn Phe Gly Phe Lys Asp Leu
                660                 665                 670

Glu Glu Tyr Lys Asp Ser Ser Glu Phe Ile Lys Gln Val Glu Thr His
            675                 680                 685

Asn Thr Phe Met Cys Trp Ala Lys Val Ser Ser Ser Gln Leu Asp Asp
            690                 695                 700

Leu Val Lys Ser Gly Asn Gly Leu Leu Phe Glu Ile Trp Ser Glu Arg
705                 710                 715                 720

Leu Glu Ser Tyr Tyr Lys Tyr Gly Asn Glu Lys Val Leu Arg Gly Tyr
                725                 730                 735

Glu Gly Val Leu Leu Ser Ile Leu Lys Asp Glu Asn Leu Val Ser Met
            740                 745                 750

Arg Thr Leu Leu Asn Ser Arg Pro Met Leu Val Tyr Arg Pro Lys Glu
            755                 760                 765

Ser Ser Lys Pro Met Val Val His Arg Asp Gly Ser Arg Val Val Asp
        770                 775                 780

Arg Phe Asp Lys Asp Gly Lys Tyr Ile Pro Pro Glu Val His Asp Glu
785                 790                 795                 800

Leu Tyr Arg Phe Phe Asn Asn Leu Leu Ile Lys Glu Lys Leu Gly Glu
                805                 810                 815

Lys Ala Arg Lys Ile Leu Asp Asn Lys Lys Val Lys Val Lys Val Leu
                820                 825                 830

Glu Ser Glu Arg Val Lys Trp Ser Lys Phe Tyr Asp Glu Gln Phe Ala
            835                 840                 845

Val Thr Phe Ser Val Lys Lys Asn Ala Asp Cys Leu Asp Thr Thr Lys
        850                 855                 860

Asp Leu Asn Ala Glu Val Met Glu Gln Tyr Ser Glu Ser Asn Arg Leu
865                 870                 875                 880

Ile Leu Ile Arg Asn Thr Thr Asp Ile Leu Tyr Tyr Leu Val Leu Asp
                885                 890                 895
```

Lys Asn Gly Lys Val Leu Lys Gln Arg Ser Leu Asn Ile Ile Asn Asp
                900                 905                 910

Gly Ala Arg Asp Val Asp Trp Lys Glu Arg Phe Arg Gln Val Thr Lys
        915                 920                 925

Asp Arg Asn Glu Gly Tyr Asn Glu Trp Asp Tyr Ser Arg Thr Ser Asn
        930                 935                 940

Asp Leu Lys Glu Val Tyr Leu Asn Tyr Ala Leu Lys Glu Ile Ala Glu
945                 950                 955                 960

Ala Val Ile Glu Tyr Asn Ala Ile Leu Ile Ile Glu Lys Met Ser Asn
                965                 970                 975

Ala Phe Lys Asp Lys Tyr Ser Phe Leu Asp Asp Val Thr Phe Lys Gly
        980                 985                 990

Phe Glu Thr Lys Leu Leu Ala Lys Leu Ser Asp Leu His Phe Arg Gly
        995                 1000                1005

Ile Lys Asp Gly Glu Pro Cys Ser Phe Thr Asn Pro Leu Gln Leu
        1010            1015            1020

Cys Gln Asn Asp Ser Asn Lys Ile Leu Gln Asp Gly Val Ile Phe
        1025            1030            1035

Met Val Pro Asn Ser Met Thr Arg Ser Leu Asp Pro Asp Thr Gly
        1040            1045            1050

Phe Ile Phe Ala Ile Asn Asp His Asn Ile Arg Thr Lys Lys Ala
        1055            1060            1065

Lys Leu Asn Phe Leu Ser Lys Phe Asp Gln Leu Lys Val Ser Ser
        1070            1075            1080

Glu Gly Cys Leu Ile Met Lys Tyr Ser Gly Asp Ser Leu Pro Thr
        1085            1090            1095

His Asn Thr Asp Asn Arg Val Trp Asn Cys Cys Cys Asn His Pro
        1100            1105            1110

Ile Thr Asn Tyr Asp Arg Glu Thr Lys Lys Val Glu Phe Ile Glu
        1115            1120            1125

Glu Pro Val Glu Glu Leu Ser Arg Val Leu Glu Glu Asn Gly Ile
        1130            1135            1140

Glu Thr Asp Thr Glu Leu Asn Lys Leu Asn Glu Arg Glu Asn Val
        1145            1150            1155

Pro Gly Lys Val Val Asp Ala Ile Tyr Ser Leu Val Leu Asn Tyr
        1160            1165            1170

Leu Arg Gly Thr Val Ser Gly Val Ala Gly Gln Arg Ala Val Tyr
        1175            1180            1185

Tyr Ser Pro Val Thr Gly Lys Lys Tyr Asp Ile Ser Phe Ile Gln
        1190            1195            1200

Ala Met Asn Leu Asn Arg Lys Cys Asp Tyr Tyr Arg Ile Gly Ser
        1205            1210            1215

Lys Glu Arg Gly Glu Trp Thr Asp Phe Val Ala Gln Leu Ile Asn
        1220            1225            1230

<210> SEQ ID NO 232
<211> LENGTH: 1246
<212> TYPE: PRT
<213> ORGANISM: Lachnospiraceae bacterium ND2006

<400> SEQUENCE: 232

Met Leu Lys Asn Val Gly Ile Asp Arg Leu Asp Val Glu Lys Gly Arg
1               5                   10                  15

Lys Asn Met Ser Lys Leu Glu Lys Phe Thr Asn Cys Tyr Ser Leu Ser
                20                  25                  30

```
Lys Thr Leu Arg Phe Lys Ala Ile Pro Val Gly Lys Thr Gln Glu Asn
         35                  40                  45

Ile Asp Asn Lys Arg Leu Leu Val Glu Asp Glu Lys Arg Ala Glu Asp
    50                  55                  60

Tyr Lys Gly Val Lys Lys Leu Leu Asp Arg Tyr Tyr Leu Ser Phe Ile
65                  70                  75                  80

Asn Asp Val Leu His Ser Ile Lys Leu Lys Asn Leu Asn Asn Tyr Ile
                85                  90                  95

Ser Leu Phe Arg Lys Lys Thr Arg Thr Glu Lys Glu Asn Lys Glu Leu
            100                 105                 110

Glu Asn Leu Glu Ile Asn Leu Arg Lys Glu Ile Ala Lys Ala Phe Lys
            115                 120                 125

Gly Asn Glu Gly Tyr Lys Ser Leu Phe Lys Lys Asp Ile Ile Glu Thr
            130                 135                 140

Ile Leu Pro Glu Phe Leu Asp Asp Lys Asp Glu Ile Ala Leu Val Asn
145                 150                 155                 160

Ser Phe Asn Gly Phe Thr Thr Ala Phe Thr Gly Phe Phe Asp Asn Arg
                165                 170                 175

Glu Asn Met Phe Ser Glu Glu Ala Lys Ser Thr Ser Ile Ala Phe Arg
            180                 185                 190

Cys Ile Asn Glu Asn Leu Thr Arg Tyr Ile Ser Asn Met Asp Ile Phe
            195                 200                 205

Glu Lys Val Asp Ala Ile Phe Asp Lys His Glu Val Gln Glu Ile Lys
            210                 215                 220

Glu Lys Ile Leu Asn Ser Asp Tyr Asp Val Glu Asp Phe Phe Glu Gly
225                 230                 235                 240

Glu Phe Phe Asn Phe Val Leu Thr Gln Glu Gly Ile Asp Val Tyr Asn
                245                 250                 255

Ala Ile Ile Gly Gly Phe Val Thr Glu Ser Gly Glu Lys Ile Lys Gly
            260                 265                 270

Leu Asn Glu Tyr Ile Asn Leu Tyr Asn Gln Lys Thr Lys Gln Lys Leu
            275                 280                 285

Pro Lys Phe Lys Pro Leu Tyr Lys Gln Val Leu Ser Asp Arg Glu Ser
            290                 295                 300

Leu Ser Phe Tyr Gly Glu Gly Tyr Thr Ser Asp Glu Glu Val Leu Glu
305                 310                 315                 320

Val Phe Arg Asn Thr Leu Asn Lys Asn Ser Glu Ile Phe Ser Ser Ile
                325                 330                 335

Lys Lys Leu Glu Lys Leu Phe Lys Asn Phe Asp Glu Tyr Ser Ser Ala
            340                 345                 350

Gly Ile Phe Val Lys Asn Gly Pro Ala Ile Ser Thr Ile Ser Lys Asp
            355                 360                 365

Ile Phe Gly Glu Trp Asn Val Ile Arg Asp Lys Trp Asn Ala Glu Tyr
            370                 375                 380

Asp Asp Ile His Leu Lys Lys Lys Ala Val Val Thr Glu Lys Tyr Glu
385                 390                 395                 400

Asp Asp Arg Arg Lys Ser Phe Lys Lys Ile Gly Ser Phe Ser Leu Glu
                405                 410                 415

Gln Leu Gln Glu Tyr Ala Asp Ala Asp Leu Ser Val Val Glu Lys Leu
            420                 425                 430

Lys Glu Ile Ile Ile Gln Lys Val Asp Glu Ile Tyr Lys Val Tyr Gly
            435                 440                 445
```

```
Ser Ser Glu Lys Leu Phe Asp Ala Asp Phe Val Leu Glu Lys Ser Leu
    450                 455                 460
Lys Lys Asn Asp Ala Val Val Ala Ile Met Lys Asp Leu Leu Asp Ser
465                 470                 475                 480
Val Lys Ser Phe Glu Asn Tyr Ile Lys Ala Phe Phe Gly Glu Gly Lys
                485                 490                 495
Glu Thr Asn Arg Asp Glu Ser Phe Tyr Gly Asp Phe Val Leu Ala Tyr
            500                 505                 510
Asp Ile Leu Leu Lys Val Asp His Ile Tyr Asp Ala Ile Arg Asn Tyr
        515                 520                 525
Val Thr Gln Lys Pro Tyr Ser Lys Asp Lys Phe Lys Leu Tyr Phe Gln
    530                 535                 540
Asn Pro Gln Phe Met Gly Gly Trp Asp Lys Asp Lys Glu Thr Asp Tyr
545                 550                 555                 560
Arg Ala Thr Ile Leu Arg Tyr Gly Ser Lys Tyr Tyr Leu Ala Ile Met
                565                 570                 575
Asp Lys Lys Tyr Ala Lys Cys Leu Gln Lys Ile Asp Lys Asp Asp Val
            580                 585                 590
Asn Gly Asn Tyr Glu Lys Ile Asn Tyr Lys Leu Leu Pro Gly Pro Asn
        595                 600                 605
Lys Met Leu Pro Lys Val Phe Phe Ser Lys Lys Trp Met Ala Tyr Tyr
    610                 615                 620
Asn Pro Ser Glu Asp Ile Gln Lys Ile Tyr Lys Asn Gly Thr Phe Lys
625                 630                 635                 640
Lys Gly Asp Met Phe Asn Leu Asn Asp Cys His Lys Leu Ile Asp Phe
                645                 650                 655
Phe Lys Asp Ser Ile Ser Arg Tyr Pro Lys Trp Ser Asn Ala Tyr Asp
            660                 665                 670
Phe Asn Phe Ser Glu Thr Glu Lys Tyr Lys Asp Ile Ala Gly Phe Tyr
        675                 680                 685
Arg Glu Val Glu Glu Gln Gly Tyr Lys Val Ser Phe Glu Ser Ala Ser
    690                 695                 700
Lys Lys Glu Val Asp Lys Leu Val Glu Gly Lys Leu Tyr Met Phe
705                 710                 715                 720
Gln Ile Tyr Asn Lys Asp Phe Ser Asp Lys Ser His Gly Thr Pro Asn
                725                 730                 735
Leu His Thr Met Tyr Phe Lys Leu Leu Phe Asp Glu Asn Asn His Gly
            740                 745                 750
Gln Ile Arg Leu Ser Gly Gly Ala Glu Leu Phe Met Arg Arg Ala Ser
        755                 760                 765
Leu Lys Lys Glu Glu Leu Val Val His Pro Ala Asn Ser Pro Ile Ala
    770                 775                 780
Asn Lys Asn Pro Asp Asn Pro Lys Lys Thr Thr Thr Leu Ser Tyr Asp
785                 790                 795                 800
Val Tyr Lys Asp Lys Arg Phe Ser Glu Asp Gln Tyr Glu Leu His Ile
                805                 810                 815
Pro Ile Ala Ile Asn Lys Cys Pro Lys Asn Ile Phe Lys Ile Asn Thr
            820                 825                 830
Glu Val Arg Val Leu Leu Lys His Asp Asp Asn Pro Tyr Val Ile Gly
        835                 840                 845
Ile Asp Arg Gly Glu Arg Asn Leu Leu Tyr Ile Val Val Val Asp Gly
    850                 855                 860
Lys Gly Asn Ile Val Glu Gln Tyr Ser Leu Asn Glu Ile Ile Asn Asn
```

```
                865               870               875               880
Phe Asn Gly Ile Arg Ile Lys Thr Asp Tyr His Ser Leu Leu Asp Lys
                885               890               895
Lys Glu Lys Glu Arg Phe Glu Ala Arg Gln Asn Trp Thr Ser Ile Glu
                900               905               910
Asn Ile Lys Glu Leu Lys Ala Gly Tyr Ile Ser Gln Val Val His Lys
                915               920               925
Ile Cys Glu Leu Val Glu Lys Tyr Asp Ala Val Ile Ala Leu Glu Asp
                930               935               940
Leu Asn Ser Gly Phe Lys Asn Ser Arg Val Lys Val Glu Lys Gln Val
945               950               955               960
Tyr Gln Lys Phe Glu Lys Met Leu Ile Asp Lys Leu Asn Tyr Met Val
                965               970               975
Asp Lys Lys Ser Asn Pro Cys Ala Thr Gly Gly Ala Leu Lys Gly Tyr
                980               985               990
Gln Ile Thr Asn Lys Phe Glu Ser Phe Lys Ser Met Ser Thr Gln Asn
                995               1000              1005
Gly Phe Ile Phe Tyr Ile Pro Ala Trp Leu Thr Ser Lys Ile Asp
        1010              1015              1020
Pro Ser Thr Gly Phe Val Asn Leu Leu Lys Thr Lys Tyr Thr Ser
        1025              1030              1035
Ile Ala Asp Ser Lys Lys Phe Ile Ser Ser Phe Asp Arg Ile Met
        1040              1045              1050
Tyr Val Pro Glu Glu Asp Leu Phe Glu Phe Ala Leu Asp Tyr Lys
        1055              1060              1065
Asn Phe Ser Arg Thr Asp Ala Asp Tyr Ile Lys Lys Trp Lys Leu
        1070              1075              1080
Tyr Ser Tyr Gly Asn Arg Ile Arg Ile Phe Arg Asn Pro Lys Lys
        1085              1090              1095
Asn Asn Val Phe Asp Trp Glu Glu Val Cys Leu Thr Ser Ala Tyr
        1100              1105              1110
Lys Glu Leu Phe Asn Lys Tyr Gly Ile Asn Tyr Gln Gln Gly Asp
        1115              1120              1125
Ile Arg Ala Leu Leu Cys Glu Gln Ser Asp Lys Ala Phe Tyr Ser
        1130              1135              1140
Ser Phe Met Ala Leu Met Ser Leu Met Leu Gln Met Arg Asn Ser
        1145              1150              1155
Ile Thr Gly Arg Thr Asp Val Asp Phe Leu Ile Ser Pro Val Lys
        1160              1165              1170
Asn Ser Asp Gly Ile Phe Tyr Asp Ser Arg Asn Tyr Glu Ala Gln
        1175              1180              1185
Glu Asn Ala Ile Leu Pro Lys Asn Ala Asp Ala Asn Gly Ala Tyr
        1190              1195              1200
Asn Ile Ala Arg Lys Val Leu Trp Ala Ile Gly Gln Phe Lys Lys
        1205              1210              1215
Ala Glu Asp Glu Lys Leu Asp Lys Val Lys Ile Ala Ile Ser Asn
        1220              1225              1230
Lys Glu Trp Leu Glu Tyr Ala Gln Thr Ser Val Lys His
        1235              1240              1245

<210> SEQ ID NO 233
<211> LENGTH: 1228
<212> TYPE: PRT
<213> ORGANISM: Lachnospiraceae bacterium ND2006
```

<400> SEQUENCE: 233

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu

-continued

```
                405                 410                 415
Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
            435                 440                 445

Asn Asp Ala Val Val Ala Ile Met Lys Asp Leu Leu Asp Ser Val Lys
            450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
            515                 520                 525

Gln Phe Met Gly Gly Trp Asp Lys Asp Lys Glu Thr Asp Tyr Arg Ala
            530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
            595                 600                 605

Ser Glu Asp Ile Gln Lys Ile Tyr Lys Asn Gly Thr Phe Lys Lys Gly
            610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
            675                 680                 685

Glu Val Asp Lys Leu Val Glu Glu Gly Lys Leu Tyr Met Phe Gln Ile
            690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
            755                 760                 765

Asn Pro Asp Asn Pro Lys Lys Thr Thr Thr Leu Ser Tyr Asp Val Tyr
            770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830
```

Arg Gly Glu Arg Asn Leu Leu Tyr Ile Val Val Asp Gly Lys Gly
            835                 840                 845

Asn Ile Val Glu Gln Tyr Ser Leu Asn Glu Ile Ile Asn Asn Phe Asn
850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
                900                 905                 910

Glu Leu Val Glu Lys Tyr Asp Ala Val Ile Ala Leu Glu Asp Leu Asn
                915                 920                 925

Ser Gly Phe Lys Asn Ser Arg Val Lys Val Glu Lys Gln Val Tyr Gln
        930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
                980                 985                 990

Ile Phe Tyr Ile Pro Ala Trp Leu Thr Ser Lys Ile Asp Pro Ser Thr
            995                 1000                1005

Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His
    1220                1225

<210> SEQ ID NO 234
<211> LENGTH: 1300
<212> TYPE: PRT
<213> ORGANISM: Francisella tularensis subsp. Novicida U112

<400> SEQUENCE: 234

```
Met Ser Ile Tyr Gln Glu Phe Val Asn Lys Tyr Ser Leu Ser Lys Thr
1               5                   10                  15
Leu Arg Phe Glu Leu Ile Pro Gln Gly Lys Thr Leu Glu Asn Ile Lys
            20                  25                  30
Ala Arg Gly Leu Ile Leu Asp Asp Glu Lys Arg Ala Lys Asp Tyr Lys
        35                  40                  45
Lys Ala Lys Gln Ile Ile Asp Lys Tyr His Gln Phe Phe Ile Glu Glu
    50                  55                  60
Ile Leu Ser Ser Val Cys Ile Ser Glu Asp Leu Leu Gln Asn Tyr Ser
65                  70                  75                  80
Asp Val Tyr Phe Lys Leu Lys Lys Ser Asp Asp Asn Leu Gln Lys
            85                  90                  95
Asp Phe Lys Ser Ala Lys Asp Thr Ile Lys Lys Gln Ile Ser Glu Tyr
            100                 105                 110
Ile Lys Asp Ser Glu Lys Phe Lys Asn Leu Phe Asn Gln Asn Leu Ile
        115                 120                 125
Asp Ala Lys Lys Gly Gln Glu Ser Asp Leu Ile Leu Trp Leu Lys Gln
    130                 135                 140
Ser Lys Asp Asn Gly Ile Glu Leu Phe Lys Ala Asn Ser Asp Ile Thr
145                 150                 155                 160
Asp Ile Asp Glu Ala Leu Glu Ile Ile Lys Ser Phe Lys Gly Trp Thr
                165                 170                 175
Thr Tyr Phe Lys Gly Phe His Glu Asn Arg Lys Asn Val Tyr Ser Ser
            180                 185                 190
Asn Asp Ile Pro Thr Ser Ile Ile Tyr Arg Ile Val Asp Asp Asn Leu
        195                 200                 205
Pro Lys Phe Leu Glu Asn Lys Ala Lys Tyr Glu Ser Leu Lys Asp Lys
    210                 215                 220
Ala Pro Glu Ala Ile Asn Tyr Glu Gln Ile Lys Lys Asp Leu Ala Glu
225                 230                 235                 240
Glu Leu Thr Phe Asp Ile Asp Tyr Lys Thr Ser Glu Val Asn Gln Arg
                245                 250                 255
Val Phe Ser Leu Asp Glu Val Phe Glu Ile Ala Asn Phe Asn Asn Tyr
            260                 265                 270
Leu Asn Gln Ser Gly Ile Thr Lys Phe Asn Thr Ile Ile Gly Gly Lys
        275                 280                 285
Phe Val Asn Gly Glu Asn Thr Lys Arg Lys Gly Ile Asn Glu Tyr Ile
    290                 295                 300
Asn Leu Tyr Ser Gln Gln Ile Asn Asp Lys Thr Leu Lys Lys Tyr Lys
305                 310                 315                 320
Met Ser Val Leu Phe Lys Gln Ile Leu Ser Asp Thr Glu Ser Lys Ser
                325                 330                 335
Phe Val Ile Asp Lys Leu Glu Asp Asp Ser Asp Val Val Thr Thr Met
            340                 345                 350
Gln Ser Phe Tyr Glu Gln Ile Ala Ala Phe Lys Thr Val Glu Glu Lys
        355                 360                 365
Ser Ile Lys Glu Thr Leu Ser Leu Leu Phe Asp Asp Leu Lys Ala Gln
    370                 375                 380
```

```
Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
            405                 410                 415

Val Leu Glu Tyr Ile Thr Gln Gln Ile Ala Pro Lys Asn Leu Asp Asn
        420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800
```

```
Pro Asn Leu His Thr Leu Tyr Trp Lys Ala Leu Phe Asp Glu Arg Asn
            805                 810                 815

Leu Gln Asp Val Val Tyr Lys Leu Asn Gly Glu Ala Glu Leu Phe Tyr
        820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
            885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
            915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
            965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Glu Asp Leu
            995                 1000                1005

Asn Phe Gly Phe Lys Arg Gly Arg Phe Lys Val Glu Lys Gln Val
    1010                1015                1020

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
```

-continued

```
                1205                1210                1215

Asn Ser Lys Thr Gly Thr Glu Leu Asp Tyr Leu Ile Ser Pro Val
        1220                1225                1230

Ala Asp Val Asn Gly Asn Phe Phe Asp Ser Arg Gln Ala Pro Lys
        1235                1240                1245

Asn Met Pro Gln Asp Ala Asp Ala Asn Gly Ala Tyr His Ile Gly
        1250                1255                1260

Leu Lys Gly Leu Met Leu Leu Gly Arg Ile Lys Asn Asn Gln Glu
        1265                1270                1275

Gly Lys Lys Leu Asn Leu Val Ile Lys Asn Glu Glu Tyr Phe Glu
        1280                1285                1290

Phe Val Gln Asn Arg Asn Asn
        1295                1300

<210> SEQ ID NO 235
<211> LENGTH: 1477
<212> TYPE: PRT
<213> ORGANISM: Peregrinibacteria bacterium GW2011_GWA_33_10

<400> SEQUENCE: 235

Met Ser Asn Phe Phe Lys Asn Phe Thr Asn Leu Tyr Glu Leu Ser Lys
1               5                   10                  15

Thr Leu Arg Phe Glu Leu Lys Pro Val Gly Asp Thr Leu Thr Asn Met
            20                  25                  30

Lys Asp His Leu Glu Tyr Asp Glu Lys Leu Gln Thr Phe Leu Lys Asp
        35                  40                  45

Gln Asn Ile Asp Asp Ala Tyr Gln Ala Leu Lys Pro Gln Phe Asp Glu
    50                  55                  60

Ile His Glu Glu Phe Ile Thr Asp Ser Leu Glu Ser Lys Lys Ala Lys
65                  70                  75                  80

Glu Ile Asp Phe Ser Glu Tyr Leu Asp Leu Phe Gln Glu Lys Lys Glu
                85                  90                  95

Leu Asn Asp Ser Glu Lys Lys Leu Arg Asn Lys Ile Gly Glu Thr Phe
            100                 105                 110

Asn Lys Ala Gly Glu Lys Trp Lys Lys Glu Lys Tyr Pro Gln Tyr Glu
        115                 120                 125

Trp Lys Lys Gly Ser Lys Ile Ala Asn Gly Ala Asp Ile Leu Ser Cys
    130                 135                 140

Gln Asp Met Leu Gln Phe Ile Lys Tyr Lys Asn Pro Glu Asp Glu Lys
145                 150                 155                 160

Ile Lys Asn Tyr Ile Asp Asp Thr Leu Lys Gly Phe Phe Thr Tyr Phe
                165                 170                 175

Gly Gly Phe Asn Gln Asn Arg Ala Asn Tyr Tyr Glu Thr Lys Lys Glu
            180                 185                 190

Ala Ser Thr Ala Val Ala Thr Arg Ile Val His Glu Asn Leu Pro Lys
        195                 200                 205

Phe Cys Asp Asn Val Ile Gln Phe Lys His Ile Ile Lys Arg Lys Lys
    210                 215                 220

Asp Gly Thr Val Glu Lys Thr Glu Arg Lys Thr Glu Tyr Leu Asn Ala
225                 230                 235                 240

Tyr Gln Tyr Leu Lys Asn Asn Asn Lys Ile Thr Gln Ile Lys Asp Ala
                245                 250                 255

Glu Thr Glu Lys Met Ile Glu Ser Thr Pro Ile Ala Glu Lys Ile Phe
            260                 265                 270
```

-continued

Asp Val Tyr Tyr Phe Ser Ser Cys Leu Ser Gln Lys Gln Ile Glu Glu
        275                 280                 285

Tyr Asn Arg Ile Ile Gly His Tyr Asn Leu Leu Ile Asn Leu Tyr Asn
        290                 295                 300

Gln Ala Lys Arg Ser Glu Gly Lys His Leu Ser Ala Asn Glu Lys Lys
305                 310                 315                 320

Tyr Lys Asp Leu Pro Lys Phe Lys Thr Leu Tyr Lys Gln Ile Gly Cys
                325                 330                 335

Gly Lys Lys Lys Asp Leu Phe Tyr Thr Ile Lys Cys Asp Thr Glu Glu
            340                 345                 350

Glu Ala Asn Lys Ser Arg Asn Glu Gly Lys Glu Ser His Ser Val Glu
        355                 360                 365

Glu Ile Ile Asn Lys Ala Gln Glu Ala Ile Asn Lys Tyr Phe Lys Ser
        370                 375                 380

Asn Asn Asp Cys Glu Asn Ile Asn Thr Val Pro Asp Phe Ile Asn Tyr
385                 390                 395                 400

Ile Leu Thr Lys Glu Asn Tyr Glu Gly Val Tyr Trp Ser Lys Ala Ala
                405                 410                 415

Met Asn Thr Ile Ser Asp Lys Tyr Phe Ala Asn Tyr His Asp Leu Gln
            420                 425                 430

Asp Arg Leu Lys Glu Ala Lys Val Phe Gln Lys Ala Asp Lys Lys Ser
        435                 440                 445

Glu Asp Asp Ile Lys Ile Pro Glu Ala Ile Glu Leu Ser Gly Leu Phe
        450                 455                 460

Gly Val Leu Asp Ser Leu Ala Asp Trp Gln Thr Thr Leu Phe Lys Ser
465                 470                 475                 480

Ser Ile Leu Ser Asn Glu Asp Lys Leu Lys Ile Ile Thr Asp Ser Gln
                485                 490                 495

Thr Pro Ser Glu Ala Leu Leu Lys Met Ile Phe Asn Asp Ile Glu Lys
            500                 505                 510

Asn Met Glu Ser Phe Leu Lys Glu Thr Asn Asp Ile Ile Thr Leu Lys
        515                 520                 525

Lys Tyr Lys Gly Asn Lys Glu Gly Thr Glu Lys Ile Lys Gln Trp Phe
        530                 535                 540

Asp Tyr Thr Leu Ala Ile Asn Arg Met Leu Lys Tyr Phe Leu Val Lys
545                 550                 555                 560

Glu Asn Lys Ile Lys Gly Asn Ser Leu Asp Thr Asn Ile Ser Glu Ala
                565                 570                 575

Leu Lys Thr Leu Ile Tyr Ser Asp Asp Ala Glu Trp Phe Lys Trp Tyr
            580                 585                 590

Asp Ala Leu Arg Asn Tyr Leu Thr Gln Lys Pro Gln Asp Glu Ala Lys
        595                 600                 605

Glu Asn Lys Leu Lys Leu Asn Phe Asp Asn Pro Ser Leu Ala Gly Gly
        610                 615                 620

Trp Asp Val Asn Lys Glu Cys Ser Asn Phe Cys Val Ile Leu Lys Asp
625                 630                 635                 640

Lys Asn Glu Lys Lys Tyr Leu Ala Ile Met Lys Lys Gly Glu Asn Thr
                645                 650                 655

Leu Phe Gln Lys Glu Trp Thr Glu Gly Arg Gly Lys Asn Leu Thr Lys
            660                 665                 670

Lys Ser Asn Pro Leu Phe Glu Ile Asn Asn Cys Glu Ile Leu Ser Lys
        675                 680                 685

Met Glu Tyr Asp Phe Trp Ala Asp Val Ser Lys Met Ile Pro Lys Cys

```
            690                 695                 700
Ser Thr Gln Leu Lys Ala Val Val Asn His Phe Lys Gln Ser Asp Asn
705                 710                 715                 720

Glu Phe Ile Phe Pro Ile Gly Tyr Lys Val Thr Ser Gly Glu Lys Phe
                725                 730                 735

Arg Glu Glu Cys Lys Ile Ser Lys Gln Asp Phe Glu Leu Asn Asn Lys
                740                 745                 750

Val Phe Asn Lys Asn Glu Leu Ser Val Thr Ala Met Arg Tyr Asp Leu
            755                 760                 765

Ser Ser Thr Gln Glu Lys Gln Tyr Ile Lys Ala Phe Gln Lys Glu Tyr
770                 775                 780

Trp Glu Leu Leu Phe Lys Gln Glu Lys Arg Asp Thr Lys Leu Thr Asn
785                 790                 795                 800

Asn Glu Ile Phe Asn Glu Trp Ile Asn Phe Cys Asn Lys Lys Tyr Ser
                805                 810                 815

Glu Leu Leu Ser Trp Glu Arg Lys Tyr Lys Asp Ala Leu Thr Asn Trp
            820                 825                 830

Ile Asn Phe Cys Lys Tyr Phe Leu Ser Lys Tyr Pro Lys Thr Thr Leu
            835                 840                 845

Phe Asn Tyr Ser Phe Lys Glu Ser Glu Asn Tyr Asn Ser Leu Asp Glu
850                 855                 860

Phe Tyr Arg Asp Val Asp Ile Cys Ser Tyr Lys Leu Asn Ile Asn Thr
865                 870                 875                 880

Thr Ile Asn Lys Ser Ile Leu Asp Arg Leu Val Glu Glu Gly Lys Leu
                885                 890                 895

Tyr Leu Phe Glu Ile Lys Asn Gln Asp Ser Asn Asp Gly Lys Ser Ile
            900                 905                 910

Gly His Lys Asn Asn Leu His Thr Ile Tyr Trp Asn Ala Ile Phe Glu
            915                 920                 925

Asn Phe Asp Asn Arg Pro Lys Leu Asn Gly Glu Ala Glu Ile Phe Tyr
930                 935                 940

Arg Lys Ala Ile Ser Lys Asp Lys Leu Gly Ile Val Lys Gly Lys Lys
945                 950                 955                 960

Thr Lys Asn Gly Thr Glu Ile Ile Lys Asn Tyr Arg Phe Ser Lys Glu
                965                 970                 975

Lys Phe Ile Leu His Val Pro Ile Thr Leu Asn Phe Cys Ser Asn Asn
            980                 985                 990

Glu Tyr Val Asn Asp Ile Val Asn  Thr Lys Phe Tyr Asn  Phe Ser Asn
            995                 1000                1005

Leu His  Phe Leu Gly Ile Asp  Arg Gly Glu Lys His  Leu Ala Tyr
1010                1015                1020

Tyr Ser  Leu Val Asn Lys Asn  Gly Glu Ile Val Asp  Gln Gly Thr
    1025                1030                1035

Leu Asn  Leu Pro Phe Thr Asp  Lys Asp Gly Asn Gln  Arg Ser Ile
    1040                1045                1050

Lys Lys  Glu Lys Tyr Phe Tyr  Asn Lys Gln Glu Asp  Lys Trp Glu
    1055                1060                1065

Ala Lys  Glu Val Asp Cys Trp  Asn Tyr Asn Asp Leu  Leu Asp Ala
    1070                1075                1080

Met Ala  Ser Asn Arg Asp Met  Ala Arg Lys Asn Trp  Gln Arg Ile
    1085                1090                1095

Gly Thr  Ile Lys Glu Ala Lys  Asn Gly Tyr Val Ser  Leu Val Ile
    1100                1105                1110
```

```
Arg Lys Ile Ala Asp Leu Ala Val Asn Glu Arg Pro Ala Phe
1115                1120                1125

Ile Val Leu Glu Asp Leu Asn Thr Gly Phe Lys Arg Ser Arg Gln
1130                1135                1140

Lys Ile Asp Lys Ser Val Tyr Gln Lys Phe Glu Leu Ala Leu Ala
1145                1150                1155

Lys Lys Leu Asn Phe Leu Val Asp Lys Asn Ala Lys Arg Asp Glu
1160                1165                1170

Ile Gly Ser Pro Thr Lys Ala Leu Gln Leu Thr Pro Pro Val Asn
1175                1180                1185

Asn Tyr Gly Asp Ile Glu Asn Lys Lys Gln Ala Gly Ile Met Leu
1190                1195                1200

Tyr Thr Arg Ala Asn Tyr Thr Ser Gln Thr Asp Pro Ala Thr Gly
1205                1210                1215

Trp Arg Lys Thr Ile Tyr Leu Lys Ala Gly Pro Glu Glu Thr Thr
1220                1225                1230

Tyr Lys Lys Asp Gly Lys Ile Lys Asn Lys Ser Val Lys Asp Gln
1235                1240                1245

Ile Ile Glu Thr Phe Thr Asp Ile Gly Phe Asp Gly Lys Asp Tyr
1250                1255                1260

Tyr Phe Glu Tyr Asp Lys Gly Glu Phe Val Asp Glu Lys Thr Gly
1265                1270                1275

Glu Ile Lys Pro Lys Lys Trp Arg Leu Tyr Ser Gly Glu Asn Gly
1280                1285                1290

Lys Ser Leu Asp Arg Phe Arg Gly Glu Arg Glu Lys Asp Lys Tyr
1295                1300                1305

Glu Trp Lys Ile Asp Lys Ile Asp Ile Val Lys Ile Leu Asp Asp
1310                1315                1320

Leu Phe Val Asn Phe Asp Lys Asn Ile Ser Leu Leu Lys Gln Leu
1325                1330                1335

Lys Glu Gly Val Glu Leu Thr Arg Asn Asn Glu His Gly Thr Gly
1340                1345                1350

Glu Ser Leu Arg Phe Ala Ile Asn Leu Ile Gln Gln Ile Arg Asn
1355                1360                1365

Thr Gly Asn Asn Glu Arg Asp Asn Asp Phe Ile Leu Ser Pro Val
1370                1375                1380

Arg Asp Glu Asn Gly Lys His Phe Asp Ser Arg Glu Tyr Trp Asp
1385                1390                1395

Lys Glu Thr Lys Gly Glu Lys Ile Ser Met Pro Ser Ser Gly Asp
1400                1405                1410

Ala Asn Gly Ala Phe Asn Ile Ala Arg Lys Gly Ile Ile Met Asn
1415                1420                1425

Ala His Ile Leu Ala Asn Ser Asp Ser Lys Asp Leu Ser Leu Phe
1430                1435                1440

Val Ser Asp Glu Glu Trp Asp Leu His Leu Asn Asn Lys Thr Glu
1445                1450                1455

Trp Lys Lys Gln Leu Asn Ile Phe Ser Ser Arg Lys Ala Met Ala
1460                1465                1470

Lys Arg Lys Lys
1475
```

<210> SEQ ID NO 236
<211> LENGTH: 1352

<212> TYPE: PRT
<213> ORGANISM: Parcubacteria bacterium GWC2011_GWC2_44_17

<400> SEQUENCE: 236

```
Met Glu Asn Ile Phe Asp Gln Phe Ile Gly Lys Tyr Ser Leu Ser Lys
1               5                   10                  15

Thr Leu Arg Phe Glu Leu Lys Pro Val Gly Lys Thr Glu Asp Phe Leu
            20                  25                  30

Lys Ile Asn Lys Val Phe Glu Lys Asp Gln Thr Ile Asp Asp Ser Tyr
        35                  40                  45

Asn Gln Ala Lys Phe Tyr Phe Asp Ser Leu His Gln Lys Phe Ile Asp
    50                  55                  60

Ala Ala Leu Ala Ser Asp Lys Thr Ser Glu Leu Ser Phe Gln Asn Phe
65                  70                  75                  80

Ala Asp Val Leu Glu Lys Gln Asn Lys Ile Ile Leu Asp Lys Lys Arg
                85                  90                  95

Glu Met Gly Ala Leu Arg Lys Arg Asp Lys Asn Ala Val Gly Ile Asp
            100                 105                 110

Arg Leu Gln Lys Glu Ile Asn Asp Ala Glu Asp Ile Ile Gln Lys Glu
        115                 120                 125

Lys Glu Lys Ile Tyr Lys Asp Val Arg Thr Leu Phe Asp Asn Glu Ala
    130                 135                 140

Glu Ser Trp Lys Thr Tyr Tyr Gln Glu Arg Glu Val Asp Gly Lys Lys
145                 150                 155                 160

Ile Thr Phe Ser Lys Ala Asp Leu Lys Gln Lys Gly Ala Asp Phe Leu
                165                 170                 175

Thr Ala Ala Gly Ile Leu Lys Val Leu Lys Tyr Glu Phe Pro Glu Glu
            180                 185                 190

Lys Glu Lys Glu Phe Gln Ala Lys Asn Gln Pro Ser Leu Phe Val Glu
        195                 200                 205

Glu Lys Glu Asn Pro Gly Gln Lys Arg Tyr Ile Phe Asp Ser Phe Asp
    210                 215                 220

Lys Phe Ala Gly Tyr Leu Thr Lys Phe Gln Gln Thr Lys Lys Asn Leu
225                 230                 235                 240

Tyr Ala Ala Asp Gly Thr Ser Thr Ala Val Ala Thr Arg Ile Ala Asp
                245                 250                 255

Asn Phe Ile Ile Phe His Gln Asn Thr Lys Val Phe Arg Asp Lys Tyr
            260                 265                 270

Lys Asn Asn His Thr Asp Leu Gly Phe Asp Glu Glu Asn Ile Phe Glu
        275                 280                 285

Ile Glu Arg Tyr Lys Asn Cys Leu Leu Gln Arg Glu Ile Glu His Ile
    290                 295                 300

Lys Asn Glu Asn Ser Tyr Asn Lys Ile Ile Gly Arg Ile Asn Lys Lys
305                 310                 315                 320

Ile Lys Glu Tyr Arg Asp Gln Lys Ala Lys Asp Thr Lys Leu Thr Lys
                325                 330                 335

Ser Asp Phe Pro Phe Phe Lys Asn Leu Asp Lys Gln Ile Leu Gly Glu
            340                 345                 350

Val Glu Lys Glu Lys Gln Leu Ile Glu Lys Thr Arg Glu Lys Thr Glu
        355                 360                 365

Glu Asp Val Leu Ile Glu Arg Phe Lys Glu Phe Ile Glu Asn Asn Glu
    370                 375                 380

Glu Arg Phe Thr Ala Ala Lys Lys Leu Met Asn Ala Phe Cys Asn Gly
385                 390                 395                 400
```

```
Glu Phe Glu Ser Glu Tyr Gly Ile Tyr Leu Lys Asn Lys Ala Ile
            405                 410                 415

Asn Thr Ile Ser Arg Arg Trp Phe Val Ser Asp Arg Asp Phe Glu Leu
            420                 425                 430

Lys Leu Pro Gln Gln Lys Ser Lys Asn Lys Ser Glu Lys Asn Glu Pro
            435                 440                 445

Lys Val Lys Lys Phe Ile Ser Ile Ala Glu Ile Lys Asn Ala Val Glu
        450                 455                 460

Glu Leu Asp Gly Asp Ile Phe Lys Ala Val Phe Tyr Asp Lys Lys Ile
465                 470                 475                 480

Ile Ala Gln Gly Gly Ser Lys Leu Glu Gln Phe Leu Val Ile Trp Lys
                485                 490                 495

Tyr Glu Phe Glu Tyr Leu Phe Arg Asp Ile Glu Arg Glu Asn Gly Glu
                500                 505                 510

Lys Leu Leu Gly Tyr Asp Ser Cys Leu Lys Ile Ala Lys Gln Leu Gly
        515                 520                 525

Ile Phe Pro Gln Glu Lys Glu Ala Arg Glu Lys Ala Thr Ala Val Ile
        530                 535                 540

Lys Asn Tyr Ala Asp Ala Gly Leu Gly Ile Phe Gln Met Met Lys Tyr
545                 550                 555                 560

Phe Ser Leu Asp Asp Lys Asp Arg Lys Asn Thr Pro Gly Gln Leu Ser
                565                 570                 575

Thr Asn Phe Tyr Ala Glu Tyr Asp Gly Tyr Tyr Lys Asp Phe Glu Phe
                580                 585                 590

Ile Lys Tyr Tyr Asn Glu Phe Arg Asn Phe Ile Thr Lys Lys Pro Phe
                595                 600                 605

Asp Glu Asp Lys Ile Lys Leu Asn Phe Glu Asn Gly Ala Leu Leu Lys
            610                 615                 620

Gly Trp Asp Glu Asn Lys Glu Tyr Asp Phe Met Gly Val Ile Leu Lys
625                 630                 635                 640

Lys Glu Gly Arg Leu Tyr Leu Gly Ile Met His Lys Asn His Arg Lys
                645                 650                 655

Leu Phe Gln Ser Met Gly Asn Ala Lys Gly Asp Asn Ala Asn Arg Tyr
                660                 665                 670

Gln Lys Met Ile Tyr Lys Gln Ile Ala Asp Ala Ser Lys Asp Val Pro
            675                 680                 685

Arg Leu Leu Leu Thr Ser Lys Lys Ala Met Glu Lys Phe Lys Pro Ser
            690                 695                 700

Gln Glu Ile Leu Arg Ile Lys Lys Glu Lys Thr Phe Lys Arg Glu Ser
705                 710                 715                 720

Lys Asn Phe Ser Leu Arg Asp Leu His Ala Leu Ile Glu Tyr Tyr Arg
                725                 730                 735

Asn Cys Ile Pro Gln Tyr Ser Asn Trp Ser Phe Tyr Asp Phe Gln Phe
                740                 745                 750

Gln Asp Thr Gly Lys Tyr Gln Asn Ile Lys Glu Phe Thr Asp Asp Val
            755                 760                 765

Gln Lys Tyr Gly Tyr Lys Ile Ser Phe Arg Asp Ile Asp Asp Glu Tyr
        770                 775                 780

Ile Asn Gln Ala Leu Asn Glu Gly Lys Met Tyr Leu Phe Glu Val Val
785                 790                 795                 800

Asn Lys Asp Ile Tyr Asn Thr Lys Asn Gly Ser Lys Asn Leu His Thr
                805                 810                 815
```

Leu Tyr Phe Glu His Ile Leu Ser Ala Glu Asn Leu Asn Asp Pro Val
                    820                 825                 830

Phe Lys Leu Ser Gly Met Ala Glu Ile Phe Gln Arg Gln Pro Ser Val
            835                 840                 845

Asn Glu Arg Glu Lys Ile Thr Thr Gln Lys Asn Gln Cys Ile Leu Asp
        850                 855                 860

Lys Gly Asp Arg Ala Tyr Lys Tyr Arg Tyr Thr Glu Lys Lys Ile
865                 870                 875                 880

Met Phe His Met Ser Leu Val Leu Asn Thr Gly Lys Gly Glu Ile Lys
                885                 890                 895

Gln Val Gln Phe Asn Lys Ile Ile Asn Gln Arg Ile Ser Ser Ser Asp
            900                 905                 910

Asn Glu Met Arg Val Asn Val Ile Gly Ile Asp Arg Gly Glu Lys Asn
        915                 920                 925

Leu Leu Tyr Tyr Ser Val Val Lys Gln Asn Gly Glu Ile Ile Glu Gln
    930                 935                 940

Ala Ser Leu Asn Glu Ile Asn Gly Val Asn Tyr Arg Asp Lys Leu Ile
945                 950                 955                 960

Glu Arg Glu Lys Glu Arg Leu Lys Asn Arg Gln Ser Trp Lys Pro Val
                965                 970                 975

Val Lys Ile Lys Asp Leu Lys Lys Gly Tyr Ile Ser His Val Ile His
            980                 985                 990

Lys Ile Cys Gln Leu Ile Glu Lys Tyr Ser Ala Ile Val Val Leu Glu
        995                 1000                1005

Asp Leu Asn Met Arg Phe Lys Gln Ile Arg Gly Gly Ile Glu Arg
    1010                1015                1020

Ser Val Tyr Gln Gln Phe Glu Lys Ala Leu Ile Asp Lys Leu Gly
    1025                1030                1035

Tyr Leu Val Phe Lys Asp Asn Arg Asp Leu Arg Ala Pro Gly Gly
    1040                1045                1050

Val Leu Asn Gly Tyr Gln Leu Ser Ala Pro Phe Val Ser Phe Glu
    1055                1060                1065

Lys Met Arg Lys Gln Thr Gly Ile Leu Phe Tyr Thr Gln Ala Glu
    1070                1075                1080

Tyr Thr Ser Lys Thr Asp Pro Ile Thr Gly Phe Arg Lys Asn Val
    1085                1090                1095

Tyr Ile Ser Asn Ser Ala Ser Leu Asp Lys Ile Lys Glu Ala Val
    1100                1105                1110

Lys Lys Phe Asp Ala Ile Gly Trp Asp Gly Lys Glu Gln Ser Tyr
    1115                1120                1125

Phe Phe Lys Tyr Asn Pro Tyr Asn Leu Ala Asp Glu Lys Tyr Lys
    1130                1135                1140

Asn Ser Thr Val Ser Lys Glu Trp Ala Ile Phe Ala Ser Ala Pro
    1145                1150                1155

Arg Ile Arg Arg Gln Lys Gly Glu Asp Gly Tyr Trp Lys Tyr Asp
    1160                1165                1170

Arg Val Lys Val Asn Glu Glu Phe Glu Lys Leu Leu Lys Val Trp
    1175                1180                1185

Asn Phe Val Asn Pro Lys Ala Thr Asp Ile Lys Gln Glu Ile Ile
    1190                1195                1200

Lys Lys Glu Lys Ala Gly Asp Leu Gln Gly Glu Lys Glu Leu Asp
    1205                1210                1215

Gly Arg Leu Arg Asn Phe Trp His Ser Phe Ile Tyr Leu Phe Asn

```
                1220                1225                1230
Leu Val Leu Glu Leu Arg Asn Ser Phe Ser Leu Gln Ile Lys Ile
            1235                1240                1245

Lys Ala Gly Glu Val Ile Ala Val Asp Glu Gly Val Asp Phe Ile
        1250                1255                1260

Ala Ser Pro Val Lys Pro Phe Phe Thr Thr Pro Asn Pro Tyr Ile
    1265                1270                1275

Pro Ser Asn Leu Cys Trp Leu Ala Val Glu Asn Ala Asp Ala Asn
1280                1285                1290

Gly Ala Tyr Asn Ile Ala Arg Lys Gly Val Met Ile Leu Lys Lys
    1295                1300                1305

Ile Arg Glu His Ala Lys Lys Asp Pro Glu Phe Lys Lys Leu Pro
        1310                1315                1320

Asn Leu Phe Ile Ser Asn Ala Glu Trp Asp Glu Ala Ala Arg Asp
            1325                1330                1335

Trp Gly Lys Tyr Ala Gly Thr Thr Ala Leu Asn Leu Asp His
                1340                1345                1350

<210> SEQ ID NO 237
<211> LENGTH: 1206
<212> TYPE: PRT
<213> ORGANISM: Lachnospiraceae bacterium MA2020

<400> SEQUENCE: 237

Met Tyr Tyr Glu Ser Leu Thr Lys Gln Tyr Pro Val Ser Lys Thr Ile
1               5                   10                  15

Arg Asn Glu Leu Ile Pro Ile Gly Lys Thr Leu Asp Asn Ile Arg Gln
            20                  25                  30

Asn Asn Ile Leu Glu Ser Asp Val Lys Arg Lys Gln Asn Tyr Glu His
        35                  40                  45

Val Lys Gly Ile Leu Asp Glu Tyr His Lys Gln Leu Ile Asn Glu Ala
    50                  55                  60

Leu Asp Asn Cys Thr Leu Pro Ser Leu Lys Ile Ala Ala Glu Ile Tyr
65                  70                  75                  80

Leu Lys Asn Gln Lys Glu Val Ser Asp Arg Glu Asp Phe Asn Lys Thr
                85                  90                  95

Gln Asp Leu Leu Arg Lys Glu Val Val Glu Lys Leu Lys Ala His Glu
            100                 105                 110

Asn Phe Thr Lys Ile Gly Lys Lys Asp Ile Leu Asp Leu Leu Glu Lys
        115                 120                 125

Leu Pro Ser Ile Ser Glu Asp Asp Tyr Asn Ala Leu Glu Ser Phe Arg
    130                 135                 140

Asn Phe Tyr Thr Tyr Phe Thr Ser Tyr Asn Lys Val Arg Glu Asn Leu
145                 150                 155                 160

Tyr Ser Asp Lys Glu Lys Ser Ser Thr Val Ala Tyr Arg Leu Ile Asn
                165                 170                 175

Glu Asn Phe Pro Lys Phe Leu Asp Asn Val Lys Ser Tyr Arg Phe Val
            180                 185                 190

Lys Thr Ala Gly Ile Leu Ala Asp Gly Leu Gly Glu Glu Gln Asp
        195                 200                 205

Ser Leu Phe Ile Val Glu Thr Phe Asn Lys Thr Leu Thr Gln Asp Gly
    210                 215                 220

Ile Asp Thr Tyr Asn Ser Gln Val Gly Lys Ile Asn Ser Ser Ile Asn
225                 230                 235                 240
```

```
Leu Tyr Asn Gln Lys Asn Gln Lys Ala Asn Gly Phe Arg Lys Ile Pro
                245                 250                 255

Lys Met Lys Met Leu Tyr Lys Gln Ile Leu Ser Asp Arg Glu Glu Ser
            260                 265                 270

Phe Ile Asp Glu Phe Gln Ser Asp Glu Val Leu Ile Asp Asn Val Glu
        275                 280                 285

Ser Tyr Gly Ser Val Leu Ile Glu Ser Leu Lys Ser Ser Lys Val Ser
    290                 295                 300

Ala Phe Phe Asp Ala Leu Arg Glu Ser Lys Gly Lys Asn Val Tyr Val
305                 310                 315                 320

Lys Asn Asp Leu Ala Lys Thr Ala Met Ser Asn Ile Val Phe Glu Asn
                325                 330                 335

Trp Arg Thr Phe Asp Asp Leu Leu Asn Gln Glu Tyr Asp Leu Ala Asn
            340                 345                 350

Glu Asn Lys Lys Lys Asp Asp Lys Tyr Phe Glu Lys Arg Gln Lys Glu
        355                 360                 365

Leu Lys Lys Asn Lys Ser Tyr Ser Leu Glu His Leu Cys Asn Leu Ser
    370                 375                 380

Glu Asp Ser Cys Asn Leu Ile Glu Asn Tyr Ile His Gln Ile Ser Asp
385                 390                 395                 400

Asp Ile Glu Asn Ile Ile Asn Asn Glu Thr Phe Leu Arg Ile Val
                405                 410                 415

Ile Asn Glu His Asp Arg Ser Arg Lys Leu Ala Lys Asn Arg Lys Ala
            420                 425                 430

Val Lys Ala Ile Lys Asp Phe Leu Asp Ser Ile Lys Val Leu Glu Arg
        435                 440                 445

Glu Leu Lys Leu Ile Asn Ser Ser Gly Gln Glu Leu Glu Lys Asp Leu
    450                 455                 460

Ile Val Tyr Ser Ala His Glu Glu Leu Leu Val Glu Leu Lys Gln Val
465                 470                 475                 480

Asp Ser Leu Tyr Asn Met Thr Arg Asn Tyr Leu Thr Lys Lys Pro Phe
                485                 490                 495

Ser Thr Glu Lys Val Lys Leu Asn Phe Asn Arg Ser Thr Leu Leu Asn
            500                 505                 510

Gly Trp Asp Arg Asn Lys Glu Thr Asp Asn Leu Gly Val Leu Leu Leu
        515                 520                 525

Lys Asp Gly Lys Tyr Tyr Leu Gly Ile Met Asn Thr Ser Ala Asn Lys
    530                 535                 540

Ala Phe Val Asn Pro Pro Val Ala Lys Thr Glu Lys Val Phe Lys Lys
545                 550                 555                 560

Val Asp Tyr Lys Leu Leu Pro Val Pro Asn Gln Met Leu Pro Lys Val
                565                 570                 575

Phe Phe Ala Lys Ser Asn Ile Asp Phe Tyr Asn Pro Ser Ser Glu Ile
            580                 585                 590

Tyr Ser Asn Tyr Lys Lys Gly Thr His Lys Lys Gly Asn Met Phe Ser
        595                 600                 605

Leu Glu Asp Cys His Asn Leu Ile Asp Phe Phe Lys Glu Ser Ile Ser
    610                 615                 620

Lys His Glu Asp Trp Ser Lys Phe Gly Phe Lys Phe Ser Asp Thr Ala
625                 630                 635                 640

Ser Tyr Asn Asp Ile Ser Glu Phe Tyr Arg Glu Val Glu Lys Gln Gly
                645                 650                 655

Tyr Lys Leu Thr Tyr Thr Asp Ile Asp Glu Thr Tyr Ile Asn Asp Leu
```

```
              660             665             670
Ile Glu Arg Asn Glu Leu Tyr Leu Phe Gln Ile Tyr Asn Lys Asp Phe
            675             680             685

Ser Met Tyr Ser Lys Gly Lys Leu Asn Leu His Thr Leu Tyr Phe Met
            690             695             700

Met Leu Phe Asp Gln Arg Asn Ile Asp Asp Val Val Tyr Lys Leu Asn
705             710             715             720

Gly Glu Ala Glu Val Phe Tyr Arg Pro Ala Ser Ile Ser Glu Asp Glu
                725             730             735

Leu Ile Ile His Lys Ala Gly Glu Ile Lys Asn Lys Asn Pro Asn
            740             745             750

Arg Ala Arg Thr Lys Glu Thr Ser Thr Phe Ser Tyr Asp Ile Val Lys
            755             760             765

Asp Lys Arg Tyr Ser Lys Asp Lys Phe Thr Leu His Ile Pro Ile Thr
            770             775             780

Met Asn Phe Gly Val Asp Glu Val Lys Arg Phe Asn Asp Ala Val Asn
785             790             795             800

Ser Ala Ile Arg Ile Asp Glu Asn Val Asn Val Ile Gly Ile Asp Arg
                805             810             815

Gly Glu Arg Asn Leu Leu Tyr Val Val Val Ile Asp Ser Lys Gly Asn
                820             825             830

Ile Leu Glu Gln Ile Ser Leu Asn Ser Ile Ile Asn Lys Glu Tyr Asp
            835             840             845

Ile Glu Thr Asp Tyr His Ala Leu Leu Asp Glu Arg Glu Gly Gly Arg
            850             855             860

Asp Lys Ala Arg Lys Asp Trp Asn Thr Val Glu Asn Ile Arg Asp Leu
865             870             875             880

Lys Ala Gly Tyr Leu Ser Gln Val Val Asn Val Ala Lys Leu Val
                885             890             895

Leu Lys Tyr Asn Ala Ile Ile Cys Leu Glu Asp Leu Asn Phe Gly Phe
            900             905             910

Lys Arg Gly Arg Gln Lys Val Glu Lys Gln Val Tyr Gln Lys Phe Glu
            915             920             925

Lys Met Leu Ile Asp Lys Leu Asn Tyr Leu Val Ile Asp Lys Ser Arg
            930             935             940

Glu Gln Thr Ser Pro Lys Glu Leu Gly Gly Ala Leu Asn Ala Leu Gln
945             950             955             960

Leu Thr Ser Lys Phe Lys Ser Phe Lys Glu Leu Gly Lys Gln Ser Gly
                965             970             975

Val Ile Tyr Tyr Val Pro Ala Tyr Leu Thr Ser Lys Ile Asp Pro Thr
                980             985             990

Thr Gly Phe Ala Asn Leu Phe Tyr  Met Lys Cys Glu Asn  Val Glu Lys
                995              1000              1005

Ser Lys  Arg Phe Phe Asp Gly  Phe Asp Phe Ile Arg  Phe Asn Ala
     1010              1015              1020

Leu Glu  Asn Val Phe Glu Phe  Gly Phe Asp Tyr Arg  Ser Phe Thr
     1025              1030              1035

Gln Arg  Ala Cys Gly Ile Asn  Ser Lys Trp Thr Val  Cys Thr Asn
     1040              1045              1050

Gly Glu  Arg Ile Ile Lys Tyr  Arg Asn Pro Asp Lys  Asn Asn Met
     1055              1060              1065

Phe Asp  Glu Lys Val Val Val  Val Thr Asp Glu Met  Lys Asn Leu
     1070              1075              1080
```

```
Phe Glu Gln Tyr Lys Ile Pro Tyr Glu Asp Gly Arg Asn Val Lys
    1085                1090                1095

Asp Met Ile Ile Ser Asn Glu Glu Ala Glu Phe Tyr Arg Arg Leu
    1100                1105                1110

Tyr Arg Leu Leu Gln Gln Thr Leu Gln Met Arg Asn Ser Thr Ser
    1115                1120                1125

Asp Gly Thr Arg Asp Tyr Ile Ile Ser Pro Val Lys Asn Lys Arg
    1130                1135                1140

Glu Ala Tyr Phe Asn Ser Glu Leu Ser Asp Gly Ser Val Pro Lys
    1145                1150                1155

Asp Ala Asp Ala Asn Gly Ala Tyr Asn Ile Ala Arg Lys Gly Leu
    1160                1165                1170

Trp Val Leu Glu Gln Ile Arg Gln Lys Ser Glu Gly Glu Lys Ile
    1175                1180                1185

Asn Leu Ala Met Thr Asn Ala Glu Trp Leu Glu Tyr Ala Gln Thr
    1190                1195                1200

His Leu Leu
    1205

<210> SEQ ID NO 238
<211> LENGTH: 1238
<212> TYPE: PRT
<213> ORGANISM: Candidatus Methanoplasma termitum

<400> SEQUENCE: 238

Met Asn Asn Tyr Asp Glu Phe Thr Lys Leu Tyr Pro Ile Gln Lys Thr
1               5                   10                  15

Ile Arg Phe Glu Leu Lys Pro Gln Gly Arg Thr Met Glu His Leu Glu
                20                  25                  30

Thr Phe Asn Phe Phe Glu Glu Asp Arg Asp Arg Ala Glu Lys Tyr Lys
            35                  40                  45

Ile Leu Lys Glu Ala Ile Asp Glu Tyr His Lys Lys Phe Ile Asp Glu
        50                  55                  60

His Leu Thr Asn Met Ser Leu Asp Trp Asn Ser Leu Lys Gln Ile Ser
65                  70                  75                  80

Glu Lys Tyr Tyr Lys Ser Arg Glu Glu Lys Asp Lys Val Phe Leu
                85                  90                  95

Ser Glu Gln Lys Arg Met Arg Gln Glu Ile Val Ser Glu Phe Lys Lys
                100                 105                 110

Asp Asp Arg Phe Lys Asp Leu Phe Ser Lys Lys Leu Phe Ser Glu Leu
            115                 120                 125

Leu Lys Glu Glu Ile Tyr Lys Lys Gly Asn His Gln Glu Ile Asp Ala
        130                 135                 140

Leu Lys Ser Phe Asp Lys Phe Ser Gly Tyr Phe Ile Gly Leu His Glu
145                 150                 155                 160

Asn Arg Lys Asn Met Tyr Ser Asp Gly Asp Glu Ile Thr Ala Ile Ser
                165                 170                 175

Asn Arg Ile Val Asn Glu Asn Phe Pro Lys Phe Leu Asp Asn Leu Gln
            180                 185                 190

Lys Tyr Gln Glu Ala Arg Lys Lys Tyr Pro Glu Trp Ile Ile Lys Ala
        195                 200                 205

Glu Ser Ala Leu Val Ala His Asn Ile Lys Met Asp Glu Val Phe Ser
    210                 215                 220

Leu Glu Tyr Phe Asn Lys Val Leu Asn Gln Glu Gly Ile Gln Arg Tyr
```

```
                225                 230                 235                 240
            Asn Leu Ala Leu Gly Gly Tyr Val Thr Lys Ser Gly Glu Lys Met Met
                            245                 250                 255
            Gly Leu Asn Asp Ala Leu Asn Leu Ala His Gln Ser Glu Lys Ser Ser
                        260                 265                 270
            Lys Gly Arg Ile His Met Thr Pro Leu Phe Lys Gln Ile Leu Ser Glu
                        275                 280                 285
            Lys Glu Ser Phe Ser Tyr Ile Pro Asp Val Phe Thr Glu Asp Ser Gln
                    290                 295                 300
            Leu Leu Pro Ser Ile Gly Gly Phe Phe Ala Gln Ile Glu Asn Asp Lys
            305                 310                 315                 320
            Asp Gly Asn Ile Phe Asp Arg Ala Leu Glu Leu Ile Ser Ser Tyr Ala
                            325                 330                 335
            Glu Tyr Asp Thr Glu Arg Ile Tyr Ile Arg Gln Ala Asp Ile Asn Arg
                        340                 345                 350
            Val Ser Asn Val Ile Phe Gly Glu Trp Gly Thr Leu Gly Gly Leu Met
                        355                 360                 365
            Arg Glu Tyr Lys Ala Asp Ser Ile Asn Asp Ile Asn Leu Glu Arg Thr
                    370                 375                 380
            Cys Lys Lys Val Asp Lys Trp Leu Asp Ser Lys Glu Phe Ala Leu Ser
            385                 390                 395                 400
            Asp Val Leu Glu Ala Ile Lys Arg Thr Gly Asn Asn Asp Ala Phe Asn
                            405                 410                 415
            Glu Tyr Ile Ser Lys Met Arg Thr Ala Arg Glu Lys Ile Asp Ala Ala
                        420                 425                 430
            Arg Lys Glu Met Lys Phe Ile Ser Glu Lys Ile Ser Gly Asp Glu Glu
                        435                 440                 445
            Ser Ile His Ile Ile Lys Thr Leu Leu Asp Ser Val Gln Gln Phe Leu
                    450                 455                 460
            His Phe Phe Asn Leu Phe Lys Ala Arg Gln Asp Ile Pro Leu Asp Gly
            465                 470                 475                 480
            Ala Phe Tyr Ala Glu Phe Asp Glu Val His Ser Lys Leu Phe Ala Ile
                            485                 490                 495
            Val Pro Leu Tyr Asn Lys Val Arg Asn Tyr Leu Thr Lys Asn Asn Leu
                        500                 505                 510
            Asn Thr Lys Lys Ile Lys Leu Asn Phe Lys Asn Pro Thr Leu Ala Asn
                        515                 520                 525
            Gly Trp Asp Gln Asn Lys Val Tyr Asp Tyr Ala Ser Leu Ile Phe Leu
                    530                 535                 540
            Arg Asp Gly Asn Tyr Tyr Leu Gly Ile Ile Asn Pro Lys Arg Lys Lys
            545                 550                 555                 560
            Asn Ile Lys Phe Glu Gln Gly Ser Gly Asn Gly Pro Phe Tyr Arg Lys
                            565                 570                 575
            Met Val Tyr Lys Gln Ile Pro Gly Pro Asn Lys Asn Leu Pro Arg Val
                        580                 585                 590
            Phe Leu Thr Ser Thr Lys Gly Lys Lys Glu Tyr Lys Pro Ser Lys Glu
                        595                 600                 605
            Ile Ile Glu Gly Tyr Glu Ala Asp Lys His Ile Arg Gly Asp Lys Phe
                    610                 615                 620
            Asp Leu Asp Phe Cys His Lys Leu Ile Asp Phe Phe Lys Glu Ser Ile
            625                 630                 635                 640
            Glu Lys His Lys Asp Trp Ser Lys Phe Asn Phe Tyr Phe Ser Pro Thr
                            645                 650                 655
```

```
Glu Ser Tyr Gly Asp Ile Ser Glu Phe Tyr Leu Asp Val Glu Lys Gln
                660                 665                 670

Gly Tyr Arg Met His Phe Glu Asn Ile Ser Ala Glu Thr Ile Asp Glu
            675                 680                 685

Tyr Val Glu Lys Gly Asp Leu Phe Leu Phe Gln Ile Tyr Asn Lys Asp
        690                 695                 700

Phe Val Lys Ala Ala Thr Gly Lys Lys Asp Met His Thr Ile Tyr Trp
705                 710                 715                 720

Asn Ala Ala Phe Ser Pro Glu Asn Leu Gln Asp Val Val Lys Leu
                725                 730                 735

Asn Gly Glu Ala Glu Leu Phe Tyr Arg Asp Lys Ser Asp Ile Lys Glu
                740                 745                 750

Ile Val His Arg Glu Gly Glu Ile Leu Val Asn Arg Thr Tyr Asn Gly
            755                 760                 765

Arg Thr Pro Val Pro Asp Lys Ile His Lys Lys Leu Thr Asp Tyr His
            770                 775                 780

Asn Gly Arg Thr Lys Asp Leu Gly Glu Ala Lys Glu Tyr Leu Asp Lys
785                 790                 795                 800

Val Arg Tyr Phe Lys Ala His Tyr Asp Ile Thr Lys Asp Arg Arg Tyr
                805                 810                 815

Leu Asn Asp Lys Ile Tyr Phe His Val Pro Leu Thr Leu Asn Phe Lys
                820                 825                 830

Ala Asn Gly Lys Lys Asn Leu Asn Lys Met Val Ile Glu Lys Phe Leu
            835                 840                 845

Ser Asp Glu Lys Ala His Ile Ile Gly Ile Asp Arg Gly Glu Arg Asn
            850                 855                 860

Leu Leu Tyr Tyr Ser Ile Ile Asp Arg Ser Gly Lys Ile Ile Asp Gln
865                 870                 875                 880

Gln Ser Leu Asn Val Ile Asp Gly Phe Asp Tyr Arg Glu Lys Leu Asn
                885                 890                 895

Gln Arg Glu Ile Glu Met Lys Asp Ala Arg Gln Ser Trp Asn Ala Ile
            900                 905                 910

Gly Lys Ile Lys Asp Leu Lys Glu Gly Tyr Leu Ser Lys Ala Val His
            915                 920                 925

Glu Ile Thr Lys Met Ala Ile Gln Tyr Asn Ala Ile Val Val Met Glu
930                 935                 940

Glu Leu Asn Tyr Gly Phe Lys Arg Gly Arg Phe Lys Val Glu Lys Gln
945                 950                 955                 960

Ile Tyr Gln Lys Phe Glu Asn Met Leu Ile Asp Lys Met Asn Tyr Leu
                965                 970                 975

Val Phe Lys Asp Ala Pro Asp Glu Ser Pro Gly Gly Val Leu Asn Ala
                980                 985                 990

Tyr Gln Leu Thr Asn Pro Leu Glu Ser Phe Ala Lys Leu Gly Lys Gln
                995                 1000                1005

Thr Gly Ile Leu Phe Tyr Val Pro Ala Ala Tyr Thr Ser Lys Ile
        1010                1015                1020

Asp Pro Thr Thr Gly Phe Val Asn Leu Phe Asn Thr Ser Ser Lys
        1025                1030                1035

Thr Asn Ala Gln Glu Arg Lys Glu Phe Leu Gln Lys Phe Glu Ser
        1040                1045                1050

Ile Ser Tyr Ser Ala Lys Asp Gly Gly Ile Phe Ala Phe Ala Phe
        1055                1060                1065
```

```
Asp Tyr Arg Lys Phe Gly Thr Ser Lys Thr Asp His Lys Asn Val
    1070                1075                1080

Trp Thr Ala Tyr Thr Asn Gly Glu Arg Met Arg Tyr Ile Lys Glu
    1085                1090                1095

Lys Lys Arg Asn Glu Leu Phe Asp Pro Ser Lys Glu Ile Lys Glu
    1100                1105                1110

Ala Leu Thr Ser Ser Gly Ile Lys Tyr Asp Gly Gly Gln Asn Ile
    1115                1120                1125

Leu Pro Asp Ile Leu Arg Ser Asn Asn Asn Gly Leu Ile Tyr Thr
    1130                1135                1140

Met Tyr Ser Ser Phe Ile Ala Ala Ile Gln Met Arg Val Tyr Asp
    1145                1150                1155

Gly Lys Glu Asp Tyr Ile Ile Ser Pro Ile Lys Asn Ser Lys Gly
    1160                1165                1170

Glu Phe Phe Arg Thr Asp Pro Lys Arg Arg Glu Leu Pro Ile Asp
    1175                1180                1185

Ala Asp Ala Asn Gly Ala Tyr Asn Ile Ala Leu Arg Gly Glu Leu
    1190                1195                1200

Thr Met Arg Ala Ile Ala Glu Lys Phe Asp Pro Asp Ser Glu Lys
    1205                1210                1215

Met Ala Lys Leu Glu Leu Lys His Lys Asp Trp Phe Glu Phe Met
    1220                1225                1230

Gln Thr Arg Gly Asp
    1235

<210> SEQ ID NO 239
<211> LENGTH: 1282
<212> TYPE: PRT
<213> ORGANISM: Eubacterium eligens

<400> SEQUENCE: 239

Met Asn Gly Asn Arg Ser Ile Val Tyr Arg Glu Phe Val Gly Ile
1               5                   10                  15

Pro Val Ala Lys Thr Leu Arg Asn Glu Leu Arg Pro Val Gly His Thr
            20                  25                  30

Gln Glu His Ile Ile Gln Asn Gly Leu Ile Gln Glu Asp Glu Leu Arg
                35                  40                  45

Gln Glu Lys Ser Thr Glu Leu Lys Asn Ile Met Asp Asp Tyr Tyr Arg
    50                  55                  60

Glu Tyr Ile Asp Lys Ser Leu Ser Gly Val Thr Asp Leu Asp Phe Thr
65                  70                  75                  80

Leu Leu Phe Glu Leu Met Asn Leu Val Gln Ser Ser Pro Ser Lys Asp
                85                  90                  95

Asn Lys Lys Ala Leu Glu Lys Glu Gln Ser Lys Met Arg Glu Gln Ile
                100                 105                 110

Cys Thr His Leu Gln Ser Asp Ser Asn Tyr Lys Asn Ile Phe Asn Ala
            115                 120                 125

Lys Leu Leu Lys Glu Ile Leu Pro Asp Phe Ile Lys Asn Tyr Asn Gln
    130                 135                 140

Tyr Asp Val Lys Asp Lys Ala Gly Lys Leu Glu Thr Leu Ala Leu Phe
145                 150                 155                 160

Asn Gly Phe Ser Thr Tyr Phe Thr Asp Phe Phe Glu Lys Arg Lys Asn
                165                 170                 175

Val Phe Thr Lys Glu Ala Val Ser Thr Ser Ile Ala Tyr Arg Ile Val
                180                 185                 190
```

-continued

```
His Glu Asn Ser Leu Ile Phe Leu Ala Asn Met Thr Ser Tyr Lys Lys
            195                 200                 205
Ile Ser Glu Lys Ala Leu Asp Glu Ile Glu Val Ile Glu Lys Asn Asn
    210                 215                 220
Gln Asp Lys Met Gly Asp Trp Glu Leu Asn Gln Ile Phe Asn Pro Asp
225                 230                 235                 240
Phe Tyr Asn Met Val Leu Ile Gln Ser Gly Ile Asp Phe Tyr Asn Glu
                245                 250                 255
Ile Cys Gly Val Val Asn Ala His Met Asn Leu Tyr Cys Gln Gln Thr
            260                 265                 270
Lys Asn Asn Tyr Asn Leu Phe Lys Met Arg Lys Leu His Lys Gln Ile
    275                 280                 285
Leu Ala Tyr Thr Ser Thr Ser Phe Glu Val Pro Lys Met Phe Glu Asp
290                 295                 300
Asp Met Ser Val Tyr Asn Ala Val Asn Ala Phe Ile Asp Glu Thr Glu
305                 310                 315                 320
Lys Gly Asn Ile Ile Gly Lys Leu Lys Asp Ile Val Asn Lys Tyr Asp
                325                 330                 335
Glu Leu Asp Glu Lys Arg Ile Tyr Ile Ser Lys Asp Phe Tyr Glu Thr
            340                 345                 350
Leu Ser Cys Phe Met Ser Gly Asn Trp Asn Leu Ile Thr Gly Cys Val
    355                 360                 365
Glu Asn Phe Tyr Asp Glu Asn Ile His Ala Lys Gly Lys Ser Lys Glu
    370                 375                 380
Glu Lys Val Lys Lys Ala Val Lys Glu Asp Lys Tyr Lys Ser Ile Asn
385                 390                 395                 400
Asp Val Asn Asp Leu Val Glu Lys Tyr Ile Asp Glu Lys Glu Arg Asn
                405                 410                 415
Glu Phe Lys Asn Ser Asn Ala Lys Gln Tyr Ile Arg Glu Ile Ser Asn
            420                 425                 430
Ile Ile Thr Asp Thr Glu Thr Ala His Leu Glu Tyr Asp Asp His Ile
    435                 440                 445
Ser Leu Ile Glu Ser Glu Glu Lys Ala Asp Glu Met Lys Lys Arg Leu
    450                 455                 460
Asp Met Tyr Met Asn Met Tyr His Trp Ala Lys Ala Phe Ile Val Asp
465                 470                 475                 480
Glu Val Leu Asp Arg Asp Glu Met Phe Tyr Ser Asp Ile Asp Ile
                485                 490                 495
Tyr Asn Ile Leu Glu Asn Ile Val Pro Leu Tyr Asn Arg Val Arg Asn
            500                 505                 510
Tyr Val Thr Gln Lys Pro Tyr Asn Ser Lys Lys Ile Lys Leu Asn Phe
    515                 520                 525
Gln Ser Pro Thr Leu Ala Asn Gly Trp Ser Gln Ser Lys Glu Phe Asp
530                 535                 540
Asn Asn Ala Ile Ile Leu Ile Arg Asp Asn Lys Tyr Tyr Leu Ala Ile
545                 550                 555                 560
Phe Asn Ala Lys Asn Lys Pro Asp Lys Lys Ile Ile Gln Gly Asn Ser
                565                 570                 575
Asp Lys Lys Asn Asp Asn Asp Tyr Lys Lys Met Val Tyr Asn Leu Leu
            580                 585                 590
Pro Gly Ala Asn Lys Met Leu Pro Lys Val Phe Leu Ser Lys Lys Gly
    595                 600                 605
```

```
Ile Glu Thr Phe Lys Pro Ser Asp Tyr Ile Ile Ser Gly Tyr Asn Ala
610                 615                 620

His Lys His Ile Lys Thr Ser Glu Asn Phe Asp Ile Ser Phe Cys Arg
625                 630                 635                 640

Asp Leu Ile Asp Tyr Phe Lys Asn Ser Ile Glu Lys His Ala Glu Trp
            645                 650                 655

Arg Lys Tyr Glu Phe Lys Phe Ser Ala Thr Asp Ser Tyr Ser Asp Ile
            660                 665                 670

Ser Glu Phe Tyr Arg Glu Val Glu Met Gln Gly Tyr Arg Ile Asp Trp
        675                 680                 685

Thr Tyr Ile Ser Glu Ala Asp Ile Asn Lys Leu Asp Glu Gly Lys
690                 695                 700

Ile Tyr Leu Phe Gln Ile Tyr Asn Lys Asp Phe Ala Glu Asn Ser Thr
705                 710                 715                 720

Gly Lys Glu Asn Leu His Thr Met Tyr Phe Lys Asn Ile Phe Ser Glu
                725                 730                 735

Glu Asn Leu Lys Asp Ile Ile Lys Leu Asn Gly Gln Ala Glu Leu
            740                 745                 750

Phe Tyr Arg Arg Ala Ser Val Lys Asn Pro Val Lys His Lys Lys Asp
        755                 760                 765

Ser Val Leu Val Asn Lys Thr Tyr Lys Asn Gln Leu Asp Asn Gly Asp
770                 775                 780

Val Val Arg Ile Pro Ile Pro Asp Asp Ile Tyr Asn Glu Ile Tyr Lys
785                 790                 795                 800

Met Tyr Asn Gly Tyr Ile Lys Glu Ser Asp Leu Ser Glu Ala Ala Lys
                805                 810                 815

Glu Tyr Leu Asp Lys Val Glu Val Arg Thr Ala Gln Lys Asp Ile Val
            820                 825                 830

Lys Asp Tyr Arg Tyr Thr Val Asp Lys Tyr Phe Ile His Thr Pro Ile
        835                 840                 845

Thr Ile Asn Tyr Lys Val Thr Ala Arg Asn Asn Val Asn Asp Met Val
850                 855                 860

Val Lys Tyr Ile Ala Gln Asn Asp Asp Ile His Val Ile Gly Ile Asp
865                 870                 875                 880

Arg Gly Glu Arg Asn Leu Ile Tyr Ile Ser Val Ile Asp Ser His Gly
                885                 890                 895

Asn Ile Val Lys Gln Lys Ser Tyr Asn Ile Leu Asn Asn Tyr Asp Tyr
            900                 905                 910

Lys Lys Lys Leu Val Glu Lys Glu Lys Thr Arg Glu Tyr Ala Arg Lys
        915                 920                 925

Asn Trp Lys Ser Ile Gly Asn Ile Lys Glu Leu Lys Glu Gly Tyr Ile
930                 935                 940

Ser Gly Val Val His Glu Ile Ala Met Leu Ile Val Glu Tyr Asn Ala
945                 950                 955                 960

Ile Ile Ala Met Glu Asp Leu Asn Tyr Gly Phe Lys Arg Gly Arg Phe
                965                 970                 975

Lys Val Glu Arg Gln Val Tyr Gln Lys Phe Glu Ser Met Leu Ile Asn
            980                 985                 990

Lys Leu Asn Tyr Phe Ala Ser Lys Glu Lys Ser Val Asp Glu Pro Gly
        995                 1000                1005

Gly Leu Leu Lys Gly Tyr Gln Leu Thr Tyr Val Pro Asp Asn Ile
        1010                1015                1020

Lys Asn Leu Gly Lys Gln Cys Gly Val Ile Phe Tyr Val Pro Ala
```

```
              1025                1030                1035
Ala Phe Thr Ser Lys Ile Asp Pro Ser Thr Gly Phe Ile Ser Ala
         1040                1045                1050

Phe Asn Phe Lys Ser Ile Ser Thr Asn Ala Ser Arg Lys Gln Phe
         1055                1060                1065

Phe Met Gln Phe Asp Glu Ile Arg Tyr Cys Ala Glu Lys Asp Met
         1070                1075                1080

Phe Ser Phe Gly Phe Asp Tyr Asn Asn Phe Asp Thr Tyr Asn Ile
         1085                1090                1095

Thr Met Gly Lys Thr Gln Trp Thr Val Tyr Thr Asn Gly Glu Arg
         1100                1105                1110

Leu Gln Ser Glu Phe Asn Asn Ala Arg Arg Thr Gly Lys Thr Lys
         1115                1120                1125

Ser Ile Asn Leu Thr Glu Thr Ile Lys Leu Leu Leu Glu Asp Asn
         1130                1135                1140

Glu Ile Asn Tyr Ala Asp Gly His Asp Ile Arg Ile Asp Met Glu
         1145                1150                1155

Lys Met Asp Glu Asp Lys Lys Ser Glu Phe Phe Ala Gln Leu Leu
         1160                1165                1170

Ser Leu Tyr Lys Leu Thr Val Gln Met Arg Asn Ser Tyr Thr Glu
         1175                1180                1185

Ala Glu Glu Gln Glu Asn Gly Ile Ser Tyr Asp Lys Ile Ile Ser
         1190                1195                1200

Pro Val Ile Asn Asp Glu Gly Glu Phe Phe Asp Ser Asp Asn Tyr
         1205                1210                1215

Lys Glu Ser Asp Asp Lys Glu Cys Lys Met Pro Lys Asp Ala Asp
         1220                1225                1230

Ala Asn Gly Ala Tyr Cys Ile Ala Leu Lys Gly Leu Tyr Glu Val
         1235                1240                1245

Leu Lys Ile Lys Ser Glu Trp Thr Glu Asp Gly Phe Asp Arg Asn
         1250                1255                1260

Cys Leu Lys Leu Pro His Ala Glu Trp Leu Asp Phe Ile Gln Asn
         1265                1270                1275

Lys Arg Tyr Glu
         1280

<210> SEQ ID NO 240
<211> LENGTH: 1373
<212> TYPE: PRT
<213> ORGANISM: Moraxella bovoculi 237

<400> SEQUENCE: 240

Met Leu Phe Gln Asp Phe Thr His Leu Tyr Pro Leu Ser Lys Thr Val
1               5                   10                  15

Arg Phe Glu Leu Lys Pro Ile Asp Arg Thr Leu Glu His Ile His Ala
                20                  25                  30

Lys Asn Phe Leu Ser Gln Asp Glu Thr Met Ala Asp Met His Gln Lys
            35                  40                  45

Val Lys Val Ile Leu Asp Asp Tyr His Arg Asp Phe Ile Ala Asp Met
        50                  55                  60

Met Gly Glu Val Lys Leu Thr Lys Leu Ala Glu Phe Tyr Asp Val Tyr
    65                  70                  75                  80

Leu Lys Phe Arg Lys Asn Pro Lys Asp Asp Glu Leu Gln Lys Gln Leu
                85                  90                  95
```

-continued

Lys Asp Leu Gln Ala Val Leu Arg Lys Glu Ile Val Lys Pro Ile Gly
            100                 105                 110

Asn Gly Gly Lys Tyr Lys Ala Gly Tyr Asp Arg Leu Phe Gly Ala Lys
        115                 120                 125

Leu Phe Lys Asp Gly Lys Glu Leu Gly Asp Leu Ala Lys Phe Val Ile
    130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
            180                 185                 190

His Glu Asn Leu Pro Arg Phe Ile Asp Asn Leu Gln Ile Leu Thr Thr
        195                 200                 205

Ile Lys Gln Lys His Ser Ala Leu Tyr Asp Gln Ile Ile Asn Glu Leu
    210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Thr Leu Leu
                245                 250                 255

Gly Gly Ile Ser Gly Glu Ala Gly Ser Pro Lys Ile Gln Gly Ile Asn
            260                 265                 270

Glu Leu Ile Asn Ser His His Asn Gln His Cys His Lys Ser Glu Arg
        275                 280                 285

Ile Ala Lys Leu Arg Pro Leu His Lys Gln Ile Leu Ser Asp Gly Met
    290                 295                 300

Ser Val Ser Phe Leu Pro Ser Lys Phe Ala Asp Asp Ser Glu Met Cys
305                 310                 315                 320

Gln Ala Val Asn Glu Phe Tyr Arg His Tyr Ala Asp Val Phe Ala Lys
                325                 330                 335

Val Gln Ser Leu Phe Asp Gly Phe Asp Asp His Gln Lys Asp Gly Ile
            340                 345                 350

Tyr Val Glu His Lys Asn Leu Asn Glu Leu Ser Lys Gln Ala Phe Gly
        355                 360                 365

Asp Phe Ala Leu Leu Gly Arg Val Leu Asp Gly Tyr Tyr Val Asp Val
    370                 375                 380

Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
                405                 410                 415

His Ser Leu Ala Ser Leu Glu Gln Ala Ile Glu His Tyr Thr Ala Arg
            420                 425                 430

His Asp Asp Glu Ser Val Gln Ala Gly Lys Leu Gly Gln Tyr Phe Lys
        435                 440                 445

His Gly Leu Ala Gly Val Asp Asn Pro Ile Gln Lys Ile His Asn Asn
    450                 455                 460

His Ser Thr Ile Lys Gly Phe Leu Glu Arg Glu Arg Pro Ala Gly Glu
465                 470                 475                 480

Arg Ala Leu Pro Lys Ile Lys Ser Gly Lys Asn Pro Glu Met Thr Gln
                485                 490                 495

Leu Arg Gln Leu Lys Glu Leu Leu Asp Asn Ala Leu Asn Val Ala His
            500                 505                 510

Phe Ala Lys Leu Leu Thr Thr Lys Thr Thr Leu Asp Asn Gln Asp Gly

-continued

```
              515                 520                 525
Asn Phe Tyr Gly Glu Phe Gly Val Leu Tyr Asp Glu Leu Ala Lys Ile
            530                 535                 540
Pro Thr Leu Tyr Asn Lys Val Arg Asp Tyr Leu Ser Gln Lys Pro Phe
545                 550                 555                 560
Ser Thr Glu Lys Tyr Lys Leu Asn Phe Gly Asn Pro Thr Leu Leu Asn
                565                 570                 575
Gly Trp Asp Leu Asn Lys Glu Lys Asp Asn Phe Gly Val Ile Leu Gln
            580                 585                 590
Lys Asp Gly Cys Tyr Tyr Leu Ala Leu Leu Asp Lys Ala His Lys Lys
            595                 600                 605
Val Phe Asp Asn Ala Pro Asn Thr Gly Lys Ser Ile Tyr Gln Lys Met
610                 615                 620
Ile Tyr Lys Tyr Leu Glu Val Arg Lys Gln Phe Pro Lys Val Phe Phe
625                 630                 635                 640
Ser Lys Glu Ala Ile Ala Ile Asn Tyr His Pro Ser Lys Glu Leu Val
                645                 650                 655
Glu Ile Lys Asp Lys Gly Arg Gln Arg Ser Asp Asp Glu Arg Leu Lys
                660                 665                 670
Leu Tyr Arg Phe Ile Leu Glu Cys Leu Lys Ile His Pro Lys Tyr Asp
            675                 680                 685
Lys Lys Phe Glu Gly Ala Ile Gly Asp Ile Gln Leu Phe Lys Lys Asp
690                 695                 700
Lys Lys Gly Arg Glu Val Pro Ile Ser Glu Lys Asp Leu Phe Asp Lys
705                 710                 715                 720
Ile Asn Gly Ile Phe Ser Ser Lys Pro Lys Leu Glu Met Glu Asp Phe
                725                 730                 735
Phe Ile Gly Glu Phe Lys Arg Tyr Asn Pro Ser Gln Asp Leu Val Asp
            740                 745                 750
Gln Tyr Asn Ile Tyr Lys Lys Ile Asp Ser Asn Asp Asn Arg Lys Lys
            755                 760                 765
Glu Asn Phe Tyr Asn Asn His Pro Lys Phe Lys Lys Asp Leu Val Arg
770                 775                 780
Tyr Tyr Tyr Glu Ser Met Cys Lys His Glu Glu Trp Glu Glu Ser Phe
785                 790                 795                 800
Glu Phe Ser Lys Lys Leu Gln Asp Ile Gly Cys Tyr Val Asp Val Asn
                805                 810                 815
Glu Leu Phe Thr Glu Ile Glu Thr Arg Arg Leu Asn Tyr Lys Ile Ser
                820                 825                 830
Phe Cys Asn Ile Asn Ala Asp Tyr Ile Asp Glu Leu Val Glu Gln Gly
            835                 840                 845
Gln Leu Tyr Leu Phe Gln Ile Tyr Asn Lys Asp Phe Ser Pro Lys Ala
            850                 855                 860
His Gly Lys Pro Asn Leu His Thr Leu Tyr Phe Lys Ala Leu Phe Ser
865                 870                 875                 880
Glu Asp Asn Leu Ala Asp Pro Ile Tyr Lys Leu Asn Gly Glu Ala Gln
                885                 890                 895
Ile Phe Tyr Arg Lys Ala Ser Leu Asp Met Asn Glu Thr Thr Ile His
            900                 905                 910
Arg Ala Gly Glu Val Leu Glu Asn Lys Asn Pro Asp Asn Pro Lys Lys
            915                 920                 925
Arg Gln Phe Val Tyr Asp Ile Ile Lys Asp Lys Arg Tyr Thr Gln Asp
            930                 935                 940
```

Lys Phe Met Leu His Val Pro Ile Thr Met Asn Phe Gly Val Gln Gly
945                 950                 955                 960

Met Thr Ile Lys Glu Phe Asn Lys Lys Val Asn Gln Ser Ile Gln Gln
            965                 970                 975

Tyr Asp Glu Val Asn Val Ile Gly Ile Asp Arg Gly Glu Arg His Leu
        980                 985                 990

Leu Tyr Leu Thr Val Ile Asn Ser Lys Gly Glu Ile Leu Glu Gln Cys
    995                 1000                1005

Ser Leu Asn Asp Ile Thr Thr Ala Ser Ala Asn Gly Thr Gln Met
    1010                1015                1020

Thr Thr Pro Tyr His Lys Ile Leu Asp Lys Arg Glu Ile Glu Arg
    1025                1030                1035

Leu Asn Ala Arg Val Gly Trp Gly Glu Ile Glu Thr Ile Lys Glu
    1040                1045                1050

Leu Lys Ser Gly Tyr Leu Ser His Val Val His Gln Ile Ser Gln
    1055                1060                1065

Leu Met Leu Lys Tyr Asn Ala Ile Val Val Leu Glu Asp Leu Asn
    1070                1075                1080

Phe Gly Phe Lys Arg Gly Arg Phe Lys Val Glu Lys Gln Ile Tyr
    1085                1090                1095

Gln Asn Phe Glu Asn Ala Leu Ile Lys Lys Leu Asn His Leu Val
    1100                1105                1110

Leu Lys Asp Lys Ala Asp Asp Glu Ile Gly Ser Tyr Lys Asn Ala
    1115                1120                1125

Leu Gln Leu Thr Asn Asn Phe Thr Asp Leu Lys Ser Ile Gly Lys
    1130                1135                1140

Gln Thr Gly Phe Leu Phe Tyr Val Pro Ala Trp Asn Thr Ser Lys
    1145                1150                1155

Ile Asp Pro Glu Thr Gly Phe Val Asp Leu Leu Lys Pro Arg Tyr
    1160                1165                1170

Glu Asn Ile Ala Gln Ser Gln Ala Phe Phe Gly Lys Phe Asp Lys
    1175                1180                1185

Ile Cys Tyr Asn Ala Asp Lys Asp Tyr Phe Glu Phe His Ile Asp
    1190                1195                1200

Tyr Ala Lys Phe Thr Asp Lys Ala Lys Asn Ser Arg Gln Ile Trp
    1205                1210                1215

Thr Ile Cys Ser His Gly Asp Lys Arg Tyr Val Tyr Asp Lys Thr
    1220                1225                1230

Ala Asn Gln Asn Lys Gly Ala Ala Lys Gly Ile Asn Val Asn Asp
    1235                1240                1245

Glu Leu Lys Ser Leu Phe Ala Arg His His Ile Asn Glu Lys Gln
    1250                1255                1260

Pro Asn Leu Val Met Asp Ile Cys Gln Asn Asn Asp Lys Glu Phe
    1265                1270                1275

His Lys Ser Leu Met Tyr Leu Leu Lys Thr Leu Leu Ala Leu Arg
    1280                1285                1290

Tyr Ser Asn Ala Ser Ser Asp Glu Asp Phe Ile Leu Ser Pro Val
    1295                1300                1305

Ala Asn Asp Glu Gly Val Phe Phe Asn Ser Ala Leu Ala Asp Asp
    1310                1315                1320

Thr Gln Pro Gln Asn Ala Asp Ala Asn Gly Ala Tyr His Ile Ala
    1325                1330                1335

Leu Lys Gly Leu Trp Leu Leu Asn Glu Leu Lys Asn Ser Asp Asp
    1340                1345                1350

Leu Asn Lys Val Lys Leu Ala Ile Asp Asn Gln Thr Trp Leu Asn
    1355                1360                1365

Phe Ala Gln Asn Arg
    1370

<210> SEQ ID NO 241
<211> LENGTH: 1323
<212> TYPE: PRT
<213> ORGANISM: Prevotella disiens

<400> SEQUENCE: 241

Met Glu Asn Tyr Gln Glu Phe Thr Asn Leu Phe Gln Leu Asn Lys Thr
1               5                   10                  15

Leu Arg Phe Glu Leu Lys Pro Ile Gly Lys Thr Cys Glu Leu Leu Glu
            20                  25                  30

Glu Gly Lys Ile Phe Ala Ser Gly Ser Phe Leu Glu Lys Asp Lys Val
        35                  40                  45

Arg Ala Asp Asn Val Ser Tyr Val Lys Lys Glu Ile Asp Lys Lys His
    50                  55                  60

Lys Ile Phe Ile Glu Glu Thr Leu Ser Ser Phe Ser Ile Ser Asn Asp
65                  70                  75                  80

Leu Leu Lys Gln Tyr Phe Asp Cys Tyr Asn Glu Leu Lys Ala Phe Lys
                85                  90                  95

Lys Asp Cys Lys Ser Asp Glu Glu Val Lys Lys Thr Ala Leu Arg
            100                 105                 110

Asn Lys Cys Thr Ser Ile Gln Arg Ala Met Arg Glu Ala Ile Ser Gln
        115                 120                 125

Ala Phe Leu Lys Ser Pro Gln Lys Lys Leu Leu Ala Ile Lys Asn Leu
    130                 135                 140

Ile Glu Asn Val Phe Lys Ala Asp Glu Asn Val Gln His Phe Ser Glu
145                 150                 155                 160

Phe Thr Ser Tyr Phe Ser Gly Phe Glu Thr Asn Arg Glu Asn Phe Tyr
                165                 170                 175

Ser Asp Glu Glu Lys Ser Thr Ser Ile Ala Tyr Arg Leu Val His Asp
            180                 185                 190

Asn Leu Pro Ile Phe Ile Lys Asn Ile Tyr Ile Phe Glu Lys Leu Lys
        195                 200                 205

Glu Gln Phe Asp Ala Lys Thr Leu Ser Glu Ile Phe Glu Asn Tyr Lys
    210                 215                 220

Leu Tyr Val Ala Gly Ser Ser Leu Asp Glu Val Phe Ser Leu Glu Tyr
225                 230                 235                 240

Phe Asn Asn Thr Leu Thr Gln Lys Gly Ile Asp Asn Tyr Asn Ala Val
                245                 250                 255

Ile Gly Lys Ile Val Lys Glu Asp Lys Gln Glu Ile Gln Gly Leu Asn
            260                 265                 270

Glu His Ile Asn Leu Tyr Asn Gln Lys His Lys Asp Arg Arg Leu Pro
        275                 280                 285

Phe Phe Ile Ser Leu Lys Lys Gln Ile Leu Ser Asp Arg Glu Ala Leu
    290                 295                 300

Ser Trp Leu Pro Asp Met Phe Lys Asn Asp Ser Glu Val Ile Lys Ala
305                 310                 315                 320

Leu Lys Gly Phe Tyr Ile Glu Asp Gly Phe Glu Asn Asn Val Leu Thr
                325                 330                 335

```
Pro Leu Ala Thr Leu Leu Ser Ser Leu Asp Lys Tyr Asn Leu Asn Gly
            340                 345                 350

Ile Phe Ile Arg Asn Asn Glu Ala Leu Ser Ser Leu Ser Gln Asn Val
            355                 360                 365

Tyr Arg Asn Phe Ser Ile Asp Glu Ala Ile Asp Ala Asn Ala Glu Leu
            370                 375                 380

Gln Thr Phe Asn Asn Tyr Glu Leu Ile Ala Asn Ala Leu Arg Ala Lys
385                 390                 395                 400

Ile Lys Lys Glu Thr Lys Gln Gly Arg Lys Ser Phe Glu Lys Tyr Glu
            405                 410                 415

Glu Tyr Ile Asp Lys Lys Val Lys Ala Ile Asp Ser Leu Ser Ile Gln
            420                 425                 430

Glu Ile Asn Glu Leu Val Glu Asn Tyr Val Ser Glu Phe Asn Ser Asn
            435                 440                 445

Ser Gly Asn Met Pro Arg Lys Val Glu Asp Tyr Phe Ser Leu Met Arg
    450                 455                 460

Lys Gly Asp Phe Gly Ser Asn Asp Leu Ile Glu Asn Ile Lys Thr Lys
465                 470                 475                 480

Leu Ser Ala Ala Glu Lys Leu Leu Gly Thr Lys Tyr Gln Glu Thr Ala
                485                 490                 495

Lys Asp Ile Phe Lys Lys Asp Glu Asn Ser Lys Leu Ile Lys Glu Leu
            500                 505                 510

Leu Asp Ala Thr Lys Gln Phe Gln His Phe Ile Lys Pro Leu Leu Gly
            515                 520                 525

Thr Gly Glu Glu Ala Asp Arg Asp Leu Val Phe Tyr Gly Asp Phe Leu
    530                 535                 540

Pro Leu Tyr Glu Lys Phe Glu Glu Leu Thr Leu Leu Tyr Asn Lys Val
545                 550                 555                 560

Arg Asn Arg Leu Thr Gln Lys Pro Tyr Ser Lys Asp Lys Ile Arg Leu
                565                 570                 575

Cys Phe Asn Lys Pro Lys Leu Met Thr Gly Trp Val Asp Ser Lys Thr
            580                 585                 590

Glu Lys Ser Asp Asn Gly Thr Gln Tyr Gly Gly Tyr Leu Phe Arg Lys
            595                 600                 605

Lys Asn Glu Ile Gly Glu Tyr Asp Tyr Phe Leu Gly Ile Ser Ser Lys
    610                 615                 620

Ala Gln Leu Phe Arg Lys Asn Glu Ala Val Ile Gly Asp Tyr Glu Arg
625                 630                 635                 640

Leu Asp Tyr Tyr Gln Pro Lys Ala Asn Thr Ile Tyr Gly Ser Ala Tyr
                645                 650                 655

Glu Gly Glu Asn Ser Tyr Lys Glu Asp Lys Lys Arg Leu Asn Lys Val
            660                 665                 670

Ile Ile Ala Tyr Ile Glu Gln Ile Lys Gln Thr Asn Ile Lys Lys Ser
            675                 680                 685

Ile Ile Glu Ser Ile Ser Lys Tyr Pro Asn Ile Ser Asp Asp Asp Lys
            690                 695                 700

Val Thr Pro Ser Ser Leu Leu Glu Lys Ile Lys Lys Val Ser Ile Asp
705                 710                 715                 720

Ser Tyr Asn Gly Ile Leu Ser Phe Lys Ser Phe Gln Ser Val Asn Lys
                725                 730                 735

Glu Val Ile Asp Asn Leu Leu Lys Thr Ile Ser Pro Leu Lys Asn Lys
            740                 745                 750
```

```
Ala Glu Phe Leu Asp Leu Ile Asn Lys Asp Tyr Gln Ile Phe Thr Glu
            755                 760                 765

Val Gln Ala Val Ile Asp Glu Ile Cys Lys Gln Lys Thr Phe Ile Tyr
    770                 775                 780

Phe Pro Ile Ser Asn Val Glu Leu Glu Lys Glu Met Gly Asp Lys Asp
785                 790                 795                 800

Lys Pro Leu Cys Leu Phe Gln Ile Ser Asn Lys Asp Leu Ser Phe Ala
            805                 810                 815

Lys Thr Phe Ser Ala Asn Leu Arg Lys Lys Arg Gly Ala Glu Asn Leu
            820                 825                 830

His Thr Met Leu Phe Lys Ala Leu Met Glu Gly Asn Gln Asp Asn Leu
            835                 840                 845

Asp Leu Gly Ser Gly Ala Ile Phe Tyr Arg Ala Lys Ser Leu Asp Gly
            850                 855                 860

Asn Lys Pro Thr His Pro Ala Asn Glu Ala Ile Lys Cys Arg Asn Val
865                 870                 875                 880

Ala Asn Lys Asp Lys Val Ser Leu Phe Thr Tyr Asp Ile Tyr Lys Asn
            885                 890                 895

Arg Arg Tyr Met Glu Asn Lys Phe Leu Phe His Leu Ser Ile Val Gln
            900                 905                 910

Asn Tyr Lys Ala Ala Asn Asp Ser Ala Gln Leu Asn Ser Ser Ala Thr
            915                 920                 925

Glu Tyr Ile Arg Lys Ala Asp Asp Leu His Ile Ile Gly Ile Asp Arg
            930                 935                 940

Gly Glu Arg Asn Leu Leu Tyr Tyr Ser Val Ile Asp Met Lys Gly Asn
945                 950                 955                 960

Ile Val Glu Gln Asp Ser Leu Asn Ile Ile Arg Asn Asn Asp Leu Glu
            965                 970                 975

Thr Asp Tyr His Asp Leu Leu Asp Lys Arg Glu Lys Glu Arg Lys Ala
            980                 985                 990

Asn Arg Gln Asn Trp Glu Ala Val Glu Gly Ile Lys Asp Leu Lys Lys
            995                1000                1005

Gly Tyr Leu Ser Gln Ala Val His Gln Ile Ala Gln Leu Met Leu
            1010                1015                1020

Lys Tyr Asn Ala Ile Ile Ala Leu Glu Asp Leu Gly Gln Met Phe
            1025                1030                1035

Val Thr Arg Gly Gln Lys Ile Glu Lys Ala Val Tyr Gln Gln Phe
            1040                1045                1050

Glu Lys Ser Leu Val Asp Lys Leu Ser Tyr Leu Val Asp Lys Lys
            1055                1060                1065

Arg Pro Tyr Asn Glu Leu Gly Gly Ile Leu Lys Ala Tyr Gln Leu
            1070                1075                1080

Ala Ser Ser Ile Thr Lys Asn Asn Ser Asp Lys Gln Asn Gly Phe
            1085                1090                1095

Leu Phe Tyr Val Pro Ala Trp Asn Thr Ser Lys Ile Asp Pro Val
            1100                1105                1110

Thr Gly Phe Thr Asp Leu Leu Arg Pro Lys Ala Met Thr Ile Lys
            1115                1120                1125

Glu Ala Gln Asp Phe Phe Gly Ala Phe Asp Asn Ile Ser Tyr Asn
            1130                1135                1140

Asp Lys Gly Tyr Phe Glu Phe Glu Thr Asn Tyr Asp Lys Phe Lys
            1145                1150                1155

Ile Arg Met Lys Ser Ala Gln Thr Arg Trp Thr Ile Cys Thr Phe
```

```
        1160                1165                1170

Gly Asn Arg Ile Lys Arg Lys Lys Asp Lys Asn Tyr Trp Asn Tyr
        1175                1180                1185

Glu Glu Val Glu Leu Thr Glu Glu Phe Lys Lys Leu Phe Lys Asp
        1190                1195                1200

Ser Asn Ile Asp Tyr Glu Asn Cys Asn Leu Lys Glu Ile Gln
        1205                1210                1215

Asn Lys Asp Asn Arg Lys Phe Phe Asp Asp Leu Ile Lys Leu Leu
        1220                1225                1230

Gln Leu Thr Leu Gln Met Arg Asn Ser Asp Asp Lys Gly Asn Asp
        1235                1240                1245

Tyr Ile Ile Ser Pro Val Ala Asn Ala Glu Gly Gln Phe Phe Asp
        1250                1255                1260

Ser Arg Asn Gly Asp Lys Lys Leu Pro Leu Asp Ala Asp Ala Asn
        1265                1270                1275

Gly Ala Tyr Asn Ile Ala Arg Lys Gly Leu Trp Asn Ile Arg Gln
        1280                1285                1290

Ile Lys Gln Thr Lys Asn Asp Lys Lys Leu Asn Leu Ser Ile Ser
        1295                1300                1305

Ser Thr Glu Trp Leu Asp Phe Val Arg Glu Lys Pro Tyr Leu Lys
        1310                1315                1320

<210> SEQ ID NO 242
<211> LENGTH: 39
<212> TYPE: DNA
<213> ORGANISM: Homo sapiens

<400> SEQUENCE: 242
tatctgtttg gagctgttgg catcatgttc ctggggctc                            39

<210> SEQ ID NO 243
<211> LENGTH: 39
<212> TYPE: DNA
<213> ORGANISM: Homo sapiens

<400> SEQUENCE: 243
gagccccagg aacatgatgc caacagctcc aaacagata                            39

<210> SEQ ID NO 244
<211> LENGTH: 43
<212> TYPE: RNA
<213> ORGANISM: Artificial Sequence
<220> FEATURE:
<223> OTHER INFORMATION: crRNA sequence for genomic safe harbor locus
      shown in FIG. 1. The crRNA can be modified at the 3' end with an
      18 atom oligoethylene glycol spacer and a 3' terminal thiol.

<400> SEQUENCE: 244
uaauuucuac ucuuguagau gagcuguugg caucauguuc cug                       43

<210> SEQ ID NO 245
<211> LENGTH: 92
<212> TYPE: DNA
<213> ORGANISM: Homo sapiens

<400> SEQUENCE: 245
gagggattcc ctacctcccg tgctatctgt ttggagctgt tggcatcatg ttcctggggc     60
tccgaagctg ctgggaaaca ggagtgttct gc                                   92
```

```
<210> SEQ ID NO 246
<211> LENGTH: 92
<212> TYPE: DNA
<213> ORGANISM: Homo sapiens

<400> SEQUENCE: 246
gcagaacact cctgtttccc agcagcttcg gagccccagg aacatgatgc caacagctcc      60
aaacagatag cacgggaggt agggaatccc tc                                   92

<210> SEQ ID NO 247
<211> LENGTH: 100
<212> TYPE: DNA
<213> ORGANISM: Artificial Sequence
<220> FEATURE:
<223> OTHER INFORMATION: Synthetic homology template for target sequence
      of GSH locus shown in FIG. 1 with PAM mutation

<400> SEQUENCE: 247
gagggattcc ctacctcccg tgctatctgt tcggagctgt tggcatcatg gcggccgctt      60
cctggggctc cgaagctgct gggaaacagg agtgttctgc                           100

<210> SEQ ID NO 248
<211> LENGTH: 100
<212> TYPE: DNA
<213> ORGANISM: Artificial Sequence
<220> FEATURE:
<223> OTHER INFORMATION: Synthetic homology template for non-target
      sequence of GSH locus shown in FIG. 1 with PAM mutation. The
      synthetic homology template can be modified at the 3' end with an
      18 atom oligoethylene glycol spacer and a 3' terminal thiol.

<400> SEQUENCE: 248
gcagaacact cctgtttccc agcagcttcg gagccccagg aagcggccgc catgatgcca      60
acagctccga acagatagca cgggaggtag ggaatccctc                           100

<210> SEQ ID NO 249
<211> LENGTH: 27
<212> TYPE: DNA
<213> ORGANISM: Homo sapiens

<400> SEQUENCE: 249
tttggagctg ttggcatcat gttcctg                                         27

<210> SEQ ID NO 250
<211> LENGTH: 27
<212> TYPE: DNA
<213> ORGANISM: Homo sapiens

<400> SEQUENCE: 250
tttggagctg ttggcatctt gttcctg                                         27

<210> SEQ ID NO 251
<211> LENGTH: 37
<212> TYPE: DNA
<213> ORGANISM: Homo sapiens

<400> SEQUENCE: 251
ttgttgttta tccaaacctc ctaaatgata cgtgttt                              37

<210> SEQ ID NO 252
<211> LENGTH: 37
<212> TYPE: DNA
<213> ORGANISM: Homo sapiens
```

<400> SEQUENCE: 252
aaacacgtat catttaggag gtttggataa acaacaa                                37

<210> SEQ ID NO 253
<211> LENGTH: 41
<212> TYPE: RNA
<213> ORGANISM: Artificial Sequence
<220> FEATURE:
<223> OTHER INFORMATION: crRNA sequence for GSH locus shown in FIG. 3.
      The crRNA can be modified at the 3' end with an 18 atom
      oligoethylene glycol spacer and a 3' terminal thiol.

<400> SEQUENCE: 253
uaauuucuac ucuuguagau uccaaaccuc cuaaaugaua c                           41

<210> SEQ ID NO 254
<211> LENGTH: 92
<212> TYPE: DNA
<213> ORGANISM: Homo sapiens

<400> SEQUENCE: 254
gcttagtgct tatttatttt aggttgttgt ttatccaaac ctcctaaatg atacgtgttt       60
ggaacaagta acagcattgt tccttgatgt tg                                    92

<210> SEQ ID NO 255
<211> LENGTH: 92
<212> TYPE: DNA
<213> ORGANISM: Homo sapiens

<400> SEQUENCE: 255
caacatcaag gaacaatgct gttacttgtt ccaaacacgt atcatttagg aggtttggat      60
aaacaacaac ctaaaataaa taagcactaa gc                                    92

<210> SEQ ID NO 256
<211> LENGTH: 100
<212> TYPE: DNA
<213> ORGANISM: Artificial Sequence
<220> FEATURE:
<223> OTHER INFORMATION: Synthetic homology template for target sequence
      of GSH locus shown in FIG. 3 with PAM mutation

<400> SEQUENCE: 256
gcttagtgct tatttatttt aggttgttgt tcatccaaac ctcctaaatg gcggccgcat      60
acgtgtttgg aacaagtaac agcattgttc cttgatgttg                           100

<210> SEQ ID NO 257
<211> LENGTH: 100
<212> TYPE: DNA
<213> ORGANISM: Artificial Sequence
<220> FEATURE:
<223> OTHER INFORMATION: Synthetic homology template for non-target
      sequence of GSH locus shown in FIG. 3 with PAM mutation. The
      synthetic homology template can be modified at the 3' end with an
      18 atom oligoethylene glycol spacer and a 3' terminal thiol.

<400> SEQUENCE: 257
caacatcaag gaacaatgct gttacttgtt ccaaacacgt atgcggccgc catttaggag      60
gtttggatga acaacaacct aaaataaata agcactaagc                           100

<210> SEQ ID NO 258
<211> LENGTH: 53
<212> TYPE: DNA
<213> ORGANISM: Homo sapiens

<400> SEQUENCE: 258
gcgagcaagc tcagtttaca cccgatccac tggggagcag gaaatatctg tgg         53

<210> SEQ ID NO 259
<211> LENGTH: 53
<212> TYPE: DNA
<213> ORGANISM: Homo sapiens

<400> SEQUENCE: 259
ccacagatat ttcctgctcc ccagtggatc gggtgtaaac tgagcttgct cgc         53

<210> SEQ ID NO 260
<211> LENGTH: 41
<212> TYPE: RNA
<213> ORGANISM: Artificial Sequence
<220> FEATURE:
<223> OTHER INFORMATION: crRNA sequence for GSH locus shown in FIG. 4.
      The crRNA can be modified at the 3' end with an 18 atom
      oligoethylene glycol spacer and a 3' terminal thiol.

<400> SEQUENCE: 260
uaauuucuac ucuuguagau cacccgaucc acuggggagc a                       41

<210> SEQ ID NO 261
<211> LENGTH: 88
<212> TYPE: DNA
<213> ORGANISM: Artificial Sequence
<220> FEATURE:
<223> OTHER INFORMATION: Synthetic homology template for non-target
      sequence of GSH locus shown in FIG. 4

<400> SEQUENCE: 261
ccacttgagt ccgtgtcaca agcccacaga tatttcctgc gcggccgctc cccagtggat   60
cgggtgtaaa ctgagcttgc tcgctcgg                                      88

<210> SEQ ID NO 262
<211> LENGTH: 88
<212> TYPE: DNA
<213> ORGANISM: Artificial Sequence
<220> FEATURE:
<223> OTHER INFORMATION: Synthetic homology template for target sequence
      of GSH locus shown in FIG. 4

<400> SEQUENCE: 262
cgagcaagct cagttcacac ccgatccact ggggagcagg gcggccgcaa atatctgtgg   60
gcttgtgaca cggactcaag tgggctgg                                      88

<210> SEQ ID NO 263
<211> LENGTH: 43
<212> TYPE: DNA
<213> ORGANISM: Homo sapiens

<400> SEQUENCE: 263
aagctcagtt tacacccgat ccactgggga gcaggaaata tct                     43

<210> SEQ ID NO 264
<211> LENGTH: 36
<212> TYPE: RNA
<213> ORGANISM: Artificial Sequence
<220> FEATURE:
<223> OTHER INFORMATION: crRNA to use with Cas9 described in Example 1.
      The crRNA can be modified at the 5' end with an 18 atom
      oligoethylene glycol spacer and a 5' terminal thiol.

```
<400> SEQUENCE: 264
cacccgaucc acugggagc guuuuagagc uaugcu                    36
```